United States Patent
Kang et al.

(10) Patent No.: US 10,435,423 B2
(45) Date of Patent: Oct. 8, 2019

(54) FUNCTIONALIZED PHOSPHONATES VIA MICHAEL ADDITION

(71) Applicant: The Board of Regents of the Nevada System of Higher Education on Behalf of the University of Nevada, Las Vegas, Las Vegas, NV (US)

(72) Inventors: Jun Yong Kang, Henderson, NV (US); Hai Huang, Las Vegas, NV (US); Nagaraju Molleti, Las Vegas, NV (US)

(73) Assignee: The Board of Regents of the Nevada System of Higher Education on Behalf of the University of Nevada, Las Vegas, Las Vegas, NV (US)

( * ) Notice: Subject to any disclaimer, the term of this patent is extended or adjusted under 35 U.S.C. 154(b) by 0 days.

(21) Appl. No.: 15/650,417

(22) Filed: Jul. 14, 2017

(65) Prior Publication Data

US 2018/0051044 A1 Feb. 22, 2018

Related U.S. Application Data

(60) Provisional application No. 62/376,213, filed on Aug. 17, 2016.

(51) Int. Cl.
| | |
|---|---|
| *C07F 9/50* | (2006.01) |
| *C07F 9/53* | (2006.01) |
| *C07F 9/6584* | (2006.01) |
| *C07D 403/04* | (2006.01) |

(52) U.S. Cl.
CPC .......... *C07F 9/6584* (2013.01); *C07D 403/04* (2013.01); *C07F 9/505* (2013.01); *C07F 9/53* (2013.01)

(58) Field of Classification Search
None
See application file for complete search history.

(56) References Cited

U.S. PATENT DOCUMENTS 5,789,434 A 8/1998 Kluender et al.

OTHER PUBLICATIONS

STN Registry database entry for CAS RN 1838153-30-2, entered STN Dec. 28, 2015, accessed Sep. 5, 2018.*
Abbaraju, S. et al., Quinidine Thiourea-Catalyzed Enantioselective Synthesis of β-Nitrophosphonates: Beneficial Effects of Molecular Sieves. Tetrahedron. 2011; 67(39):7479-84.
Alcaine, A. et al., Thiourea Catalyzed Organocatalytic Enantioselective Michael Addition of Diphenyl Phosphite to Nitroalkenes. Org Biomol Chem. 2011; 9(8):2777-83.
Andaloussi, M. et al., Design, Synthesis, and X-Ray Crystallographic Studies of α-Aryl Sustituted Fosmidomycin Analogues as Inhibitors of *Mycobacterium tuberculosis* 1-Deoxy-$_D$-xylulose 5-Phosphate Reductoisomerase. J Med Chem. 2011; 54:4964-76.
Bernacki, A.L. et al., A Selective and Convenient Method for the Synthesis of 2-Phenylaminothiazolines. Org Lett. 2010; 12(23):5526-9.
Bigge, C.F. et al., Exploration of N-Phosphonoalkyl-, N-Phosphonoalkenyl-, and N-(Phosphonoalkyl)phenyl-spaced α-amino Acids as Competitive N-Methyl-$_D$-aspartic Acid Antagonists. J Med Chem. 1992; 35(8):1371-84.
Blom, K.F. et al., Preparative LC-MSS Purification: Improved Compound Specific Method Optimization. J Combi Chem. 2004; 6(6):874-83.
Braunstein, P. and Naud F., Hemilability of Hybrid Ligands and the Coordination Chemistry of Oxazoline-Based Systems. Angew Chem Int Ed. 2001; 40(4):680-99.
Cai, Y. et al., Regioselective $BF_3 \cdot Et_2O$-Catalyzed C—H Functionalization of Indoles and Pyrrole with Reaction of α-Diazophosphonates. RSC Adv. 2016; 6(73):69352-6.
Dalcanale, E. and Montanari, F., Selective Oxidation of Aldehydes to Carboxylic Acids with Sodium Chlorite-Hydrogen Peroxide. J Org Chem. 1986; 51(4):567-9.
Dingwall, J.G. et al., Diethoxymethylphosphinties and Phosphinates. Intermediates for the Synthesis of α, β- and δ-Aminoalkylphosphonous Acids. Tetrahedron. 1989; 45(12):6787-808.
Enders, D. et al., Asymmetric Synthesis of α-Substituted β-Nitrophosphonic Acids by Phospha-Analogous Michael Addition to Aromatic Nitroalkenes. Angew Chem Int Ed. 2000; 39(24):4605-7.
Enders, D. et al., The Phospha-Michael Addition in Organic Synthesis. Eur J Org Chem. 2006; 2006(1):29-49.
Fu, X. et al., Bicyclic Guanidine-Catalyzed Enantioselective Phospha-Michael Reaction: Synthesis of Chiral ß-Aminophosphine Oxides and ß-Aminophosphines. Chem Commun. 2007; 2007(47):5058-60.
Hanaya, T. et al., Orientation of the Addition of Dimethyl Phosphonate to 5,6-Dideoxy-6-nitro-$_D$-hex-5-enofuranoses. Bull Chem Soc Jpn. 1992; 65:1154-6.
Hosseini-Sarvari, M. and Etemad, S., Nanosized Zinc Oxide as a Catalyst for the Rapid and Green Synthesis of β-Phosphono Malonates. Tetrahedron. 2008; 64(23):5519-23.
Ikemura, K. et al., Design of New Phosphonic Acid Monomers for Dental Adhesives—Synthesis of (Meth)acryloxyalkyl 3-Phosphonopropionates and Evaluation of their Adhesion-Promoting Functions. Dent Mater J. 2006; 25(3):566-75.
Jiang, Z. et al., P—C Bond Formation via Direct and Three-Component Conjugate Addition Catalyzed by 1,5,7-Triazabicyclo[4.4.0]dec-5-ene (TBD). Tetrahedron Lett. 2007; 48(1):51-4.
Jomaa, H. et al., Inhibitors of the Nonmevalonate Pathway of Isoprenoid Biosynthesis as Antimalarial Drugs. Science. 1999; 285(5433):1573-6.
Kinney, W.A. et al., Bioisosteric Replacement of the a-Amino Carboxylic Acid Functionality in 2-Amino-5-Phosphonopentanoic Acid Yields Unique 3,4-Diamino-3-Cyclobutene-1,2-Dione Containing NMDA Antagonists. J Med Chem. 1992. 35(25):4720-6.
Kinney, W.A. et al., Design and Synthesis of [2-(8,9-Dioxo-2,6-diazabicyclo[5.2.0]non-1(7)-en-2-yl)-ethyl] Phosphonic Acid (EAA-090), a Potent N-Methyl-D-aspartate Antagonist, via the Use of 3-Cyclobutene-1,2-dione as an Achiral α-Amino Acid Bioisotere. J Med Chem. 1998; 41:236-46.

(Continued)

*Primary Examiner* — Alicia L Otton
(74) *Attorney, Agent, or Firm* — Ballard Spahr LLP

(57) ABSTRACT

Provided herein are functionalized phosphonates and methods for making same via phosphite addition to an atom alpha to an electron withdrawing group. This abstract is intended as a scanning tool for purposes of searching in the particular art and is not intended to be limiting of the present invention.

12 Claims, No Drawings

(56) References Cited

OTHER PUBLICATIONS

Laghzizil, A. et al., Removal of Fluoride from Moroccan Phosphate and Synthetic Fluoroapatites. J Fluorine Chem. 2000; 101(1):69-73.
Lenker, H.K. et al., Phospha-Michael Additions to Activated Internal Alkenes: Steric and Electronic Effects. J Org Chem. 2012; 77(3):1378-85.
Li, G. et al., Chiral Ytterbium Silylamide Catalyzed Enantioselective Phospha-Michael Addition of Diethyl Phosphite to Chalcones. Tetrahedron: Asymmetry. 2014; 25(13-14):989-96.
Li, Y.-G. et al., Synthesis and Stereochemistry of α-Aryl-β-Nitroalkylphosphinates. Phosphorus, Sulfur, Silicon, Relat Elem. 1990; 47(1):229-42.
Li, Z. et al., Novel Ionic Tagged Amine Anchored on Magnetic Nanoparticles: An Efficient and Magnetically Recyclable Catalyst for Phospha-Michael Addition. Catal Lett. 2014; 144(11):1810-8.
Luo, X. et al., Enantioselective Organocatalytic Phospha-Michael Reaction of α,β-Unsaturated Aldehydes. RSC Adv. 2011; 1(4):698-705.
Maerten, E. et al., Organocatalytic Asymmetric Direct Phosphonylation of α,β-Unsaturated Aldehydes: Mechanism, Scope, and Application in Synthesis. J Org Chem. 2007; 72(23):8893-903.
Moiseev, D.V. et al., New Tertiary Phosphines from Cinnamaldehydes and Diphenylphosphine. Inorg Chem. 2007; 46(26):11467-74.
Moonen, K. et al., One-Pot Tandem 1,4-1,2-Addition of Phosphites to α,β-Unsaturated Imines for the Synthesis of Glutamic Acid Analogues. Angew Chem Int Ed. 2005; 44(45):7407-11.
Mulla, K. and Kang, J.Y., 1,3,2-Diazaphospholidine (N-Heterocyclic Phosphine)-Mediated Carbon-Phosphorus Bond-Forming, One-Pot Tandem Reaction: A Route to α-Amino Phosphonates. J Org Chem. 2016; 81(11):4550-8.
Mulla, K. et al., Utility of Bifunctional N-Heterocyclic Phosphine (NHP)-Thioreas for Metal-Fre Carbon-Phosphorus Bond Construction Toward Regio- and Stereoselective Formation of Vinylphosphonates. J Org Chem. 2016; 81(1):77-88.
Palacois, F. et al., Synthesis of β-Aminophosphonates and -Phosphinates. Chem Rev. 2001; 105(3):899-932.
Peturssion, S. et al., Protecting groups in Carbohydrate Chemistry. J Chem Educ. 1997; 74(11):1297.
Pudovik, A.N. and Konovalova, I.V., Addition Reactions of Esters of Phosphorus(III) Acids with Unsaturated Systems. Synthesis. 1979; 1979(2):81-96.
Radwan-Olszewska, K. et al., Selective Synthesis of α-Fluoro-β-keto- and α-Fluoro-β-aminophosphonates via Electrophilic Fluorination by Selectfluor. J Org Chem. 2011; 76(4):1170-3.
Rai, V. and Namboothiri, I.N.N., Enantioselective Conjugate Addition of Dialkyl Phosphites to Nitroalkenes. Tetrahedron: Asymmetry. 2008; 19(20):2335-8.
Robbie, A.J. et al., Complexes of Sterically-Hindered Diaminophosphinothiolate Ligands with Rh(I), Ni(II) and Pd(II). Polyhedron. 2011; 30(11):1849-56.
Rulev, A.Y., Recent Advances in Michael Addition of H-Phosphonates. RSC Adv. 2014; 4:26002-12.
Russo, A. et al., Asymmetric Organocatalytic Conjugate Addition of Diarylphosphane Oxides to Chalcones. Eur J Org Chem. 2010; 2010:6736-9.
Schweitzer, B.A. et al., Design and Synthesis of β-Carboxamido Phosphonates as Potent Inhibitors of Imidazole Glycerol Phosphate Dehydratase. Bioorg Med Chem Lett. 1999; 9(14):2053-8.
Schwender, C. et al., 1-Naphthylmethylphosphonic Acid Derivatives as Osteoclastic Acid Phosphatase Inhibitors. Bioorg Med Chem Lett. 1995; 5(16):1801-6.
Simoni, D. et al., Tetramethylguanidine (TMG)-Catalyzed Addition to Dialkyl Phosphites to α,β-Unsaturated Carbonyl Compounds, Alkenenitriles, Aldehydes, Ketones and Imines. Tetrahedron Lett. 1998; 39(41):7615-8.
Sobhani, S. et al., Phospha-Michael Addition of Diethyl Phosphite to α,β-Unsaturated Malonates Catalyzed by Nano γ-$Fe_2O_3$-Pyridine Based Catalyst as a New Magnetically Recyclable Heterogeneous Organic Base. Appl Catal, A. 2013; 454:145-51.
Sobhani, S. et al., Phospha-Michael Addition of Phosphorus Nucleophiles to α,β-Unsaturated Malonates Using 3-Aminopropylated Silica Gel as an Efficient and Recyclable Catalyst. J Organomet Chem. 2011; 696:813-7.
Sohtome, Y. et al., Enantioselective Phospha-Michael Reaction of Diphenyl Phosphonate with Nitroolefins Utilizing Conformationally Flexible Guanindinium/Bisthiourea Organocatalyst: Assembly-State Tunability in Asymmetric Organocatalysis. Adv Synth catal. 2011; 353(14-15):2631-6.
Sommen, G.L. et al., Selenium-Containing Heterocycles from Isoselenocyanates: Synthesis of 1,3-Selenazolidine and Perhydro-1,3-selenazine Derivatives. Eur J Org Chem. 2005; 2005 (14):3128-37.
Strappaveccia, G. et al., PS-BEMP as a basic Catalyst for the Phospha-Michael Addition to Electron-Poor Alkenes. Org Biomol Chem. 2016; 14(14):3521-5.
Terada, M. et al., Enantioselective 1,4-Addition Reactions of Diphenyl Phosphite to Nitroalkenes Catalyzed by an Axially Chiral Guanidine. J Am Chem Soc. 2007; 129(46):14112-3.
Tronchet, J.M.J. et al., Some Novel Types of Nitrosugars. J Carbohydr Chem. 1985; 4:29-52.
Trost, B.M., Atom Economy—A Challenge for Organic Synthesis: Homogeneous Catalysis Leads the Way. Angew Chem Int Ed Engl. 1995; 34:259-81.
Trost, B.M., The Atom Economy—a Search for Synthetic Efficiency. Science. 1991; 254(5037):1471-7.
Turcheniuk, K.V. et al., Efficient Asymmetric Synthesis of Trifluoromethylated β-Aminophosphonates and Their Incorporation into Dipeptides. Chem commun. 2012; 48(94):11519-21.
Wang, F. et al., Novel Lanthanide Amides Incorporating Neural Pyrrole Ligand in a Constrained Geometry Architecture: Synthesis, Characterization, Reaction, and Catalytic Activity. Organometallics. 2013; 32(14):3920-31.
Wang, J. et al., Quinine-Catalyzed Enantioselective Michael Addition of Diphenyl Phosphite to Nitroolefins: Synthesis of Chiral Precursors of α-Substituted β-Aminophosphonates. Adv Synth Catal. 2007; 349(7):1052-6.
Wen, S. et al., Enantioselective Organocatalytic Phospha-Michael Reaction of α, β-Unsaturated Ketones. Chem Commun. 2010; 46(26):4806-8.
Wester, R.T. et al., Preparation of a Novel Series of Phosphonate Nortatine Renin Inhibitors. Bioorg Med Chem Lett. 1994; 4(16):2005-10.
Yamamoto, H. et al., Synthesis and Structural Analysis of 5-Deoxy-5-C-(hydroxyphosphinyl)-$_D$-xylo- and -glucopyranoses. J Org Chem. 1985; 50(19):3516-21.
Yamashita, M. et al., First X-Ray Study on Orientation of Addition of Phorphorus Compounds to 3-O-Alkyl-5,6-dideoxy-1,2-O-isopropylidene-6-C-nitro-α-D-xylo-hexo-5-(Z)-enofuranoses. Chem Lett. 1987; 16:1407-8.
Yamashita, M. et al., Synthesis of Dimethyl (1-Nitromethylakyl)phosphonates and Their Conversion to Dimethyl (1-Formylalkyl)phosphonates by Oxidation with Ozone. Synthesis. 1987; 1987(1):62-4.
Yang, Q. et al., Palladium-Catalyzed Migratory Insertion of Isocyanides for Synthesis of C-Phosphonoketenimines. ACS Catal. 2016; 6(7):4715-9.
Yokomatsu, T. et al., Lipase-Catalyzed Enantioselective Acylation of Prochiral 2-(ω-Phosphono)alkyl-1,3-Propanediols: Application to the Enantioselective Synthesis of ω-Phosphono-a-Amino Acids. Tetrahedron: Asymmetry. 1996; 7(9):2743-54.
Zhang, A. et al., Lanthanide-Catalyzed Selective Addition of Diethyl Phosphite to Chalcones. Heteroat Chem. 2013; 24(5):345-54.
Zhao, D. et al., Highly Enantioselective 1,4-Addition of Diethyl Phosphite to Enones Using a Dinuclear Zn Catalyst. Chem Eur J. 2009; 15(12):2738-41.
Zhu, Y. et al., Squaramide-Catalyzed Enantioselective Michael Addition of Diphenyl Phosphite to Nitroalkenes. Angew Chem Int Ed. 2010; 49:153-6.

* cited by examiner

FUNCTIONALIZED PHOSPHONATES VIA MICHAEL ADDITION

CROSS-REFERENCE TO RELATED APPLICATIONS

This Application claims the benefit of U.S. Provisional Application No. 62/376,213, filed on Aug. 17, 2016, which is incorporated herein by reference in its entirety.

BACKGROUND

The phospha-Michael addition reaction has emerged one of the most versatile and powerful synthetic tools for carbon-phosphorus bond formation because of its atom and step economic approach as well as many different products available with various substitution patterns, depending on both the acceptor and the donor nucleophiles (Trost (1991) *Science* 254: 1471-1477; Trost (1995) *Angew. Chem. Int. Ed.* 34: 259-281; Rulev (2014) *RSC Adv.* 4: 26002-26012; Enders et al. (2006) *Eur. J. Org. Chem.* 2006: 29-49). Highly functionalized and valuable phospha-Michael adducts are generated under the reaction conditions in one step (Maerten et al. (2007) *J. Org. Chem.* 72: 8893-8903; Moonen et al. (2005) *Angew. Chem. Int. Ed.* 44: 7407-7411; Laghzizil et al. (2000) *J. Fluorine Chem.* 101: 69-73; Moiseev et al. (2007) *Inorg. Chem.* 46: 11467-11474; Luo et al. (2011) *RSC Adv.* 1: 698-705; Zhao et al. (2009) *Chem. Eur. J.* 15: 2738-2741; Simoni et al. (1998) *Tetrahedron Lett.* 39: 7615-7618; Li et al. (2014) *Tetrahedron: Asymmetry* 25: 989-996; Strappaveccia et al. (2016) *Org. Biomol. Chem.* 14: 3521-3525; Wen et al. (2010) *Chem. Comm.* 46: 4806-4808; Russo et al. (2010) *Eur. J. Org. Chem.* 2010: 6736-6739; Rai and Namboothiri (2008) *Tetrahedron: Asymmetry* 19: 2335-2338; Zhu et al. (2010) *Angew. Chem. Int. Ed.* 49: 153-156; Fu et al. (2007) *Chem. Commun.* 5058-5060; Wang et al. (2007) *Adv. Synth. Catal.* 349: 1052-1056; Lenker et al. (2012) *J. Org. Chem.* 77: 1378-1385; Li et al. (2014) *Catal. Lett.* 144: 1810-1818; Sobhani et al. (2013) *Appl. Catal., A* 454: 145-151; Sobhani et al. (2011) *J. Organomet. Chem.* 696: 813-817; Hosseini-Sarvari and Etemad (2008) *Tetrahedron* 64: 5519-5523).

Among the phospha-Michael adducts, γ-ketophosphonates and their phosphonic acid derivatives have received significant attention in recent years owing to their both biological properties and pharmaceutical applications. They exhibit a wide range of enzyme inhibitions such as matrix metalloprotease (MMP-2) inhibitor (Kluender et al. In U.S. Pat. Appl. U.S. 95-539409 951106, Chem. Abstr 1998, p. 161412) and osteoclastic acid phosphatase (OAP) inhibitor (Schwender et al. (1995) *Bioorg. Med. Chem. Lett.* 5: 1801-1806). In addition, they are versatile precursors for the synthesis of important γ-aminophosphonate compounds of anti-malarial drugs including Fosmidomycin and FR-900098 (Maerten et al. (2007) *J. Org. Chem.* 72: 8893-8903; Jomaa et al. (1999) *Science* 285: 1573-1576; Andaloussi et al. (2011) *J. Med. Chem.* 54: 4964-4976). Furthermore, 3-phosphonopropionate has been identified as a promising dental adhesive (Ikemura et al. (2006) *Dent. Mater. J.* 25: 566-575).

Dialkyl phosphonate or trialkyl phosphites are the common Michael donors of this phospha-Michael addition in which only the trivalent phosphite form of the active nucleophile undergoes 1,4-addition to α,β-unsaturated carbonyls to form the γ-ketophosphonates (Zhao et al. (2009) *Chem. Eur. J.* 15: 2738-2741; Russo et al. (2010) *Eur. J. Org. Chem.* 2010: 6736-6739). With various methods available for the tautomerism in favor of the phosphite form between the phosphite and phosphonate equilibrium, dialkyl phosphonate Michael donors have been successfully applied for the synthesis of γ-ketophosphonates (Zhao et al. (2009) *Chem. Eur. J.* 15: 2738-2741; Simoni et al. (1998) *Tetrahedron Lett.* 39: 7615-7618; Li et al. (2014) *Tetrahedron: Asymmetry* 25: 989-996; Strappaveccia et al. (2016) *Org. Biomol. Chem.* 14: 3521-3525). On the other hand, application of the trialkyl phosphites to the phospha-Michael reaction is limited to a handful of examples and currently requires complex reaction conditions (Maerten et al. (2007) *J. Org. Chem.* 72: 8893-8903; Moonen et al. (2005) *Angew. Chem. Int. Ed.* 44: 7407-7411). In 2007, Jørgensen and co-workers reported pyrrolidine-catalyzed enantioselective phospha-Michael addition of trialkyl phosphite (P(O-i-Pr)$_3$) to the α,β-unsaturated aldehydes for β-phosphonylation, in combination of Brønsted acid (PhCO$_2$H) and an external nucleophile (NaI) (Maerten et al. (2007) *J. Org. Chem.* 72: 8893-8903). In addition, synthetic application of the precedent amine-catalyzed phospha-Michael reaction of the trialkyl phosphites to α,β-unsaturated aldehydes still faces two major synthetic hurdles: 1) The crucial step, the transformation of P(III) to P(V) (Maerten et al. (2007) *J. Org. Chem.* 72: 8893-8903), must be performed via nucleophilic attack by additives. 2) Chemoselectivity is also another inherent difficulty in this type of addition due to the reversibility of the nucleophilic attack and competition between 1,2- and 1,4-addition (Maerten et al. (2007) *J. Org. Chem.* 72: 8893-8903; Moonen et al. (2005) *Angew. Chem. Int. Ed.* 44: 7407-7411; Moiseev et al. (2007) *Inorg. Chem.* 46: 11467-11474; Luo et al. (2011) *RSC Adv.* 1: 698-705; Strappaveccia et al. (2016) *Org. Biomol. Chem.* 14: 3521-3525).

Despite the plethora of known applications of phospha-Michael adducts, the preparation of these compounds has remained limited due to the use of additives and competing reaction products. Consequently, the development of a selective method of phosphonylation for accessing functionalized phosphonates is highly desirable in synthetic organic chemistry. These needs and others are met by the present invention.

SUMMARY

In accordance with the purpose(s) of the invention, as embodied and broadly described herein, the invention, in one aspect, relates to functionalized phosphonates and methods of preparing these compounds via, for example, a phospha-Michael addition of an N-heterocyclic phosphines.

Disclosed are methods for preparing a product compound having a structure represented by a formula:

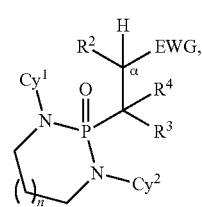

wherein n is 0 or 1; wherein each of $Cy^1$ and $Cy^2$ is independently selected from: aryl substituted with 0, 1, 2, or 3 groups independently selected from halogen, hydroxyl, amine, alkylamino, dialkylamino, C1-C4 alkyl, and C1-C4 alkoxy; a 5- or 6-membered heteroaryl having 1, 2, or 3 ring-members selected from O, S, and $NR^1$ and substituted with 0, 1, 2, or 3 groups independently selected from halogen, hydroxyl, amine, alkylamino, dialkylamino, C1-C4 alkyl, and C1-C4 alkoxy; a 5- or 6-membered cycloalkyl substituted with 0, 1, 2, or 3 groups independently selected from halogen, hydroxyl, amine, alkylamino, dialkylamino, C1-C4 alkyl, and C1-C4 alkoxy; and a 5- or 6-membered heterocycloalkyl having 1, 2, or 3 ring-members selected from O, S, and $NR^1$ and substituted with 0, 1, 2, or 3 groups independently selected from halogen, hydroxyl, amine, alkylamino, dialkylamino, C1-C4 alkyl, and C1-C4 alkoxy; wherein each $R^1$ is independently selected from hydrogen, C1-C4 alkyl, aryl, 5- or 6-membered heteroaryl, 5- or 6-membered cycloalkyl, and —(C1-C4 alkyl)aryl, and substituted with 0, 1, 2, or 3 groups independently selected from halogen, hydroxyl, amine, alkylamino, dialkylamino, C1-C4 alkyl, and C1-C4 alkoxy; wherein $R^2$ is selected from hydrogen, halogen, hydroxyl, amine, alkylamino, dialkylamino, C1-C4 alkyl, C1-C4 alkoxy, and an electron-withdrawing group; and wherein $R^3$ is selected from hydrogen, hydroxyl, amine, alkyl amine, dialkylamine, C1-C4 alkyl, C1-C8 alkenyl, C1-C4 alkoxy, —C(O)OH, —C(O)$OR^5$, —C(O)$R^5$, —C(O)$NHR^6$, aryl, a 5- or 6-membered heteroaryl having 1, 2, or 3 ring-members selected from O, S, and $NR^1$, a 5- or 6-membered cycloalkyl, (C1-C4 alkyl)aryl, and (C1-C4 alkenyl)aryl, and substituted with 0, 1, 2, or 3 groups independently selected from halogen, hydroxyl, amine, alkylamino, dialkylamino, C1-C4 alkyl, and C1-C4 alkoxy; or wherein $R^2$ and $R^3$, together with the intervening atoms, comprise a 5- or 6-membered cycloalkyl or a 5- or 6-membered heterocycloalkyl having 1, 2, or 3 ring-members selected from O, S, and $NR^1$, substituted with 0, 1, 2, or 3 groups independently selected from oxo, hydroxyl, halogen, C1-C4 alkyl, C1-C4 alkoxy, —C(O)OH, —C(O)$OR^5$, —C(O)$R^5$, and —C(O)$NHR^6$; wherein EWG is an electron-withdrawing group; and wherein $R^4$ is selected from hydrogen, hydroxyl, amine, alkyl amine, dialkylamine, C1-C4 alkyl, C1-C8 alkenyl, C1-C4 alkoxy, —C(O)OH, —C(O)$OR^5$, —C(O)$R^5$, —C(O)$NHR^6$, aryl, a 5- or 6-membered heteroaryl having 1, 2, or 3 ring-members selected from O, S, and $NR^1$, a 5- or 6-membered cycloalkyl, (C1-C4 alkyl)aryl, and (C1-C4 alkenyl)aryl, and substituted with 0, 1, 2, or 3 groups independently selected from halogen, hydroxyl, amine, alkylamino, dialkylamino, C1-C4 alkyl, and C1-C4 alkoxy; or wherein EWG and $R^4$, together with the intervening atoms, comprise a 5- or 6-membered cycloalkyl or a 5- or 6-membered heterocycloalkyl having 1 or 2 ring-members selected from O, S, and $NR^1$, substituted with 0, 1, 2, or 3 groups independently selected from hydroxyl, halogen, oxo, C1-C4 alkyl, C1-C4 alkoxy, —C(O)OH, —C(O)$R^5$, —C(O)$OR^5$, and —C(O)$NHR^6$; provided that the first atom of EWG adjacent to the position denoted a is substituted with oxo; wherein each $R^5$ is independently selected from hydrogen and C1-C4 alkyl; and wherein each $R^6$ is independently selected from hydrogen, C1-C4 alkyl, and aryl substituted with 0, 1, 2, or 3 groups independently selected from halogen, hydroxyl, amine, alkylamino, dialkylamino, C1-C4 alkyl, and C1-C4 alkoxy; the method comprising the step of reacting a first compound having a structure represented by a formula:

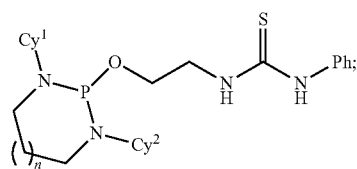

with a second compound having a structure represented by a formula:

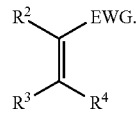

Also disclosed are compounds having a structure represented by a formula:

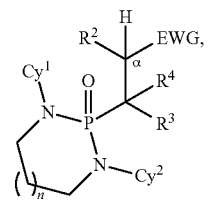

wherein n is 0 or 1; wherein each of $Cy^1$ and $Cy^2$ is independently selected from: aryl substituted with 0, 1, 2, or 3 groups independently selected from halogen, hydroxyl, amine, alkylamino, dialkylamino, C1-C4 alkyl, and C1-C4 alkoxy; a 5- or 6-membered heteroaryl having 1, 2, or 3 ring-members selected from O, S, and $NR^1$ and substituted with 0, 1, 2, or 3 groups independently selected from halogen, hydroxyl, amine, alkylamino, dialkylamino, C1-C4 alkyl, and C1-C4 alkoxy; a 5- or 6-membered cycloalkyl substituted with 0, 1, 2, or 3 groups independently selected from halogen, hydroxyl, amine, alkylamino, dialkylamino, C1-C4 alkyl, and C1-C4 alkoxy; and a 5- or 6-membered heterocycloalkyl having 1, 2, or 3 ring-members selected from O, S, and $NR^1$ and substituted with 0, 1, 2, or 3 groups independently selected from halogen, hydroxyl, amine, alkylamino, dialkylamino, C1-C4 alkyl, and C1-C4 alkoxy; wherein each $R^1$ is independently selected from hydrogen, C1-C4 alkyl, aryl, 5- or 6-membered heteroaryl, 5- or 6-membered cycloalkyl, and —(C1-C4 alkyl)aryl, and substituted with 0, 1, 2, or 3 groups independently selected from halogen, hydroxyl, amine, alkylamino, dialkylamino, C1-C4 alkyl, and C1-C4 alkoxy; wherein $R^2$ is selected from hydrogen, halogen, hydroxyl, amine, alkylamino, dialkylamino, C1-C4 alkyl, C1-C4 alkoxy, and an electron-withdrawing group; and wherein $R^3$ is selected from hydrogen, hydroxyl, amine, alkyl amine, dialkylamine, C1-C4 alkyl, C1-C8 alkenyl, C1-C4 alkoxy, —C(O)OH, —C(O)$OR^5$, —C(O)$R^5$, —C(O)$NHR^6$, aryl, a 5- or 6-membered heteroaryl having 1, 2, or 3 ring-members selected from O, S, and $NR^1$, a 5- or 6-membered cycloalkyl, (C1-C4 alkyl)aryl, and (C1-C4 alkenyl)aryl, and substituted with 0, 1, 2, or 3 groups independently selected from halogen, hydroxyl, amine, alkylamino, dialkylamino, C1-C4 alkyl, and C1-C4 alkoxy; or wherein $R^2$ and $R^3$, together with the intervening atoms, comprise a 5- or 6-membered cycloalkyl or a 5- or 6-membered heterocycloalkyl having 1, 2, or 3 ring-members selected from O, S, and $Nr^1$, substituted with 0, 1, 2, or 3 groups independently selected from oxo, hydroxyl, halogen, C1-C4 alkyl, C1-C4 alkoxy, —C(O)OH, —C(O)$OR^5$, —C(O)$R^5$, and —C(O)$NHR^6$; wherein EWG is an electron-withdrawing group; and wherein $R^4$ is selected from hydrogen, hydroxyl, amine, alkyl amine, dialkylamine, C1-C4 alkyl, C1-C8 alkenyl, C1-C4 alkoxy, —C(O)OH, —C(O)$OR^5$, —C(O)$R^5$, —C(O)$NHR^6$, aryl, a 5- or 6-membered heteroaryl having 1, 2, or 3 ring-members selected from O, S, and NR$^1$, a 5- or 6-membered cycloalkyl, (C1-C4 alkyl)aryl, and (C1-C4 alkenyl)aryl, and substituted with 0, 1, 2, or 3 groups independently selected from halogen, hydroxyl, amine, alkylamino, dialkylamino, C1-C4 alkyl, and C1-C4 alkoxy; or wherein EWG and R$^4$, together with the intervening atoms, comprise a 5- or 6-membered cycloalkyl or a 5- or 6-membered heterocycloalkyl having 1 or 2 ring-members selected from O, S, and NR$^1$, substituted with 0, 1, 2, or 3 groups independently selected from hydroxyl, halogen, oxo, C1-C4 alkyl, C1-C4 alkoxy, —C(O)OH, —C(O)R$^5$, —C(O)OR$^5$, and —C(O)NHR$^6$; provided that the first atom of EWG adjacent to the position denoted a is substituted with oxo; wherein each R$^5$ is independently selected from hydrogen and C1-C4 alkyl; and wherein each R$^6$ is independently selected from hydrogen, C1-C4 alkyl, and aryl substituted with 0, 1, 2, or 3 groups independently selected from halogen, hydroxyl, amine, alkylamino, dialkylamino, C1-C4 alkyl, and C1-C4 alkoxy.

Also disclosed are methods for preparing a product compound having a structure represented by a formula:

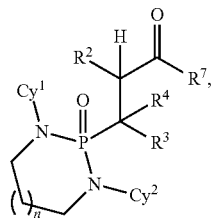

wherein n is 0 or 1; wherein each of Cy$^1$ and Cy$^2$ is independently selected from: aryl substituted with 0, 1, 2, or 3 groups independently selected from halogen, hydroxyl, amine, alkylamino, dialkylamino, C1-C4 alkyl, and C1-C4 alkoxy; a 5- or 6-membered heteroaryl having 1, 2, or 3 ring-members selected from O, S, and NR$^1$ and substituted with 0, 1, 2, or 3 groups independently selected from halogen, hydroxyl, amine, alkylamino, dialkylamino, C1-C4 alkyl, and C1-C4 alkoxy; a 5- or 6-membered cycloalkyl substituted with 0, 1, 2, or 3 groups independently selected from halogen, hydroxyl, amine, alkylamino, dialkylamino, C1-C4 alkyl, and C1-C4 alkoxy; and a 5- or 6-membered heterocycloalkyl having 1, 2, or 3 ring-members selected from O, S, and NR$^1$ and substituted with 0, 1, 2, or 3 groups independently selected from halogen, hydroxyl, amine, alkylamino, dialkylamino, C1-C4 alkyl, and C1-C4 alkoxy; wherein each R$^1$ is independently selected from hydrogen, C1-C4 alkyl, aryl, 5- or 6-membered heteroaryl, 5- or 6-membered cycloalkyl, and —(C1-C4 alkyl)aryl, and substituted with 0, 1, 2, or 3 groups independently selected from halogen, hydroxyl, amine, alkylamino, dialkylamino, C1-C4 alkyl, and C1-C4 alkoxy; wherein R$^2$ is selected from hydrogen, halogen, hydroxyl, amine, alkylamino, dialkylamino, C1-C4 alkyl, C1-C4 alkoxy, and an electron-withdrawing group; and wherein R$^3$ is selected from hydrogen, hydroxyl, amine, alkyl amine, dialkylamine, C1-C4 alkyl, C1-C8 alkenyl, C1-C4 alkoxy, —C(O)OH, —C(O)OR$^5$, —C(O)R$^5$, —C(O)NHR$^6$, aryl, a 5- or 6-membered heteroaryl having 1, 2, or 3 ring-members selected from O, S, and NR$^1$, a 5- or 6-membered cycloalkyl, (C1-C4 alkyl)aryl, and (C1-C4 alkenyl)aryl, and substituted with 0, 1, 2, or 3 groups independently selected from halogen, hydroxyl, amine, alkylamino, dialkylamino, C1-C4 alkyl, and C1-C4 alkoxy; or wherein R$^2$ and R$^3$, together with the intervening atoms, comprise a 5- or 6-membered cycloalkyl or a 5- or 6-membered heterocycloalkyl having 1, 2, or 3 ring-members selected from O, S, and NR$^1$, substituted with 0, 1, 2, or 3 groups independently selected from oxo, hydroxyl, halogen, C1-C4 alkyl, C1-C4 alkoxy, —C(O)OH, —C(O)OR$^5$, —C(O)R$^5$, and —C(O)NHR$^6$; wherein R$^7$ is selected from hydrogen, hydroxyl, amine, alkyl amine, dialkylamine, C1-C4 alkyl, and C1-C4 alkoxy; and wherein R$^4$ is selected from hydrogen, hydroxyl, amine, alkyl amine, dialkylamine, C1-C4 alkyl, C1-C8 alkenyl, C1-C4 alkoxy, —C(O)OH, —C(O)OR$^5$, —C(O)R$^5$, —C(O)NHR$^6$, aryl, a 5- or 6-membered heteroaryl having 1, 2, or 3 ring-members selected from O, S, and NR$^1$, a 5- or 6-membered cycloalkyl, (C1-C4 alkyl)aryl, and (C1-C4 alkenyl)aryl, and substituted with 0, 1, 2, or 3 groups independently selected from halogen, hydroxyl, amine, alkylamino, dialkylamino, C1-C4 alkyl, and C1-C4 alkoxy; or wherein R$^7$ and R$^4$, together with the intervening atoms, comprise a 5- or 6-membered cycloalkyl or a 5- or 6-membered heterocycloalkyl having 1 or 2 ring-members selected from O, S, and NR$^1$, substituted with 0, 1, 2, or 3 groups independently selected from hydroxyl, halogen, oxo, C1-C4 alkyl, C1-C4 alkoxy, —C(O)OH, —C(O)R$^5$, —C(O)OR$^5$, and —C(O)NHR$^6$; wherein each R$^5$ is independently selected from hydrogen and C1-C4 alkyl; and wherein each R$^6$ is independently selected from hydrogen, C1-C4 alkyl, and aryl substituted with 0, 1, 2, or 3 groups independently selected from halogen, hydroxyl, amine, alkylamino, dialkylamino, C1-C4 alkyl, and C1-C4 alkoxy; the method comprising the step of reacting a first compound having a structure represented by a formula:

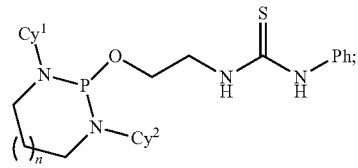

with a second compound having a structure represented by a formula:

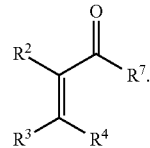

Also disclosed are compounds having a structure represented by a formula:

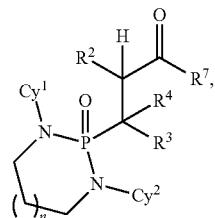

wherein n is 0 or 1; wherein each of Cy$^1$ and Cy$^2$ is independently selected from: aryl substituted with 0, 1, 2, or 3 groups independently selected from halogen, hydroxyl, amine, alkylamino, dialkylamino, C1-C4 alkyl, and C1-C4 alkoxy; a 5- or 6-membered heteroaryl having 1, 2, or 3 ring-members selected from O, S, and NR¹ and substituted with 0, 1, 2, or 3 groups independently selected from halogen, hydroxyl, amine, alkylamino, dialkylamino, C1-C4 alkyl, and C1-C4 alkoxy; a 5- or 6-membered cycloalkyl substituted with 0, 1, 2, or 3 groups independently selected from halogen, hydroxyl, amine, alkylamino, dialkylamino, C1-C4 alkyl, and C1-C4 alkoxy; and a 5- or 6-membered heterocycloalkyl having 1, 2, or 3 ring-members selected from O, S, and NR¹ and substituted with 0, 1, 2, or 3 groups independently selected from halogen, hydroxyl, amine, alkylamino, dialkylamino, C1-C4 alkyl, and C1-C4 alkoxy; wherein each R¹ is independently selected from hydrogen, C1-C4 alkyl, aryl, 5- or 6-membered heteroaryl, 5- or 6-membered cycloalkyl, and —(C1-C4 alkyl)aryl, and substituted with 0, 1, 2, or 3 groups independently selected from halogen, hydroxyl, amine, alkylamino, dialkylamino, C1-C4 alkyl, and C1-C4 alkoxy; wherein R² is selected from hydrogen, halogen, hydroxyl, amine, alkylamino, dialkylamino, C1-C4 alkyl, C1-C4 alkoxy, and an electron-withdrawing group; and wherein R³ is selected from hydrogen, hydroxyl, amine, alkyl amine, dialkylamine, C1-C4 alkyl, C1-C8 alkenyl, C1-C4 alkoxy, —C(O)OH, —C(O)OR⁵, —C(O)R⁵, —C(O)NHR⁶, aryl, a 5- or 6-membered heteroaryl having 1, 2, or 3 ring-members selected from O, S, and NR¹, a 5- or 6-membered cycloalkyl, (C1-C4 alkyl)aryl, and (C1-C4 alkenyl)aryl, and substituted with 0, 1, 2, or 3 groups independently selected from halogen, hydroxyl, amine, alkylamino, dialkylamino, C1-C4 alkyl, and C1-C4 alkoxy; or wherein R² and R³, together with the intervening atoms, comprise a 5- or 6-membered cycloalkyl or a 5- or 6-membered heterocycloalkyl having 1, 2, or 3 ring-members selected from O, S, and NR¹, substituted with 0, 1, 2, or 3 groups independently selected from oxo, hydroxyl, halogen, C1-C4 alkyl, C1-C4 alkoxy, —C(O)OH, —C(O)OR⁵, —C(O)R⁵, and —C(O)NHR⁶; wherein R⁷ is selected from hydrogen, hydroxyl, amine, alkyl amine, dialkylamine, C1-C4 alkyl, and C1-C4 alkoxy; and wherein R⁴ is selected from hydrogen, hydroxyl, amine, alkyl amine, dialkylamine, C1-C4 alkyl, C1-C8 alkenyl, C1-C4 alkoxy, —C(O)OH, —C(O)OR⁵, —C(O)R⁵, —C(O)NHR⁶, aryl, a 5- or 6-membered heteroaryl having 1, 2, or 3 ring-members selected from O, S, and NR¹, a 5- or 6-membered cycloalkyl, (C1-C4 alkyl)aryl, and (C1-C4 alkenyl)aryl, and substituted with 0, 1, 2, or 3 groups independently selected from halogen, hydroxyl, amine, alkylamino, dialkylamino, C1-C4 alkyl, and C1-C4 alkoxy; or wherein R⁷ and R⁴, together with the intervening atoms, comprise a 5- or 6-membered cycloalkyl or a 5- or 6-membered heterocycloalkyl having 1 or 2 ring-members selected from O, S, and NR¹, substituted with 0, 1, 2, or 3 groups independently selected from hydroxyl, halogen, oxo, C1-C4 alkyl, C1-C4 alkoxy, —C(O)OH, —C(O)R⁵, —C(O)OR⁵, and —C(O)NHR⁶; wherein each R⁵ is independently selected from hydrogen and C1-C4 alkyl; and wherein each R⁶ is independently selected from hydrogen, C1-C4 alkyl, and aryl substituted with 0, 1, 2, or 3 groups independently selected from halogen, hydroxyl, amine, alkylamino, dialkylamino, C1-C4 alkyl, and C1-C4 alkoxy.

Also disclosed are methods for preparing a compound having a structure represented by a formula:

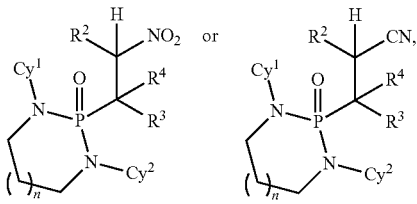

wherein n is 0 or 1; wherein each of Cy¹ and Cy² is independently selected from: aryl substituted with 0, 1, 2, or 3 groups independently selected from halogen, hydroxyl, amine, alkylamino, dialkylamino, C1-C4 alkyl, and C1-C4 alkoxy; a 5- or 6-membered heteroaryl having 1, 2, or 3 ring-members selected from O, S, and NR¹ and substituted with 0, 1, 2, or 3 groups independently selected from halogen, hydroxyl, amine, alkylamino, dialkylamino, C1-C4 alkyl, and C1-C4 alkoxy; a 5- or 6-membered cycloalkyl substituted with 0, 1, 2, or 3 groups independently selected from halogen, hydroxyl, amine, alkylamino, dialkylamino, C1-C4 alkyl, and C1-C4 alkoxy; and a 5- or 6-membered heterocycloalkyl having 1, 2, or 3 ring-members selected from O, S, and NR¹ and substituted with 0, 1, 2, or 3 groups independently selected from halogen, hydroxyl, amine, alkylamino, dialkylamino, C1-C4 alkyl, and C1-C4 alkoxy; wherein each R¹ is independently selected from hydrogen, C1-C4 alkyl, aryl, 5- or 6-membered heteroaryl, 5- or 6-membered cycloalkyl, and —(C1-C4 alkyl)aryl, and substituted with 0, 1, 2, or 3 groups independently selected from halogen, hydroxyl, amine, alkylamino, dialkylamino, C1-C4 alkyl, and C1-C4 alkoxy; wherein R² is selected from hydrogen, halogen, hydroxyl, amine, alkylamino, dialkylamino, C1-C4 alkyl, C1-C4 alkoxy, and an electron-withdrawing group; and wherein R³ is selected from hydrogen, hydroxyl, amine, alkyl amine, dialkylamine, C1-C4 alkyl, C1-C8 alkenyl, C1-C4 alkoxy, —C(O)OH, —C(O)OR⁵, —C(O)R⁵, —C(O)NHR⁶, aryl, a 5- or 6-membered heteroaryl having 1, 2, or 3 ring-members selected from O, S, and NR¹, a 5- or 6-membered cycloalkyl, (C1-C4 alkyl)aryl, and (C1-C4 alkenyl)aryl, and substituted with 0, 1, 2, or 3 groups independently selected from halogen, hydroxyl, amine, alkylamino, dialkylamino, C1-C4 alkyl, and C1-C4 alkoxy; or wherein R² and R³, together with the intervening atoms, comprise a 5- or 6-membered cycloalkyl or a 5- or 6-membered heterocycloalkyl having 1, 2, or 3 ring-members selected from O, S, and NR¹, substituted with 0, 1, 2, or 3 groups independently selected from oxo, hydroxyl, halogen, C1-C4 alkyl, C1-C4 alkoxy, —C(O)OH, —C(O)OR⁵, —C(O)R⁵, and —C(O)NHR⁶; wherein R⁴ is selected from hydrogen, hydroxyl, amine, alkyl amine, dialkylamine, C1-C4 alkyl, C1-C8 alkenyl, C1-C4 alkoxy, —C(O)OH, —C(O)OR⁵, —C(O)R⁵, —C(O)NHR⁶, aryl, a 5- or 6-membered heteroaryl having 1, 2, or 3 ring-members selected from O, S, and NR¹, a 5- or 6-membered cycloalkyl, (C1-C4 alkyl)aryl, and (C1-C4 alkenyl)aryl, and substituted with 0, 1, 2, or 3 groups independently selected from halogen, hydroxyl, amine, alkylamino, dialkylamino, C1-C4 alkyl, and C1-C4 alkoxy; wherein each R⁵ is independently selected from hydrogen and C1-C4 alkyl; and wherein each R⁶ is independently selected from hydrogen, C1-C4 alkyl, and aryl substituted with 0, 1, 2, or 3 groups independently selected from halogen, hydroxyl, amine, alkylamino, dialkylamino, C1-C4 alkyl, and C1-C4 alkoxy; the method comprising the step of reacting a first compound having a structure represented by a formula:

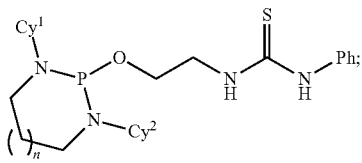

with a second compound having a structure represented by a formula:

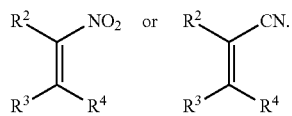

Also disclosed are compounds having a structure represented by a formula:

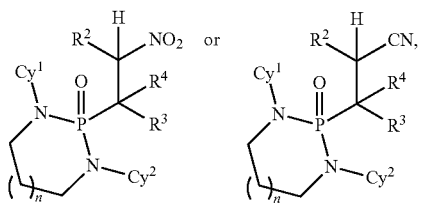

wherein n is 0 or 1; wherein each of $Cy^1$ and $Cy^2$ is independently selected from: aryl substituted with 0, 1, 2, or 3 groups independently selected from halogen, hydroxyl, amine, alkylamino, dialkylamino, C1-C4 alkyl, and C1-C4 alkoxy; a 5- or 6-membered heteroaryl having 1, 2, or 3 ring-members selected from O, S, and $NR^1$ and substituted with 0, 1, 2, or 3 groups independently selected from halogen, hydroxyl, amine, alkylamino, dialkylamino, C1-C4 alkyl, and C1-C4 alkoxy; a 5- or 6-membered cycloalkyl substituted with 0, 1, 2, or 3 groups independently selected from halogen, hydroxyl, amine, alkylamino, dialkylamino, C1-C4 alkyl, and C1-C4 alkoxy; and a 5- or 6-membered heterocycloalkyl having 1, 2, or 3 ring-members selected from O, S, and $NR^1$ and substituted with 0, 1, 2, or 3 groups independently selected from halogen, hydroxyl, amine, alkylamino, dialkylamino, C1-C4 alkyl, and C1-C4 alkoxy; wherein each $R^1$ is independently selected from hydrogen, C1-C4 alkyl, aryl, 5- or 6-membered heteroaryl, 5- or 6-membered cycloalkyl, and —(C1-C4 alkyl)aryl, and substituted with 0, 1, 2, or 3 groups independently selected from halogen, hydroxyl, amine, alkylamino, dialkylamino, C1-C4 alkyl, and C1-C4 alkoxy; wherein $R^2$ is selected from hydrogen, halogen, hydroxyl, amine, alkylamino, dialkylamino, C1-C4 alkyl, C1-C4 alkoxy, and an electron-withdrawing group; and wherein $R^3$ is selected from hydrogen, hydroxyl, amine, alkyl amine, dialkylamine, C1-C4 alkyl, C1-C8 alkenyl, C1-C4 alkoxy, —C(O)OH, —C(O)OR$^5$, —C(O)R$^5$, —C(O)NHR$^6$, aryl, a 5- or 6-membered heteroaryl having 1, 2, or 3 ring-members selected from O, S, and $NR^1$, a 5- or 6-membered cycloalkyl, (C1-C4 alkyl)aryl, and (C1-C4 alkenyl)aryl, and substituted with 0, 1, 2, or 3 groups independently selected from halogen, hydroxyl, amine, alkylamino, dialkylamino, C1-C4 alkyl, and C1-C4 alkoxy; or wherein $R^2$ and $R^3$, together with the intervening atoms, comprise a 5- or 6-membered cycloalkyl or a 5- or 6-membered heterocycloalkyl having 1, 2, or 3 ring-members selected from O, S, and $NR^1$, substituted with 0, 1, 2, or 3 groups independently selected from oxo, hydroxyl, halogen, C1-C4 alkyl, C1-C4 alkoxy, —C(O)OH, —C(O)OR$^5$, —C(O)R$^5$, and —C(O)NHR$^6$; wherein $R^4$ is selected from hydrogen, hydroxyl, amine, alkyl amine, dialkylamine, C1-C4 alkyl, C1-C8 alkenyl, C1-C4 alkoxy, —C(O)OH, —C(O)OR$^5$, —C(O)R$^5$, —C(O)NHR$^6$, aryl, a 5- or 6-membered heteroaryl having 1, 2, or 3 ring-members selected from O, S, and $NR^1$, a 5- or 6-membered cycloalkyl, (C1-C4 alkyl)aryl, and (C1-C4 alkenyl)aryl, and substituted with 0, 1, 2, or 3 groups independently selected from halogen, hydroxyl, amine, alkylamino, dialkylamino, C1-C4 alkyl, and C1-C4 alkoxy; wherein each $R^5$ is independently selected from hydrogen and C1-C4 alkyl; and wherein each $R^6$ is independently selected from hydrogen, C1-C4 alkyl, and aryl substituted with 0, 1, 2, or 3 groups independently selected from halogen, hydroxyl, amine, alkylamino, dialkylamino, C1-C4 alkyl, and C1-C4 alkoxy.

Also disclosed are compounds prepared by a disclosed method.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. Definitions

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

It is appreciated that certain features of the disclosure, which are, for clarity, described in the context of separate aspects, can also be provided in combination in a single aspect. Conversely, various features of the disclosure which are, for brevity, described in the context of a single aspect, can also be provided separately or in any suitable subcombination.

For the terms "for example" and "such as," and grammatical equivalences thereof, the phrase "and without limitation" is understood to follow unless explicitly stated otherwise.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

All compounds, and salts thereof (e.g., pharmaceutically acceptable salts), can be found together with other substances such as water and solvents (e.g., hydrates and solvates).

Compounds provided herein also can include tautomeric forms. Tautomeric forms result from the swapping of a single bond with an adjacent double bond together with the concomitant migration of a proton. Tautomeric forms include prototropic tautomers that are isomeric protonation states having the same empirical formula and total charge. Example prototropic tautomers include ketone—enol pairs, amide—imidic acid pairs, lactam—lactim pairs, enamine—imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds provided herein can also include all isotopes of atoms occurring in the intermediates or final compounds. Isotopes include those atoms having the same atomic number but different mass numbers. For example, isotopes of hydrogen include hydrogen, tritium, and deuterium.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

Also provided herein are pharmaceutically acceptable salts of the compounds described herein. As used herein, the term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the compounds provided herein include the conventional non-toxic salts of the parent compound formed, for example, from non-toxic inorganic or organic acids. The pharmaceutically acceptable salts of the compounds provided herein can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. In various aspects, a non-aqueous media like ether, ethyl acetate, alcohols (e.g., methanol, ethanol, iso-propanol, or butanol) or acetonitrile (ACN) can be used. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977). Conventional methods for preparing salt forms are described, for example, in *Handbook of Pharmaceutical Salts: Properties, Selection, and Use,* Wiley-VCH, 2002.

In various aspects, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

As used herein, chemical structures that contain one or more stereocenters depicted with dashed and bold bonds (i.e., ⋮|) are meant to indicate absolute stereochemistry of the stereocenter(s) present in the chemical structure. As used herein, bonds symbolized by a simple line do not indicate a stereo-preference. Unless otherwise indicated to the contrary, chemical structures, which include one or more stereocenters, illustrated herein without indicating absolute or relative stereochemistry encompass all possible stereoisomeric forms of the compound (e.g., diastereomers and enantiomers) and mixtures thereof. Structures with a single bold or dashed line, and at least one additional simple line, encompass a single enantiomeric series of all possible diastereomers.

Resolution of racemic mixtures of compounds can be carried out using appropriate methods. An exemplary method includes fractional recrystallization using a chiral resolving acid that is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid, or the various optically active camphorsulfonic acids such as camphorsulfonic acid. Other resolving agents suitable for fractional crystallization methods include stereoisomerically pure forms of methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent compositions can be determined by one skilled in the art.

The expressions "ambient temperature" and "room temperature" as used herein are understood in the art and refer generally to a temperature, e.g., a reaction temperature, that is about the temperature of the room in which the reaction is carried out, for example, a temperature from about 20° C. to about 30° C.

At various places in the present specification, divalent linking substituents are described. It is specifically intended that each divalent linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. As used herein, the term "substituted" means that a hydrogen atom is removed and replaced by a substituent. It is to be understood that substitution at a given atom is limited by valency.

Throughout the definitions, the terms "$C_{n-m}$" and "Cn-Cm" indicate a range that includes the endpoints, wherein n and m are integers and indicate the number of carbons. Examples include $C_{1-4}$, $C_{1-6}$, and the like.

As used herein, the terms "$C_{n-m}$ alkyl" and "Cn-Cm alkyl," employed alone or in combination with other terms, refer to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In various aspects, the alkyl group contains from 1 to 6 carbon atoms, from 1 to 4 carbon atoms, from 1 to 3 carbon atoms, or 1 to 2 carbon atoms.

As used herein, "$C_{n-m}$ alkenyl" and "Cn-Cm alkenyl" refer to an alkyl group having one or more double carbon-carbon bonds and having n to m carbons. Example alkenyl groups include, but are not limited to, ethenyl, n-propenyl, isopropenyl, n-butenyl, sec-butenyl, and the like. In various aspects, the alkenyl moiety contains 2 to 6, 2 to 4, or 2 to 3 carbon atoms.

As used herein, "$C_{n-m}$ alkynyl" and "Cn-Cm alkynyl" refer to an alkyl group having one or more triple carbon-carbon bonds and having n to m carbons. Example alkynyl groups include, but are not limited to, ethynyl, propyn-1-yl, propyn-2-yl, and the like. In various aspects, the alkynyl moiety contains 2 to 6, 2 to 4, or 2 to 3 carbon atoms.

As used herein, the terms "$C_{n-m}$ alkylene" and "Cn-Cm alkylene," employed alone or in combination with other terms, refers to a divalent alkyl linking group having n to m carbons. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methylpropan-1,3-diyl, and the like. In various aspects, the alkylene moiety contains 2 to 6, 2 to 4, 2 to 3, 1 to 6, 1 to 4, or 1 to 2 carbon atoms.

As used herein, the terms "$C_{n-m}$ alkoxy" and "Cn-Cm alkoxy," employed alone or in combination with other terms, refers to a group of formula —O-alkyl, wherein the alkyl group has n to m carbons. Example alkoxy groups include methoxy, ethoxy, propoxy (e.g., n-propoxy and isopropoxy), tert-butoxy, and the like. In various aspects, the alkyl group has 1 to 6, 1 to 4, or 1 to 3 carbon atoms.

As used herein, the terms "$C_{n-m}$ alkylamino" and "Cn-Cm alkylamino" refers to a group of formula —NH(alkyl), wherein the alkyl group has n to m carbon atoms. In various aspects, the alkyl group has 1 to 6, 1 to 4, or 1 to 3 carbon atoms.

As used herein, the terms "$C_{n-m}$ alkoxycarbonyl" and "Cn-Cm alkoxycarbonyl" refers to a group of formula —C(O)O-alkyl, wherein the alkyl group has n to m carbon atoms. In various aspects, the alkyl group has 1 to 6, 1 to 4, or 1 to 3 carbon atoms.

As used herein, the terms "$C_{n-m}$ alkylcarbonyl" and "Cn-Cm alkylcarbonyl" refers to a group of formula —C(O)-alkyl, wherein the alkyl group has n to m carbon atoms. In various aspects, the alkyl group has 1 to 6, 1 to 4, or 1 to 3 carbon atoms.

As used herein, the terms "$C_{n-m}$ alkylcarbonylamino" and "Cn-Cm alkylcarbonylamino" refer to a group of formula —NHC(O)-alkyl, wherein the alkyl group has n to m carbon atoms. In various aspects, the alkyl group has 1 to 6, 1 to 4, or 1 to 3 carbon atoms.

As used herein, the terms "$C_{n-m}$ alkylsulfonylamino" and "Cn-Cm alkylsulfonylamino" refer to a group of formula —NHS(O)$_2$-alkyl, wherein the alkyl group has n to m carbon atoms. In various aspects, the alkyl group has 1 to 6, 1 to 4, or 1 to 3 carbon atoms.

As used herein, the term "aminosulfonyl" refers to a group of formula —S(O)$_2$NH$_2$.

As used herein, the terms "$C_{n-m}$ alkylaminosulfonyl" and "Cn-Cm alkylaminosulfonyl" refer to a group of formula —S(O)$_2$NH(alkyl), wherein the alkyl group has n to m carbon atoms. In various aspects, the alkyl group has 1 to 6, 1 to 4, or 1 to 3 carbon atoms.

As used herein, the terms "di($C_{n-m}$ alkyl)aminosulfonyl" and "di(Cn-Cm alkyl)aminosulfonyl" refer to a group of formula —S(O)$_2$N(alkyl)$_2$, wherein each alkyl group independently has n to m carbon atoms. In various aspects, each alkyl group has, independently, 1 to 6, 1 to 4, or 1 to 3 carbon atoms.

As used herein, the term "aminosulfonylamino" refers to a group of formula —NHS(O)$_2$NH$_2$.

As used herein, the terms "$C_{n-m}$ alkylaminosulfonylamino" and "Cn-Cm alkylaminosulfonylamino" refer to a group of formula —NHS(O)$_2$NH(alkyl), wherein the alkyl group has n to m carbon atoms. In various aspects, the alkyl group has 1 to 6, 1 to 4, or 1 to 3 carbon atoms.

As used herein, the terms "di($C_{n-m}$ alkyl)aminosulfonylamino" and "di(Cn-Cm alkyl)aminosulfonylamino" refer to a group of formula —NHS(O)$_2$N(alkyl)$_2$, wherein each alkyl group independently has n to m carbon atoms. In various aspects, each alkyl group has, independently, 1 to 6, 1 to 4, or 1 to 3 carbon atoms.

As used herein, the term "aminocarbonylamino," employed alone or in combination with other terms, refers to a group of formula —NHC(O)NH$_2$.

As used herein, the terms "$C_{n-m}$ alkylaminocarbonylamino" and "Cn-Cm alkylaminocarbonylamino" refer to a group of formula —NHC(O)NH(alkyl), wherein the alkyl group has n to m carbon atoms. In various aspects, the alkyl group has 1 to 6, 1 to 4, or 1 to 3 carbon atoms.

As used herein, the terms "di($C_{n-m}$ alkyl)aminocarbonylamino" and "di(Cn-Cm alkyl)aminocarbonylamino" refer to a group of formula —NHC(O)N(alkyl)$_2$, wherein each alkyl group independently has n to m carbon atoms. In various aspects, each alkyl group has, independently, 1 to 6, 1 to 4, or 1 to 3 carbon atoms.

As used herein, the terms "$C_{n-m}$ alkylcarbamyl" and "Cn-Cm alkylcarbamyl" refer to a group of formula —C(O)—NH(alkyl), wherein the alkyl group has n to m carbon atoms. In various aspects, the alkyl group has 1 to 6, 1 to 4, or 1 to 3 carbon atoms.

As used herein, the term "thio" refers to a group of formula —SH.

As used herein, the terms "$C_{n-m}$ alkylthio" and "Cn-Cm alkylthio" refer to a group of formula —S-alkyl, wherein the alkyl group has n to m carbon atoms. In various aspects, the alkyl group has 1 to 6, 1 to 4, or 1 to 3 carbon atoms.

As used herein, the terms "$C_{n-m}$ alkylsulfinyl" and "Cn-Cm alkylsulfinyl" refer to a group of formula —S(O)-alkyl, wherein the alkyl group has n to m carbon atoms. In various aspects, the alkyl group has 1 to 6, 1 to 4, or 1 to 3 carbon atoms.

As used herein, the terms "$C_{n-m}$ alkylsulfonyl" and "Cn-Cm alkylsulfonyl" refer to a group of formula —S(O)$_2$-alkyl, wherein the alkyl group has n to m carbon atoms. In various aspects, the alkyl group has 1 to 6, 1 to 4, or 1 to 3 carbon atoms.

As used herein, the term "amino" refers to a group of formula —NH$_2$.

As used herein, the term "carbamyl" to a group of formula —C(O)NH$_2$.

As used herein, the term "carbonyl," employed alone or in combination with other terms, refers to a —C(=O)— group, which may also be written as C(O).

As used herein, the terms "cyano-$C_{1-3}$ alkyl" and "cyano-C1-C3 alkyl" refer to a group of formula —($C_{1-3}$ alkylene)-CN.

As used herein, the terms "HO—$C_{1-3}$ alkyl" and "HO—C1-C3 alkyl" refer to a group of formula —($C_{1-3}$ alkylene)-OH.

As used herein, the terms "$C_{1-3}$ alkoxy-$C_{1-3}$ alkyl" and "C1-C3 alkoxy-C1-C3 alkyl" refer to a group of formula —($C_{1-3}$ alkylene)-O($C_{1-3}$ alkyl).

As used herein, the term "carboxy" refers to a group of formula —C(O)OH.

As used herein, the terms "di($C_{n-m}$-alkyl)amino" and "di(Cn-Cm-alkyl)amino" refer to a group of formula —N(alkyl)$_2$, wherein the two alkyl groups each has, independently, n to m carbon atoms. In various aspects, each alkyl group independently has 1 to 6, 1 to 4, or 1 to 3 carbon atoms.

As used herein, the terms "di($C_{n-m}$-alkyl)carbamyl" and "di(Cn-Cm-alkyl)carbamyl" refer to a group of formula —C(O)N(alkyl)$_2$, wherein the two alkyl groups each has, independently, n to m carbon atoms. In various aspects, each alkyl group independently has 1 to 6, 1 to 4, or 1 to 3 carbon atoms.

As used herein, "halo" refers to F, Cl, Br, or I. In various aspects, the halo group is F or Cl.

As used herein, "$C_{n-m}$ haloalkoxy" and "Cn-Cm haloalkoxy" refer to a group of formula —O-haloalkyl having n to m carbon atoms. An example haloalkoxy group is OCF$_3$. In various aspects, the haloalkoxy group is fluorinated only. In various aspects, the alkyl group has 1 to 6, 1 to 4, or 1 to 3 carbon atoms.

As used herein, the terms "$C_{n-m}$ haloalkyl" and "Cn-Cm haloalkyl," employed alone or in combination with other terms, refer to an alkyl group having from one halogen atom to 2s+1 halogen atoms which may be the same or different, where "s" is the number of carbon atoms in the alkyl group, wherein the alkyl group has n to m carbon atoms. In various aspects, the haloalkyl group is fluorinated only. In various aspects, the alkyl group has 1 to 6, 1 to 4, or 1 to 3 carbon atoms.

As used herein, the term "amine base" refers to a mono-substituted amine group (i.e., primary amine base), di-substituted amine group (i.e., secondary amine base), or a tri-substituted amine group (i.e., tertiary amine base). Example mono-substituted amine bases include methyl amine, ethyl amine, propyl amine, butyl amine, and the like. Example di-substituted amine bases include dimethylamine, diethylamine, dipropylamine, dibutylamine, pyrrolidine, piperidine, azepane, morpholine, and the like. In various aspects, the tertiary amine has the formula $N(R')_3$, wherein each R' is independently $C_{1-6}$ alkyl, 3-10 member cycloalkyl, 4-10 membered heterocycloalkyl, 1-10 membered heteroaryl, and 5-10 membered aryl, wherein the 3-10 member cycloalkyl, 4-10 membered heterocycloalkyl, 1-10 membered heteroaryl, and 5-10 membered aryl are optionally substituted by 1, 2, 3, 4, 5, or 6 $C_{1-6}$ alkyl groups. Example tertiary amine bases include trimethylamine, triethylamine, tripropylamine, triisopropylamine, tributylamine, tri-tert-butylamine, N,N-dimethylethanamine, N-ethyl-N-methylpropan-2-amine, N-ethyl-N-isopropylpropan-2-amine, morpholine, N-methylmorpholine, and the like. In various aspects, the term "tertiary amine base" refers to a group of formula $N(R)_3$, wherein each R is independently a linear or branched $C_{1-6}$ alkyl group.

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Cycloalkyl groups can have 3, 4, 5, 6, 7, 8, 9, or 10 ring-forming carbons ($C_{3-10}$). Ring-forming carbon atoms of a cycloalkyl group can be optionally substituted by oxo or sulfido (e.g., C(O) or C(S)). Cycloalkyl groups also include cycloalkylidenes. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like. In various aspects, cycloalkyl is cyclopropyl, cyclobutyl, cyclopentyl, cyclohexyl, cyclopentyl, or adamantyl. In various aspects, the cycloalkyl has 6-10 ring-forming carbon atoms. In various aspects, cycloalkyl is cyclohexyl or adamantyl. Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, and 7-membered heterocycloalkyl groups. Heterocycloalkyl groups can also include spirocycles. Example heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by oxo or sulfido (e.g., C(O), S(O), C(S), or $S(O)_2$, etc.). The heterocycloalkyl group can be attached through a ring-forming carbon atom or a ring-forming heteroatom. In various aspects, the heterocycloalkyl group contains 0 to 3 double bonds. In various aspects, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In various aspects, the heterocycloalkyl has 4-10, 4-7 or 4-6 ring atoms with 1 or 2 heteroatoms independently selected from nitrogen, oxygen, or sulfur and having one or more oxidized ring members.

As used herein, the term "aryl," employed alone or in combination with other terms, refers to an aromatic hydrocarbon group, which may be monocyclic or polycyclic (e.g., having 2, 3 or 4 fused rings). The terms "$C_{n-m}$ aryl" and "Cn-Cm aryl" refer to an aryl group having from n to m ring carbon atoms. Aryl groups include, e.g., phenyl, naphthyl, anthracenyl, phenanthrenyl, indanyl, indenyl, and the like. In various aspects, aryl groups have from 6 to about 20 carbon atoms, from 6 to about 15 carbon atoms, or from 6 to about 10 carbon atoms. In various aspects, the aryl group is a substituted or unsubstituted phenyl.

As used herein, "heteroaryl" refers to a monocyclic or polycyclic aromatic heterocycle having at least one heteroatom ring member selected from sulfur, oxygen, and nitrogen. In various aspects, the heteroaryl ring has 1, 2, 3, or 4 heteroatom ring members independently selected from nitrogen, sulfur and oxygen. In various aspects, any ring-forming N in a heteroaryl moiety can be an N-oxide. In various aspects, the heteroaryl has 5-10 ring atoms and 1, 2, 3 or 4 heteroatom ring members independently selected from nitrogen, sulfur and oxygen. In various aspects, the heteroaryl has 5-6 ring atoms and 1 or 2 heteroatom ring members independently selected from nitrogen, sulfur and oxygen. In various aspects, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl.

At certain places, the definitions or aspects refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

As used herein, the term "electron withdrawing group" (EWG), employed alone or in combination with other terms, refers to an atom or group of atoms that draws electron density through induction (e.g., withdrawing electron density about a σ-bond) or resonance (e.g., withdrawing electron density about a π-bond or π-system). Example electron withdrawing groups include, but are not limited to, halo groups (e.g., fluoro, chloro, bromo, iodo), nitriles (e.g., —CN), carbonyl groups (e.g., aldehydes, ketones, carboxylic acids, acid chlorides, esters, and the like), nitro groups (e.g., —NO$_2$), alkenyl groups (e.g., vinyl), alkynyl groups (e.g., ethynyl), sulfonyl groups (e.g., S(O)R, S(O)$_2$R), sulfonate groups (e.g., —SO$_3$H), and sulfonamide groups (e.g., S(O)N(R)$_2$, S(O)$_2$N(R)$_2$). In various aspects, the electron withdrawing group is selected from nitro, cyano, —S(O)R$^5$, —SO$_2$R$^5$, —P(O)(R$^5$)$_2$, —P(O)(OR$^5$)$_2$, —C(O)OH, —C(O)R$^5$, —C(O)OR$^5$, and —C(O)NHR$^6$.

Preparation of the compounds described herein can involve a reaction in the presence of an acid or a base. Example acids can be inorganic or organic acids and include, but are not limited to, strong and weak acids. Example acids include, but are not limited to, hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Example weak acids include, but are not limited to, acetic acid, propionic acid, butanoic acid, benzoic acid, tartaric acid, pentanoic acid, hexanoic acid, heptanoic acid, octanoic acid, nonanoic acid, and decanoic acid. Example bases include, without limitation, lithium hydroxide, sodium hydroxide, potassium hydroxide, lithium carbonate, sodium carbonate, potassium carbonate, sodium bicarbonate, and amine bases. Example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, iso-propyl, n-butyl, t-butyl, trimethylsilyl and cyclohexyl substituted amides (e.g., lithium N-isopropylcyclohexylamide).

The following abbreviations may be used herein: AcOH (acetic acid); aq. (aqueous); atm. (atmosphere(s)); Br$_2$ (bromine); Bn (benzyl); calc. (calculated); d (doublet); dd (doublet of doublets); DCM (dichloromethane); DMF (N,N-dimethylformamide); Et (ethyl); Et$_2$O (diethyl ether); EtOAc (ethyl acetate); EtOH (ethanol); EWG (electron withdrawing group); g (gram(s)); h (hour(s)); H$_2$ (hydrogen gas); HCl (hydrochloric acid/hydrogen choride); HPLC (high performance liquid chromatography); H$_2$SO$_4$ (sulfuric acid); Hz (hertz); I$_2$ (iodine); IPA (isopropyl alcohol); J (coupling constant); KOH (potassium hydroxide); K$_3$PO$_4$ (potassium phosphate); LCMS (liquid chromatography—mass spectrometry); LiICA (lithium N-isopropylcyclohexylamide); m (multiplet); M (molar); MS (Mass spectrometry); Me (methyl); MeCN (acetonitrile); MeOH (methanol); mg (milligram(s)); min. (minutes(s)); mL (milliliter(s)); mmol (millimole(s)); N (normal); NaBH$_3$CN (sodium cyanoborohydride); NHP (N-heterocyclic phosphine); NHP-Cl (N-heterocyclic phosphine chloride); Na$_2$CO$_3$ (sodium carbonate); NaHCO$_3$ (sodium bicarbonate); NaOH (sodium hydroxide); Na$_2$SO$_4$ (sodium sulfate); nM (nanomolar); NMR (nuclear magnetic resonance spectroscopy); PCl$_3$ (trichlorophosphine); PMP (4-methoxyphenyl); RP-HPLC (reverse phase high performance liquid chromatography); t (triplet or tertiary); t-Bu (tert-butyl); TEA (triethylamine); TFA (trifluoroacetic acid); THF (tetrahydrofuran); TLC (thin layer chromatography); (microgram(s)); μL (microliter(s)); μM (micromolar); wt % (weight percent).

B. Functionalized Phosphonates

In one aspect, the invention relates to functionalized phosphonates useful as synthetic intermediates in, for example, the synthesis of biologically active compounds. For example, phosphonic acid derivatives have demonstrated utility as matrix metalloprotease inhibitors (Kluender et al. In US Pat. Appl. US 95-539409 951106, Chem. Abst 1998, p. 16142), osteoclastic acid phosphatase inhibitors (Schwender et al. (1995) *Bioorg. Med. Chem. Lett.* 5: 1801-1806), N-methyl-D-aspartate antagonists (Yokomatsu et al. (1996) *Tetrahedron: Asymmetry* 7: 2743-2754; Bigge et al. (1992) *J. Med. Chem.* 35: 1371-1384; Kinney et al. (1998) *J. Med. Chem.* 41: 236-246; Kinney et al. (1992) *J. Med. Chem.* 35: 4720-4726), imidazole glycerol phosphate dehydratase inhibitors (Schweitzer et al. (1999) *Bioorg. Med. Chem. Lett.* 9: 2053-2058), and norstatine renin inhibitors (Wester et al. (1994) *Bioorg. Med. Chem. Lett.* 4: 2005-2010). The use of the disclosed functionalized phosphonates as intermediates in the synthesis of other pharmaceutically active compounds is also envisioned.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, disclosed are compounds having a structure represented by a formula:

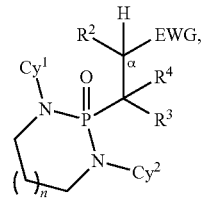

wherein n is 0 or 1; wherein each of Cy$^1$ and Cy$^2$ is independently selected from: aryl substituted with 0, 1, 2, or 3 groups independently selected from halogen, hydroxyl, amine, alkylamino, dialkylamino, C1-C4 alkyl, and C1-C4 alkoxy; a 5- or 6-membered heteroaryl having 1, 2, or 3 ring-members selected from O, S, and NR$^1$ and substituted with 0, 1, 2, or 3 groups independently selected from halogen, hydroxyl, amine, alkylamino, dialkylamino, C1-C4 alkyl, and C1-C4 alkoxy; a 5- or 6-membered cycloalkyl substituted with 0, 1, 2, or 3 groups independently selected from halogen, hydroxyl, amine, alkylamino, dialkylamino, C1-C4 alkyl, and C1-C4 alkoxy; and a 5- or 6-membered heterocycloalkyl having 1, 2, or 3 ring-members selected from O, S, and NR$^1$ and substituted with 0, 1, 2, or 3 groups independently selected from halogen, hydroxyl, amine, alkylamino, dialkylamino, C1-C4 alkyl, and C1-C4 alkoxy; wherein each R$^1$ is independently selected from hydrogen, C1-C4 alkyl, aryl, 5- or 6-membered heteroaryl, 5- or 6-membered cycloalkyl, and —(C1-C4 alkyl)aryl, and substituted with 0, 1, 2, or 3 groups independently selected from halogen, hydroxyl, amine, alkylamino, dialkylamino, C1-C4 alkyl, and C1-C4 alkoxy; wherein R$^2$ is selected from hydrogen, halogen, hydroxyl, amine, alkylamino, dialkylamino, C1-C4 alkyl, C1-C4 alkoxy, and an electron-withdrawing group; and wherein R$^3$ is selected from hydrogen, hydroxyl, amine, alkyl amine, dialkylamine, C1-C4 alkyl, C1-C8 alkenyl, C1-C4 alkoxy, —C(O)OH, —C(O)OR$^5$, —C(O)R$^5$, —C(O)NHR$^6$, aryl, a 5- or 6-membered heteroaryl having 1, 2, or 3 ring-members selected from O, S, and NR$^1$, a 5- or 6-membered cycloalkyl, (C1-C4 alkyl)aryl, and (C1-C4 alkenyl)aryl, and substituted with 0, 1, 2, or 3 groups independently selected from halogen, hydroxyl, amine, alkylamino, dialkylamino, C1-C4 alkyl, and C1-C4 alkoxy; or wherein $R^2$ and $R^3$, together with the intervening atoms, comprise a 5- or 6-membered cycloalkyl or a 5- or 6-membered heterocycloalkyl having 1, 2, or 3 ring-members selected from O, S, and $NR^1$, substituted with 0, 1, 2, or 3 groups independently selected from oxo, hydroxyl, halogen, C1-C4 alkyl, C1-C4 alkoxy, —C(O)OH, —C(O)OR$^5$, —C(O)R$^5$, and —C(O)NHR$^6$; wherein EWG is an electron-withdrawing group; and wherein $R^4$ is selected from hydrogen, hydroxyl, amine, alkyl amine, dialkylamine, C1-C4 alkyl, C1-C8 alkenyl, C1-C4 alkoxy, —C(O)OH, —C(O)OR$^5$, —C(O)R$^5$, —C(O)NHR$^6$, aryl, a 5- or 6-membered heteroaryl having 1, 2, or 3 ring-members selected from O, S, and $NR^1$, a 5- or 6-membered cycloalkyl, (C1-C4 alkyl)aryl, and (C1-C4 alkenyl)aryl, and substituted with 0, 1, 2, or 3 groups independently selected from halogen, hydroxyl, amine, alkylamino, dialkylamino, C1-C4 alkyl, and C1-C4 alkoxy; or wherein EWG and $R^4$, together with the intervening atoms, comprise a 5- or 6-membered cycloalkyl or a 5- or 6-membered heterocycloalkyl having 1 or 2 ring-members selected from O, S, and $NR^1$, substituted with 0, 1, 2, or 3 groups independently selected from hydroxyl, halogen, oxo, C1-C4 alkyl, C1-C4 alkoxy, —C(O)OH, —C(O)R$^5$, —C(O)OR$^5$, and —C(O)NHR$^6$; provided that the first atom of EWG adjacent to the position denoted a is substituted with oxo; wherein each $R^5$ is independently selected from hydrogen and C1-C4 alkyl; and wherein each $R^6$ is independently selected from hydrogen, C1-C4 alkyl, and aryl substituted with 0, 1, 2, or 3 groups independently selected from halogen, hydroxyl, amine, alkylamino, dialkylamino, C1-C4 alkyl, and C1-C4 alkoxy.

In one aspect, disclosed are compounds having a structure represented by a formula:

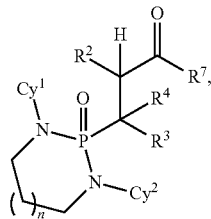

wherein n is 0 or 1; wherein each of $Cy^1$ and $Cy^2$ is independently selected from: aryl substituted with 0, 1, 2, or 3 groups independently selected from halogen, hydroxyl, amine, alkylamino, dialkylamino, C1-C4 alkyl, and C1-C4 alkoxy; a 5- or 6-membered heteroaryl having 1, 2, or 3 ring-members selected from O, S, and $NR^1$ and substituted with 0, 1, 2, or 3 groups independently selected from halogen, hydroxyl, amine, alkylamino, dialkylamino, C1-C4 alkyl, and C1-C4 alkoxy; a 5- or 6-membered cycloalkyl substituted with 0, 1, 2, or 3 groups independently selected from halogen, hydroxyl, amine, alkylamino, dialkylamino, C1-C4 alkyl, and C1-C4 alkoxy; and a 5- or 6-membered heterocycloalkyl having 1, 2, or 3 ring-members selected from O, S, and $NR^1$ and substituted with 0, 1, 2, or 3 groups independently selected from halogen, hydroxyl, amine, alkylamino, dialkylamino, C1-C4 alkyl, and C1-C4 alkoxy; wherein each $R^1$ is independently selected from hydrogen, C1-C4 alkyl, aryl, 5- or 6-membered heteroaryl, 5- or 6-membered cycloalkyl, and —(C1-C4 alkyl)aryl, and substituted with 0, 1, 2, or 3 groups independently selected from halogen, hydroxyl, amine, alkylamino, dialkylamino, C1-C4 alkyl, and C1-C4 alkoxy; wherein $R^2$ is selected from hydrogen, halogen, hydroxyl, amine, alkylamino, dialkylamino, C1-C4 alkyl, C1-C4 alkoxy, and an electron-withdrawing group; and wherein $R^3$ is selected from hydrogen, hydroxyl, amine, alkyl amine, dialkylamine, C1-C4 alkyl, C1-C8 alkenyl, C1-C4 alkoxy, —C(O)OH, —C(O)OR$^5$, —C(O)R$^5$, —C(O)NHR$^6$, aryl, a 5- or 6-membered heteroaryl having 1, 2, or 3 ring-members selected from O, S, and $NR^1$, a 5- or 6-membered cycloalkyl, (C1-C4 alkyl)aryl, and (C1-C4 alkenyl)aryl, and substituted with 0, 1, 2, or 3 groups independently selected from halogen, hydroxyl, amine, alkylamino, dialkylamino, C1-C4 alkyl, and C1-C4 alkoxy; or wherein $R^2$ and $R^3$, together with the intervening atoms, comprise a 5- or 6-membered cycloalkyl or a 5- or 6-membered heterocycloalkyl having 1, 2, or 3 ring-members selected from O, S, and $NR^1$, substituted with 0, 1, 2, or 3 groups independently selected from oxo, hydroxyl, halogen, C1-C4 alkyl, C1-C4 alkoxy, —C(O)OH, —C(O)OR$^5$, —C(O)R$^5$, and —C(O)NHR$^6$; wherein $R^7$ is selected from hydrogen, hydroxyl, amine, alkyl amine, dialkylamine, C1-C4 alkyl, and C1-C4 alkoxy; and wherein $R^4$ is selected from hydrogen, hydroxyl, amine, alkyl amine, dialkylamine, C1-C4 alkyl, C1-C8 alkenyl, C1-C4 alkoxy, —C(O)OH, —C(O)OR$^5$, —C(O)R$^5$, —C(O)NHR$^6$, aryl, a 5- or 6-membered heteroaryl having 1, 2, or 3 ring-members selected from O, S, and $NR^1$, a 5- or 6-membered cycloalkyl, (C1-C4 alkyl)aryl, and (C1-C4 alkenyl)aryl, and substituted with 0, 1, 2, or 3 groups independently selected from halogen, hydroxyl, amine, alkylamino, dialkylamino, C1-C4 alkyl, and C1-C4 alkoxy; or wherein $R^7$ and $R^4$, together with the intervening atoms, comprise a 5- or 6-membered cycloalkyl or a 5- or 6-membered heterocycloalkyl having 1 or 2 ring-members selected from O, S, and $NR^1$, substituted with 0, 1, 2, or 3 groups independently selected from hydroxyl, halogen, oxo, C1-C4 alkyl, C1-C4 alkoxy, —C(O)OH, —C(O)R$^5$, —C(O)OR$^5$, and —C(O)NHR$^6$; wherein each $R^5$ is independently selected from hydrogen and C1-C4 alkyl; and wherein each $R^6$ is independently selected from hydrogen, C1-C4 alkyl, and aryl substituted with 0, 1, 2, or 3 groups independently selected from halogen, hydroxyl, amine, alkylamino, dialkylamino, C1-C4 alkyl, and C1-C4 alkoxy.

In one aspect, disclosed are compounds having a structure represented by a formula:

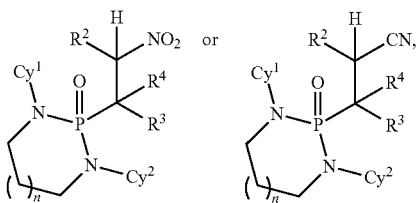

wherein n is 0 or 1; wherein each of $Cy^1$ and $Cy^2$ is independently selected from: aryl substituted with 0, 1, 2, or 3 groups independently selected from halogen, hydroxyl, amine, alkylamino, dialkylamino, C1-C4 alkyl, and C1-C4 alkoxy; a 5- or 6-membered heteroaryl having 1, 2, or 3 ring-members selected from O, S, and $NR^1$ and substituted with 0, 1, 2, or 3 groups independently selected from halogen, hydroxyl, amine, alkylamino, dialkylamino, C1-C4 alkyl, and C1-C4 alkoxy; a 5- or 6-membered cycloalkyl substituted with 0, 1, 2, or 3 groups independently selected from halogen, hydroxyl, amine, alkylamino, dialkylamino, C1-C4 alkyl, and C1-C4 alkoxy; and a 5- or 6-membered heterocycloalkyl having 1, 2, or 3 ring-members selected from O, S, and NR$^1$ and substituted with 0, 1, 2, or 3 groups independently selected from halogen, hydroxyl, amine, alkylamino, dialkylamino, C1-C4 alkyl, and C1-C4 alkoxy; wherein each R$^1$ is independently selected from hydrogen, C1-C4 alkyl, aryl, 5- or 6-membered heteroaryl, 5- or 6-membered cycloalkyl, and —(C1-C4 alkyl)aryl, and substituted with 0, 1, 2, or 3 groups independently selected from halogen, hydroxyl, amine, alkylamino, dialkylamino, C1-C4 alkyl, and C1-C4 alkoxy; wherein R$^2$ is selected from hydrogen, halogen, hydroxyl, amine, alkylamino, dialkylamino, C1-C4 alkyl, C1-C4 alkoxy, and an electron-withdrawing group; and wherein R$^3$ is selected from hydrogen, hydroxyl, amine, alkyl amine, dialkylamine, C1-C4 alkyl, C1-C8 alkenyl, C1-C4 alkoxy, —C(O)OH, —C(O)OR$^5$, —C(O)R$^5$, —C(O)NHR$^6$, aryl, a 5- or 6-membered heteroaryl having 1, 2, or 3 ring-members selected from O, S, and NR$^1$, a 5- or 6-membered cycloalkyl, (C1-C4 alkyl)aryl, and (C1-C4 alkenyl)aryl, and substituted with 0, 1, 2, or 3 groups independently selected from halogen, hydroxyl, amine, alkylamino, dialkylamino, C1-C4 alkyl, and C1-C4 alkoxy; or wherein R$^2$ and R$^3$, together with the intervening atoms, comprise a 5- or 6-membered cycloalkyl or a 5- or 6-membered heterocycloalkyl having 1, 2, or 3 ring-members selected from O, S, and NR$^1$, substituted with 0, 1, 2, or 3 groups independently selected from oxo, hydroxyl, halogen, C1-C4 alkyl, C1-C4 alkoxy, —C(O)OH, —C(O)OR$^5$, —C(O)R$^5$, and —C(O)NHR$^6$; wherein R$^4$ is selected from hydrogen, hydroxyl, amine, alkyl amine, dialkylamine, C1-C4 alkyl, C1-C8 alkenyl, C1-C4 alkoxy, —C(O)OH, —C(O)OR$^5$, —C(O)R$^5$, —C(O)NHR$^6$, aryl, a 5- or 6-membered heteroaryl having 1, 2, or 3 ring-members selected from O, S, and NR$^1$, a 5- or 6-membered cycloalkyl, (C1-C4 alkyl)aryl, and (C1-C4 alkenyl)aryl, and substituted with 0, 1, 2, or 3 groups independently selected from halogen, hydroxyl, amine, alkylamino, dialkylamino, C1-C4 alkyl, and C1-C4 alkoxy; wherein each R$^5$ is independently selected from hydrogen and C1-C4 alkyl; and wherein each R$^6$ is independently selected from hydrogen, C1-C4 alkyl, and aryl substituted with 0, 1, 2, or 3 groups independently selected from halogen, hydroxyl, amine, alkylamino, dialkylamino, C1-C4 alkyl, and C1-C4 alkoxy.

In one aspect, disclosed are compounds prepared by a disclosed method.

In a further aspect, the compound has a structure represented by a formula selected from:

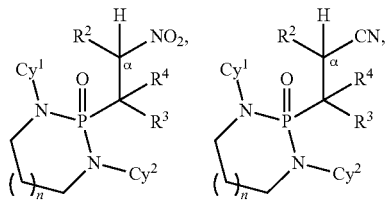

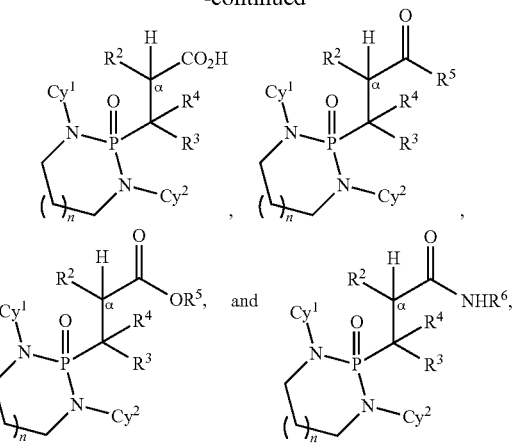

or a salt thereof.

In a further aspect, the compound has a structure represented by a formula selected from:

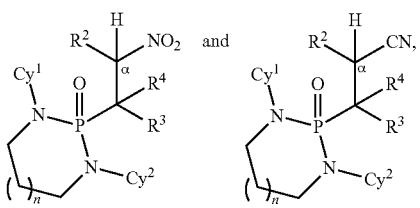

or a salt thereof.

In a further aspect, the compound has a structure represented by a formula:

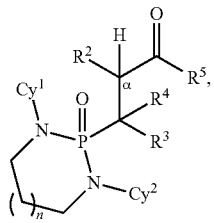

or a salt thereof.

In a further aspect, the compound has a structure represented by a formula selected from:

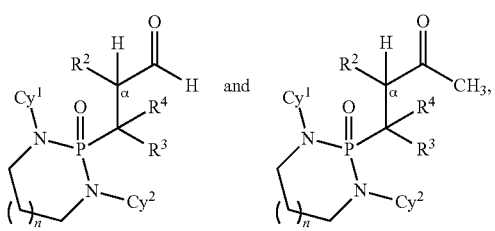

or a salt thereof.

In a further aspect, the compound has a structure represented by a formula:

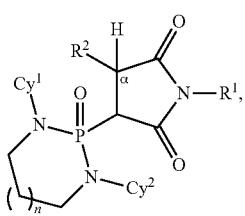

or a salt thereof.

In a further aspect, the compound has a structure represented by a formula:

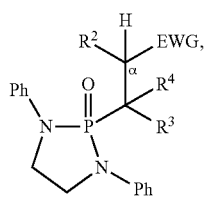

or a salt thereof.

In a further aspect, the compound has a structure represented by a formula selected from:

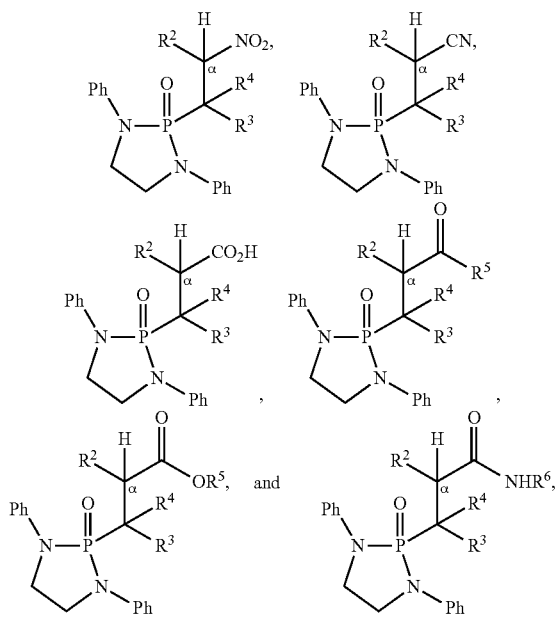

or a salt thereof.

In a further aspect, the compound has a structure represented by a formula selected from:

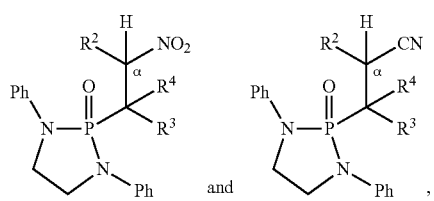

or a salt thereof.

In a further aspect, the compound has a structure represented by a formula:

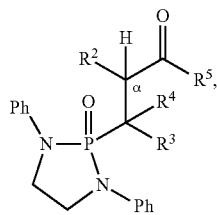

or a salt thereof.

In a further aspect, the compound has a structure represented by a formula selected from:

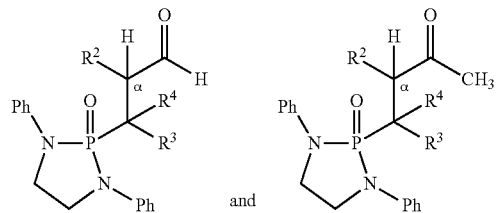

or a salt thereof.

In a further aspect, the compound has a structure represented by a formula:

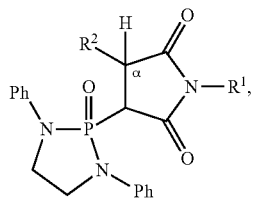

or a salt thereof.

In one aspect, n is 0 or 1. In a further aspect, n is 0. In a still further aspect, n is 1.

a. EWG Groups

In one aspect, EWG is an electron-withdrawing group. Examples of electro-withdrawing groups include, but are not limited to, nitro, cyano, carboxylic acid, ester, ketone, aldehyde, amide, and sulfonyl groups. In a further aspect, the electron-withdrawing group is selected from nitro, cyano, —S(O)$R^5$, —SO$_2$$R^5$, —P(O)($R^5$)$_2$, —P(O)(O$R^5$)$_2$, —C(O)OH, —C(O)$R^5$, —C(O)O$R^5$, and —C(O)NH$R^6$.

In a further aspect, the electron-withdrawing group is selected from —S(O)$R^5$ and —SO$_2$$R^5$. In a still further aspect, the electron-withdrawing group is —S(O)$R^5$. In yet a further aspect, the electron-withdrawing group is SO$_2$$R^5$.

In a further aspect, the electron-withdrawing group is selected from —P(O)($R^5$)$_2$ and —P(O)(O$R^5$)$_2$. In a still further aspect, the electron-withdrawing group is —P(O)($R^5$)$_2$. In yet a further aspect, the electron-withdrawing group is —P(O)(O$R^5$)$_2$.

In a further aspect, the electron-withdrawing group is selected from —C(O)OH, —C(O)$R^5$, —C(O)O$R^5$, and —C(O)NH$R^6$. In a still further aspect, the electron-withdrawing group is selected from —C(O)$R^5$, —C(O)O$R^5$, and —C(O)NHR$^6$. In yet a further aspect, the electron-withdrawing group is selected from —C(O)R$^5$ and —C(O)NHR$^6$. In an even further aspect, the electron-withdrawing group is selected from —C(O)OR$^5$ and —C(O)NHR$^6$. In a still further aspect, the electron-withdrawing group is —C(O)OH. In yet a further aspect, the electron-withdrawing group is —C(O)R$^5$. In an even further aspect, the electron-withdrawing group is —C(O)OR$^5$. In a still further aspect, the electron-withdrawing group is —C(O)NHR$^6$.

In a further aspect, the electron-withdrawing group is selected from nitro and cyano. In a still further aspect, the electron-withdrawing group is nitro. In yet a further aspect, the electron-withdrawing group is cyano.

b. R$^1$ Groups

In one aspect, each R$^1$ is independently selected from hydrogen, C1-C4 alkyl, aryl, 5- or 6-membered heteroaryl, 5- or 6-membered cycloalkyl, and —(C1-C4 alkyl)aryl, and substituted with 0, 1, 2, or 3 groups independently selected from halogen, hydroxyl, amine, alkylamino, dialkylamino, C1-C4 alkyl, and C1-C4 alkoxy. In a further aspect, each R$^1$ is hydrogen.

In a further aspect, each R$^1$ is independently selected from hydrogen, C1-C4 alkyl, aryl, 5- or 6-membered heteroaryl, 5- or 6-membered cycloalkyl, and —(C1-C4 alkyl)aryl, and substituted with 0, 1, or 2 groups independently selected from halogen, hydroxyl, amine, alkylamino, dialkylamino, C1-C4 alkyl, and C1-C4 alkoxy. In a still further aspect, each R$^1$ is independently selected from hydrogen, C1-C4 alkyl, aryl, 5- or 6-membered heteroaryl, 5- or 6-membered cycloalkyl, and —(C1-C4 alkyl)aryl, and substituted with 0 or 1 group selected from halogen, hydroxyl, amine, alkylamino, dialkylamino, C1-C4 alkyl, and C1-C4 alkoxy. In yet a further aspect, each R$^1$ is independently selected from hydrogen, C1-C4 alkyl, aryl, 5- or 6-membered heteroaryl, 5- or 6-membered cycloalkyl, and —(C1-C4 alkyl)aryl, and unsubstituted.

In a further aspect, each R$^1$ is independently selected from hydrogen and C1-C4 alkyl. In a still further aspect, each R$^1$ is independently selected from hydrogen, i-propyl, n-propyl, ethyl, and methyl. In yet a further aspect, each R$^1$ is independently selected from hydrogen, ethyl, and methyl. In an even further aspect, each R$^1$ is independently selected from hydrogen and ethyl. In a still further aspect, each R$^1$ is independently selected from hydrogen and methyl.

In a further aspect, each R$^1$ is independently selected from aryl, 5- or 6-membered heteroaryl, 5- or 6-membered cycloalkyl, and —(C1-C4 alkyl)aryl, and substituted with 0, 1, 2, or 3 groups independently selected from halogen, hydroxyl, amine, alkylamino, dialkylamino, C1-C4 alkyl, and C1-C4 alkoxy. In a still further aspect, each R$^1$ is independently selected from aryl, 5- or 6-membered heteroaryl, 5- or 6-membered cycloalkyl, and —(C1-C4 alkyl)aryl, and substituted with 0, 1, or 2 groups independently selected from halogen, hydroxyl, amine, alkylamino, dialkylamino, C1-C4 alkyl, and C1-C4 alkoxy. In yet a further aspect, each R$^1$ is independently selected from aryl, 5- or 6-membered heteroaryl, 5- or 6-membered cycloalkyl, and —(C1-C4 alkyl)aryl, and substituted with 0 or 1 group selected from halogen, hydroxyl, amine, alkylamino, dialkylamino, C1-C4 alkyl, and C1-C4 alkoxy. In an even further aspect, each R$^1$ is independently selected from aryl, 5- or 6-membered heteroaryl, 5- or 6-membered cycloalkyl, and —(C1-C4 alkyl)aryl, and monosubstituted with a group selected from halogen, hydroxyl, amine, alkylamino, dialkylamino, C1-C4 alkyl, and C1-C4 alkoxy. In a still further aspect, each R$^1$ is independently selected from aryl, 5- or 6-membered heteroaryl, 5- or 6-membered cycloalkyl, and —(C1-C4 alkyl)aryl, and unsubstituted.

In a further aspect, each R$^1$ is independently selected from aryl and 5- or 6-membered heteroaryl and substituted with 0, 1, 2, or 3 groups independently selected from halogen, hydroxyl, amine, alkylamino, dialkylamino, C1-C4 alkyl, and C1-C4 alkoxy. In a still further aspect, each R$^1$ is independently selected from aryl and 5- or 6-membered heteroaryl and substituted with 0, 1, or 2 groups independently selected from halogen, hydroxyl, amine, alkylamino, dialkylamino, C1-C4 alkyl, and C1-C4 alkoxy. In yet a further aspect, each R$^1$ is independently selected from aryl and 5- or 6-membered heteroaryl and substituted with 0 or 1 group selected from halogen, hydroxyl, amine, alkylamino, dialkylamino, C1-C4 alkyl, and C1-C4 alkoxy. In an even further aspect, each R$^1$ is independently selected from aryl and 5- or 6-membered heteroaryl and monosubstituted with a group selected from halogen, hydroxyl, amine, alkylamino, dialkylamino, C1-C4 alkyl, and C1-C4 alkoxy. In a still further aspect, each R$^1$ is independently selected from aryl and 5- or 6-membered heteroaryl and unsubstituted.

In a further aspect, each R$^1$ is independently selected from aryl substituted with 0, 1, 2, or 3 groups independently selected from halogen, hydroxyl, amine, alkylamino, dialkylamino, C1-C4 alkyl, and C1-C4 alkoxy. In a still further aspect, each R$^1$ is independently selected from aryl substituted with 0, 1, or 2 groups independently selected from halogen, hydroxyl, amine, alkylamino, dialkylamino, C1-C4 alkyl, and C1-C4 alkoxy. In yet a further aspect, each R$^1$ is independently selected from aryl substituted with 0 or 1 group selected from halogen, hydroxyl, amine, alkylamino, dialkylamino, C1-C4 alkyl, and C1-C4 alkoxy. In an even further aspect, each R$^1$ is independently selected from aryl monosubstituted with a group selected from halogen, hydroxyl, amine, alkylamino, dialkylamino, C1-C4 alkyl, and C1-C4 alkoxy. In a still further aspect, each R$^1$ is unsubstituted aryl.

In a further aspect, each R$^1$ is phenyl substituted with 0, 1, 2, or 3 groups independently selected from halogen, hydroxyl, amine, alkylamino, dialkylamino, C1-C4 alkyl, and C1-C4 alkoxy. In a still further aspect, each R$^1$ is phenyl substituted with 0, 1, or 2 groups independently selected from halogen, hydroxyl, amine, alkylamino, dialkylamino, C1-C4 alkyl, and C1-C4 alkoxy. In yet a further aspect, each R$^1$ is phenyl substituted with 0 or 1 group selected from halogen, hydroxyl, amine, alkylamino, dialkylamino, C1-C4 alkyl, and C1-C4 alkoxy. In an even further aspect, each R$^1$ is phenyl monosubstituted with a group selected from halogen, hydroxyl, amine, alkylamino, dialkylamino, C1-C4 alkyl, and C1-C4 alkoxy. In a still further aspect, each R$^1$ is unsubstituted phenyl.

In a further aspect, each R$^1$ is independently selected from 5- or 6-membered heteroaryl substituted with 0, 1, 2, or 3 groups independently selected from halogen, hydroxyl, amine, alkylamino, dialkylamino, C1-C4 alkyl, and C1-C4 alkoxy. In a still further aspect, each R$^1$ is independently selected from 5- or 6-membered heteroaryl substituted with 0, 1, or 2 groups independently selected from halogen, hydroxyl, amine, alkylamino, dialkylamino, C1-C4 alkyl, and C1-C4 alkoxy. In yet a further aspect, each R$^1$ is independently selected from 5- or 6-membered heteroaryl substituted with 0 or 1 group selected from halogen, hydroxyl, amine, alkylamino, dialkylamino, C1-C4 alkyl, and C1-C4 alkoxy. In an even further aspect, each R$^1$ is independently selected from 5- or 6-membered heteroaryl monosubstituted with a group selected from halogen, hydroxyl, amine, alkylamino, dialkylamino, C1-C4 alkyl, and C1-C4 alkoxy. In a still further aspect, each $R^1$ is independently selected from 5- or 6-membered heteroaryl and unsubstituted.

In a further aspect, each $R^1$ is independently selected from 6-membered heteroaryl substituted with 0, 1, 2, or 3 groups independently selected from halogen, hydroxyl, amine, alkylamino, dialkylamino, C1-C4 alkyl, and C1-C4 alkoxy. In a still further aspect, each $R^1$ is independently selected from 6-membered heteroaryl substituted with 0, 1, or 2 groups independently selected from halogen, hydroxyl, amine, alkylamino, dialkylamino, C1-C4 alkyl, and C1-C4 alkoxy. In yet a further aspect, each $R^1$ is independently selected from 6-membered heteroaryl substituted with 0 or 1 group selected from halogen, hydroxyl, amine, alkylamino, dialkylamino, C1-C4 alkyl, and C1-C4 alkoxy. In an even further aspect, each $R^1$ is independently selected from 6-membered heteroaryl monosubstituted with a group selected from halogen, hydroxyl, amine, alkylamino, dialkylamino, C1-C4 alkyl, and C1-C4 alkoxy. In a still further aspect, each $R^1$ is independently selected from 6-membered heteroaryl and unsubstituted.

In a further aspect, each $R^1$ is pyridinyl substituted with 0, 1, 2, or 3 groups independently selected from halogen, hydroxyl, amine, alkylamino, dialkylamino, C1-C4 alkyl, and C1-C4 alkoxy. In a still further aspect, each $R^1$ is pyridinyl substituted with 0, 1, or 2 groups independently selected from halogen, hydroxyl, amine, alkylamino, dialkylamino, C1-C4 alkyl, and C1-C4 alkoxy. In yet a further aspect, each $R^1$ is pyridinyl substituted with 0 or 1 group selected from halogen, hydroxyl, amine, alkylamino, dialkylamino, C1-C4 alkyl, and C1-C4 alkoxy. In an even further aspect, each $R^1$ is pyridinyl monosubstituted with a group selected from halogen, hydroxyl, amine, alkylamino, dialkylamino, C1-C4 alkyl, and C1-C4 alkoxy. In a still further aspect, each $R^1$ is unsubstituted pyridinyl.

In a further aspect, each $R^1$ is independently selected from 5- or 6-membered cycloalkyl and substituted with 0, 1, 2, or 3 groups independently selected from halogen, hydroxyl, amine, alkylamino, dialkylamino, C1-C4 alkyl, and C1-C4 alkoxy. In a still further aspect, each $R^1$ is independently selected from 5- or 6-membered cycloalkyl and substituted with 0, 1, or 2 groups independently selected from halogen, hydroxyl, amine, alkylamino, dialkylamino, C1-C4 alkyl, and C1-C4 alkoxy. In yet a further aspect, each $R^1$ is independently selected from 5- or 6-membered cycloalkyl and substituted with 0 or 1 group selected from halogen, hydroxyl, amine, alkylamino, dialkylamino, C1-C4 alkyl, and C1-C4 alkoxy. In an even further aspect, each $R^1$ is independently selected from 5- or 6-membered cycloalkyl and monosubstituted with a group selected from halogen, hydroxyl, amine, alkylamino, dialkylamino, C1-C4 alkyl, and C1-C4 alkoxy. In a still further aspect, each $R^1$ is independently selected from 5- or 6-membered cycloalkyl and unsubstituted.

In a further aspect, each $R^1$ is cyclohexyl substituted with 0, 1, 2, or 3 groups independently selected from halogen, hydroxyl, amine, alkylamino, dialkylamino, C1-C4 alkyl, and C1-C4 alkoxy. In a still further aspect, each $R^1$ is cyclohexyl substituted with 0, 1, or 2 groups independently selected from halogen, hydroxyl, amine, alkylamino, dialkylamino, C1-C4 alkyl, and C1-C4 alkoxy. In yet a further aspect, each $R^1$ is cyclohexyl substituted with 0 or 1 group selected from halogen, hydroxyl, amine, alkylamino, dialkylamino, C1-C4 alkyl, and C1-C4 alkoxy. In an even further aspect, each $R^1$ is cyclohexyl monosubstituted with a group selected from halogen, hydroxyl, amine, alkylamino, dialkylamino, C1-C4 alkyl, and C1-C4 alkoxy. In a still further aspect, each $R^1$ is unsubstituted cyclohexyl.

In a further aspect, each $R^1$ is independently selected from —(C1-C4 alkyl)aryl and substituted with 0, 1, 2, or 3 groups independently selected from halogen, hydroxyl, amine, alkylamino, dialkylamino, C1-C4 alkyl, and C1-C4 alkoxy. In a still further aspect, each $R^1$ is independently selected from —(C1-C4 alkyl)aryl and substituted with 0, 1, or 2 groups independently selected from halogen, hydroxyl, amine, alkylamino, dialkylamino, C1-C4 alkyl, and C1-C4 alkoxy. In yet a further aspect, each $R^1$ is independently selected from —(C1-C4 alkyl)aryl and substituted with 0 or 1 group selected from halogen, hydroxyl, amine, alkylamino, dialkylamino, C1-C4 alkyl, and C1-C4 alkoxy. In an even further aspect, each $R^1$ is independently selected from —(C1-C4 alkyl)aryl and monosubstituted with a group selected from halogen, hydroxyl, amine, alkylamino, dialkylamino, C1-C4 alkyl, and C1-C4 alkoxy. In a still further aspect, each $R^1$ is independently selected from —(C1-C4 alkyl)aryl and unsubstituted.

In a further aspect, each $R^1$ is —$CH_2Ph$ substituted with 0, 1, 2, or 3 groups independently selected from halogen, hydroxyl, amine, alkylamino, dialkylamino, C1-C4 alkyl, and C1-C4 alkoxy. In a still further aspect, each $R^1$ is —$CH_2Ph$ substituted with 0, 1, or 2 groups independently selected from halogen, hydroxyl, amine, alkylamino, dialkylamino, C1-C4 alkyl, and C1-C4 alkoxy. In yet a further aspect, each $R^1$ is —$CH_2Ph$ substituted with 0 or 1 group selected from halogen, hydroxyl, amine, alkylamino, dialkylamino, C1-C4 alkyl, and C1-C4 alkoxy. In an even further aspect, each $R^1$ is —$CH_2Ph$ monosubstituted with a group selected from halogen, hydroxyl, amine, alkylamino, dialkylamino, C1-C4 alkyl, and C1-C4 alkoxy. In a still further aspect, each $R^1$ is unsubstituted —$CH_2Ph$.

c. $R^2$ and $R^3$ Groups

In one aspect, $R^2$ is selected from hydrogen, halogen, hydroxyl, amine, alkylamino, dialkylamino, C1-C4 alkyl, C1-C4 alkoxy, and an electron-withdrawing group; and wherein $R^3$ is selected from hydrogen, hydroxyl, amine, alkyl amine, dialkylamine, C1-C4 alkyl, C1-C8 alkenyl, C1-C4 alkoxy, —C(O)OH, —C(O)$OR^5$, —C(O)$R^5$, —C(O)$NHR^6$, aryl, a 5- or 6-membered heteroaryl having 1, 2, or 3 ring-members selected from O, S, and $NR^1$, a 5- or 6-membered cycloalkyl, (C1-C4 alkyl)aryl, and (C1-C4 alkenyl)aryl, and substituted with 0, 1, 2, or 3 groups independently selected from halogen, hydroxyl, amine, alkylamino, dialkylamino, C1-C4 alkyl, and C1-C4 alkoxy; or wherein $R^2$ and $R^3$, together with the intervening atoms, comprise a 5- or 6-membered cycloalkyl or a 5- or 6-membered heterocycloalkyl having 1, 2, or 3 ring-members selected from O, S, and $NR^1$, substituted with 0, 1, 2, or 3 groups independently selected from oxo, hydroxyl, halogen, C1-C4 alkyl, C1-C4 alkoxy, —C(O)OH, —C(O)$OR^5$, —C(O)$R^5$, and —C(O)$NHR^6$.

In one aspect, $R^2$ is selected from hydrogen, halogen, hydroxyl, amine, alkylamino, dialkylamino, C1-C4 alkyl, C1-C4 alkoxy, and an electron-withdrawing group; and wherein $R^3$ is selected from hydrogen, hydroxyl, amine, alkyl amine, dialkylamine, C1-C4 alkyl, C1-C4 alkoxy, —C(O)OH, —C(O)$OR^5$, —C(O)$R^5$, and —C(O)$NHR^6$; or wherein $R^2$ and $R^3$, together with the intervening atoms, comprise a 5- or 6-membered cycloalkyl or a 5- or 6-membered heterocycloalkyl having 1, 2, or 3 ring-members selected from O, S, and $NR^1$, substituted with 0, 1, 2, or 3 groups independently selected from oxo, hydroxyl, halogen, C1-C4 alkyl, C1-C4 alkoxy, —C(O)OH, —C(O)$OR^5$, —C(O)$R^5$, and —C(O)$NHR^6$.

In a further aspect, $R^2$ is selected from hydrogen, halogen, hydroxyl, amine, alkylamino, dialkylamino, C1-C4 alkyl, C1-C4 alkoxy, and an electron-withdrawing group. In a still further aspect, $R^2$ is selected from hydrogen, halogen, hydroxyl, amine, alkylamino, dialkylamino, C1-C4 alkyl, C1-C4 alkoxy, nitro, cyano, —C(O)OH, —C(O)$R^5$, —C(O)O$R^5$, and —C(O)NH$R^6$. In yet a further aspect, $R^2$ is hydrogen.

In a further aspect, $R^2$ is selected from hydrogen, halogen, hydroxyl, amine, alkylamino, and dialkylamino. In a still further aspect, $R^2$ is selected from hydrogen, —F, —Cl, hydroxyl, amine, —NH(CH$_2$CH$_2$CH$_3$), —NH(CH(CH$_3$)$_2$), —NH(CH$_2$CH$_3$), —NH(CH$_3$), —N(CH$_2$CH$_2$CH$_3$)$_2$, —N(CH(CH$_3$)$_2$)$_2$, —N(CH$_2$CH$_3$)$_2$, —N(CH$_3$)$_2$, and —N(CH$_2$CH$_3$)(CH$_3$). In yet a further aspect, $R^2$ is selected from hydrogen, —F, —Cl, hydroxyl, amine, —NH(CH$_2$CH$_3$), —NH(CH$_3$), —N(CH$_2$CH$_3$)$_2$, —N(CH$_3$)$_2$, and —N(CH$_2$CH$_3$)(CH$_3$). In an even further aspect, $R^2$ is selected from hydrogen, —F, —Cl, hydroxyl, amine, —NH(CH$_3$), and —N(CH$_3$)$_2$.

In a further aspect, $R^2$ is selected from hydrogen, halogen, hydroxyl, amine, C1-C4 alkyl, and C1-C4 alkoxy. In a still further aspect, $R^2$ is selected from hydrogen, —F, —Cl, hydroxyl, amine, i-propyl, n-propyl, ethyl, methyl, i-propoxy, n-propyoxy, ethoxy, and methoxy. In yet a further aspect, $R^2$ is selected from hydrogen, —F, —Cl, hydroxyl, amine, ethyl, methyl, ethoxy, and methoxy. In an even further aspect, $R^2$ is selected from hydrogen, —F, —Cl, hydroxyl, amine, methyl, and methoxy.

In a further aspect, $R^2$ is selected from C1-C4 alkyl and C1-C4 alkoxy. In a still further aspect, $R^2$ is selected from i-propyl, n-propyl, ethyl, methyl, i-propoxy, n-propyoxy, ethoxy, and methoxy. In yet a further aspect, $R^2$ is selected from ethyl, methyl, ethoxy, and methoxy. In an even further aspect, $R^2$ is selected from methyl and methoxy.

In a further aspect, $R^2$ is selected from hydrogen and halogen. In a still further aspect, $R^2$ is selected from hydrogen, —F, —Br, and —Cl. In yet a further aspect, $R^2$ is selected from hydrogen, —F, and —Cl. In an even further aspect, $R^2$ is selected from hydrogen and —Cl. In yet a further aspect, $R^2$ is selected from hydrogen and —F.

In a further aspect, $R^3$ is selected from hydrogen, hydroxyl, amine, alkyl amine, dialkylamine, C1-C4 alkyl, C1-C8 alkenyl, C1-C4 alkoxy, —C(O)OH, —C(O)O$R^5$, —C(O)$R^5$, —C(O)NH$R^6$, aryl, a 5- or 6-membered heteroaryl having 1, 2, or 3 ring-members selected from O, S, and NR$^1$, a 5- or 6-membered cycloalkyl, (C1-C4 alkyl)aryl, and (C1-C4 alkenyl)aryl, and substituted with 0, 1, 2, or 3 groups independently selected from halogen, hydroxyl, amine, alkylamino, dialkylamino, C1-C4 alkyl, and C1-C4 alkoxy. In a still further aspect, $R^3$ is selected from hydrogen, hydroxyl, amine, alkyl amine, dialkylamine, C1-C4 alkyl, C1-C4 alkenyl, C1-C4 alkoxy, —C(O)OH, —C(O)O$R^5$, —C(O)$R^5$, —C(O)NH$R^6$, aryl, a 5- or 6-membered heteroaryl having 1, 2, or 3 ring-members selected from O, S, and NR$^1$, a 5- or 6-membered cycloalkyl, (C1-C4 alkyl)aryl, and (C1-C4 alkenyl)aryl, and substituted with 0, 1, 2, or 3 groups independently selected from halogen, hydroxyl, amine, alkylamino, dialkylamino, C1-C4 alkyl, and C1-C4 alkoxy.

In a further aspect, $R^3$ is selected from aryl, a 5- or 6-membered heteroaryl having 1, 2, or 3 ring-members selected from O, S, and NR$^1$, a 5- or 6-membered cycloalkyl, (C1-C4 alkyl)aryl, and (C1-C4 alkenyl)aryl, and substituted with 0, 1, 2, or 3 groups independently selected from halogen, hydroxyl, amine, alkylamino, dialkylamino, C1-C4 alkyl, and C1-C4 alkoxy. In a still further aspect, $R^3$ is selected from aryl, a 5- or 6-membered heteroaryl having 1, 2, or 3 ring-members selected from O, S, and NR$^1$, a 5- or 6-membered cycloalkyl, (C1-C4 alkyl)aryl, and (C1-C4 alkenyl)aryl, and substituted with 0 or 1 group selected from halogen, hydroxyl, amine, alkylamino, dialkylamino, C1-C4 alkyl, and C1-C4 alkoxy. In an even further aspect, $R^3$ is selected from aryl, a 5- or 6-membered heteroaryl having 1, 2, or 3 ring-members selected from O, S, and NR$^1$, a 5- or 6-membered cycloalkyl, (C1-C4 alkyl)aryl, and (C1-C4 alkenyl)aryl, and monosubstituted with a group selected from halogen, hydroxyl, amine, alkylamino, dialkylamino, C1-C4 alkyl, and C1-C4 alkoxy. In a still further aspect, $R^3$ is selected from aryl, a 5- or 6-membered heteroaryl having 1, 2, or 3 ring-members selected from O, S, and NR$^1$, a 5- or 6-membered cycloalkyl, (C1-C4 alkyl)aryl, and (C1-C4 alkenyl)aryl, and unsubstituted.

In a further aspect, $R^3$ is selected from aryl and a 5- or 6-membered heteroaryl having 1, 2, or 3 ring-members selected from O, S, and NR$^1$, and substituted with 0, 1, 2, or 3 groups independently selected from halogen, hydroxyl, amine, alkylamino, dialkylamino, C1-C4 alkyl, and C1-C4 alkoxy. In a still further aspect, $R^3$ is selected from aryl and a 5- or 6-membered heteroaryl having 1, 2, or 3 ring-members selected from O, S, and NR$^1$, and substituted with 0, 1, or 2 groups independently selected from halogen, hydroxyl, amine, alkylamino, dialkylamino, C1-C4 alkyl, and C1-C4 alkoxy. In yet a further aspect, $R^3$ is selected from aryl and a 5- or 6-membered heteroaryl having 1, 2, or 3 ring-members selected from O, S, and NR$^1$, and substituted with 0 or 1 group selected from halogen, hydroxyl, amine, alkylamino, dialkylamino, C1-C4 alkyl, and C1-C4 alkoxy. In an even further aspect, $R^3$ is selected from aryl and a 5- or 6-membered heteroaryl having 1, 2, or 3 ring-members selected from O, S, and NR$^1$, and monosubstituted with a group selected from halogen, hydroxyl, amine, alkylamino, dialkylamino, C1-C4 alkyl, and C1-C4 alkoxy. In a still further aspect, $R^3$ is selected from aryl and a 5- or 6-membered heteroaryl having 1, 2, or 3 ring-members selected from O, S, and NR$^1$, and unsubstituted.

In a further aspect, $R^3$ is aryl substituted with 0, 1, 2, or 3 groups independently selected from halogen, hydroxyl, amine, alkylamino, dialkylamino, C1-C4 alkyl, and C1-C4 alkoxy. In a still further aspect, $R^3$ aryl substituted with 0, 1, or 2 groups independently selected from halogen, hydroxyl, amine, alkylamino, dialkylamino, C1-C4 alkyl, and C1-C4 alkoxy. In yet a further aspect, $R^3$ is aryl substituted with 0 or 1 group selected from halogen, hydroxyl, amine, alkylamino, dialkylamino, C1-C4 alkyl, and C1-C4 alkoxy. In an even further aspect, $R^3$ is aryl monosubstituted with a group selected from halogen, hydroxyl, amine, alkylamino, dialkylamino, C1-C4 alkyl, and C1-C4 alkoxy. In a still further aspect, $R^3$ is unsubstituted aryl.

In a further aspect, $R^3$ is phenyl substituted with 0, 1, 2, or 3 groups independently selected from halogen, hydroxyl, amine, alkylamino, dialkylamino, C1-C4 alkyl, and C1-C4 alkoxy. In a still further aspect, $R^3$ phenyl substituted with 0, 1, or 2 groups independently selected from halogen, hydroxyl, amine, alkylamino, dialkylamino, C1-C4 alkyl, and C1-C4 alkoxy. In yet a further aspect, $R^3$ is phenyl substituted with 0 or 1 group selected from halogen, hydroxyl, amine, alkylamino, dialkylamino, C1-C4 alkyl, and C1-C4 alkoxy. In an even further aspect, $R^3$ is phenyl monosubstituted with a group selected from halogen, hydroxyl, amine, alkylamino, dialkylamino, C1-C4 alkyl, and C1-C4 alkoxy. In a still further aspect, $R^3$ is unsubstituted phenyl.

In a further aspect, $R^3$ is a 5- or 6-membered heteroaryl having 1, 2, or 3 ring-members selected from O, S, and $NR^1$, and substituted with 0, 1, 2, or 3 groups independently selected from halogen, hydroxyl, amine, alkylamino, dialkylamino, C1-C4 alkyl, and C1-C4 alkoxy. In a still further aspect, $R^3$ is a 5- or 6-membered heteroaryl having 1, 2, or 3 ring-members selected from O, S, and $NR^1$, and substituted with 0, 1, or 2 groups independently selected from halogen, hydroxyl, amine, alkylamino, dialkylamino, C1-C4 alkyl, and C1-C4 alkoxy. In yet a further aspect, $R^3$ is a 5- or 6-membered heteroaryl having 1, 2, or 3 ring-members selected from O, S, and $NR^1$, and substituted with 0 or 1 group selected from halogen, hydroxyl, amine, alkylamino, dialkylamino, C1-C4 alkyl, and C1-C4 alkoxy. In an even further aspect, $R^3$ is a 5- or 6-membered heteroaryl having 1, 2, or 3 ring-members selected from O, S, and $NR^1$, and monosubstituted with a group selected from halogen, hydroxyl, amine, alkylamino, dialkylamino, C1-C4 alkyl, and C1-C4 alkoxy. In a still further aspect, $R^3$ is a 5- or 6-membered heteroaryl having 1, 2, or 3 ring-members selected from O, S, and $NR^1$, and unsubstituted.

In a further aspect, $R^3$ is pyridinyl substituted with 0, 1, 2, or 3 groups independently selected from halogen, hydroxyl, amine, alkylamino, dialkylamino, C1-C4 alkyl, and C1-C4 alkoxy. In a still further aspect, $R^3$ pyridinyl substituted with 0, 1, or 2 groups independently selected from halogen, hydroxyl, amine, alkylamino, dialkylamino, C1-C4 alkyl, and C1-C4 alkoxy. In yet a further aspect, $R^3$ is pyridinyl substituted with 0 or 1 group selected from halogen, hydroxyl, amine, alkylamino, dialkylamino, C1-C4 alkyl, and C1-C4 alkoxy. In an even further aspect, $R^3$ is pyridinyl monosubstituted with a group selected from halogen, hydroxyl, amine, alkylamino, dialkylamino, C1-C4 alkyl, and C1-C4 alkoxy. In a still further aspect, $R^3$ is unsubstituted pyridinyl.

In a further aspect, $R^3$ is a 5- or 6-membered cycloalkyl substituted with 0, 1, 2, or 3 groups independently selected from halogen, hydroxyl, amine, alkylamino, dialkylamino, C1-C4 alkyl, and C1-C4 alkoxy. In a still further aspect, $R^3$ is a 5- or 6-membered cycloalkyl substituted with 0, 1, or 2 groups independently selected from halogen, hydroxyl, amine, alkylamino, dialkylamino, C1-C4 alkyl, and C1-C4 alkoxy. In yet a further aspect, $R^3$ is a 5- or 6-membered cycloalkyl substituted with 0 or 1 group selected from halogen, hydroxyl, amine, alkylamino, dialkylamino, C1-C4 alkyl, and C1-C4 alkoxy. In an even further aspect, $R^3$ is a 5- or 6-membered cycloalkyl monosubstituted with a group selected from halogen, hydroxyl, amine, alkylamino, dialkylamino, C1-C4 alkyl, and C1-C4 alkoxy. In a still further aspect, $R^3$ is an unsubstituted 5- or 6-membered cycloalkyl.

In a further aspect, $R^3$ is selected from (C1-C4 alkyl)aryl and (C1-C4 alkenyl)aryl, and substituted with 0, 1, 2, or 3 groups independently selected from halogen, hydroxyl, amine, alkylamino, dialkylamino, C1-C4 alkyl, and C1-C4 alkoxy. In a still further aspect, $R^3$ is selected from (C1-C4 alkyl)aryl and (C1-C4 alkenyl)aryl, and substituted with 0, 1, or 2 groups independently selected from halogen, hydroxyl, amine, alkylamino, dialkylamino, C1-C4 alkyl, and C1-C4 alkoxy. In yet a further aspect, $R^3$ is selected from (C1-C4 alkyl)aryl and (C1-C4 alkenyl)aryl, and substituted with 0 or 1 group selected from halogen, hydroxyl, amine, alkylamino, dialkylamino, C1-C4 alkyl, and C1-C4 alkoxy. In an even further aspect, $R^3$ is selected from (C1-C4 alkyl)aryl and (C1-C4 alkenyl)aryl, and monosubstituted with a group selected from halogen, hydroxyl, amine, alkylamino, dialkylamino, C1-C4 alkyl, and C1-C4 alkoxy. In a still further aspect, $R^3$ is selected from (C1-C4 alkyl)aryl and (C1-C4 alkenyl)aryl, and unsubstituted.

In a further aspect, $R^3$ is selected from —$CH_2Ph$ and —CH=CHPh, and substituted with 0, 1, 2, or 3 groups independently selected from halogen, hydroxyl, amine, alkylamino, dialkylamino, C1-C4 alkyl, and C1-C4 alkoxy. In a still further aspect, $R^3$ is selected from —$CH_2Ph$ and —CH=CHPh, and substituted with 0, 1, or 2 groups independently selected from halogen, hydroxyl, amine, alkylamino, dialkylamino, C1-C4 alkyl, and C1-C4 alkoxy. In yet a further aspect, $R^3$ is selected from —$CH_2Ph$ and —CH=CHPh, and substituted with 0 or 1 group selected from halogen, hydroxyl, amine, alkylamino, dialkylamino, C1-C4 alkyl, and C1-C4 alkoxy. In an even further aspect, $R^3$ is selected from —$CH_2Ph$ and —CH=CHPh, and monosubstituted with a group selected from halogen, hydroxyl, amine, alkylamino, dialkylamino, C1-C4 alkyl, and C1-C4 alkoxy. In a still further aspect, $R^3$ is selected from —$CH_2Ph$ and —CH=CHPh, and unsubstituted.

In a further aspect, $R^3$ is selected from hydrogen, hydroxyl, amine, alkyl amine, dialkylamine, C1-C4 alkyl, C1-C4 alkoxy, —C(O)OH, —C(O)$OR^5$, —C(O)$R^5$, and —C(O)$NHR^6$. In a still further aspect, $R^3$ is hydrogen.

In a further aspect, $R^3$ is selected from hydrogen, hydroxyl, amine, —C(O)OH, —C(O)$OR^5$, —C(O)$R^5$, and —C(O)$NHR^6$. In a still further aspect, $R^3$ is selected from hydrogen, —C(O)OH, —C(O)$OR^5$, —C(O)$R^5$, and —C(O)$NHR^6$.

In a further aspect, $R^3$ is selected from hydrogen, hydroxyl, amine, alkyl amine, and dialkylamine. In a still further aspect, $R^3$ is selected from hydrogen, hydroxyl, amine, —NH($CH_2CH_2CH_3$), —NH(CH($CH_3)_2$), —NH($CH_2CH_3$), —NH($CH_3$), —N($CH_2CH_2CH_3)_2$, —N(CH($CH_3)_2)_2$, —N($CH_2CH_3)_2$, —N($CH_3)_2$, and —N($CH_2CH_3$)($CH_3$). In yet a further aspect, $R^3$ is selected from hydrogen, hydroxyl, amine, —NH($CH_2CH_3$), —NH($CH_3$), —N($CH_2CH_3)_2$, —N($CH_3)_2$, and —N($CH_2CH_3$)($CH_3$). In an even further aspect, $R^3$ is selected from hydrogen, -hydroxyl, amine, —NH($CH_3$), and —N($CH_3)_2$.

In a further aspect, $R^3$ is selected from hydrogen, hydroxyl, amine, C1-C4 alkyl, and C1-C4 alkoxy. In a still further aspect, $R^3$ is selected from hydrogen, hydroxyl, amine, i-propyl, n-propyl, ethyl, methyl, i-propoxy, n-propyoxy, ethoxy, and methoxy. In yet a further aspect, $R^3$ is selected from hydrogen, hydroxyl, amine, ethyl, methyl, ethoxy, and methoxy. In an even further aspect, $R^3$ is selected from hydrogen, hydroxyl, amine, methyl, and methoxy.

In a further aspect, $R^3$ is selected from C1-C4 alkyl and C1-C4 alkoxy. In a still further aspect, $R^3$ is selected from i-propyl, n-propyl, ethyl, methyl, i-propoxy, n-propyoxy, ethoxy, and methoxy. In yet a further aspect, $R^3$ is selected from ethyl, methyl, ethoxy, and methoxy. In an even further aspect, $R^3$ is selected from methyl and methoxy.

In a further aspect, $R^2$ and $R^3$, together with the intervening atoms, comprise a 5- or 6-membered cycloalkyl or a 5- or 6-membered heterocycloalkyl having 1, 2, or 3 ring-members selected from O, S, and $NR^1$, substituted with 0, 1, 2, or 3 groups independently selected from oxo, hydroxyl, halogen, C1-C4 alkyl, C1-C4 alkoxy, —C(O)OH, —C(O)$OR^5$, —C(O)$R^5$, and —C(O)$NHR^6$. In a still further aspect, $R^2$ and $R^3$, together with the intervening atoms, comprise a 5- or 6-membered cycloalkyl or a 5- or 6-membered heterocycloalkyl having 1, 2, or 3 ring-members selected from O, S, and $NR^1$, substituted with 0, 1, or 2 groups independently selected from oxo, hydroxyl, halogen, C1-C4 alkyl, C1-C4 alkoxy, —C(O)OH, —C(O)$OR^5$, —C(O)$R^5$, and —C(O)$NHR^6$. In yet a further aspect, $R^2$ and $R^3$, together with the intervening atoms, comprise a 5- or 6-membered cycloalkyl or a 5- or 6-membered heterocycloalkyl having 1, 2, or 3 ring-members selected from O, S, and $NR^1$, substituted with 0 or 1 group selected from oxo, hydroxyl, halogen, C1-C4 alkyl, C1-C4 alkoxy, —C(O)OH, —C(O)$OR^5$, —C(O)$R^5$, and —C(O)$NHR^6$. In an even further aspect, $R^2$ and $R^3$, together with the intervening atoms, comprise a 5- or 6-membered cycloalkyl or a 5- or 6-membered heterocycloalkyl having 1, 2, or 3 ring-members selected from O, S, and $NR^1$, monosubstituted with a group selected from oxo, hydroxyl, halogen, C1-C4 alkyl, C1-C4 alkoxy, —C(O)OH, —C(O)$OR^5$, —C(O)$R^5$, and —C(O)$NHR^6$. In a still further aspect, $R^2$ and $R^3$, together with the intervening atoms, comprise a 5- or 6-membered cycloalkyl or a 5- or 6-membered heterocycloalkyl having 1, 2, or 3 ring-members selected from O, S, and $NR^1$, and unsubstituted.

In a further aspect, $R^2$ and $R^3$, together with the intervening atoms, comprise a 5- or 6-membered cycloalkyl or a 5- or 6-membered heterocycloalkyl having 1 or 2 ring-members selected from O, S, and $NR^1$, substituted with 0, 1, 2, or 3 groups independently selected from oxo, hydroxyl, halogen, C1-C4 alkyl, C1-C4 alkoxy, —C(O)OH, —C(O)$OR^5$, —C(O)$R^5$, and —C(O)$NHR^6$. In a still further aspect, $R^2$ and $R^3$, together with the intervening atoms, comprise a 5- or 6-membered cycloalkyl or a 5- or 6-membered heterocycloalkyl having 3 ring-members selected from O, S, and $NR^1$, substituted with 0, 1, 2, or 3 groups independently selected from oxo, hydroxyl, halogen, C1-C4 alkyl, C1-C4 alkoxy, —C(O)OH, —C(O)$OR^5$, —C(O)$R^5$, and —C(O)$NHR^6$. In yet a further aspect, $R^2$ and $R^3$, together with the intervening atoms, comprise a 5- or 6-membered cycloalkyl or a 5- or 6-membered heterocycloalkyl having 2 ring-members selected from O, S, and $NR^1$, substituted with 0, 1, 2, or 3 groups independently selected from oxo, hydroxyl, halogen, C1-C4 alkyl, C1-C4 alkoxy, —C(O)OH, —C(O)$OR^5$, —C(O)$R^5$, and —C(O)$NHR^6$. In an even further aspect, $R^2$ and $R^3$, together with the intervening atoms, comprise a 5- or 6-membered cycloalkyl or a 5- or 6-membered heterocycloalkyl having 1 ring-member selected from O, S, and $NR^1$, substituted with 0, 1, 2, or 3 groups independently selected from oxo, hydroxyl, halogen, C1-C4 alkyl, C1-C4 alkoxy, —C(O)OH, —C(O)$OR^5$, —C(O)$R^5$, and —C(O)$NHR^6$.

In a further aspect, $R^2$ and $R^3$, together with the intervening atoms, comprise a 5- or 6-membered cycloalkyl having 1, 2, or 3 ring-members selected from O, S, and $NR^1$, substituted with 0, 1, 2, or 3 groups independently selected from oxo, hydroxyl, halogen, C1-C4 alkyl, C1-C4 alkoxy, —C(O)OH, —C(O)$OR^5$, —C(O)$R^5$, and —C(O)$NHR^6$. In a still further aspect, $R^2$ and $R^3$, together with the intervening atoms, comprise a 5- or 6-membered cycloalkyl having 1, 2, or 3 ring-members selected from O, S, and $NR^1$, substituted with 0, 1, or 2 groups independently selected from oxo, hydroxyl, halogen, C1-C4 alkyl, C1-C4 alkoxy, —C(O)OH, —C(O)$OR^5$, —C(O)$R^5$, and —C(O)$NHR^6$. In yet a further aspect, $R^2$ and $R^3$, together with the intervening atoms, comprise a 5- or 6-membered cycloalkyl having 1, 2, or 3 ring-members selected from O, S, and $NR^1$, substituted with 0 or 1 group selected from oxo, hydroxyl, halogen, C1-C4 alkyl, C1-C4 alkoxy, —C(O)OH, —C(O)$OR^5$, —C(O)$R^5$, and —C(O)$NHR^6$. In an even further aspect, $R^2$ and $R^3$, together with the intervening atoms, comprise a 5- or 6-membered cycloalkyl having 1, 2, or 3 ring-members selected from O, S, and $NR^1$, monosubstituted with a group selected from oxo, hydroxyl, halogen, C1-C4 alkyl, C1-C4 alkoxy, —C(O)OH, —C(O)$OR^5$, —C(O)$R^5$, and —C(O)$NHR^6$. In a still further aspect, $R^2$ and $R^3$, together with the intervening atoms, comprise a 5- or 6-membered cycloalkyl having 1, 2, or 3 ring-members selected from O, S, and $NR^1$, and unsubstituted.

In a further aspect, $R^2$ and $R^3$, together with the intervening atoms, comprise a 5- or 6-membered heterocycloalkyl having 1, 2, or 3 ring-members selected from O, S, and $NR^1$, substituted with 0, 1, 2, or 3 groups independently selected from oxo, hydroxyl, halogen, C1-C4 alkyl, C1-C4 alkoxy, —C(O)OH, —C(O)$OR^5$, —C(O)$R^5$, and —C(O)$NHR^6$. In a still further aspect, $R^2$ and $R^3$, together with the intervening atoms, comprise a 5- or 6-membered heterocycloalkyl having 1, 2, or 3 ring-members selected from O, S, and $NR^1$, substituted with 0, 1, or 2 groups independently selected from oxo, hydroxyl, halogen, C1-C4 alkyl, C1-C4 alkoxy, —C(O)OH, —C(O)$OR^5$, —C(O)$R^5$, and —C(O)$NHR^6$. In yet a further aspect, $R^2$ and $R^3$, together with the intervening atoms, comprise a 5- or 6-membered heterocycloalkyl having 1, 2, or 3 ring-members selected from O, S, and $NR^1$, substituted with 0 or 1 group selected from oxo, hydroxyl, halogen, C1-C4 alkyl, C1-C4 alkoxy, —C(O)OH, —C(O)$OR^5$, —C(O)$R^5$, and —C(O)$NHR^6$. In an even further aspect, $R^2$ and $R^3$, together with the intervening atoms, comprise a 5- or 6-membered heterocycloalkyl having 1, 2, or 3 ring-members selected from O, S, and $NR^1$, monosubstituted with a group selected from oxo, hydroxyl, halogen, C1-C4 alkyl, C1-C4 alkoxy, —C(O)OH, —C(O)$OR^5$, —C(O)$R^5$, and —C(O)$NHR^6$. In a still further aspect, $R^2$ and $R^3$, together with the intervening atoms, comprise a 5- or 6-membered heterocycloalkyl having 1, 2, or 3 ring-members selected from O, S, and $NR^1$, and unsubstituted.

d. $R^4$ Groups

In one aspect, $R^4$ is selected from hydrogen, hydroxyl, amine, alkyl amine, dialkylamine, C1-C4 alkyl, C1-C8 alkenyl, C1-C4 alkoxy, —C(O)OH, —C(O)$OR^5$, —C(O)$R^5$, —C(O)$NHR^6$, aryl, a 5- or 6-membered heteroaryl having 1, 2, or 3 ring-members selected from O, S, and $NR^1$, a 5- or 6-membered cycloalkyl, (C1-C4 alkyl)aryl, and (C1-C4 alkenyl)aryl, and substituted with 0, 1, 2, or 3 groups independently selected from halogen, hydroxyl, amine, alkylamino, dialkylamino, C1-C4 alkyl, and C1-C4 alkoxy; or EWG and $R^4$, together with the intervening atoms, comprise a 5- or 6-membered cycloalkyl or a 5- or 6-membered heterocycloalkyl having 1 or 2 ring-members selected from O, S, and $NR^1$, substituted with 0, 1, 2, or 3 groups independently selected from hydroxyl, halogen, oxo, C1-C4 alkyl, C1-C4 alkoxy, —C(O)OH, —C(O)$R^5$, —C(O)$OR^5$, and —C(O)$NHR^6$; provided that the first atom of EWG adjacent to the position denoted α is substituted with oxo.

In one aspect, $R^4$ is selected from hydrogen, hydroxyl, amine, alkyl amine, dialkylamine, C1-C4 alkyl, C1-C4 alkoxy, —C(O)OH, —C(O)$OR^5$, —C(O)$R^5$, and —C(O)$NHR^6$; or EWG and $R^4$, together with the intervening atoms, comprise a 5- or 6-membered cycloalkyl or a 5- or 6-membered heterocycloalkyl having 1 or 2 ring-members selected from O, S, and $NR^1$, substituted with 0, 1, 2, or 3 groups independently selected from hydroxyl, halogen, oxo, C1-C4 alkyl, C1-C4 alkoxy, —C(O)OH, —C(O)$R^5$, —C(O)$OR^5$, and —C(O)$NHR^6$; provided that the first atom of EWG adjacent to the position denoted a is substituted with oxo. In a further aspect, $R^4$ is hydrogen.

In a further aspect, $R^4$ is selected from hydrogen, hydroxyl, amine, alkyl amine, dialkylamine, C1-C4 alkyl, C1-C8 alkenyl, C1-C4 alkoxy, —C(O)OH, —C(O)OR$^5$, —C(O)R$^5$, —C(O)NHR$^6$, aryl, a 5- or 6-membered heteroaryl having 1, 2, or 3 ring-members selected from O, S, and NR$^1$, a 5- or 6-membered cycloalkyl, (C1-C4 alkyl)aryl, and (C1-C4 alkenyl)aryl, and substituted with 0, 1, 2, or 3 groups independently selected from halogen, hydroxyl, amine, alkylamino, dialkylamino, C1-C4 alkyl, and C1-C4 alkoxy. In a still further aspect, $R^4$ is selected from hydrogen, hydroxyl, amine, alkyl amine, dialkylamine, C1-C4 alkyl, C1-C4 alkenyl, C1-C4 alkoxy, —C(O)OH, —C(O)OR$^5$, —C(O)R$^5$, —C(O)NHR$^6$, aryl, a 5- or 6-membered heteroaryl having 1, 2, or 3 ring-members selected from O, S, and NR$^1$, a 5- or 6-membered cycloalkyl, (C1-C4 alkyl)aryl, and (C1-C4 alkenyl)aryl, and substituted with 0, 1, 2, or 3 groups independently selected from halogen, hydroxyl, amine, alkylamino, dialkylamino, C1-C4 alkyl, and C1-C4 alkoxy.

In a further aspect, $R^4$ is selected from aryl, a 5- or 6-membered heteroaryl having 1, 2, or 3 ring-members selected from O, S, and NR$^1$, a 5- or 6-membered cycloalkyl, (C1-C4 alkyl)aryl, and (C1-C4 alkenyl)aryl, and substituted with 0, 1, 2, or 3 groups independently selected from halogen, hydroxyl, amine, alkylamino, dialkylamino, C1-C4 alkyl, and C1-C4 alkoxy. In a still further aspect, $R^4$ is selected from aryl, a 5- or 6-membered heteroaryl having 1, 2, or 3 ring-members selected from O, S, and NR$^1$, a 5- or 6-membered cycloalkyl, (C1-C4 alkyl)aryl, and (C1-C4 alkenyl)aryl, and substituted with 0, 1, or 2 groups independently selected from halogen, hydroxyl, amine, alkylamino, dialkylamino, C1-C4 alkyl, and C1-C4 alkoxy. In yet a further aspect, $R^4$ is selected from aryl, a 5- or 6-membered heteroaryl having 1, 2, or 3 ring-members selected from O, S, and NR$^1$, a 5- or 6-membered cycloalkyl, (C1-C4 alkyl)aryl, and (C1-C4 alkenyl)aryl, and substituted with 0 or 1 group selected from halogen, hydroxyl, amine, alkylamino, dialkylamino, C1-C4 alkyl, and C1-C4 alkoxy. In an even further aspect, $R^4$ is selected from aryl, a 5- or 6-membered heteroaryl having 1, 2, or 3 ring-members selected from O, S, and NR$^1$, a 5- or 6-membered cycloalkyl, (C1-C4 alkyl)aryl, and (C1-C4 alkenyl)aryl, and monosubstituted with a group selected from halogen, hydroxyl, amine, alkylamino, dialkylamino, C1-C4 alkyl, and C1-C4 alkoxy. In a still further aspect, $R^4$ is selected from aryl, a 5- or 6-membered heteroaryl having 1, 2, or 3 ring-members selected from O, S, and NR$^1$, a 5- or 6-membered cycloalkyl, (C1-C4 alkyl)aryl, and (C1-C4 alkenyl)aryl, and unsubstituted.

In a further aspect, $R^4$ is selected from aryl and a 5- or 6-membered heteroaryl having 1, 2, or 3 ring-members selected from O, S, and NR$^1$, and substituted with 0, 1, 2, or 3 groups independently selected from halogen, hydroxyl, amine, alkylamino, dialkylamino, C1-C4 alkyl, and C1-C4 alkoxy. In a still further aspect, $R^4$ is selected from aryl and a 5- or 6-membered heteroaryl having 1, 2, or 3 ring-members selected from O, S, and NR$^1$, and substituted with 0, 1, or 2 groups independently selected from halogen, hydroxyl, amine, alkylamino, dialkylamino, C1-C4 alkyl, and C1-C4 alkoxy. In yet a further aspect, $R^4$ is selected from aryl and a 5- or 6-membered heteroaryl having 1, 2, or 3 ring-members selected from O, S, and NR$^1$, and substituted with 0 or 1 group selected from halogen, hydroxyl, amine, alkylamino, dialkylamino, C1-C4 alkyl, and C1-C4 alkoxy. In an even further aspect, $R^4$ is selected from aryl and a 5- or 6-membered heteroaryl having 1, 2, or 3 ring-members selected from O, S, and NR$^1$, and monosubstituted with a group selected from halogen, hydroxyl, amine, alkylamino, dialkylamino, C1-C4 alkyl, and C1-C4 alkoxy. In a still further aspect, $R^4$ is selected from aryl and a 5- or 6-membered heteroaryl having 1, 2, or 3 ring-members selected from O, S, and NR$^1$, and unsubstituted.

In a further aspect, $R^4$ is aryl substituted with 0, 1, 2, or 3 groups independently selected from halogen, hydroxyl, amine, alkylamino, dialkylamino, C1-C4 alkyl, and C1-C4 alkoxy. In a still further aspect, $R^4$ is aryl substituted with 0, 1, or 2 groups independently selected from halogen, hydroxyl, amine, alkylamino, dialkylamino, C1-C4 alkyl, and C1-C4 alkoxy. In yet a further aspect, $R^4$ is aryl substituted with 0 or 1 group selected from halogen, hydroxyl, amine, alkylamino, dialkylamino, C1-C4 alkyl, and C1-C4 alkoxy. In an even further aspect, $R^4$ is aryl monosubstituted with a group selected from halogen, hydroxyl, amine, alkylamino, dialkylamino, C1-C4 alkyl, and C1-C4 alkoxy. In a still further aspect, $R^4$ is unsubstituted aryl.

In a further aspect, $R^4$ is phenyl substituted with 0, 1, 2, or 3 groups independently selected from halogen, hydroxyl, amine, alkylamino, dialkylamino, C1-C4 alkyl, and C1-C4 alkoxy. In a still further aspect, $R^4$ is phenyl substituted with 0, 1, or 2 groups independently selected from halogen, hydroxyl, amine, alkylamino, dialkylamino, C1-C4 alkyl, and C1-C4 alkoxy. In yet a further aspect, $R^4$ is phenyl substituted with 0 or 1 group selected from halogen, hydroxyl, amine, alkylamino, dialkylamino, C1-C4 alkyl, and C1-C4 alkoxy. In an even further aspect, $R^4$ is phenyl monosubstituted with a group selected from halogen, hydroxyl, amine, alkylamino, dialkylamino, C1-C4 alkyl, and C1-C4 alkoxy. In a still further aspect, $R^4$ is unsubstituted phenyl.

In a further aspect, $R^4$ is a 5- or 6-membered heteroaryl having 1, 2, or 3 ring-members selected from O, S, and NR$^1$, and substituted with 0, 1, 2, or 3 groups independently selected from halogen, hydroxyl, amine, alkylamino, dialkylamino, C1-C4 alkyl, and C1-C4 alkoxy. In a still further aspect, $R^4$ is a 5- or 6-membered heteroaryl having 1, 2, or 3 ring-members selected from O, S, and NR$^1$, and substituted with 0, 1, or 2 groups independently selected from halogen, hydroxyl, amine, alkylamino, dialkylamino, C1-C4 alkyl, and C1-C4 alkoxy. In yet a further aspect, $R^4$ is a 5- or 6-membered heteroaryl having 1, 2, or 3 ring-members selected from O, S, and NR$^1$, and substituted with 0 or 1 group selected from halogen, hydroxyl, amine, alkylamino, dialkylamino, C1-C4 alkyl, and C1-C4 alkoxy. In an even further aspect, $R^4$ is a 5- or 6-membered heteroaryl having 1, 2, or 3 ring-members selected from O, S, and NR$^1$, and monosubstituted with a group selected from halogen, hydroxyl, amine, alkylamino, dialkylamino, C1-C4 alkyl, and C1-C4 alkoxy. In a still further aspect, $R^4$ is a 5- or 6-membered heteroaryl having 1, 2, or 3 ring-members selected from O, S, and NR$^1$, and unsubstituted.

In a further aspect, $R^4$ is pyridinyl substituted with 0, 1, 2, or 3 groups independently selected from halogen, hydroxyl, amine, alkylamino, dialkylamino, C1-C4 alkyl, and C1-C4 alkoxy. In a still further aspect, $R^4$ is pyridinyl substituted with 0, 1, or 2 groups independently selected from halogen, hydroxyl, amine, alkylamino, dialkylamino, C1-C4 alkyl, and C1-C4 alkoxy. In yet a further aspect, $R^4$ is pyridinyl substituted with 0 or 1 group selected from halogen, hydroxyl, amine, alkylamino, dialkylamino, C1-C4 alkyl, and C1-C4 alkoxy. In an even further aspect, $R^4$ is pyridinyl monosubstituted with a group selected from halogen, hydroxyl, amine, alkylamino, dialkylamino, C1-C4 alkyl, and C1-C4 alkoxy. In a still further aspect, $R^4$ is unsubstituted pyridinyl.

In a further aspect, $R^4$ is a 5- or 6-membered cycloalkyl substituted with 0, 1, 2, or 3 groups independently selected from halogen, hydroxyl, amine, alkylamino, dialkylamino, C1-C4 alkyl, and C1-C4 alkoxy. In a still further aspect, $R^4$ is a 5- or 6-membered cycloalkyl substituted with 0, 1, or 2 groups independently selected from halogen, hydroxyl, amine, alkylamino, dialkylamino, C1-C4 alkyl, and C1-C4 alkoxy. In yet a further aspect, $R^4$ is a 5- or 6-membered cycloalkyl substituted with 0 or 1 group selected from halogen, hydroxyl, amine, alkylamino, dialkylamino, C1-C4 alkyl, and C1-C4 alkoxy. In an even further aspect, $R^4$ is a 5- or 6-membered cycloalkyl monosubstituted with a group selected from halogen, hydroxyl, amine, alkylamino, dialkylamino, C1-C4 alkyl, and C1-C4 alkoxy. In a still further aspect, $R^4$ is an unsubstituted 5- or 6-membered cycloalkyl.

In a further aspect, $R^4$ is selected from (C1-C4 alkyl)aryl and (C1-C4 alkenyl)aryl, and substituted with 0, 1, 2, or 3 groups independently selected from halogen, hydroxyl, amine, alkylamino, dialkylamino, C1-C4 alkyl, and C1-C4 alkoxy. In a still further aspect, $R^4$ is selected from (C1-C4 alkyl)aryl and (C1-C4 alkenyl)aryl, and substituted with 0, 1, or 2 groups independently selected from halogen, hydroxyl, amine, alkylamino, dialkylamino, C1-C4 alkyl, and C1-C4 alkoxy. In yet a further aspect, $R^4$ is selected from (C1-C4 alkyl)aryl and (C1-C4 alkenyl)aryl, and substituted with 0 or 1 group selected from halogen, hydroxyl, amine, alkylamino, dialkylamino, C1-C4 alkyl, and C1-C4 alkoxy. In an even further aspect, $R^4$ is selected from (C1-C4 alkyl)aryl and (C1-C4 alkenyl)aryl, and monosubstituted with a group selected from halogen, hydroxyl, amine, alkylamino, dialkylamino, C1-C4 alkyl, and C1-C4 alkoxy. In a still further aspect, $R^4$ is selected from (C1-C4 alkyl)aryl and (C1-C4 alkenyl)aryl, and unsubstituted.

In a further aspect, $R^4$ is selected from —CH$_2$Ph and —CH=CHPh, and substituted with 0, 1, 2, or 3 groups independently selected from halogen, hydroxyl, amine, alkylamino, dialkylamino, C1-C4 alkyl, and C1-C4 alkoxy. In a still further aspect, $R^4$ is selected from —CH$_2$Ph and —CH=CHPh, and substituted with 0, 1, or 2 groups independently selected from halogen, hydroxyl, amine, alkylamino, dialkylamino, C1-C4 alkyl, and C1-C4 alkoxy. In yet a further aspect, $R^4$ is selected from —CH$_2$Ph and —CH=CHPh, and substituted with 0 or 1 group selected from halogen, hydroxyl, amine, alkylamino, dialkylamino, C1-C4 alkyl, and C1-C4 alkoxy. In an even further aspect, $R^4$ is selected from —CH$_2$Ph and —CH=CHPh, and monosubstituted with a group selected from halogen, hydroxyl, amine, alkylamino, dialkylamino, C1-C4 alkyl, and C1-C4 alkoxy. In a still further aspect, $R^4$ is selected from —CH$_2$Ph and —CH=CHPh, and unsubstituted.

In a further aspect, $R^4$ is selected from hydrogen, hydroxyl, amine, alkyl amine, dialkylamine, C1-C4 alkyl, C1-C4 alkoxy, —C(O)OH, —C(O)OR$^5$, —C(O)R$^5$, and —C(O)NHR$^6$. In a still further aspect, $R^4$ is selected from hydrogen, hydroxyl, amine, —C(O)OH, —C(O)OR$^5$, —C(O)R$^5$, and —C(O)NHR$^6$. In yet a further aspect, $R^4$ is selected from hydrogen, —C(O)OH, —C(O)OR$^5$, —C(O)R$^5$, and —C(O)NHR$^6$.

In a further aspect, $R^4$ is selected from hydrogen, hydroxyl, amine, alkyl amine, and dialkylamine. In a still further aspect, $R^4$ is selected from hydrogen, hydroxyl, amine, —NH(CH$_2$CH$_2$CH$_3$), —NH(CH(CH$_3$)$_2$), —NH(CH$_2$CH$_3$), —NH(CH$_3$), —N(CH$_2$CH$_2$CH$_3$)$_2$, —N(CH(CH$_3$)$_2$)$_2$, —N(CH$_2$CH$_3$)$_2$, —N(CH$_3$)$_2$, and —N(CH$_2$CH$_3$)(CH$_3$). In yet a further aspect, $R^4$ is selected from hydrogen, hydroxyl, amine, —NH(CH$_2$CH$_3$), —NH(CH$_3$), —N(CH$_2$CH$_3$)$_2$, —N(CH$_3$)$_2$, and —N(CH$_2$CH$_3$)(CH$_3$). In an even further aspect, $R^4$ is selected from hydrogen, hydroxyl, amine, —NH(CH$_3$), and —N(CH$_3$)$_2$.

In a further aspect, $R^4$ is selected from hydrogen, hydroxyl, amine, C1-C4 alkyl, and C1-C4 alkoxy. In a still further aspect, $R^4$ is selected from hydrogen, hydroxyl, amine, i-propyl, n-propyl, ethyl, methyl, i-propoxy, n-propyoxy, ethoxy, and methoxy. In yet a further aspect, $R^4$ is selected from hydrogen, hydroxyl, amine, ethyl, methyl, ethoxy, and methoxy. In an even further aspect, $R^4$ is selected from hydrogen, hydroxyl, amine, methyl, and methoxy.

In a further aspect, $R^4$ is selected from C1-C4 alkyl and C1-C4 alkoxy. In a still further aspect, $R^4$ is selected from i-propyl, n-propyl, ethyl, methyl, i-propoxy, n-propyoxy, ethoxy, and methoxy. In yet a further aspect, $R^4$ is selected from ethyl, methyl, ethoxy, and methoxy. In an even further aspect, $R^4$ is selected from methyl and methoxy.

In a further aspect, EWG and $R^4$, together with the intervening atoms, comprise a 5- or 6-membered cycloalkyl or a 5- or 6-membered heterocycloalkyl having 1 or 2 ring-members selected from O, S, and NR$^1$, substituted with 0, 1, 2, or 3 groups independently selected from hydroxyl, halogen, oxo, C1-C4 alkyl, C1-C4 alkoxy, —C(O)OH, —C(O)R$^5$, —C(O)OR$^5$, and —C(O)NHR$^6$. In a still further aspect, EWG and $R^4$, together with the intervening atoms, comprise a 5- or 6-membered cycloalkyl or a 5- or 6-membered heterocycloalkyl having 2 ring-members selected from O, S, and NR$^1$, substituted with 0, 1, 2, or 3 groups independently selected from hydroxyl, halogen, oxo, C1-C4 alkyl, C1-C4 alkoxy, —C(O)OH, —C(O)R$^5$, —C(O)OR$^5$, and —C(O)NHR$^6$. In yet a further aspect, EWG and $R^4$, together with the intervening atoms, comprise a 5- or 6-membered cycloalkyl or a 5- or 6-membered heterocycloalkyl having 1 ring-member selected from O, S, and NR$^1$, substituted with 0, 1, 2, or 3 groups independently selected from hydroxyl, halogen, oxo, C1-C4 alkyl, C1-C4 alkoxy, —C(O)OH, —C(O)R$^5$, —C(O)OR$^5$, and —C(O)NHR$^6$.

In a further aspect, EWG and $R^4$, together with the intervening atoms, comprise a 5- or 6-membered cycloalkyl or a 5- or 6-membered heterocycloalkyl having 1 or 2 ring-members selected from O, S, and NR$^1$, substituted with 0, 1, or 2 groups independently selected from hydroxyl, halogen, oxo, C1-C4 alkyl, C1-C4 alkoxy, —C(O)OH, —C(O)R$^5$, —C(O)OR$^5$, and —C(O)NHR$^6$. In a still further aspect, EWG and $R^4$, together with the intervening atoms, comprise a 5- or 6-membered cycloalkyl or a 5- or 6-membered heterocycloalkyl having 1 or 2 ring-members selected from O, S, and NR$^1$, substituted with 0, or 1 group selected from hydroxyl, halogen, oxo, C1-C4 alkyl, C1-C4 alkoxy, —C(O)OH, —C(O)R$^5$, —C(O)OR$^5$, and —C(O)NHR$^6$. In yet a further aspect, EWG and $R^4$, together with the intervening atoms, comprise a 5- or 6-membered cycloalkyl or a 5- or 6-membered heterocycloalkyl having 1 or 2 ring-members selected from O, S, and NR$^1$, monosubstituted with a group selected from hydroxyl, halogen, oxo, C1-C4 alkyl, C1-C4 alkoxy, —C(O)OH, —C(O)R$^5$, —C(O)OR$^5$, and —C(O)NHR$^6$. In an even further aspect, EWG and $R^4$, together with the intervening atoms, comprise a 5- or 6-membered cycloalkyl or a 5- or 6-membered heterocycloalkyl having 1 or 2 ring-members selected from O, S, and NR$^1$, and unsubstituted.

In a further aspect, EWG and $R^4$, together with the intervening atoms, comprise a 5- or 6-membered cycloalkyl substituted with 0, 1, 2, or 3 groups independently selected from hydroxyl, halogen, oxo, C1-C4 alkyl, C1-C4 alkoxy, —C(O)OH, —C(O)R$^5$, —C(O)OR$^5$, and —C(O)NHR$^6$. In a still further aspect, EWG and $R^4$, together with the intervening atoms, comprise a 5- or 6-membered cycloalkyl substituted with 0, 1, or 2 groups independently selected from hydroxyl, halogen, oxo, C1-C4 alkyl, C1-C4 alkoxy, —C(O)OH, —C(O)R$^5$, —C(O)OR$^5$, and —C(O)NHR$^6$. In yet a further aspect, EWG and R$^4$, together with the intervening atoms, comprise a 5- or 6-membered cycloalkyl substituted with 0 or 1 group selected from hydroxyl, halogen, oxo, C1-C4 alkyl, C1-C4 alkoxy, —C(O)OH, —C(O)R$^5$, —C(O)OR$^5$, and —C(O)NHR$^6$. In an even further aspect, EWG and R$^4$, together with the intervening atoms, comprise a 5- or 6-membered cycloalkyl monosubstituted with a group selected from hydroxyl, halogen, oxo, C1-C4 alkyl, C1-C4 alkoxy, —C(O)OH, —C(O)R$^5$, —C(O)OR$^5$, and —C(O)NHR$^6$. In a still further aspect, EWG and R$^4$, together with the intervening atoms, comprise an unsubstituted 5- or 6-membered cycloalkyl.

In a further aspect, EWG and R$^4$, together with the intervening atoms, comprise a 5-membered cycloalkyl substituted with 0, 1, 2, or 3 groups independently selected from hydroxyl, halogen, oxo, C1-C4 alkyl, C1-C4 alkoxy, —C(O)OH, —C(O)R$^5$, —C(O)OR$^5$, and —C(O)NHR$^6$. In a still further aspect, EWG and R$^4$, together with the intervening atoms, comprise a 5-membered cycloalkyl substituted with 0, 1, or 2 groups independently selected from hydroxyl, halogen, oxo, C1-C4 alkyl, C1-C4 alkoxy, —C(O)OH, —C(O)R$^5$, —C(O)OR$^5$, and —C(O)NHR$^6$. In yet a further aspect, EWG and R$^4$, together with the intervening atoms, comprise a 5-membered cycloalkyl substituted with 0 or 1 group selected from hydroxyl, halogen, oxo, C1-C4 alkyl, C1-C4 alkoxy, —C(O)OH, —C(O)R$^5$, —C(O)OR$^5$, and —C(O)NHR$^6$. In an even further aspect, EWG and R$^4$, together with the intervening atoms, comprise a 5-membered cycloalkyl monosubstituted with a group selected from hydroxyl, halogen, oxo, C1-C4 alkyl, C1-C4 alkoxy, —C(O)OH, —C(O)R$^5$, —C(O)OR$^5$, and —C(O)NHR$^6$. In a still further aspect, EWG and R$^4$, together with the intervening atoms, comprise an unsubstituted 5-membered cycloalkyl.

In a further aspect, EWG and R$^4$, together with the intervening atoms, comprise a 6-membered cycloalkyl substituted with 0, 1, 2, or 3 groups independently selected from hydroxyl, halogen, oxo, C1-C4 alkyl, C1-C4 alkoxy, —C(O)OH, —C(O)R$^5$, —C(O)OR$^5$, and —C(O)NHR$^6$. In a still further aspect, EWG and R$^4$, together with the intervening atoms, comprise a 6-membered cycloalkyl substituted with 0, 1, or 2 groups independently selected from hydroxyl, halogen, oxo, C1-C4 alkyl, C1-C4 alkoxy, —C(O)OH, —C(O)R$^5$, —C(O)OR$^5$, and —C(O)NHR$^6$. In yet a further aspect, EWG and R$^4$, together with the intervening atoms, comprise a 6-membered cycloalkyl substituted with 0 or 1 group selected from hydroxyl, halogen, oxo, C1-C4 alkyl, C1-C4 alkoxy, —C(O)OH, —C(O)R$^5$, —C(O)OR$^5$, and —C(O)NHR$^6$. In an even further aspect, EWG and R$^4$, together with the intervening atoms, comprise a 6-membered cycloalkyl monosubstituted with a group selected from hydroxyl, halogen, oxo, C1-C4 alkyl, C1-C4 alkoxy, —C(O)OH, —C(O)R$^5$, —C(O)OR$^5$, and —C(O)NHR$^6$. In a still further aspect, EWG and R$^4$, together with the intervening atoms, comprise an unsubstituted 6-membered cycloalkyl.

In a further aspect, EWG and R$^4$, together with the intervening atoms, comprise a 5- or 6-membered heterocycloalkyl having 1 or 2 ring-members selected from O, S, and NR$^1$, substituted with 0, 1, 2, or 3 groups independently selected from hydroxyl, halogen, oxo, C1-C4 alkyl, C1-C4 alkoxy, —C(O)OH, —C(O)R$^5$, —C(O)OR$^5$, and —C(O)NHR$^6$. In a still further aspect, EWG and R$^4$, together with the intervening atoms, comprise a 5- or 6-membered heterocycloalkyl having 1 or 2 ring-members selected from O, S, and NR$^1$, substituted with 0, 1, or 2 groups independently selected from hydroxyl, halogen, oxo, C1-C4 alkyl, C1-C4 alkoxy, —C(O)OH, —C(O)R$^5$, —C(O)OR$^5$, and —C(O)NHR$^6$. In yet a further aspect, EWG and R$^4$, together with the intervening atoms, comprise a 5- or 6-membered heterocycloalkyl having 1 or 2 ring-members selected from O, S, and NR$^1$, substituted with 0 or 1 group selected from hydroxyl, halogen, oxo, C1-C4 alkyl, C1-C4 alkoxy, —C(O)OH, —C(O)R$^5$, —C(O)OR$^5$, and —C(O)NHR$^6$. In an even further aspect, EWG and R$^4$, together with the intervening atoms, comprise a 5- or 6-membered heterocycloalkyl having 1 or 2 ring-members selected from O, S, and NR$^1$, monosubstituted with a group selected from hydroxyl, halogen, oxo, C1-C4 alkyl, C1-C4 alkoxy, —C(O)OH, —C(O)R$^5$, —C(O)OR$^5$, and —C(O)NHR$^6$. In a still further aspect, EWG and R$^4$, together with the intervening atoms, comprise an unsubstituted 5- or 6-membered heterocycloalkyl having 1 or 2 ring-members selected from O, S, and NR$^1$.

In a further aspect, EWG and R$^4$, together with the intervening atoms, comprise a 5-membered heterocycloalkyl having 1 or 2 ring-members selected from O, S, and NR$^1$, substituted with 0, 1, 2, or 3 groups independently selected from hydroxyl, halogen, oxo, C1-C4 alkyl, C1-C4 alkoxy, —C(O)OH, —C(O)R$^5$, —C(O)OR$^5$, and —C(O)NHR$^6$. In a still further aspect, EWG and R$^4$, together with the intervening atoms, comprise a 5-membered heterocycloalkyl having 1 or 2 ring-members selected from O, S, and NR$^1$, substituted with 0, 1, or 2 groups independently selected from hydroxyl, halogen, oxo, C1-C4 alkyl, C1-C4 alkoxy, —C(O)OH, —C(O)R$^5$, —C(O)OR$^5$, and —C(O)NHR$^6$. In yet a further aspect, EWG and R$^4$, together with the intervening atoms, comprise a 5-membered heterocycloalkyl having 1 or 2 ring-members selected from O, S, and NR$^1$, substituted with 0 or 1 group selected from hydroxyl, halogen, oxo, C1-C4 alkyl, C1-C4 alkoxy, —C(O)OH, —C(O)R$^5$, —C(O)OR$^5$, and —C(O)NHR$^6$. In an even further aspect, EWG and R$^4$, together with the intervening atoms, comprise a 5-membered heterocycloalkyl having 1 or 2 ring-members selected from O, S, and NR$^1$, monosubstituted with a group selected from hydroxyl, halogen, oxo, C1-C4 alkyl, C1-C4 alkoxy, —C(O)OH, —C(O)R$^5$, —C(O)OR$^5$, and —C(O)NHR$^6$. In a still further aspect, EWG and R$^4$, together with the intervening atoms, comprise an unsubstituted 5-membered heterocycloalkyl having 1 or 2 ring-members selected from O, S, and NR$^1$.

In a further aspect, EWG and R$^4$, together with the intervening atoms, comprise a 5-membered heterocycloalkyl having 2 ring-members selected from O, S, and NR$^1$, substituted with 0, 1, 2, or 3 groups independently selected from hydroxyl, halogen, oxo, C1-C4 alkyl, C1-C4 alkoxy, —C(O)OH, —C(O)R$^5$, —C(O)OR$^5$, and —C(O)NHR$^6$. In a still further aspect, In a further aspect, EWG and R$^4$, together with the intervening atoms, comprise a 5-membered heterocycloalkyl having 1 ring-member selected from O, S, and NR$^1$, substituted with 0, 1, 2, or 3 groups independently selected from hydroxyl, halogen, oxo, C1-C4 alkyl, C1-C4 alkoxy, —C(O)OH, —C(O)R$^5$, —C(O)OR$^5$, and —C(O)NHR$^6$. In yet a further aspect, EWG and R$^4$, together with the intervening atoms, comprise a 5-membered heterocycloalkyl having 1 O ring-member, substituted with 0, 1, 2, or 3 groups independently selected from hydroxyl, halogen, oxo, C1-C4 alkyl, C1-C4 alkoxy, —C(O)OH, —C(O)R$^5$, —C(O)OR$^5$, and —C(O)NHR$^6$. In an even further aspect, EWG and R$^4$, together with the intervening atoms, comprise a 5-membered heterocycloalkyl having 1 S ring-member, substituted with 0, 1, 2, or 3 groups independently selected from hydroxyl, halogen, oxo, C1-C4 alkyl, C1-C4 alkoxy, —C(O)OH, —C(O)$R^5$, —C(O)O$R^5$, and —C(O)NH$R^6$. In a still further aspect, EWG and $R^4$, together with the intervening atoms, comprise a 5-membered heterocycloalkyl having 1 N$R^1$ ring-member, substituted with 0, 1, 2, or 3 groups independently selected from hydroxyl, halogen, oxo, C1-C4 alkyl, C1-C4 alkoxy, —C(O)OH, —C(O)$R^5$, —C(O)O$R^5$, and —C(O)NH$R^6$.

In a further aspect, EWG and $R^4$, together with the intervening atoms, comprise a 6-membered heterocycloalkyl having 1 or 2 ring-members selected from O, S, and N$R^1$, substituted with 0, 1, 2, or 3 groups independently selected from hydroxyl, halogen, oxo, C1-C4 alkyl, C1-C4 alkoxy, —C(O)OH, —C(O)$R^5$, —C(O)O$R^5$, and —C(O)NH$R^6$. In a still further aspect, EWG and $R^4$, together with the intervening atoms, comprise a 6-membered heterocycloalkyl having 1 or 2 ring-members selected from O, S, and N$R^1$, substituted with 0, 1, or 2 groups independently selected from hydroxyl, halogen, oxo, C1-C4 alkyl, C1-C4 alkoxy, —C(O)OH, —C(O)$R^5$, —C(O)O$R^5$, and —C(O)NH$R^6$. In yet a further aspect, EWG and $R^4$, together with the intervening atoms, comprise a 6-membered heterocycloalkyl having 1 or 2 ring-members selected from O, S, and N$R^1$, substituted with 0 or 1 group selected from hydroxyl, halogen, oxo, C1-C4 alkyl, C1-C4 alkoxy, —C(O)OH, —C(O)$R^5$, —C(O)O$R^5$, and —C(O)NH$R^6$. In an even further aspect, EWG and $R^4$, together with the intervening atoms, comprise a 6-membered heterocycloalkyl having 1 or 2 ring-members selected from O, S, and N$R^1$, monosubstituted with a group selected from hydroxyl, halogen, oxo, C1-C4 alkyl, C1-C4 alkoxy, —C(O)OH, —C(O)$R^5$, —C(O)O$R^5$, and —C(O)NH$R^6$. In a still further aspect, EWG and $R^4$, together with the intervening atoms, comprise an unsubstituted 6-membered heterocycloalkyl having 1 or 2 ring-members selected from O, S, and N$R^1$.

e. $R^5$ Groups

In one aspect, each $R^5$ is independently selected from hydrogen and C1-C4 alkyl. In a further aspect, each $R^5$ is hydrogen.

In a further aspect, each $R^5$ is independently selected from hydrogen, methyl, ethyl, n-propyl, i-propyl, n-butyl, i-butyl, s-butyl, and t-butyl. In a still further aspect, each $R^5$ is independently selected from hydrogen, methyl, ethyl, n-propyl, and i-propyl. In yet a further aspect, each $R^5$ is independently selected from hydrogen, methyl, and ethyl. In an even further aspect, each $R^5$ is independently selected from hydrogen and ethyl. In a still further aspect, each $R^5$ is independently selected from hydrogen and methyl.

f. $R^6$ Groups

In one aspect, each $R^6$ is independently selected from hydrogen, C1-C4 alkyl, and aryl substituted with 0, 1, 2, or 3 groups independently selected from halogen, hydroxyl, amine, alkylamino, dialkylamino, C1-C4 alkyl, and C1-C4 alkoxy. In a further aspect, each $R^6$ is hydrogen.

In a further aspect, each $R^6$ is independently selected from hydrogen and C1-C4 alkyl. In a still further aspect, each $R^6$ is independently selected from hydrogen, methyl, ethyl, n-propyl, and i-propyl. In yet a further aspect, each $R^6$ is independently selected from hydrogen, methyl, and ethyl. In an even further aspect, each $R^6$ is independently selected from hydrogen and ethyl. In a still further aspect, each $R^6$ is independently selected from hydrogen and methyl.

In a further aspect, each $R^6$ is aryl substituted with 0, 1, 2, or 3 groups independently selected from halogen, hydroxyl, amine, alkylamino, dialkylamino, C1-C4 alkyl, and C1-C4 alkoxy. In a still further aspect, each $R^6$ is aryl substituted with 0, 1, or 2 groups independently selected from halogen, hydroxyl, amine, alkylamino, dialkylamino, C1-C4 alkyl, and C1-C4 alkoxy. In yet a further aspect, each $R^6$ is aryl substituted with 0 or 1 group selected from halogen, hydroxyl, amine, alkylamino, dialkylamino, C1-C4 alkyl, and C1-C4 alkoxy. In a still further aspect, each $R^6$ is aryl monosubstituted with a group selected from halogen, hydroxyl, amine, alkylamino, dialkylamino, C1-C4 alkyl, and C1-C4 alkoxy. In an even further aspect, each $R^6$ is unsubstituted aryl.

g. $R^7$ Groups

In one aspect, $R^7$ is selected from hydrogen, hydroxyl, amine, alkylamine, dialkylamine, C1-C4 alkyl, and C1-C4 alkoxy. In a further aspect, $R^7$ is hydrogen.

In one aspect, $R^7$ and $R^4$, together with the intervening atoms, comprise a 5- or 6-membered cycloalkyl or a 5- or 6-membered heterocycloalkyl having 1 or 2 ring-members selected from O, S, and N$R^1$, substituted with 0, 1, 2, or 3 groups independently selected from hydroxyl, halogen, oxo, C1-C4 alkyl, C1-C4 alkoxy, —C(O)OH, —C(O)$R^5$, —C(O)O$R^5$, and —C(O)NH$R^6$.

In a further aspect, $R^7$ is selected from hydrogen, hydroxyl, amine, C1-C4 alkyl, and C1-C4 alkoxy. In a still further aspect, $R^7$ is selected from hydrogen, hydroxyl, amine, i-propyl, n-propyl, ethyl, methyl, i-propoxy, n-propyoxy, ethoxy, and methoxy. In yet a further aspect, $R^7$ is selected from hydrogen, hydroxyl, amine, ethyl, methyl, ethoxy, and methoxy. In an even further aspect, $R^7$ is selected from hydrogen, hydroxyl, amine, methyl, and methoxy.

In a further aspect, $R^7$ is selected from C1-C4 alkyl and C1-C4 alkoxy. In a still further aspect, $R^7$ is selected from i-propyl, n-propyl, ethyl, methyl, i-propoxy, n-propyoxy, ethoxy, and methoxy. In yet a further aspect, $R^7$ is selected from ethyl, methyl, ethoxy, and methoxy. In an even further aspect, $R^7$ is selected from methyl and methoxy.

In a further aspect, $R^7$ is selected from hydrogen, hydroxyl, amine, alkylamine, and dialkylamine. In a still further aspect, In a still further aspect, $R^7$ is selected from hydrogen, hydroxyl, amine, —NH(CH$_2$CH$_2$CH$_3$), —NH(CH(CH$_3$)$_2$), —NH(CH$_2$CH$_3$), —NH(CH$_3$), —N(CH$_2$CH$_2$CH$_3$)$_2$, —N(CH(CH$_3$)$_2$)$_2$, —N(CH$_2$CH$_3$)$_2$, —N(CH$_3$)$_2$, and —N(CH$_2$CH$_3$)(CH$_3$). In yet a further aspect, $R^7$ is selected from hydrogen, hydroxyl, amine, —NH(CH$_2$CH$_3$), —NH(CH$_3$), —N(CH$_2$CH$_3$)$_2$, —N(CH$_3$)$_2$, and —N(CH$_2$CH$_3$)(CH$_3$). In an even further aspect, $R^7$ is selected from hydrogen, hydroxyl, amine, —NH(CH$_3$), and —N(CH$_3$)$_2$.

In a further aspect, $R^7$ is selected from alkylamine and dialkylamine. In a still further aspect, In a still further aspect, $R^7$ is selected from —NH(CH$_2$CH$_2$CH$_3$), —NH(CH(CH$_3$)$_2$), —NH(CH$_2$CH$_3$), —NH(CH$_3$), —N(CH$_2$CH$_2$CH$_3$)$_2$, —N(CH(CH$_3$)$_2$)$_2$, —N(CH$_2$CH$_3$)$_2$, —N(CH$_3$)$_2$, and —N(CH$_2$CH$_3$)(CH$_3$). In yet a further aspect, $R^7$ is selected from —NH(CH$_2$CH$_3$), —NH(CH$_3$), —N(CH$_2$CH$_3$)$_2$, —N(CH$_3$)$_2$, and —N(CH$_2$CH$_3$)(CH$_3$). In an even further aspect, $R^7$ is selected from —NH(CH$_3$) and —N(CH$_3$)$_2$.

In a further aspect, $R^7$ and $R^4$, together with the intervening atoms, comprise a 5- or 6-membered cycloalkyl or a 5- or 6-membered heterocycloalkyl having 1 or 2 ring-members selected from O, S, and N$R^1$, substituted with 0, 1, or 2 groups independently selected from hydroxyl, halogen, oxo, C1-C4 alkyl, C1-C4 alkoxy, —C(O)OH, —C(O)$R^5$, —C(O)O$R^5$, and —C(O)NH$R^6$. In a still further aspect, $R^7$ and $R^4$, together with the intervening atoms, comprise a 5- or 6-membered cycloalkyl or a 5- or 6-membered heterocycloalkyl having 1 or 2 ring-members selected from O, S, and NR$^1$, substituted with 0 or 1 group selected from hydroxyl, halogen, oxo, C1-C4 alkyl, C1-C4 alkoxy, —C(O)OH, —C(O)R$^5$, —C(O)OR$^5$, and —C(O)NHR$^6$. In yet a further aspect, R$^7$ and R$^4$, together with the intervening atoms, comprise a 5- or 6-membered cycloalkyl or a 5- or 6-membered heterocycloalkyl having 1 or 2 ring-members selected from O, S, and NR$^1$, monosubstituted with a group selected from hydroxyl, halogen, oxo, C1-C4 alkyl, C1-C4 alkoxy, —C(O)OH, —C(O)R$^5$, —C(O)OR$^5$, and —C(O)NHR$^6$. In an even further aspect, R$^7$ and R$^4$, together with the intervening atoms, comprise a 5- or 6-membered cycloalkyl or a 5- or 6-membered heterocycloalkyl having 1 or 2 ring-members selected from O, S, and NR$^1$, and unsubstituted.

In a further aspect, R$^7$ and R$^4$, together with the intervening atoms, comprise a 5- or 6-membered cycloalkyl substituted with 0, 1, 2, or 3 groups independently selected from hydroxyl, halogen, oxo, C1-C4 alkyl, C1-C4 alkoxy, —C(O)OH, —C(O)R$^5$, —C(O)OR$^5$, and —C(O)NHR$^6$. In a still further aspect, R$^7$ and R$^4$, together with the intervening atoms, comprise a 5- or 6-membered cycloalkyl substituted with 0, 1, or 2 groups independently selected from hydroxyl, halogen, oxo, C1-C4 alkyl, C1-C4 alkoxy, —C(O)OH, —C(O)R$^5$, —C(O)OR$^5$, and —C(O)NHR$^6$. In yet a further aspect, R$^7$ and R$^4$, together with the intervening atoms, comprise a 5- or 6-membered cycloalkyl substituted with 0 or 1 group selected from hydroxyl, halogen, oxo, C1-C4 alkyl, C1-C4 alkoxy, —C(O)OH, —C(O)R$^5$, —C(O)OR$^5$, and —C(O)NHR$^6$. In an even further aspect, R$^7$ and R$^4$, together with the intervening atoms, comprise a 5- or 6-membered cycloalkyl monosubstituted with a group selected from hydroxyl, halogen, oxo, C1-C4 alkyl, C1-C4 alkoxy, —C(O)OH, —C(O)R$^5$, —C(O)OR$^5$, and —C(O)NHR$^6$. In a still further aspect, R$^7$ and R$^4$, together with the intervening atoms, comprise an unsubstituted 5- or 6-membered cycloalkyl.

In a further aspect, R$^7$ and R$^4$, together with the intervening atoms, comprise a 5-membered cycloalkyl substituted with 0, 1, 2, or 3 groups independently selected from hydroxyl, halogen, oxo, C1-C4 alkyl, C1-C4 alkoxy, —C(O)OH, —C(O)R$^5$, —C(O)OR$^5$, and —C(O)NHR$^6$. In a still further aspect, R$^7$ and R$^4$, together with the intervening atoms, comprise a 5-membered cycloalkyl substituted with 0, 1, or 2 groups independently selected from hydroxyl, halogen, oxo, C1-C4 alkyl, C1-C4 alkoxy, —C(O)OH, —C(O)R$^5$, —C(O)OR$^5$, and —C(O)NHR$^6$. In yet a further aspect, R$^7$ and R$^4$, together with the intervening atoms, comprise a 5-membered cycloalkyl substituted with 0 or 1 group selected from hydroxyl, halogen, oxo, C1-C4 alkyl, C1-C4 alkoxy, —C(O)OH, —C(O)R$^5$, —C(O)OR$^5$, and —C(O)NHR$^6$. In an even further aspect, R$^7$ and R$^4$, together with the intervening atoms, comprise a 5-membered cycloalkyl monosubstituted with a group selected from hydroxyl, halogen, oxo, C1-C4 alkyl, C1-C4 alkoxy, —C(O)OH, —C(O)R$^5$, —C(O)OR$^5$, and —C(O)NHR$^6$. In a still further aspect, R$^7$ and R$^4$, together with the intervening atoms, comprise an unsubstituted 5-membered cycloalkyl.

In a further aspect, R$^7$ and R$^4$, together with the intervening atoms, comprise a 6-membered cycloalkyl substituted with 0, 1, 2, or 3 groups independently selected from hydroxyl, halogen, oxo, C1-C4 alkyl, C1-C4 alkoxy, —C(O)OH, —C(O)R$^5$, —C(O)OR$^5$, and —C(O)NHR$^6$. In a still further aspect, R$^7$ and R$^4$, together with the intervening atoms, comprise a 6-membered cycloalkyl substituted with 0, 1, or 2 groups independently selected from hydroxyl, halogen, oxo, C1-C4 alkyl, C1-C4 alkoxy, —C(O)OH, —C(O)R$^5$, —C(O)OR$^5$, and —C(O)NHR$^6$. In yet a further aspect, R$^7$ and R$^4$, together with the intervening atoms, comprise a 6-membered cycloalkyl substituted with 0 or 1 group selected from hydroxyl, halogen, oxo, C1-C4 alkyl, C1-C4 alkoxy, —C(O)OH, —C(O)R$^5$, —C(O)OR$^5$, and —C(O)NHR$^6$. In an even further aspect, R$^7$ and R$^4$, together with the intervening atoms, comprise a 6-membered cycloalkyl monosubstituted with a group selected from hydroxyl, halogen, oxo, C1-C4 alkyl, C1-C4 alkoxy, —C(O)OH, —C(O)R$^5$, —C(O)OR$^5$, and —C(O)NHR$^6$. In a still further aspect, R$^7$ and R$^4$, together with the intervening atoms, comprise an unsubstituted 6-membered cycloalkyl.

In a further aspect, R$^7$ and R$^4$, together with the intervening atoms, comprise a 5- or 6-membered heterocycloalkyl having 1 or 2 ring-members selected from O, S, and NR$^1$, substituted with 0, 1, 2, or 3 groups independently selected from hydroxyl, halogen, oxo, C1-C4 alkyl, C1-C4 alkoxy, —C(O)OH, —C(O)R$^5$, —C(O)OR$^5$, and —C(O)NHR$^6$. In a still further aspect, R$^7$ and R$^4$, together with the intervening atoms, comprise a 5- or 6-membered heterocycloalkyl having 2 ring-members selected from O, S, and NR$^1$, substituted with 0, 1, 2, or 3 groups independently selected from hydroxyl, halogen, oxo, C1-C4 alkyl, C1-C4 alkoxy, —C(O)OH, —C(O)R$^5$, —C(O)OR$^5$, and —C(O)NHR$^6$. In yet a further aspect, R$^7$ and R$^4$, together with the intervening atoms, comprise a 5- or 6-membered heterocycloalkyl having 1 ring-member selected from O, S, and NR$^1$, substituted with 0, 1, 2, or 3 groups independently selected from hydroxyl, halogen, oxo, C1-C4 alkyl, C1-C4 alkoxy, —C(O)OH, —C(O)R$^5$, —C(O)OR$^5$, and —C(O)NHR$^6$.

In a further aspect, R$^7$ and R$^4$, together with the intervening atoms, comprise a 5- or 6-membered heterocycloalkyl having 1 or 2 ring-members selected from O, S, and NR$^1$, substituted with 0, 1, or 2 groups independently selected from hydroxyl, halogen, oxo, C1-C4 alkyl, C1-C4 alkoxy, —C(O)OH, —C(O)R$^5$, —C(O)OR$^5$, and —C(O)NHR$^6$. In a still further aspect, R$^7$ and R$^4$, together with the intervening atoms, comprise a 5- or 6-membered heterocycloalkyl having 1 or 2 ring-members selected from O, S, and NR$^1$, substituted with 0 or 1 group selected from hydroxyl, halogen, oxo, C1-C4 alkyl, C1-C4 alkoxy, —C(O)OH, —C(O)R$^5$, —C(O)OR$^5$, and —C(O)NHR$^6$. In yet a further aspect, R$^7$ and R$^4$, together with the intervening atoms, comprise a 5- or 6-membered heterocycloalkyl having 1 or 2 ring-members selected from O, S, and NR$^1$, monosubstituted with a group selected from hydroxyl, halogen, oxo, C1-C4 alkyl, C1-C4 alkoxy, —C(O)OH, —C(O)R$^5$, —C(O)OR$^5$, and —C(O)NHR$^6$. In an even further aspect, R$^7$ and R$^4$, together with the intervening atoms, comprise an unsubstituted 5- or 6-membered heterocycloalkyl having 1 or 2 ring-members selected from O, S, and NR$^1$.

In a further aspect, R$^7$ and R$^4$, together with the intervening atoms, comprise a 5-membered heterocycloalkyl having 1 or 2 ring-members selected from O, S, and NR$^1$, substituted with 0, 1, or 2 groups independently selected from hydroxyl, halogen, oxo, C1-C4 alkyl, C1-C4 alkoxy, —C(O)OH, —C(O)R$^5$, —C(O)OR$^5$, and —C(O)NHR$^6$. In a still further aspect, R$^7$ and R$^4$, together with the intervening atoms, comprise a 5-membered heterocycloalkyl having 1 or 2 ring-members selected from O, S, and NR$^1$, substituted with 0 or 1 group selected from hydroxyl, halogen, oxo, C1-C4 alkyl, C1-C4 alkoxy, —C(O)OH, —C(O)R$^5$, —C(O)OR$^5$, and —C(O)NHR$^6$. In yet a further aspect, R$^7$ and R$^4$, together with the intervening atoms, comprise a 5-membered heterocycloalkyl having 1 or 2 ring-members selected from O, S, and NR$^1$, monosubstituted with a group selected from hydroxyl, halogen, oxo, C1-C4 alkyl, C1-C4 alkoxy, —C(O)OH, —C(O)R$^5$, —C(O)OR$^5$, and —C(O)NHR$^6$. In an even further aspect, $R^7$ and $R^4$, together with the intervening atoms, comprise an unsubstituted 5-membered heterocycloalkyl having 1 or 2 ring-members selected from O, S, and $NR^1$.

In a further aspect, $R^7$ and $R^4$, together with the intervening atoms, comprise a 6-membered heterocycloalkyl having 1 or 2 ring-members selected from O, S, and $NR^1$, substituted with 0, 1, or 2 groups independently selected from hydroxyl, halogen, oxo, C1-C4 alkyl, C1-C4 alkoxy, —C(O)OH, —C(O)$R^5$, —C(O)O$R^5$, and —C(O)NH$R^6$. In a still further aspect, $R^7$ and $R^4$, together with the intervening atoms, comprise a 6-membered heterocycloalkyl having 1 or 2 ring-members selected from O, S, and $NR^1$, substituted with 0 or 1 group selected from hydroxyl, halogen, oxo, C1-C4 alkyl, C1-C4 alkoxy, —C(O)OH, —C(O)$R^5$, —C(O)O$R^5$, and —C(O)NH$R^6$. In yet a further aspect, $R^7$ and $R^4$, together with the intervening atoms, comprise a 6-membered heterocycloalkyl having 1 or 2 ring-members selected from O, S, and $NR^1$, monosubstituted with a group selected from hydroxyl, halogen, oxo, C1-C4 alkyl, C1-C4 alkoxy, —C(O)OH, —C(O)$R^5$, —C(O)O$R^5$, and —C(O)NH$R^6$. In an even further aspect, $R^7$ and $R^4$, together with the intervening atoms, comprise an unsubstituted 6-membered heterocycloalkyl having 1 or 2 ring-members selected from O, S, and $NR^1$.

h. $Cy^1$ and $Cy^2$ Groups

In one aspect, each of $Cy^1$ and $Cy^2$ is independently selected from: aryl substituted with 0, 1, 2, or 3 groups independently selected from halogen, hydroxyl, amine, alkylamino, dialkylamino, C1-C4 alkyl, and C1-C4 alkoxy; a 5- or 6-membered heteroaryl having 1, 2, or 3 ring-members selected from O, S, and $NR^1$ and substituted with 0, 1, 2, or 3 groups independently selected from halogen, hydroxyl, amine, alkylamino, dialkylamino, C1-C4 alkyl, and C1-C4 alkoxy; a 5- or 6-membered cycloalkyl substituted with 0, 1, 2, or 3 groups independently selected from halogen, hydroxyl, amine, alkylamino, dialkylamino, C1-C4 alkyl, and C1-C4 alkoxy; and a 5- or 6-membered heterocycloalkyl having 1, 2, or 3 ring-members selected from O, S, and $NR^1$ and substituted with 0, 1, 2, or 3 groups independently selected from halogen, hydroxyl, amine, alkylamino, dialkylamino, C1-C4 alkyl, and C1-C4 alkoxy.

In a further aspect, each of $Cy^1$ and $Cy^2$ is independently selected from: aryl substituted with 0, 1, 2, or 3 groups independently selected from halogen, hydroxyl, amine, alkylamino, dialkylamino, C1-C4 alkyl, and C1-C4 alkoxy; and a 5- or 6-membered heteroaryl having 1, 2, or 3 ring-members selected from O, S, and $NR^1$ and substituted with 0, 1, 2, or 3 groups independently selected from halogen, hydroxyl, amine, alkylamino, dialkylamino, C1-C4 alkyl, and C1-C4 alkoxy.

In a further aspect, each of $Cy^1$ and $Cy^2$ is aryl substituted with 0, 1, 2, or 3 groups independently selected from halogen, hydroxyl, amine, alkylamino, dialkylamino, C1-C4 alkyl, and C1-C4 alkoxy. In a still further aspect, each of $Cy^1$ and $Cy^2$ is aryl substituted with 0, 1, or 2 groups independently selected from halogen, hydroxyl, amine, alkylamino, dialkylamino, C1-C4 alkyl, and C1-C4 alkoxy. In yet a further aspect, each of $Cy^1$ and $Cy^2$ is aryl substituted with 0 or 1 group selected from halogen, hydroxyl, amine, alkylamino, dialkylamino, C1-C4 alkyl, and C1-C4 alkoxy. In an even further aspect, each of $Cy^1$ and $Cy^2$ is aryl monosubstituted with a group selected from halogen, hydroxyl, amine, alkylamino, dialkylamino, C1-C4 alkyl, and C1-C4 alkoxy. In a still further aspect, each of $Cy^1$ and $Cy^2$ is unsubstituted aryl.

In a further aspect, each of $Cy^1$ and $Cy^2$ is phenyl. In a still further aspect, each of $Cy^1$ and $Cy^2$ is phenyl substituted with 0, 1, 2, or 3 groups independently selected from halogen, hydroxyl, amine, alkylamino, dialkylamino, C1-C4 alkyl, and C1-C4 alkoxy. In yet a further aspect, each of $Cy^1$ and $Cy^2$ is phenyl substituted with 0, 1, or 2 groups independently selected from halogen, hydroxyl, amine, alkylamino, dialkylamino, C1-C4 alkyl, and C1-C4 alkoxy. In an even further aspect, each of $Cy^1$ and $Cy^2$ is phenyl substituted with 0 or 1 group selected from halogen, hydroxyl, amine, alkylamino, dialkylamino, C1-C4 alkyl, and C1-C4 alkoxy. In a still further aspect, each of $Cy^1$ and $Cy^2$ is phenyl monosubstituted with a group selected from halogen, hydroxyl, amine, alkylamino, dialkylamino, C1-C4 alkyl, and C1-C4 alkoxy. In yet a further aspect, each of $Cy^1$ and $Cy^2$ is unsubstituted phenyl.

In a further aspect, each of $Cy^1$ and $Cy^2$ is a 5- or 6-membered heteroaryl having 1, 2, or 3 ring-members selected from O, S, and $NR^1$ and substituted with 0, 1, 2, or 3 groups independently selected from halogen, hydroxyl, amine, alkylamino, dialkylamino, C1-C4 alkyl, and C1-C4 alkoxy. In a still further aspect, each of $Cy^1$ and $Cy^2$ is a 5- or 6-membered heteroaryl having 1 or 2 ring-members selected from O, S, and $NR^1$ and substituted with 0, 1, 2, or 3 groups independently selected from halogen, hydroxyl, amine, alkylamino, dialkylamino, C1-C4 alkyl, and C1-C4 alkoxy. In yet a further aspect, each of $Cy^1$ and $Cy^2$ is a 5- or 6-membered heteroaryl having 1 ring-member selected from O, S, and $NR^1$ and substituted with 0, 1, 2, or 3 groups independently selected from halogen, hydroxyl, amine, alkylamino, dialkylamino, C1-C4 alkyl, and C1-C4 alkoxy.

In a further aspect, each of $Cy^1$ and $Cy^2$ is a 5- or 6-membered heteroaryl having 1, 2, or 3 ring-members selected from O, S, and $NR^1$ and substituted with 0, 1, or 2 groups independently selected from halogen, hydroxyl, amine, alkylamino, dialkylamino, C1-C4 alkyl, and C1-C4 alkoxy. In a still further aspect, each of $Cy^1$ and $Cy^2$ is a 5- or 6-membered heteroaryl having 1, 2, or 3 ring-members selected from O, S, and $NR^1$ and substituted with 0 or 1 group selected from halogen, hydroxyl, amine, alkylamino, dialkylamino, C1-C4 alkyl, and C1-C4 alkoxy. In yet a further aspect, each of $Cy^1$ and $Cy^2$ is a 5- or 6-membered heteroaryl having 1, 2, or 3 ring-members selected from O, S, and $NR^1$ and monosubstituted with a group selected from halogen, hydroxyl, amine, alkylamino, dialkylamino, C1-C4 alkyl, and C1-C4 alkoxy. In an even further aspect, each of $Cy^1$ and $Cy^2$ is a 5- or 6-membered heteroaryl having 1, 2, or 3 ring-members selected from O, S, and $NR^1$ and unsubstituted.

In a further aspect, each of $Cy^1$ and $Cy^2$ is a 5-membered heteroaryl having 1, 2, or 3 ring-members selected from O, S, and $NR^1$ and substituted with 0, 1, or 2 groups independently selected from halogen, hydroxyl, amine, alkylamino, dialkylamino, C1-C4 alkyl, and C1-C4 alkoxy. In a still further aspect, each of $Cy^1$ and $Cy^2$ is a 5-membered heteroaryl having 1, 2, or 3 ring-members selected from O, S, and $NR^1$ and substituted with 0 or 1 group selected from halogen, hydroxyl, amine, alkylamino, dialkylamino, C1-C4 alkyl, and C1-C4 alkoxy. In yet a further aspect, each of $Cy^1$ and $Cy^2$ is a 5-membered heteroaryl having 1, 2, or 3 ring-members selected from O, S, and $NR^1$ and monosubstituted with a group selected from halogen, hydroxyl, amine, alkylamino, dialkylamino, C1-C4 alkyl, and C1-C4 alkoxy. In an even further aspect, each of $Cy^1$ and $Cy^2$ is a 5-membered heteroaryl having 1, 2, or 3 ring-members selected from O, S, and $NR^1$ and unsubstituted.

In a further aspect, each of $Cy^1$ and $Cy^2$ is a 6-membered heteroaryl having 1, 2, or 3 ring-members selected from O, S, and $NR^1$ and substituted with 0, 1, or 2 groups independently selected from halogen, hydroxyl, amine, alkylamino, dialkylamino, C1-C4 alkyl, and C1-C4 alkoxy. In a still further aspect, each of $Cy^1$ and $Cy^2$ is a 6-membered heteroaryl having 1, 2, or 3 ring-members selected from O, S, and $NR^1$ and substituted with 0 or 1 group selected from halogen, hydroxyl, amine, alkylamino, dialkylamino, C1-C4 alkyl, and C1-C4 alkoxy. In yet a further aspect, each of $Cy^1$ and $Cy^2$ is a 6-membered heteroaryl having 1, 2, or 3 ring-members selected from O, S, and $NR^1$ and monosubstituted with a group selected from halogen, hydroxyl, amine, alkylamino, dialkylamino, C1-C4 alkyl, and C1-C4 alkoxy. In an even further aspect, each of $Cy^1$ and $Cy^2$ is a 5-membered heteroaryl having 1, 2, or 3 ring-members selected from O, S, and $NR^1$ and unsubstituted.

In a further aspect, each of $Cy^1$ and $Cy^2$ is independently selected from: a 5- or 6-membered cycloalkyl substituted with 0, 1, 2, or 3 groups independently selected from halogen, hydroxyl, amine, alkylamino, dialkylamino, C1-C4 alkyl, and C1-C4 alkoxy; and a 5- or 6-membered heterocycloalkyl having 1, 2, or 3 ring-members selected from O, S, and $NR^1$ and substituted with 0, 1, 2, or 3 groups independently selected from halogen, hydroxyl, amine, alkylamino, dialkylamino, C1-C4 alkyl, and C1-C4 alkoxy.

In a further aspect, each of $Cy^1$ and $Cy^2$ is a 5- or 6-membered cycloalkyl substituted with 0, 1, 2, or 3 groups independently selected from halogen, hydroxyl, amine, alkylamino, dialkylamino, C1-C4 alkyl, and C1-C4 alkoxy. In a still further aspect, each of $Cy^1$ and $Cy^2$ is a 5- or 6-membered cycloalkyl substituted with 0, 1, or 2 groups independently selected from halogen, hydroxyl, amine, alkylamino, dialkylamino, C1-C4 alkyl, and C1-C4 alkoxy. In yet a further aspect, each of $Cy^1$ and $Cy^2$ is a 5- or 6-membered cycloalkyl substituted with 0 or 1 group selected from halogen, hydroxyl, amine, alkylamino, dialkylamino, C1-C4 alkyl, and C1-C4 alkoxy. In an even further aspect, each of $Cy^1$ and $Cy^2$ is a 5- or 6-membered cycloalkyl monosubstituted with a group selected from halogen, hydroxyl, amine, alkylamino, dialkylamino, C1-C4 alkyl, and C1-C4 alkoxy. In a still further aspect, each of $Cy^1$ and $Cy^2$ is an unsubstituted 5- or 6-membered cycloalkyl.

In a further aspect, each of $Cy^1$ and $Cy^2$ is a 5-membered cycloalkyl substituted with 0, 1, 2, or 3 groups independently selected from halogen, hydroxyl, amine, alkylamino, dialkylamino, C1-C4 alkyl, and C1-C4 alkoxy. In a still further aspect, each of $Cy^1$ and $Cy^2$ is a 5-membered cycloalkyl substituted with 0, 1, or 2 groups independently selected from halogen, hydroxyl, amine, alkylamino, dialkylamino, C1-C4 alkyl, and C1-C4 alkoxy. In yet a further aspect, each of $Cy^1$ and $Cy^2$ is a 5-membered cycloalkyl substituted with 0 or 1 group selected from halogen, hydroxyl, amine, alkylamino, dialkylamino, C1-C4 alkyl, and C1-C4 alkoxy. In an even further aspect, each of $Cy^1$ and $Cy^2$ is a 5-membered cycloalkyl monosubstituted with a group selected from halogen, hydroxyl, amine, alkylamino, dialkylamino, C1-C4 alkyl, and C1-C4 alkoxy. In a still further aspect, each of $Cy^1$ and $Cy^2$ is an unsubstituted 5-membered cycloalkyl.

In a further aspect, each of $Cy^1$ and $Cy^2$ is a 6-membered cycloalkyl substituted with 0, 1, 2, or 3 groups independently selected from halogen, hydroxyl, amine, alkylamino, dialkylamino, C1-C4 alkyl, and C1-C4 alkoxy. In a still further aspect, each of $Cy^1$ and $Cy^2$ is a 6-membered cycloalkyl substituted with 0, 1, or 2 groups independently selected from halogen, hydroxyl, amine, alkylamino, dialkylamino, C1-C4 alkyl, and C1-C4 alkoxy. In yet a further aspect, each of $Cy^1$ and $Cy^2$ is a 6-membered cycloalkyl substituted with 0 or 1 group selected from halogen, hydroxyl, amine, alkylamino, dialkylamino, C1-C4 alkyl, and C1-C4 alkoxy. In an even further aspect, each of $Cy^1$ and $Cy^2$ is a 6-membered cycloalkyl monosubstituted with a group selected from halogen, hydroxyl, amine, alkylamino, dialkylamino, C1-C4 alkyl, and C1-C4 alkoxy. In a still further aspect, each of $Cy^1$ and $Cy^2$ is an unsubstituted 6-membered cycloalkyl.

In a further aspect, each of $Cy^1$ and $Cy^2$ is a 5- or 6-membered heterocycloalkyl having 1, 2, or 3 ring-members selected from O, S, and $NR^1$ and substituted with 0, 1, 2, or 3 groups independently selected from halogen, hydroxyl, amine, alkylamino, dialkylamino, C1-C4 alkyl, and C1-C4 alkoxy. In a still further aspect, each of $Cy^1$ and $Cy^2$ is a 5- or 6-membered heterocycloalkyl having 1 or 2 ring-members selected from O, S, and $NR^1$ and substituted with 0, 1, 2, or 3 groups independently selected from halogen, hydroxyl, amine, alkylamino, dialkylamino, C1-C4 alkyl, and C1-C4 alkoxy. In yet a further aspect, each of $Cy^1$ and $Cy^2$ is a 5- or 6-membered heterocycloalkyl having 1 ring-member selected from O, S, and $NR^1$ and substituted with 0, 1, 2, or 3 groups independently selected from halogen, hydroxyl, amine, alkylamino, dialkylamino, C1-C4 alkyl, and C1-C4 alkoxy.

In a further aspect, each of $Cy^1$ and $Cy^2$ is a 5- or 6-membered heterocycloalkyl having 1, 2, or 3 ring-members selected from O, S, and $NR^1$ and substituted with 0, 1, or 2 groups independently selected from halogen, hydroxyl, amine, alkylamino, dialkylamino, C1-C4 alkyl, and C1-C4 alkoxy. In a still further aspect, each of $Cy^1$ and $Cy^2$ is a 5- or 6-membered heterocycloalkyl having 1, 2, or 3 ring-members selected from O, S, and $NR^1$ and substituted with 0 or 1 group selected from halogen, hydroxyl, amine, alkylamino, dialkylamino, C1-C4 alkyl, and C1-C4 alkoxy. In yet a further aspect, each of $Cy^1$ and $Cy^2$ is a 5- or 6-membered heterocycloalkyl having 1, 2, or 3 ring-members selected from O, S, and $NR^1$ and monosubstituted with a group selected from halogen, hydroxyl, amine, alkylamino, dialkylamino, C1-C4 alkyl, and C1-C4 alkoxy. In an even further aspect, each of $Cy^1$ and $Cy^2$ is a 5- or 6-membered heterocycloalkyl having 1, 2, or 3 ring-members selected from O, S, and $NR^1$ and unsubstituted.

In a further aspect, each of $Cy^1$ and $Cy^2$ is a 5-membered heterocycloalkyl having 1, 2, or 3 ring-members selected from O, S, and $NR^1$ and substituted with 0, 1, 2, or 3 groups independently selected from halogen, hydroxyl, amine, alkylamino, dialkylamino, C1-C4 alkyl, and C1-C4 alkoxy. In a still further aspect, each of $Cy^1$ and $Cy^2$ is a 5-membered heterocycloalkyl having 1, 2, or 3 ring-members selected from O, S, and $NR^1$ and substituted with 0, 1, or 2 groups independently selected from halogen, hydroxyl, amine, alkylamino, dialkylamino, C1-C4 alkyl, and C1-C4 alkoxy. In yet a further aspect, each of $Cy^1$ and $Cy^2$ is a 5-membered heterocycloalkyl having 1, 2, or 3 ring-members selected from O, S, and $NR^1$ and substituted with 0 or 1 group selected from halogen, hydroxyl, amine, alkylamino, dialkylamino, C1-C4 alkyl, and C1-C4 alkoxy. In an even further aspect, each of $Cy^1$ and $Cy^2$ is a 5-membered heterocycloalkyl having 1, 2, or 3 ring-members selected from O, S, and $NR^1$ and monosubstituted with a group selected from halogen, hydroxyl, amine, alkylamino, dialkylamino, C1-C4 alkyl, and C1-C4 alkoxy. In a still further aspect, each of $Cy^1$ and $Cy^2$ is a 5-membered heterocycloalkyl having 1, 2, or 3 ring-members selected from O, S, and $NR^1$ and unsubstituted.

In a further aspect, each of Cy¹ and Cy² is a 6-membered heterocycloalkyl having 1, 2, or 3 ring-members selected from O, S, and NR¹ and substituted with 0, 1, 2, or 3 groups independently selected from halogen, hydroxyl, amine, alkylamino, dialkylamino, C1-C4 alkyl, and C1-C4 alkoxy. In a still further aspect, each of Cy¹ and Cy² is a 6-membered heterocycloalkyl having 1, 2, or 3 ring-members selected from O, S, and NR¹ and substituted with 0, 1, or 2 groups independently selected from halogen, hydroxyl, amine, alkylamino, dialkylamino, C1-C4 alkyl, and C1-C4 alkoxy. In yet a further aspect, each of Cy¹ and Cy² is a 6-membered heterocycloalkyl having 1, 2, or 3 ring-members selected from O, S, and NR¹ and substituted with 0 or 1 group selected from halogen, hydroxyl, amine, alkylamino, dialkylamino, C1-C4 alkyl, and C1-C4 alkoxy. In an even further aspect, each of Cy¹ and Cy² is a 6-membered heterocycloalkyl having 1, 2, or 3 ring-members selected from O, S, and NR¹ and monosubstituted with a group selected from halogen, hydroxyl, amine, alkylamino, dialkylamino, C1-C4 alkyl, and C1-C4 alkoxy. In a still further aspect, each of Cy¹ and Cy² is a 6-membered heterocycloalkyl having 1, 2, or 3 ring-members selected from O, S, and NR¹ and unsubstituted.

2. Functionalized Phosphonate Examples

In one aspect, a compound is selected from:

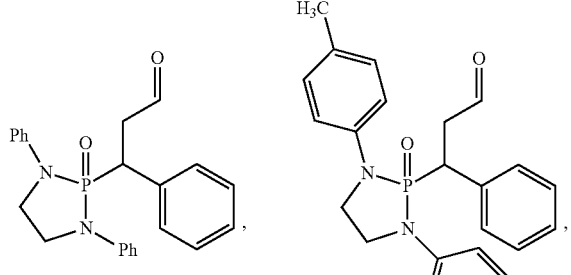

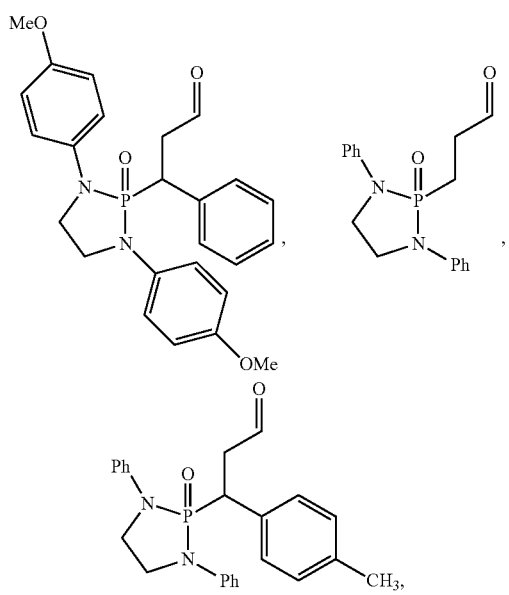

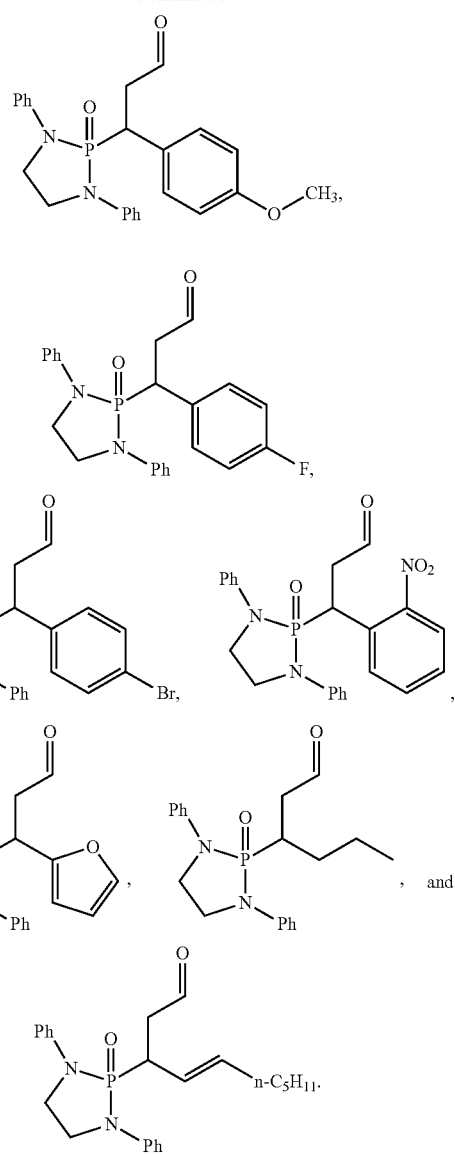

In one aspect, a compound is selected from:

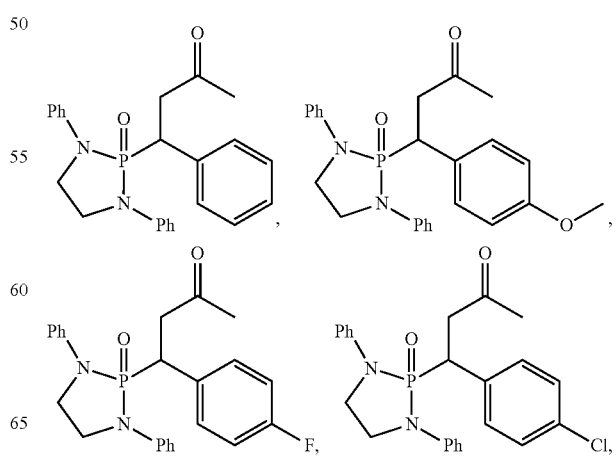

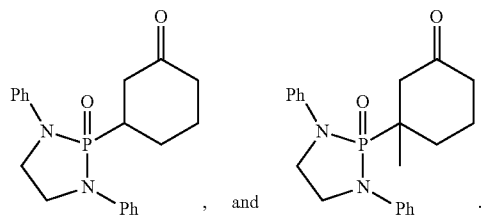
In one aspect, a compound is selected from:
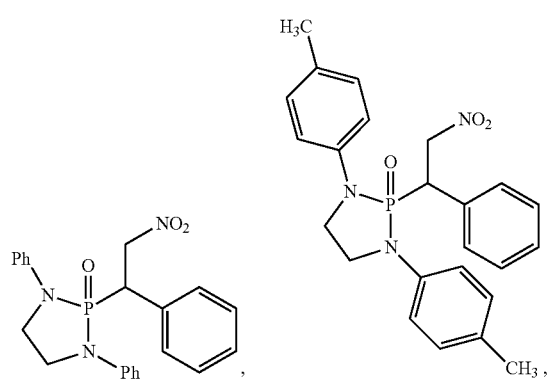
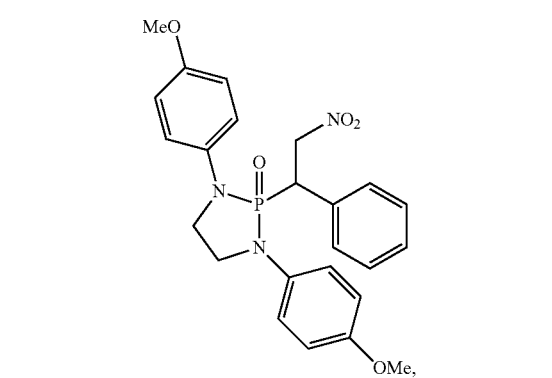
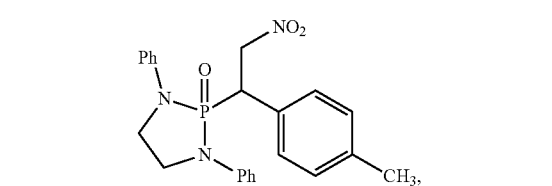
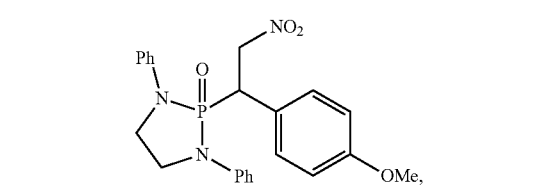
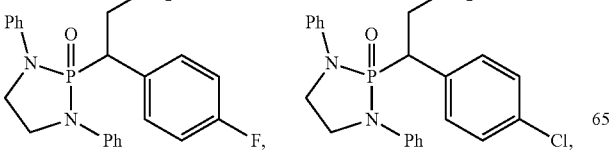
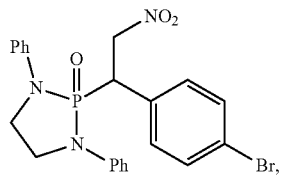
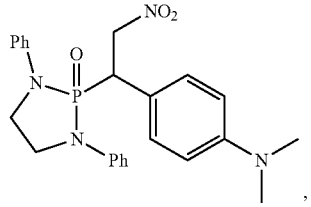
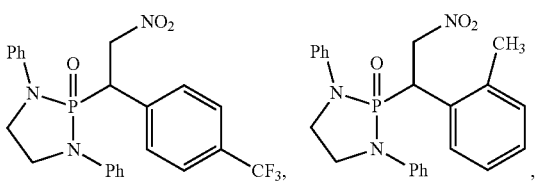
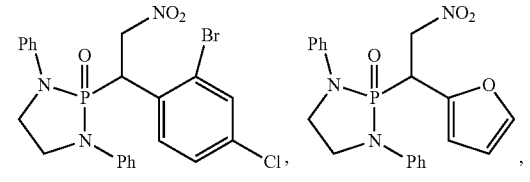
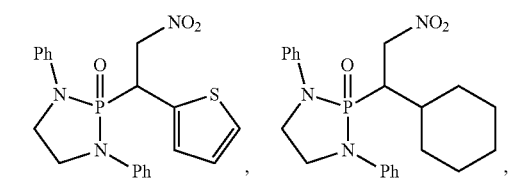
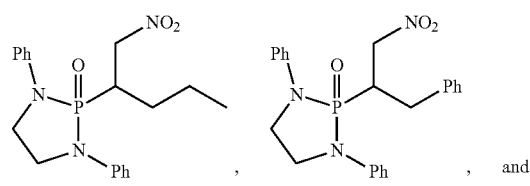
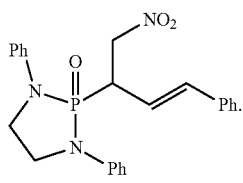

In one aspect, a compound is selected from:
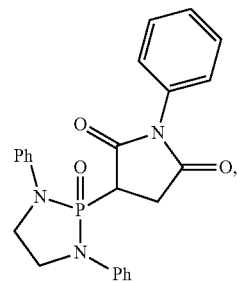 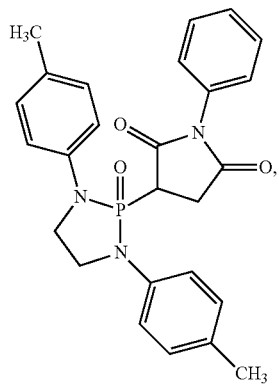
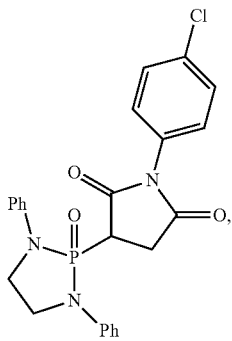 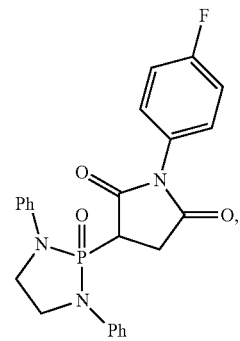
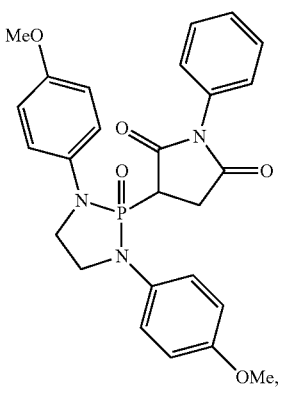 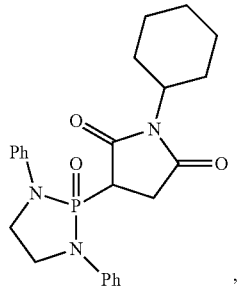
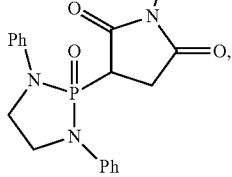 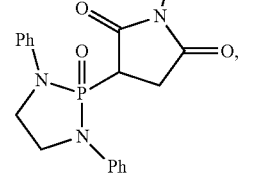
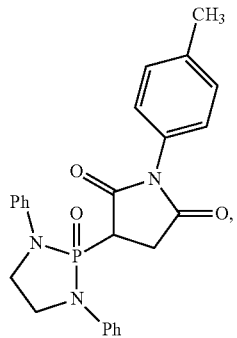 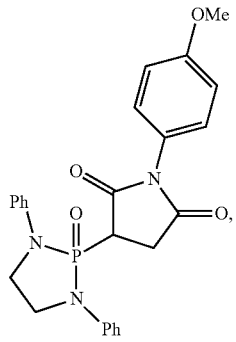
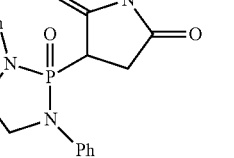 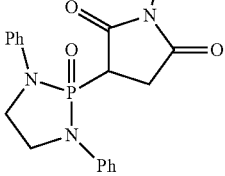
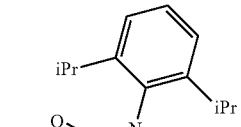 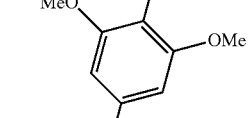
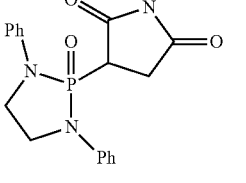 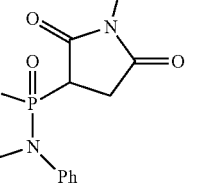, and
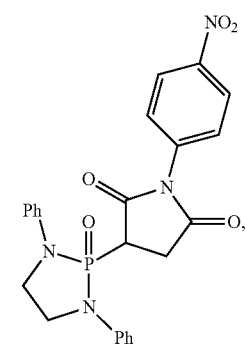 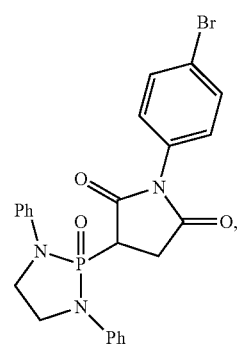
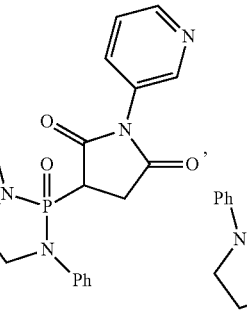

3. Prophetic Compound Examples

The following compound examples are prophetic, and can be prepared using the synthesis methods described herein above and other general methods as needed as would be known to one skilled in the art. Thus, in one aspect, a compound can be selected from:

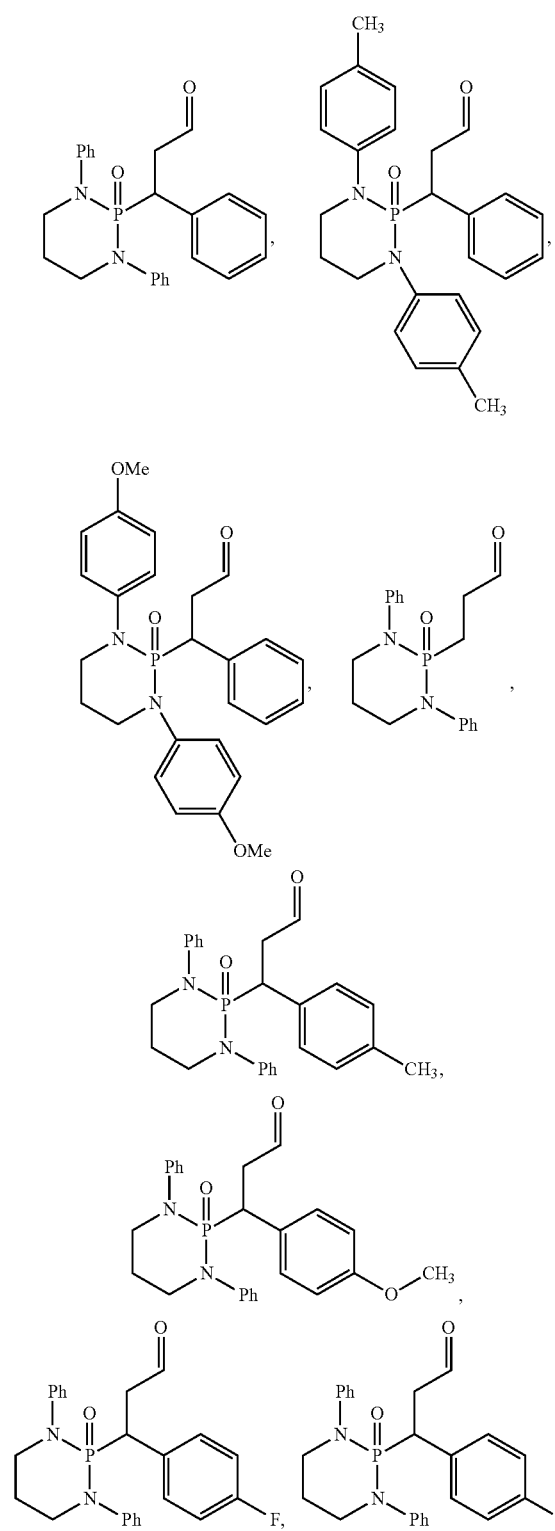

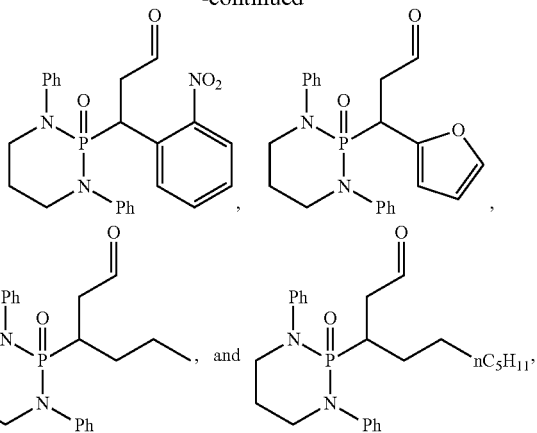

or a derivative thereof.

In one aspect, a compound can be selected from:

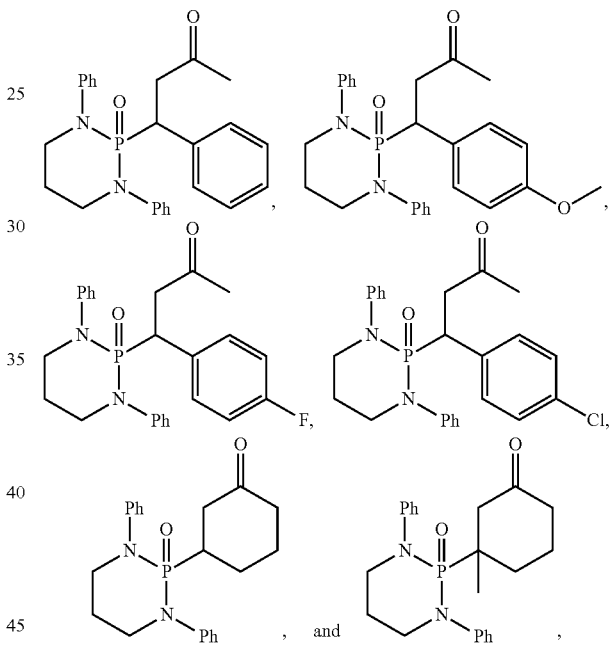

or a derivative thereof.

In one aspect, a compound can be selected from:

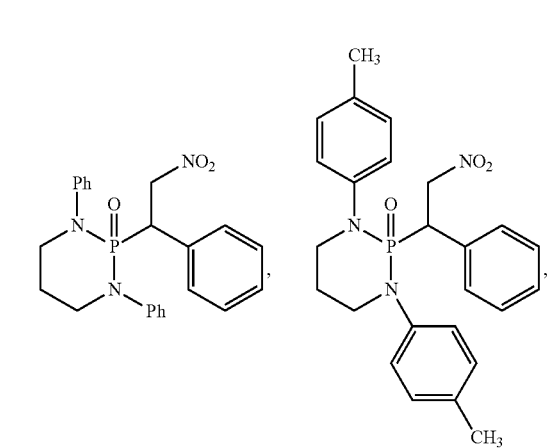

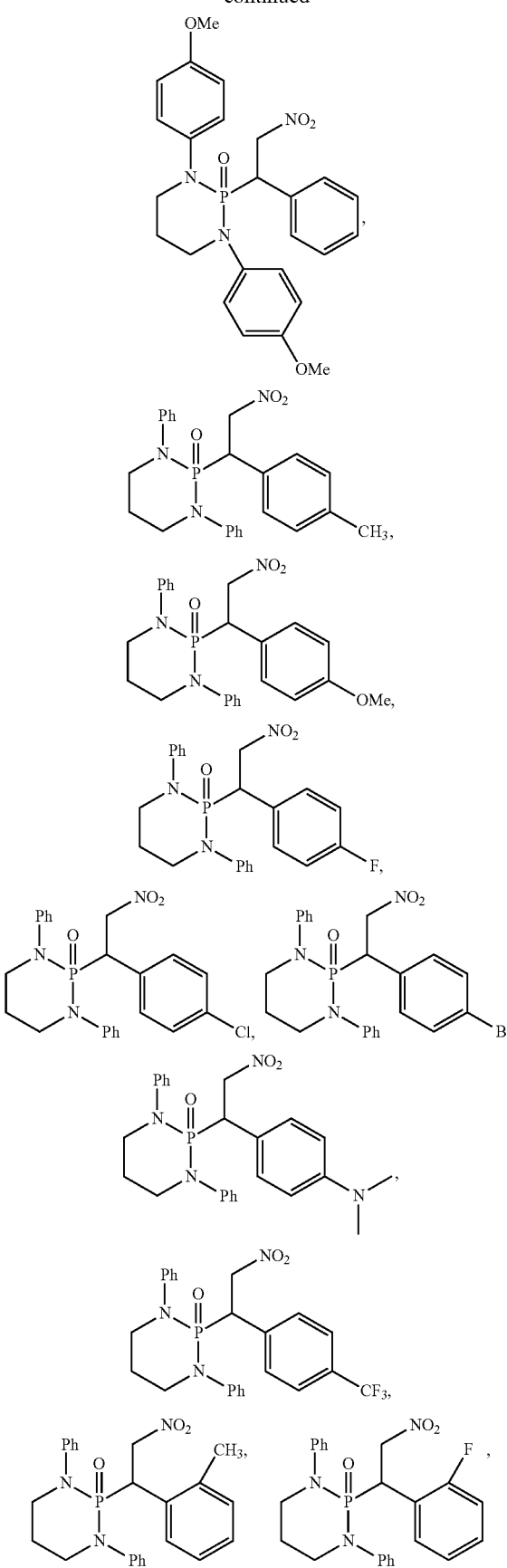
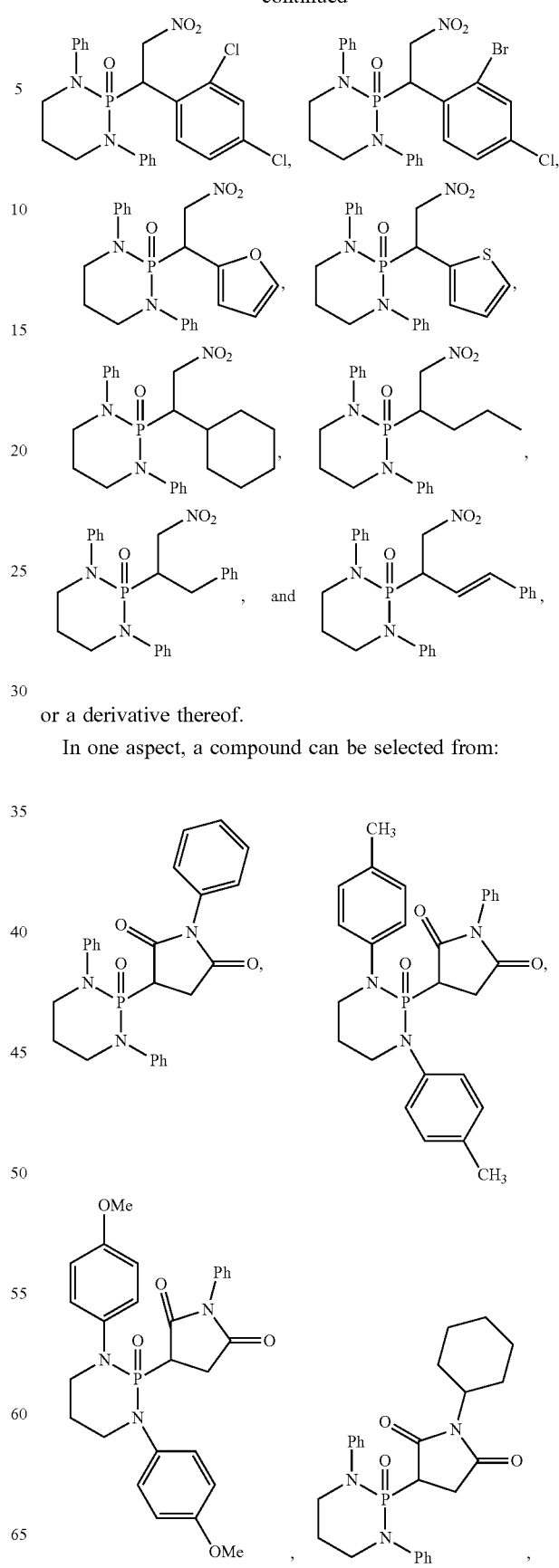
or a derivative thereof.
In one aspect, a compound can be selected from:

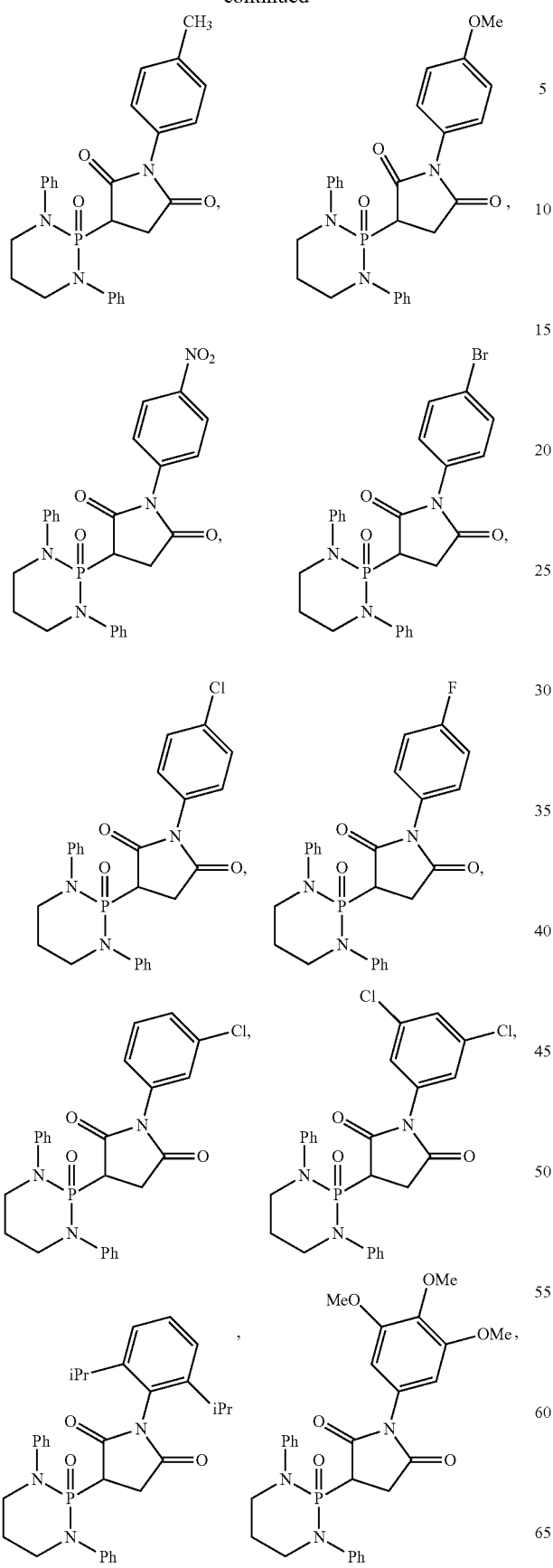
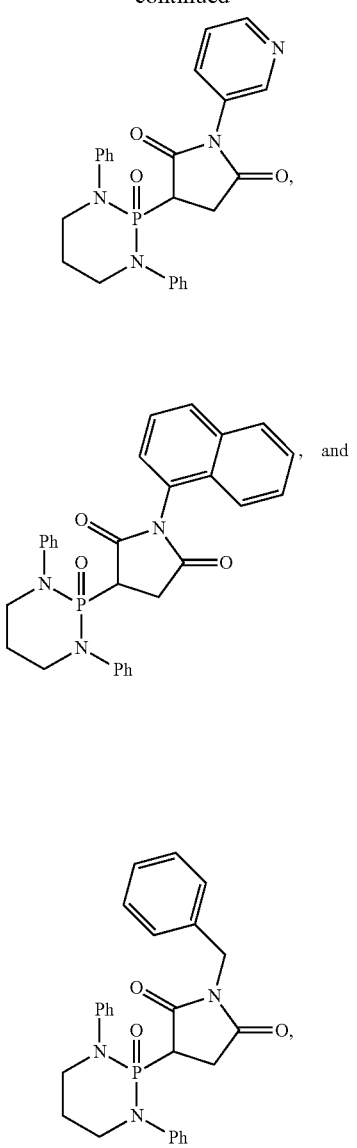
or a derivative thereof.
In one aspect, a compound can be selected from:
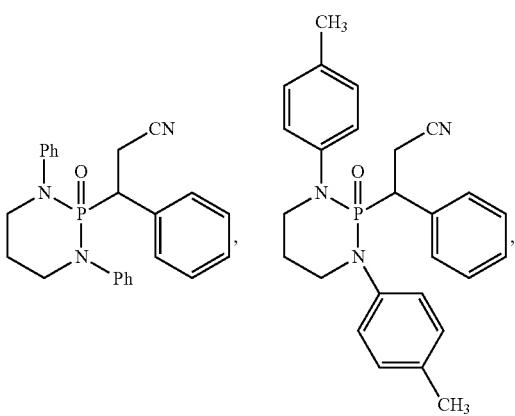

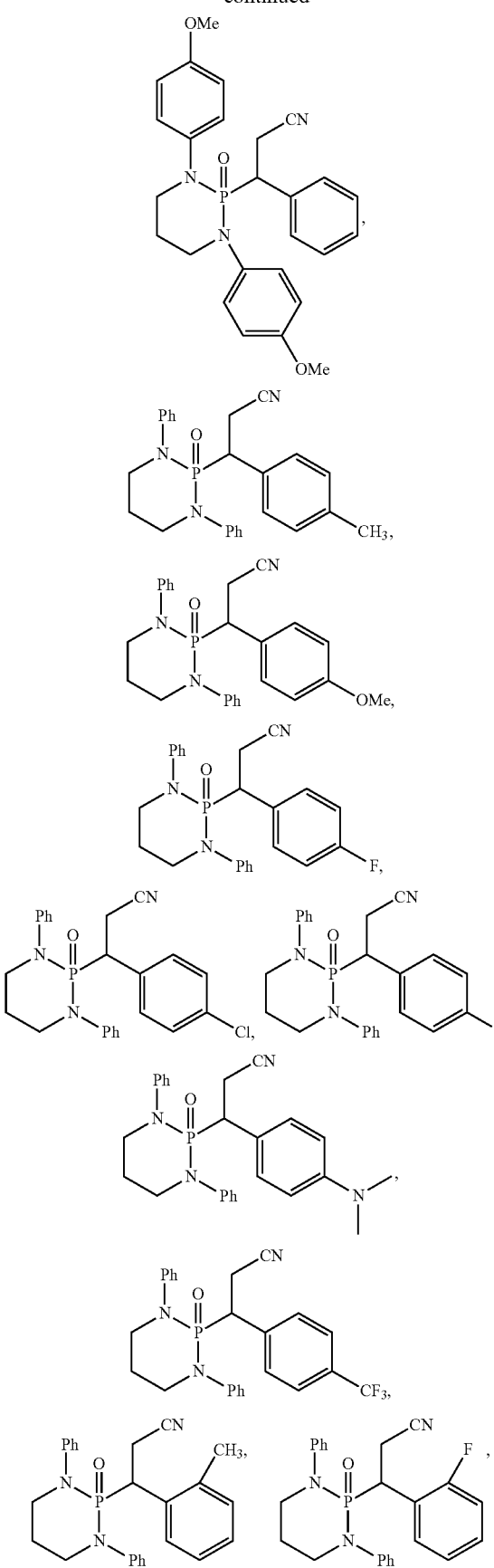
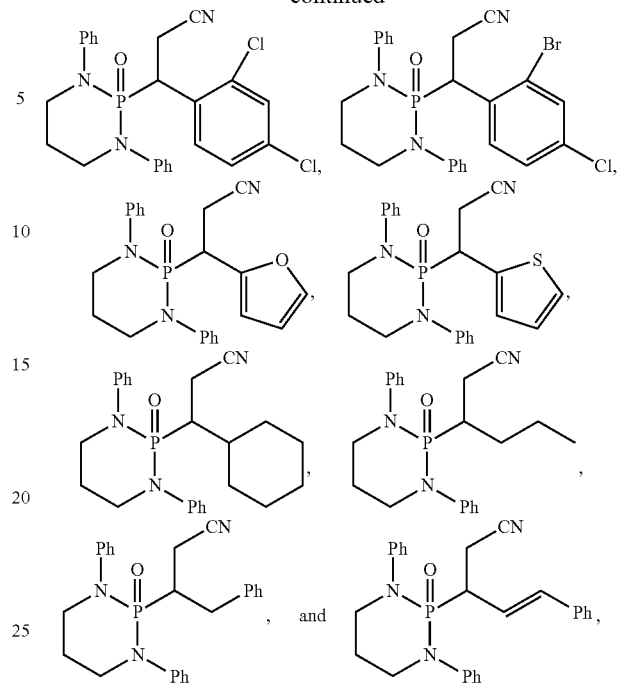
or a derivative thereof.
In one aspect, a compound can be selected from:
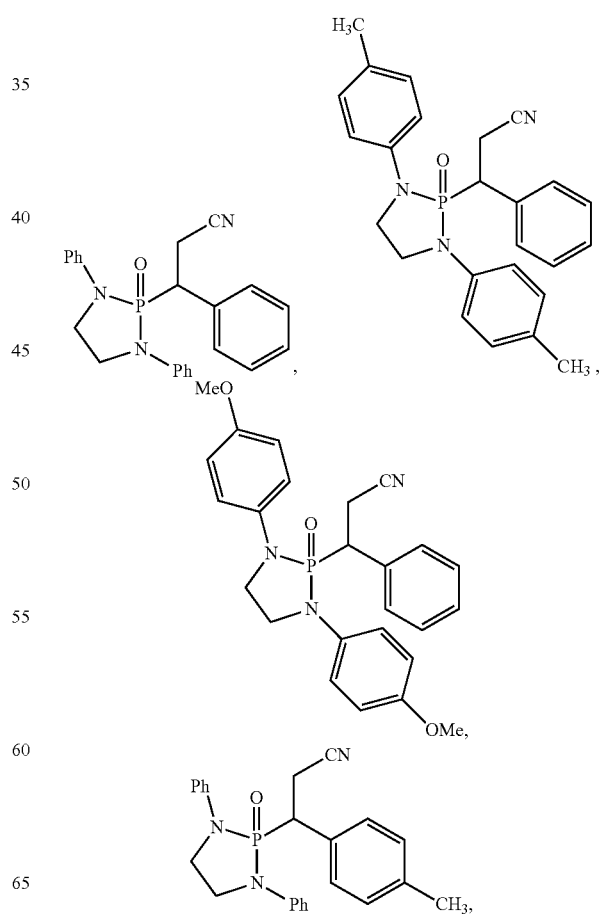

-continued

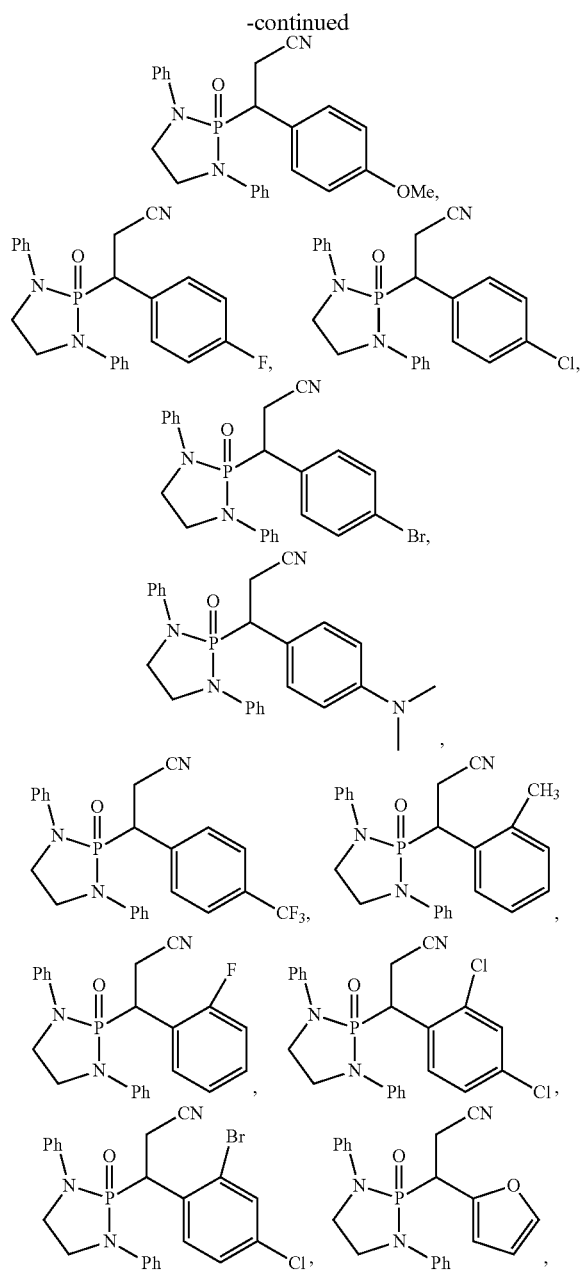

or a derivative thereof.

C. Methods of Making Functionalized Phosphonates

In one aspect, disclosed are methods for preparing a product compound having a structure represented by a formula:

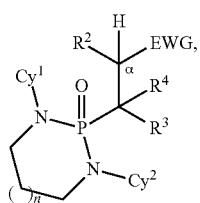

wherein n is 0 or 1; wherein each of $Cy^1$ and $Cy^2$ is independently selected from: aryl substituted with 0, 1, 2, or 3 groups independently selected from halogen, hydroxyl, amine, alkylamino, dialkylamino, C1-C4 alkyl, and C1-C4 alkoxy; a 5- or 6-membered heteroaryl having 1, 2, or 3 ring-members selected from O, S, and $NR^1$ and substituted with 0, 1, 2, or 3 groups independently selected from halogen, hydroxyl, amine, alkylamino, dialkylamino, C1-C4 alkyl, and C1-C4 alkoxy; a 5- or 6-membered cycloalkyl substituted with 0, 1, 2, or 3 groups independently selected from halogen, hydroxyl, amine, alkylamino, dialkylamino, C1-C4 alkyl, and C1-C4 alkoxy; and a 5- or 6-membered heterocycloalkyl having 1, 2, or 3 ring-members selected from O, S, and $NR^1$ and substituted with 0, 1, 2, or 3 groups independently selected from halogen, hydroxyl, amine, alkylamino, dialkylamino, C1-C4 alkyl, and C1-C4 alkoxy; wherein each $R^1$ is independently selected from hydrogen, C1-C4 alkyl, aryl, 5- or 6-membered heteroaryl, 5- or 6-membered cycloalkyl, and —(C1-C4 alkyl)aryl, and substituted with 0, 1, 2, or 3 groups independently selected from halogen, hydroxyl, amine, alkylamino, dialkylamino, C1-C4 alkyl, and C1-C4 alkoxy; wherein $R^2$ is selected from hydrogen, halogen, hydroxyl, amine, alkylamino, dialkylamino, C1-C4 alkyl, C1-C4 alkoxy, and an electron-withdrawing group; and wherein $R^3$ is selected from hydrogen, hydroxyl, amine, alkyl amine, dialkylamine, C1-C4 alkyl, C1-C8 alkenyl, C1-C4 alkoxy, —C(O)OH, —C(O)$OR^5$, —C(O)$R^5$, —C(O)$NHR^6$, aryl, a 5- or 6-membered heteroaryl having 1, 2, or 3 ring-members selected from O, S, and $NR^1$, a 5- or 6-membered cycloalkyl, (C1-C4 alkyl)aryl, and (C1-C4 alkenyl)aryl, and substituted with 0, 1, 2, or 3 groups independently selected from halogen, hydroxyl, amine, alkylamino, dialkylamino, C1-C4 alkyl, and C1-C4 alkoxy; or wherein $R^2$ and $R^3$, together with the intervening atoms, comprise a 5- or 6-membered cycloalkyl or a 5- or 6-membered heterocycloalkyl having 1, 2, or 3 ring-members selected from O, S, and $NR^1$, substituted with 0, 1, 2, or 3 groups independently selected from oxo, hydroxyl, halogen, C1-C4 alkyl, C1-C4 alkoxy, —C(O)OH, —C(O)$OR^5$, —C(O)$R^5$, and —C(O)$NHR^6$; wherein EWG is an electron-withdrawing group; and wherein $R^4$ is selected from hydrogen, hydroxyl, amine, alkyl amine, dialkylamine, C1-C4 alkyl, C1-C8 alkenyl, C1-C4 alkoxy, —C(O)OH, —C(O)$OR^5$, —C(O)$R^5$, —C(O)$NHR^6$, aryl, a 5- or 6-membered heteroaryl having 1, 2, or 3 ring-members selected from O, S, and $NR^1$, a 5- or 6-membered cycloalkyl, (C1-C4 alkyl)aryl, and (C1-C4 alkenyl)aryl, and substituted with 0, 1, 2, or 3 groups independently selected from halogen, hydroxyl, amine, alkylamino, dialkylamino, C1-C4 alkyl, and C1-C4 alkoxy; or wherein EWG and $R^4$, together with the intervening atoms, comprise a 5- or 6-membered cycloalkyl or a 5- or 6-membered heterocycloalkyl having 1 or 2 ring-members selected from O, S, and $NR^1$, substituted with 0, 1, 2, or 3 groups independently selected from hydroxyl, halogen, oxo, C1-C4 alkyl, C1-C4 alkoxy, —C(O)OH, —C(O)$R^5$, —C(O)$OR^5$, and —C(O)$NHR^6$; provided that the first atom of EWG adjacent to the position denoted a is substituted with oxo; wherein each $R^5$ is independently selected from hydrogen and C1-C4 alkyl; and wherein each $R^6$ is independently selected from hydrogen, C1-C4 alkyl, and aryl substituted with 0, 1, 2, or 3 groups independently selected from halogen, hydroxyl, amine, alkylamino, dialkylamino, C1-C4 alkyl, and C1-C4 alkoxy; the method comprising the step of reacting a first compound having a structure represented by a formula:

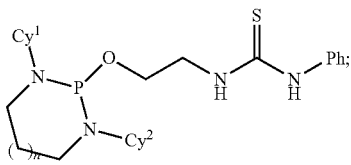

with a second compound having a structure represented by a formula:

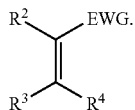

In one aspect, disclosed are methods for preparing a product compound having a structure represented by a formula:

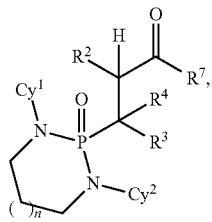

wherein n is 0 or 1; wherein each of $Cy^1$ and $Cy^2$ is independently selected from: aryl substituted with 0, 1, 2, or 3 groups independently selected from halogen, hydroxyl, amine, alkylamino, dialkylamino, C1-C4 alkyl, and C1-C4 alkoxy; a 5- or 6-membered heteroaryl having 1, 2, or 3 ring-members selected from O, S, and $NR^1$ and substituted with 0, 1, 2, or 3 groups independently selected from halogen, hydroxyl, amine, alkylamino, dialkylamino, C1-C4 alkyl, and C1-C4 alkoxy; a 5- or 6-membered cycloalkyl substituted with 0, 1, 2, or 3 groups independently selected from halogen, hydroxyl, amine, alkylamino, dialkylamino, C1-C4 alkyl, and C1-C4 alkoxy; and a 5- or 6-membered heterocycloalkyl having 1, 2, or 3 ring-members selected from O, S, and $NR^1$ and substituted with 0, 1, 2, or 3 groups independently selected from halogen, hydroxyl, amine, alkylamino, dialkylamino, C1-C4 alkyl, and C1-C4 alkoxy; wherein each $R^1$ is independently selected from hydrogen, C1-C4 alkyl, aryl, 5- or 6-membered heteroaryl, 5- or 6-membered cycloalkyl, and —(C1-C4 alkyl)aryl, and substituted with 0, 1, 2, or 3 groups independently selected from halogen, hydroxyl, amine, alkylamino, dialkylamino, C1-C4 alkyl, and C1-C4 alkoxy; wherein $R^2$ is selected from hydrogen, halogen, hydroxyl, amine, alkylamino, dialkylamino, C1-C4 alkyl, C1-C4 alkoxy, and an electron-withdrawing group; and wherein $R^3$ is selected from hydrogen, hydroxyl, amine, alkyl amine, dialkylamine, C1-C4 alkyl, C1-C8 alkenyl, C1-C4 alkoxy, —C(O)OH, —C(O)$OR^5$, —C(O)$R^5$, —C(O)$NHR^6$, aryl, a 5- or 6-membered heteroaryl having 1, 2, or 3 ring-members selected from O, S, and $NR^1$, a 5- or 6-membered cycloalkyl, (C1-C4 alkyl)aryl, and (C1-C4 alkenyl)aryl, and substituted with 0, 1, 2, or 3 groups independently selected from halogen, hydroxyl, amine, alkylamino, dialkylamino, C1-C4 alkyl, and C1-C4 alkoxy; or wherein $R^2$ and $R^3$, together with the intervening atoms, comprise a 5- or 6-membered cycloalkyl or a 5- or 6-membered heterocycloalkyl having 1, 2, or 3 ring-members selected from O, S, and $NR^1$, substituted with 0, 1, 2, or 3 groups independently selected from oxo, hydroxyl, halogen, C1-C4 alkyl, C1-C4 alkoxy, —C(O)OH, —C(O)$OR^5$, —C(O)$R^5$, and —C(O)$NHR^6$; wherein $R^7$ is selected from hydrogen, hydroxyl, amine, alkyl amine, dialkylamine, C1-C4 alkyl, and C1-C4 alkoxy; and wherein $R^4$ is selected from hydrogen, hydroxyl, amine, alkyl amine, dialkylamine, C1-C4 alkyl, C1-C8 alkenyl, C1-C4 alkoxy, —C(O)OH, —C(O)$OR^5$, —C(O)$R^5$, —C(O)$NHR^6$, aryl, a 5- or 6-membered heteroaryl having 1, 2, or 3 ring-members selected from O, S, and $NR^1$, a 5- or 6-membered cycloalkyl, (C1-C4 alkyl)aryl, and (C1-C4 alkenyl)aryl, and substituted with 0, 1, 2, or 3 groups independently selected from halogen, hydroxyl, amine, alkylamino, dialkylamino, C1-C4 alkyl, and C1-C4 alkoxy; or wherein $R^7$ and $R^4$, together with the intervening atoms, comprise a 5- or 6-membered cycloalkyl or a 5- or 6-membered heterocycloalkyl having 1 or 2 ring-members selected from O, S, and $NR^1$, substituted with 0, 1, 2, or 3 groups independently selected from hydroxyl, halogen, oxo, C1-C4 alkyl, C1-C4 alkoxy, —C(O)OH, —C(O)$R^5$, —C(O)$OR^5$, and —C(O)$NHR^6$; wherein each $R^5$ is independently selected from hydrogen and C1-C4 alkyl; and wherein each $R^6$ is independently selected from hydrogen, C1-C4 alkyl, and aryl substituted with 0, 1, 2, or 3 groups independently selected from halogen, hydroxyl, amine, alkylamino, dialkylamino, C1-C4 alkyl, and C1-C4 alkoxy; the method comprising the step of reacting a first compound having a structure represented by a formula:

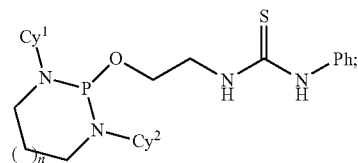

with a second compound having a structure represented by a formula:

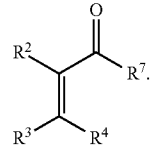

In a further aspect, reacting is in the presence of a catalyst. In a still further aspect, reacting is not in the presence of a catalyst. In yet a further aspect, the catalyst is an amine (e.g., a secondary amine, or heterocyclic amine). Examples of amine catalysts include, but are not limited to, triethylamine, N,N-Diisopropylethylamine, pyridine, DMAP, imidazole, 1-cyclohexylpiperazine, 1-phenylpiperazine, 1-(2-phenylethyl)piperazine, 1-hexylpiperazine, 1-t-butylpiperazine, 1-(4-pyridyl)piperazine, 1-[2-(dimethylamino)ethlylpiperazine, 1-(4-trifluoromethylphenyl)piperazine, and 1-ethylpiperazine. In an even further aspect, the amine catalyst is 1-cyclohexylpiperazine.

In one aspect, disclosed are methods for preparing a compound having a structure represented by a formula:

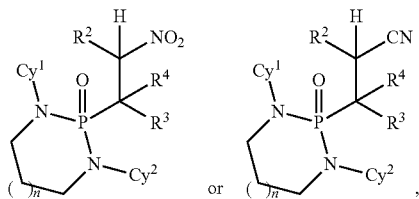 or 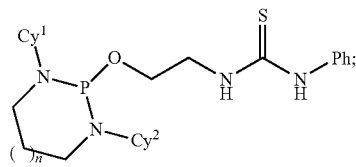, wherein n is 0 or 1; wherein each of $Cy^1$ and $Cy^2$ is independently selected from: aryl substituted with 0, 1, 2, or 3 groups independently selected from halogen, hydroxyl, amine, alkylamino, dialkylamino, C1-C4 alkyl, and C1-C4 alkoxy; a 5- or 6-membered heteroaryl having 1, 2, or 3 ring-members selected from O, S, and $NR^1$ and substituted with 0, 1, 2, or 3 groups independently selected from halogen, hydroxyl, amine, alkylamino, dialkylamino, C1-C4 alkyl, and C1-C4 alkoxy; a 5- or 6-membered cycloalkyl substituted with 0, 1, 2, or 3 groups independently selected from halogen, hydroxyl, amine, alkylamino, dialkylamino, C1-C4 alkyl, and C1-C4 alkoxy; and a 5- or 6-membered heterocycloalkyl having 1, 2, or 3 ring-members selected from O, S, and $NR^1$ and substituted with 0, 1, 2, or 3 groups independently selected from halogen, hydroxyl, amine, alkylamino, dialkylamino, C1-C4 alkyl, and C1-C4 alkoxy; wherein each $R^1$ is independently selected from hydrogen, C1-C4 alkyl, aryl, 5- or 6-membered heteroaryl, 5- or 6-membered cycloalkyl, and —(C1-C4 alkyl)aryl, and substituted with 0, 1, 2, or 3 groups independently selected from halogen, hydroxyl, amine, alkylamino, dialkylamino, C1-C4 alkyl, and C1-C4 alkoxy; wherein $R^2$ is selected from hydrogen, halogen, hydroxyl, amine, alkylamino, dialkylamino, C1-C4 alkyl, C1-C4 alkoxy, and an electron-withdrawing group; and wherein $R^3$ is selected from hydrogen, hydroxyl, amine, alkyl amine, dialkylamine, C1-C4 alkyl, C1-C8 alkenyl, C1-C4 alkoxy, —C(O)OH, —C(O)$OR^5$, —C(O)$R^5$, —C(O)$NHR^6$, aryl, a 5- or 6-membered heteroaryl having 1, 2, or 3 ring-members selected from O, S, and $NR^1$, a 5- or 6-membered cycloalkyl, (C1-C4 alkyl)aryl, and (C1-C4 alkenyl)aryl, and substituted with 0, 1, 2, or 3 groups independently selected from halogen, hydroxyl, amine, alkylamino, dialkylamino, C1-C4 alkyl, and C1-C4 alkoxy; or wherein $R^2$ and $R^3$, together with the intervening atoms, comprise a 5- or 6-membered cycloalkyl or a 5- or 6-membered heterocycloalkyl having 1, 2, or 3 ring-members selected from O, S, and $NR^1$, substituted with 0, 1, 2, or 3 groups independently selected from oxo, hydroxyl, halogen, C1-C4 alkyl, C1-C4 alkoxy, —C(O)OH, —C(O)$OR^5$, —C(O)$R^5$, and —C(O)$NHR^6$; wherein $R^4$ is selected from hydrogen, hydroxyl, amine, alkyl amine, dialkylamine, C1-C4 alkyl, C1-C8 alkenyl, C1-C4 alkoxy, —C(O)OH, —C(O)$OR^5$, —C(O)$R^5$, —C(O)$NHR^6$, aryl, a 5- or 6-membered heteroaryl having 1, 2, or 3 ring-members selected from O, S, and $NR^1$, a 5- or 6-membered cycloalkyl, (C1-C4 alkyl)aryl, and (C1-C4 alkenyl)aryl, and substituted with 0, 1, 2, or 3 groups independently selected from halogen, hydroxyl, amine, alkylamino, dialkylamino, C1-C4 alkyl, and C1-C4 alkoxy; wherein each $R^5$ is independently selected from hydrogen and C1-C4 alkyl; and wherein each $R^6$ is independently selected from hydrogen, C1-C4 alkyl, and aryl substituted with 0, 1, 2, or 3 groups independently selected from halogen, hydroxyl, amine, alkylamino, dialkylamino, C1-C4 alkyl, and C1-C4 alkoxy; the method comprising the step of reacting a first compound having a structure represented by a formula:

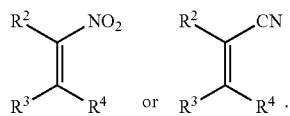

with a second compound having a structure represented by a formula:

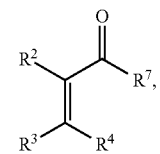

In a further aspect, EWG is an electron-withdrawing group. Examples of electro-withdrawing groups include, but are not limited to, nitro, cyano carboxylic acid, ester, ketone, aldehyde, amide, and sulfonyl groups. In a further aspect, the electron-withdrawing group is selected from nitro, cyano, —C(O)OH, —C(O)$R^5$, —C(O)$OR^5$, and —C(O)$NHR^6$.

In a further aspect, the method further comprises a reduction step.

In a further aspect, the second compound has a structure represented by a formula:

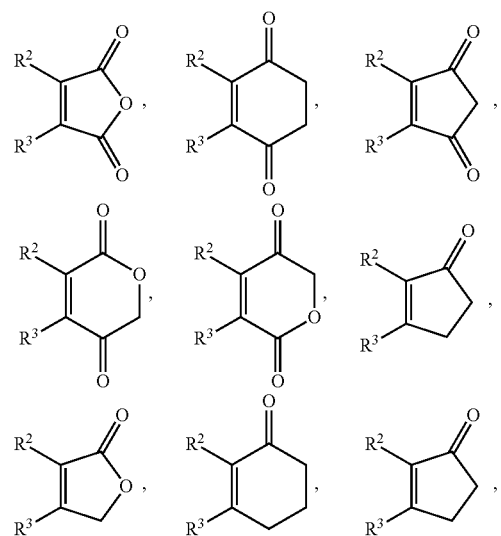

wherein $R^7$ is selected from hydrogen, hydroxyl, amine, alkyl amine, dialkylamine, C1-C4 alkyl, and C1-C4 alkoxy.

In a further aspect, the second compound has a structure selected from:

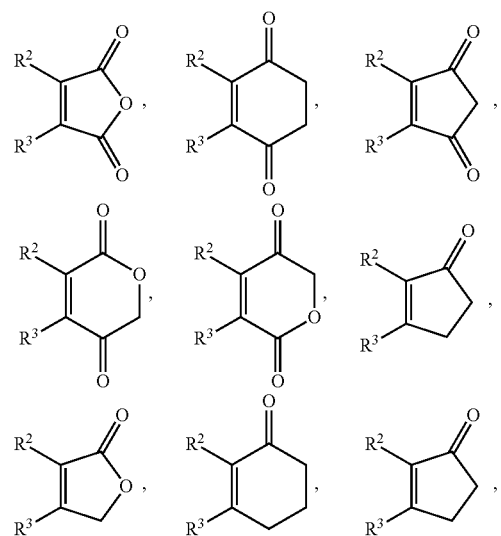

-continued

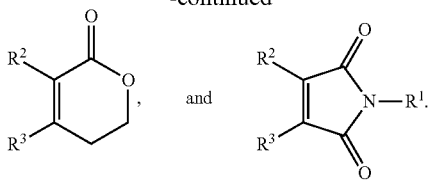

In a further aspect, the second compound has a structure selected from:

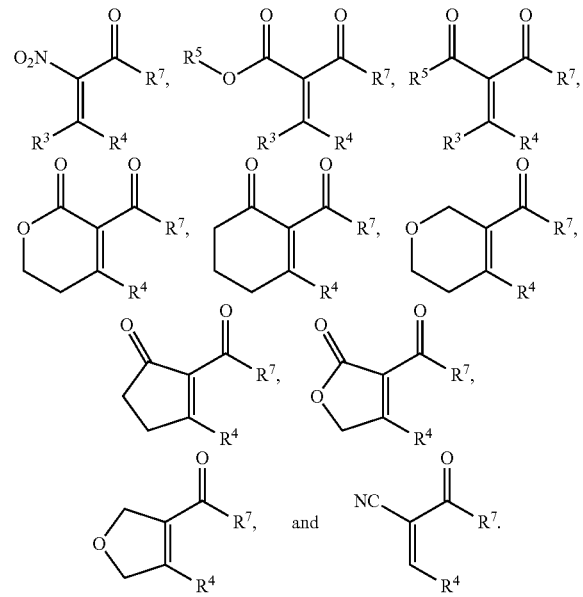

In a further aspect, the second compound has a structure represented by a formula:

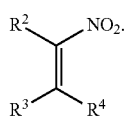

In a further aspect, the second compound has a structure represented by a formula:

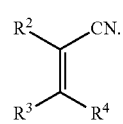

In a further aspect, the second compound has a structure represented by a formula:

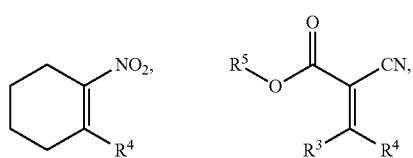

-continued

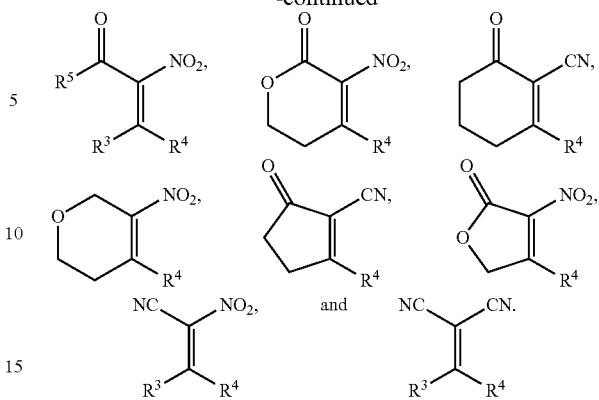

The compounds provided herein, including salts thereof, can be prepared using known organic synthesis techniques and can be synthesized according to any of numerous possible synthetic routes.

The reactions for preparing the compounds provided herein can be carried out in suitable solvents that can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of the compounds provided herein can involve the protection and deprotection of various chemical groups. The chemistry of protecting groups can be found, for example, in *Protecting Group Chemistry*, 1$^{st}$ Ed., Oxford University Press, 2000; *March's Advanced Organic Chemistry: Reactions, Mechanisms, and Structure*, 5$^{th}$ Ed., Wiley-Interscience Publication, 2001; and Peturssion, S. et al., "Protecting Groups in Carbohydrate Chemistry," *J. Chem. Educ.*, 74(11), 1297 (1997).

Reactions can be monitored using an appropriate method. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified using appropriate methods such as high performance liquid chromatography (HPLC) ("*Preparative LC-MS Purification: Improved Compound Specific Method Optimization*" K. F. Blom, et al., *J. Combi. Chem.* 6(6), 874 (2004)) and normal phase silica chromatography.

It will be appreciated by one skilled in the art that the processes described are not the exclusive means by which compounds of the invention may be synthesized and that a broad repertoire of synthetic organic reactions is available to be potentially employed in synthesizing compounds of the invention. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of*

*Heterocyclic Chemistry* Vols. 1-49 (Journal of Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, 2$^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, 6$^{th}$ Ed. (Wiley, 2007); Trost et al. (Ed.), *Comprehensive Organic Synthesis* (Pergamon Press, 1991).

1. Route I

In one aspect, substituted N-heterocyclic phosphine analogs can be prepared as shown below.

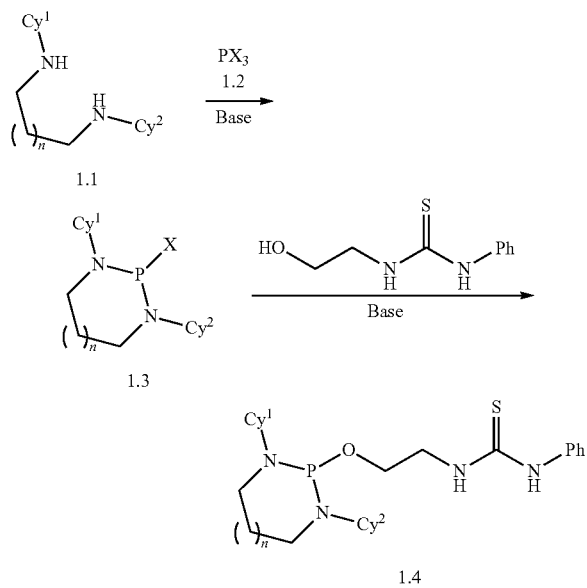

Compounds are represented in generic form, with substituents as noted in compound descriptions elsewhere herein. A more specific example is set forth below.

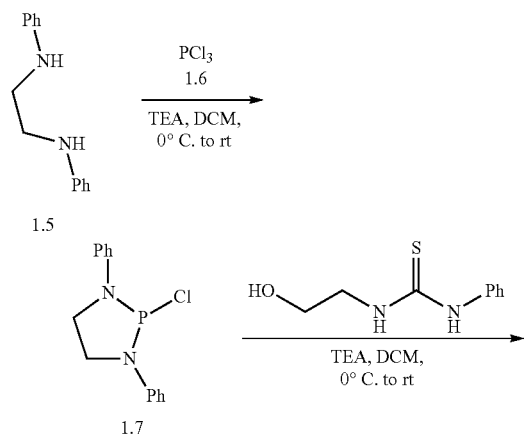

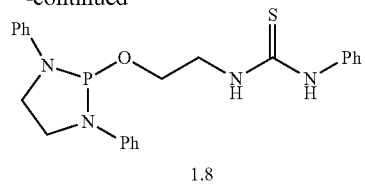

In one aspect, the synthesis of N-heterocyclic phosphine analogs can begin with an appropriate diamine, e.g., 1.5 as shown above. Diamines are commercially available or readily prepared by one skilled in the art. Thus, compounds of type 1.8, and similar compounds, can be prepared according to reaction Scheme 1B above. Compounds of type 1.7 can be prepared by a cyclization reaction of an appropriate diamine, e.g., 1.5 as shown above. The cyclization reaction is carried out in the presence of an appropriate phosphorous trihalide, e.g., 1.6 as shown above, and an appropriate base, e.g., triethylamine (TEA), in an appropriate solvent, e.g., dichloromethane (DCM). Compounds of type 1.8 can be prepared by a substitution reaction of an appropriate N-heterocyclic phosphine halide, e.g., 1.7 as shown above. The substitution reaction is carried out in the presence of an appropriate thiourea, e.g., 1-(2-hydroxyethyl)-3-phenylthiourea as shown above, and an appropriate base, e.g., triethylamine, in an appropriate solvent, e.g., dichloromethane. As can be appreciated by one skilled in the art, the above reaction provides an example of a generalized approach wherein compounds similar in structure to the specific reactants above (compounds similar to compounds of type 1.1 and 1.2), can be substituted in the reaction to provide substituted N-heterocyclic phosphine analogs similar to Formula 1.4.

2. Route II

In one aspect, substituted phosphonate analogs can be prepared as shown below.

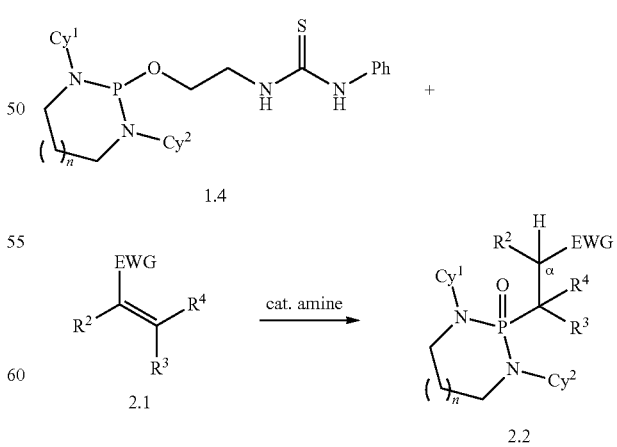

Compounds are represented in generic form, with substituents as noted in compound descriptions elsewhere herein. A more specific example is set forth below.

SCHEME 2B.

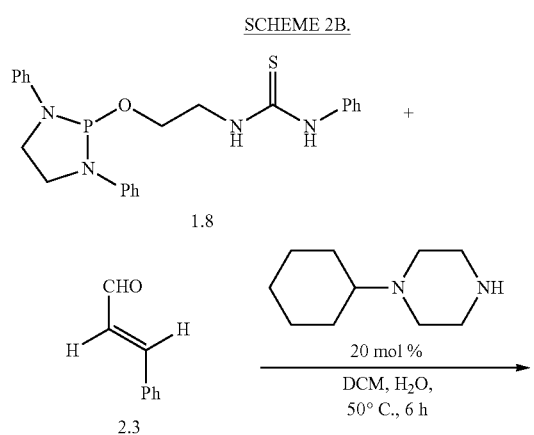

2.4

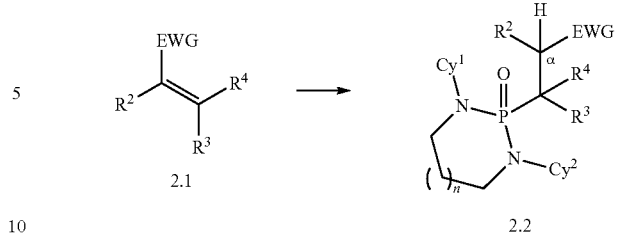

2.2

Compounds are represented in generic form, with substituents as noted in compound descriptions elsewhere herein. A more specific example is set forth below.

SCHEME 3B.

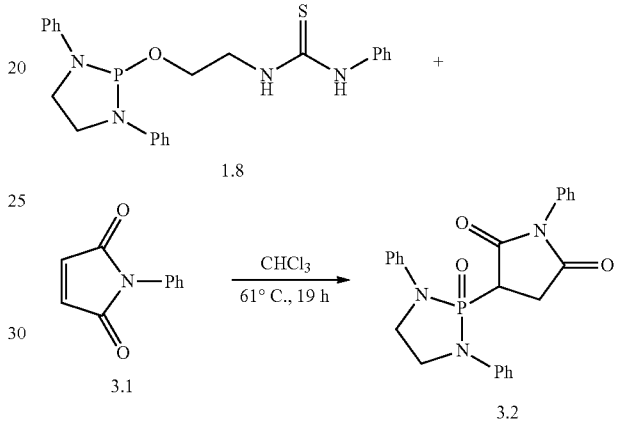

In one aspect, the synthesis of substituted phosphonate analogs can begin with an N-heterocyclic phosphine analog. N-heterocyclic phosphine analogs are commercially available or readily prepared by one skilled in the art. Thus, compounds of type 2.4, and similar compounds, can be prepared according to reaction Scheme 2B above. Compounds of type 2.4 can be prepared by a phospha-Michael addition of an appropriate N-heterocyclic phosphine analog, e.g., 1.8 as shown above. The phospha-Michael addition is carried out in the presence of an appropriate olefin, e.g., 2.3 as shown above, and an appropriate amine catalyst, e.g., 1-cyclohexylpiperazine, in an appropriate solvent system, e.g., dichloromethane and water, at an appropriate temperature, e.g., 50° C., for an appropriate period of time, e.g., 6 hours. As can be appreciated by one skilled in the art, the above reaction provides an example of a generalized approach wherein compounds similar in structure to the specific reactants above (compounds similar to compounds of type 1.4 and 2.1), can be substituted in the reaction to provide substituted phosphonate analogs similar to Formula 2.2.

3. Route III

In one aspect, substituted phosphonate analogs can be prepared as shown below.

In one aspect, the synthesis of substituted phosphonate analogs can begin with an N-heterocyclic phosphine analog. N-heterocyclic phosphine analogs are commercially available or readily prepared by one skilled in the art. Thus, compounds of type 3.2, and similar compounds, can be prepared according to reaction Scheme 3B above. Compounds of type 3.2 can be prepared by a phospha-Michael addition of an appropriate N-heterocyclic phosphine analog, e.g., 1.8 as shown above. The phospha-Michael addition is carried out in the presence of an appropriate olefin, e.g., 3.1 as shown above, in an appropriate solvent, e.g., chloroform, at an appropriate temperature, e.g., 61° C., for an appropriate period of time, e.g., 19 hours. As can be appreciated by one skilled in the art, the above reaction provides an example of a generalized approach wherein compounds similar in structure to the specific reactants above (compounds similar to compounds of type 1.4 and 2.1), can be substituted in the reaction to provide substituted phosphonate analogs similar to Formula 2.2.

4. Route IV

In one aspect, substituted phosphonate analogs can be prepared as shown below.

SCHEME 3A.

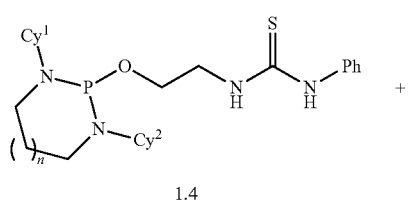

1.4

SCHEME 4A.

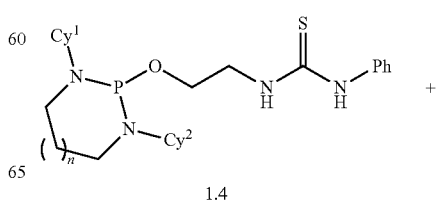

1.4

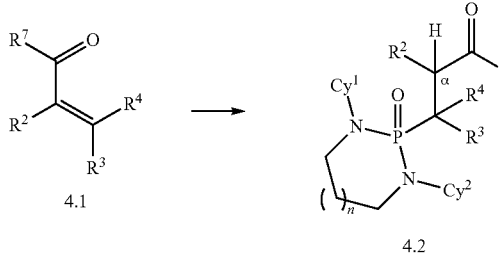

Compounds are represented in generic form, with substituents as noted in compound descriptions elsewhere herein. A more specific example is set forth below.

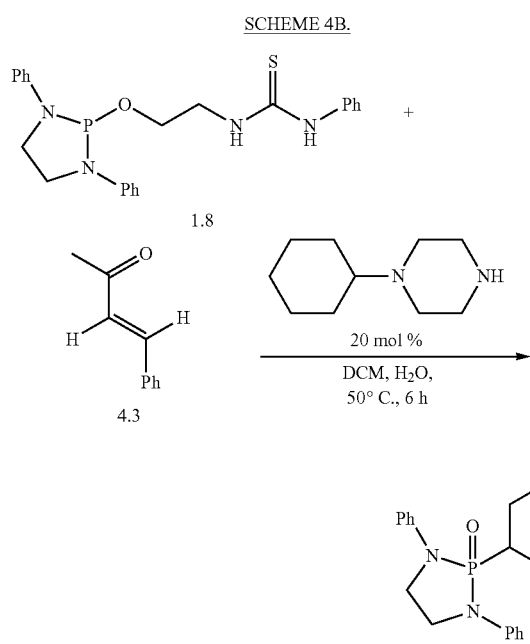

In one aspect, the synthesis of substituted phosphonate analogs can begin with an N-heterocyclic phosphine analog. N-heterocyclic phosphine analogs are commercially available or readily prepared by one skilled in the art. Thus, compounds of type 4.4, and similar compounds, can be prepared according to reaction Scheme 4B above. Compounds of type 4.4 can be prepared by a phospha-Michael addition of an appropriate N-heterocyclic phosphine analog, e.g., 1.8 as shown above. The phospha-Michael addition is carried out in the presence of an appropriate α, β-unsaturated carbonyl, e.g., 4.3 as shown above, and an appropriate amine catalyst, e.g., 1-cyclohexylpiperazine, in an appropriate solvent system, e.g., dichloromethane and water, at an appropriate temperature, e.g., 50° C., for an appropriate period of time, e.g., 6 hours. As can be appreciated by one skilled in the art, the above reaction provides an example of a generalized approach wherein compounds similar in structure to the specific reactants above (compounds similar to compounds of type 1.4 and 4.1), can be substituted in the reaction to provide substituted phosphonate analogs similar to Formula 4.2.

5. Route V

In one aspect, substituted phosphonate analogs can be prepared as shown below.

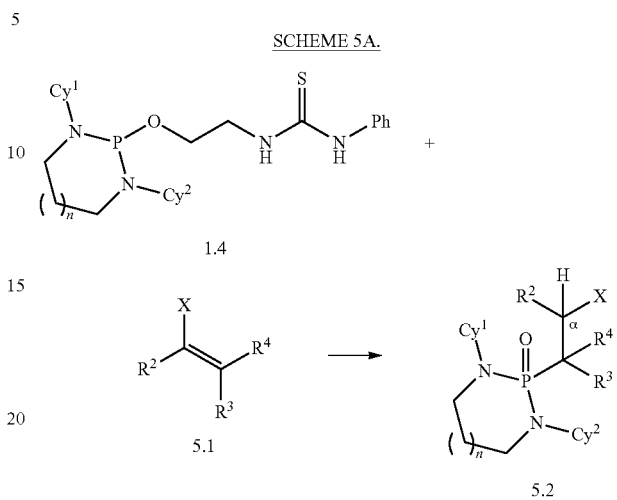

Compounds are represented in generic form, with substituents as noted in compound descriptions elsewhere herein and wherein X is selected from $NO_2$ and CN. A more specific example is set forth below.

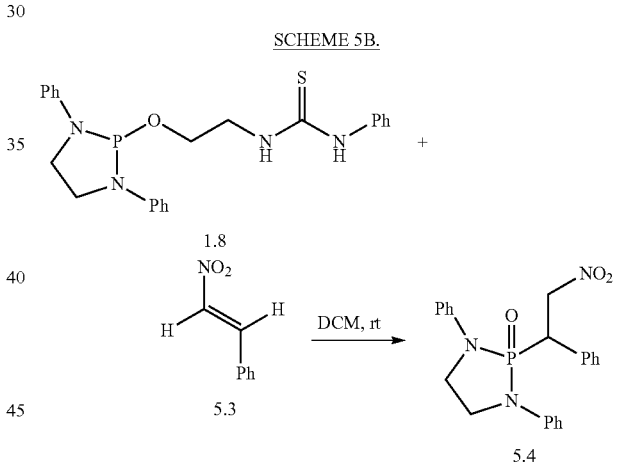

In one aspect, the synthesis of substituted phosphonate analogs can begin with an N-heterocyclic phosphine analog. N-heterocyclic phosphine analogs are commercially available or readily prepared by one skilled in the art. Thus, compounds of type 5.4, and similar compounds, can be prepared according to reaction Scheme 5B above. Compounds of type 5.4 can be prepared by a phospha-Michael addition of an appropriate N-heterocyclic phosphine analog, e.g., 1.8 as shown above. The phospha-Michael addition is carried out in the presence of an appropriate nitroolefin or cyanoolefin, e.g., 5.3 as shown above, in an appropriate solvent, e.g., dichloromethane, at an appropriate temperature, e.g., room temperature. As can be appreciated by one skilled in the art, the above reaction provides an example of a generalized approach wherein compounds similar in structure to the specific reactants above (compounds similar to compounds of type 1.4 and 5.1), can be substituted in the reaction to provide substituted phosphonate analogs similar to Formula 5.2.

D. Examples

The following examples are put forth so as to provide those of ordinary skill in the art with a complete disclosure and description of how the compounds, and/or methods disclosed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Examples are provided herein to illustrate the invention, and should not be construed as limiting the invention in any way.

1. General Experimental Methods

All reactions were carried out under an argon atmosphere in oven-dried glassware with magnetic stirring bar. Dry solvents (THF, toluene, and DCM) were obtained by solvent purification system under argon. All commercially available reagents were used as received without further purification. Purification of reaction products was carried out by flash column chromatography using silica gel 60 (230-400 mesh). Analytical thin layer chromatography was performed on 0.25 mm aluminum-backed silica gel 60-F plates. Visualization was accompanied with UV light and $KMnO_4$ solution. Concentration under reduced pressure refers to the removal of volatiles using a rotary evaporator attached to a dry diaphragm pump (10-15 mm Hg) followed by pumping to a constant weight with an oil pump (<300 mTorr). Infrared (IR) spectra were recorded on an IR spectrometer with KBr wafers or a film on KBr plate. High-resolution mass spectra (HRMS) were recorded on LCMS-IT-TOF mass spectrometer using ESI (electrospray ionization) or APCI (Atmospheric Pressure Chemical Ionization). $^1H$ NMR spectra were recorded in $CDCl_3$ on 400 MHz NMR spectrometer. The $^1H$ chemical shifts are referenced to residual solvent signals at δ 7.26 ($CHCl_3$) or δ 0.00 (TMS). $^1H$ NMR coupling constants (J) are reported in Hertz (Hz) and multiplicities are indicated as follows: s (singlet), bs (broad singlet), d (doublet), t (triplet), m (multiplet), dd (doublet of doublet), dt (doublet of triplet). $^{13}C$ NMR spectra were proton decoupled and recorded in $CDCl_3$ on 100.5 MHz NMR spectrometer. The $^{13}C$ chemical shifts are referenced to solvent signals at δ 77.16 ($CDCl_3$). $^{31}P$ NMR spectra were proton decoupled and recorded in $CDCl_3$ on 162 MHz NMR spectrometer. $^{31}P$ chemical shifts are reported relative to 85% $H_3PO_4$ (0.00 ppm) as an external standard.

2. General Procedure for the Synthesis of NHP-Thioureas

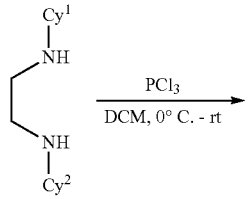

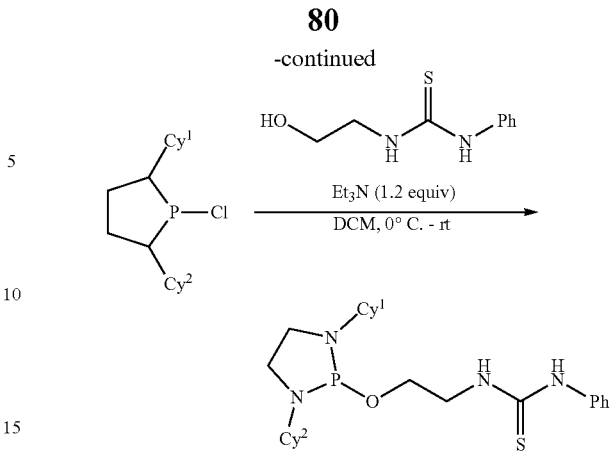

NHP-chloride was synthesized and characterized according to previously reported methodology (Robbie et al. (2011) *Polyhedron* 30: 1849-1856). To a solution of N,N'-diphenylethylenediamine (2.12 g, 10 mmol) in $CH_2Cl_2$ (40 mL) was added freshly distilled triethylamine (2.8 mL, 20 mmol). The solution was cooled to 0° C., and phosphorus trichloride (0.86 mL, 10 mmol) added dropwise over a period of 10 min giving a brown solution with small amounts of white precipitates. The solution was stirred at 0° C. for 30 min and then for 2 h at room temperature. After stirring for 2 h, volatiles were removed under reduced pressure. The orange/brown solid was extracted with THF (3×20 mL). The THF solutions were combined and evaporated to dryness in vacuo yielding NHP-Cl as a brown free-flowing solid.

NHP-thiourea was synthesized and characterized according to our previously reported methodology (Mulla et al. (2016) *J Org. Chem.* 81: 77-88). To a solution of NHP-chloride (3.62 mmol) in DCM (25 mL) were added amino substituted ethanol (3.62 mmol) and triethylamine (4.34 mmol) at 0° C. The reaction mixture was warmed up to room temperature and stirred for 2 h. After stirring for 2 h, the reaction mixture was concentrated under reduced pressure. The residue was subjected to column chromatography on silica gel (gradient eluent of Hexanes/EtOAc) to give the NHP-thiourea.

3. General Procedure for the Phosphite Addition to α, β-Unsaturated Aldehydes Employing NHP-Thioureas as Phosphonylation Reagents

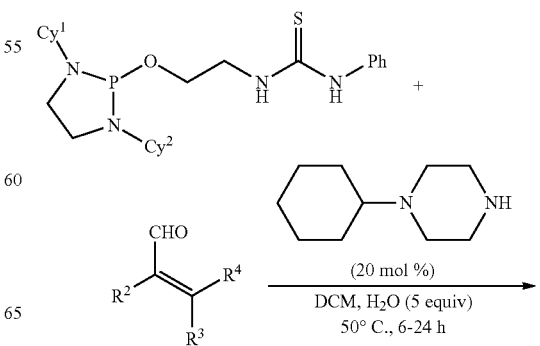

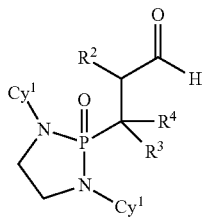

To a solution of NHP-thiourea (0.1 mmol), 1-cyclohexylpiperazine (0.02 mmol), H$_2$O (0.5 mmol) in DCM (0.5 mL) was added α,β-unsaturated aldehyde (0.3 mmol). The reaction mixture was heated in an oil bath at 50° C. for 6-24 h. After stirring for 6-24 h, the reaction mixture was cooled to room temperature and concentrated under reduced pressure. The residue was subjected to column chromatography on silica gel to give the corresponding product.

a. Synthesis of 3-(2-oxido-1,3-diphenyl-1,3,2-diazaphospholidin-2-yl)-3-phenylpropanal (3a)

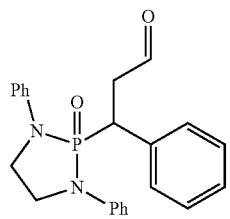

37 mg, 95% yield; white solid; mp 157-158° C.; R$_f$=0.25 (v$_{Hexane}$/v$_{EtOAc}$=1:1), v$_{Hexane}$/v$_{EtOAc}$/v$_{DCM}$ (6/2/1) for column; IR v (KBr, cm$^{-1}$) 3061, 2955, 2895, 1718, 1599, 1477, 1271, 1226, 1124, 1033, 954; $^1$H NMR (400 MHz, CDCl$_3$) δ 9.61 (t, J=1.6 Hz, 1H), 7.42-7.35 (m, 6H), 7.28 (d, J=8.4 Hz, 2H), 7.23-7.14 (m, 3H), 7.13-7.06 (m, 2H), 6.76-6.71 (m, 2H), 4.36-4.25 (m, 1H), 3.52-3.33 (m, 3H), 3.10-2.98 (m, 1H), 2.89-2.80 (m, 1H), 2.77-2.68 (m, 1H); $^{13}$C NMR (100.5 MHz, CDCl$_3$) δ 199.1 (d, J=16.4 Hz), 141.9 (dd, J=88.6, 9.0 Hz), 135.3 (d, J=6.7 Hz), 129.6 (d, J=17.1 Hz), 128.6 (d, J=5.9 Hz), 128.4 (d, J=3.7 Hz), 127.6 (d, J=3.8 Hz), 122.4 (d, J=54.3 Hz), 117.1 (dd, J=111.7, 4.5 Hz), 43.8 (d, J=8.2 Hz), 43.5, 42.5 (d, J=7.4 Hz), 40.8 (d, J=107.9 Hz); $^{31}$P NMR (162 MHz, CDCl$_3$): δ 28.91 ppm; HRMS (ESI): m/z calcd. for C$_{23}$H$_{23}$N$_2$O$_2$P ([M+H]$^+$): 391.1570; Found: 391.1567.

b. Synthesis of 3-(2-oxido-1,3-di-p-tolyl-1,3,2-diazaphospholidin-2-yl)-3-phenylpropanal (3b)

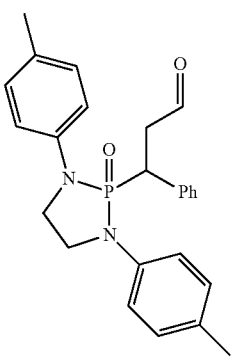

39.3 mg, 94% yield; white solid; mp 179-180° C.; R$_f$=0.32 (v$_{Hexane}$/v$_{EtOAc}$=1:1), v$_{Hexane}$/v$_{EtOAc}$/v$_{DCM}$ (6/2/1) for column; IR v (KBr, cm$^{-1}$) 3032, 2920, 2856, 1718, 1616, 1516, 1286, 1269, 1236, 1134, 960; $^1$H NMR (400 MHz, CDCl$_3$) δ 9.59 (dd, J=2.0, 0.8 Hz, 1H), 7.27 (d, J=8.4 Hz, 2H), 7.21-7.14 (m, 9H), 6.77-6.72 (m, 2H), 4.31-4.20 (m, 1H), 3.48-3.30 (m, 3H), 3.07-2.96 (m, 1H), 2.84-2.69 (m, 2H), 2.36 (s, 6H); $^{13}$C NMR (100.5 MHz, CDCl$_3$) δ 199.3 (d, J=16.4 Hz), 139.4 (dd, J=82.6, 8.2 Hz), 135.4 (d, J=6.7 Hz), 131.8 (d, J=61.8 Hz), 130.1 (d, J=14.9 Hz), 128.6 (d, J=5.9 Hz), 128.2 (d, J=3.0 Hz), 127.4 (d, J=3.7 Hz), 117.3 (dd, J=117.6, 4.5 Hz), 44.1 (d, J=7.4 Hz), 43.5, 42.7 (d, J=7.4 Hz), 40.7 (d, J=107.1 Hz), 20.7; $^{31}$P NMR (162 MHz, CDCl$_3$): δ 28.50 ppm; HRMS (ESI): m/z calcd. for C$_{25}$H$_{27}$N$_2$O$_2$P ([M+Na]$^+$): 441.1702; Found: 441.1701.

c. Synthesis of 3-(1,3-bis(4-methoxyphenyl)-2-oxido-1,3,2-diazaphospholidin-2-yl)-3-phenylpropanal (3c)

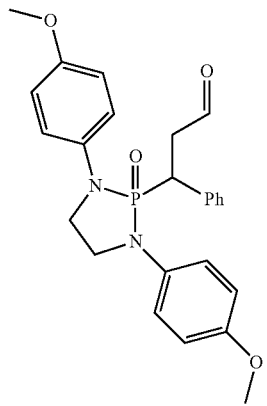

39.4 mg, 87% yield; white solid; mp 140-141° C.; R$_f$=0.14 (v$_{Hexane}$/v$_{EtOAc}$=1:1), v$_{Hexane}$/v$_{EtOAc}$/v$_{DCM}$ (1/2/4) for column; IR v (KBr, cm$^{-1}$) 3061, 2931, 2835, 1718, 1508, 1473, 1269, 1242, 1182, 1033, 960; $^1$H NMR (400 MHz, CDCl$_3$) δ 9.57 (dd, J=2.0, 0.8 Hz, 1H), 7.33 (d, J=8.8 Hz, 2H), 7.24-7.16 (m, 5H), 6.96-6.90 (m, 4H), 6.81-6.77 (m, 2H), 4.22-4.12 (m, 1H), 3.84 (d, J=2.4 Hz, 6H), 3.42-3.30 (m, 3H), 3.01-2.90 (m, 1H), 2.86-2.77 (m, 2H); $^{13}$C NMR (100.5 MHz, CDCl$_3$) δ 199.3 (d, J=16.4 Hz), 155.4 (d, J=38 Hz), 135.5 (dd, J=6.7, 3.7 Hz), 134.8 (d, J=8.2 Hz), 128.7 (d, J=5.2 Hz), 128.2 (d, J=3.0 Hz), 127.4 (d, J=3.7 Hz), 120.1 (d, J=3.7 Hz), 118.7 (d, J=4.5 Hz), 114.8 (dd, J=24.2 Hz), 55.5 (d, J=5.2 Hz), 44.9 (d, J=7.5 Hz), 43.52 (d, J=8.2 Hz), 43.5, 40.6 (d, J=108.7 Hz); $^{31}$P NMR (162 MHz, CDCl$_3$): δ 28.29 ppm; HRMS (ESI): m/z calcd. for C$_{25}$H$_{27}$N$_2$O$_4$P ([M+H]$^+$): 451.1781; Found: 451.1770.

d. Synthesis of 3-(2-oxido-1,3-diphenyl-1,3,2-diazaphospholidin-2-yl)-3-(p-tolyl)propanal (3e)

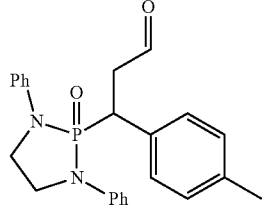

3e 37.1 mg, 92% yield; white solid; mp 138-139° C.; $R_f$=0.31 ($v_{Hexane}/v_{EtOAc}$=1:1), $v_{Hexane}/v_{EtOAc}/v_{DCM}$ (6/2/1) for column; IR v (KBr, cm$^{-1}$) 3059, 2945, 2924, 2889, 1720, 1599, 1498, 1473, 1271, 1226, 1122, 1035; $^1$H NMR (400 MHz, CDCl$_3$) δ 9.60-9.58 (m, 1H), 7.42-7.34 (m, 6H), 7.28 (d, J=8.4 Hz, 2H), 7.13-7.06 (m, 2H), 6.98 (d, J=8.4 Hz, 2H), 6.62 (dd, J=8.0, 2.8 Hz, 2H), 4.32-4.20 (m, 1H), 3.50-3.34 (m, 3H), 3.06-2.95 (m, 1H), 2.90-2.82 (m, 1H), 2.81-2.73 (m, 1H), 2.29 (d, J=4.0 Hz, 3H); $^{13}$C NMR (100.5 MHz, CDCl$_3$) δ 199.3 (d, J=16.3 Hz), 142.0 (dd, J=87.9, 8.1 Hz), 137.2 (d, J=3.7 Hz), 132.0 (d, J=6.7 Hz), 129.5 (d, J=16.4 Hz), 129.0 (d, J=3.0 Hz), 128.4 (d, J=6.0 Hz), 122.3 (d, J=53.6 Hz), 117.1 (dd, J=109.4, 3.7 Hz), 43.8 (d, J=7.5 Hz), 43.5, 42.5 (d, J=7.4 Hz), 40.4 (d, J=107.9 Hz), 21.0; $^{31}$P NMR (162 MHz, CDCl$_3$): δ 29.32 ppm; HRMS (ESI): m/z calcd. for C$_{24}$H$_{25}$N$_2$O$_2$P ([M+H]$^+$): 405.1726; Found: 405.1717.

e. Synthesis of 3-(4-methoxyphenyl)-3-(2-oxido-1,3-diphenyl-1,3,2-diazaphospholidin-2-yl)propanal (3f)

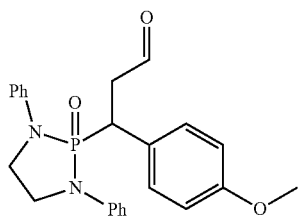

3f 38.6 mg, 92% yield; colorless oil; $R_f$=0.31 ($v_{Hexane}/v_{EtOAc}$=1:1), $v_{Hexane}/v_{EtOAc}/v_{DCM}$ (3/1/1) for column; IR v (KBr, cm$^{-1}$) 3061, 2928, 2837, 1720, 1599, 1500, 1473, 1269, 1251, 1228, 1180, 1124, 1033, 956; $^1$H NMR (400 MHz, CDCl$_3$) δ 9.60-9.57 (m, 1H), 7.42-7.34 (m, 6H), 7.28 (d, J=8.8 Hz, 2H), 7.12-7.06 (m, 2H), 6.73-6.69 (m, 2H), 6.69-6.62 (m, 2H), 4.29-4.19 (m, 1H), 3.76 (s, 3H), 3.51-3.36 (m, 3H), 3.04-2.92 (m, 1H), 2.92-2.78 (m, 2H); $^{13}$C NMR (100.5 MHz, CDCl$_3$) δ 199.3 (d, J=16.4 Hz), 158.9 (d, J=3.0 Hz), 141.9 (dd, J=87.1, 9.0 Hz), 129.6, 129.5, 129.4, 127.1 (d, J=6.7 Hz), 122.3 (d, J=53.5 Hz), 117.0 (dd, J=107.9, 3.7 Hz), 113.7 (d, J=3.0 Hz), 55.2, 43.8 (d, J=6.7 Hz), 43.7, 42.5 (d, J=8.2 Hz), 39.9 (d, J=108.7 Hz); $^{31}$P NMR (162 MHz, CDCl$_3$): δ 29.59 ppm; HRMS (ESI): m/z calcd. for C$_{24}$H$_{25}$N$_2$O$_3$P ([M+Na]$^+$): 443.1495; Found: 443.1504.

f. Synthesis of 3-(4-fluorophenyl)-3-(2-oxido-1,3-diphenyl-1,3,2-diazaphospholidin-2-yl)propanal (3g)

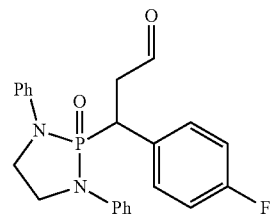

3g 34.1 mg, 84% yield; white solid; mp 170-171° C.; $R_f$=0.21 ($v_{Hexane}/v_{EtOAc}$=1:1), $v_{Hexane}/v_{EtOAc}/v_{DCM}$ (3/1/1) for column; IR v (KBr, cm$^{-1}$) 3061, 2928, 2893, 1712, 1599, 1508, 1500, 1477, 1271, 1226, 1120, 956; $^1$H NMR (400 MHz, CDCl$_3$) δ 9.60 (t, J=1.6 Hz, 1H), 7.43-7.36 (m, 6H), 7.28 (d, J=8.0 Hz, 2H), 7.14-7.07 (m, 2H), 6.88 (t, J=8.8 Hz, 2H), 6.73-6.68 (m, 2H), 4.34-4.23 (m, 1H), 3.55-3.40 (m, 3H), 3.06-2.80 (m, 3H); $^{13}$C NMR (100.5 MHz, CDCl$_3$) δ 198.7 (d, J=16.3 Hz), 162.0 (dd, J=245.6, 3.7 Hz), 141.8 (dd, J=87.8, 8.2 Hz), 131.2 (dd, J=6.7, 3.7 Hz), 130.1 (dd, J=8.2, 6.0 Hz), 129.7 (d, J=14.9 Hz), 122.6 (d, J=52.1 Hz), 117.2 (dd, J=106.4, 3.7 Hz), 115.3 (dd, J=20.9, 3.0 Hz), 44.0 (d, J=7.4 Hz), 43.8, 42.6 (d, J=8.2 Hz), 29.9 (d, J=108.7 Hz); $^{31}$P NMR (162 MHz, CDCl$_3$): δ 28.71 ppm; HRMS (ESI): m/z calcd. for C$_{23}$H$_{22}$FN$_2$O$_2$P ([M+H]$^+$): 409.1476; Found: 409.1468.

g. Synthesis of 3-(4-bromophenyl)-3-(2-oxido-1,3-diphenyl-1,3,2-diazaphospholidin-2-yl)propanal (3h)

3h 40.7 mg, 87% yield; white solid; mp 168-170° C.; $R_f$=0.27 ($v_{Hexane}/v_{EtOAc}$=1:1), $v_{Hexane}/v_{EtOAc}/v_{DCM}$ (3/1/1) for column; IR v (KBr, cm$^{-1}$) 3059, 2893, 2829, 1718, 1599, 1508, 1498, 1491, 1475, 1271, 1224, 1120, 956; $^1$H NMR (400 MHz, CDCl$_3$) δ 9.61-9.58 (m, 1H), 7.43-7.36 (m, 6H), 7.33-7.25 (m, 4H), 7.16-7.07 (m, 2H), 6.61 (dd, J=8.4, 2.4 Hz, 2H), 4.32-4.21 (m, 1H), 3.56-3.40 (m, 3H), 3.07-2.82 (m, 3H); $^{13}$C NMR (100.5 MHz, CDCl$_3$) δ 198.5 (d, J=16.4 Hz), 141.7 (dd, J=89.3, 8.2 Hz), 134.5 (d, J=6.7 Hz), 131.4 (d, J=2.9 Hz), 130.2 (d, J=5.9 Hz), 129.7 (d, J=14.9 Hz), 122.6 (d, J=51.3 Hz), 121.4 (d, J=4.4 Hz), 117.2 (dd, J=107.9, 4.4 Hz), 44.1 (d, J=7.5 Hz), 43.6, 42.7 (d, J=7.5 Hz), 40.1 (d, J=107.9 Hz); $^{31}$P NMR (162 MHz, CDCl$_3$): δ 27.94 ppm; HRMS (ESI): m/z calcd. for C$_{23}$H$_{22}$BrN$_2$O$_2$P ([M−H]$^-$: 467.0529; Found: 467.0537.

h. Synthesis of 3-(2-nitrophenyl)-3-(2-oxido-1,3-diphenyl-1,3,2-diazaphospholidin-2-yl)propanal

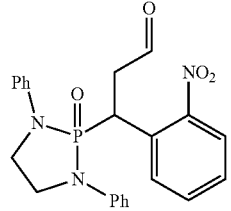

3i 39.1 mg, 90% yield; yellow oil; $R_f$=0.21 ($v_{Hexane}/v_{EtOAc}$=1:1), $v_{Hexane}/v_{EtOAc}/v_{DCM}$ (3/1/1) for column; IR v (KBr, cm$^{-1}$) 3061, 2926, 2879, 1722, 1599, 1527, 1492, 1352, 1265, 1230, 1122, 1035, 960; $^1$H NMR (400 MHz, CDCl$_3$) δ 9.49-9.47 (m, 1H), 7.65 (dd, J=8.0, 0.8 Hz, 1H), 7.37-7.29 (m, 5H), 7.26-7.07 (m, 7H), 6.97-6.91 (m, 1H), 5.27-5.17 (m, 1H), 3.66-3.59 (m, 2H), 3.56-3.46 (m, 1H), 3.33-23.21 (m, 2H), 3.19-3.07 (m, 1H); $^{13}$C NMR (100.5 MHz, CDCl$_3$) δ 198.1 (d, J=15.6 Hz), 149.8 (d, J=6.7 Hz), 141.4 (dd, J=32.7, 7.4 Hz), 132.4 (d, J=3.0 Hz), 130.3 (dd, J=19.4, 6.7 Hz), 129.3 (d, J=33.5 Hz), 127.9 (d, J=2.9 Hz), 125.0 (d, J=1.9 Hz), 122.8 (d, J=43.1 Hz), 117.6 (dd, J=29.8, 4.5 Hz), 44.7 (d, J=1.5 Hz), 43.4 (d, J=8.9 Hz), 42.9 (d, J=9.0 Hz), 35.3 (d, J=108.6 Hz); $^{31}$P NMR (162 MHz, CDCl$_3$): δ 25.36 ppm; HRMS (ESI): m/z calcd. for C$_{23}$H$_{22}$N$_3$O$_4$P ([M+Na]$^+$): 458.1240; Found: 458.1236.

i. Synthesis of 3-(furan-2-yl)-3-(2-oxido-1,3-diphenyl-1,3,2-diazaphospholidin-2-yl)propanal

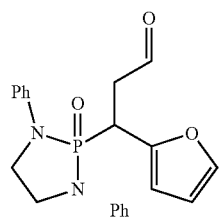

3j 24.2 mg, 64% yield; yellow oil; $R_f$=0.24 ($v_{Hexane}/v_{EtOAc}$=1:1), $v_{Hexane}/v_{EtOAc}/v_{DCM}$ (3/1/1) for column; IR v (KBr, cm$^{-1}$) 3061, 2951, 2883, 1724, 1599, 1500, 1473, 1269, 1230, 1122, 1035, 958; $^1$H NMR (400 MHz, CDCl$_3$) δ 9.57 (s, 1H), 7.40-7.36 (m, 6H), 7.30 (d, J=8.0 Hz, 2H), 7.26-7.23 (m, 1H), 7.13-7.05 (m, 2H), 6.26 (s, 1H), 5.80 (t, J=3.6 Hz, 1H), 4.39-4.28 (m, 1H), 3.66-3.58 (m, 1H), 3.55-3.46 (m, 1H), 3.36-3.23 (m, 2H), 3.10-3.02 (m, 1H), 2.99-2.88 (m, 1H); $^{13}$C NMR (100.5 MHz, CDCl$_3$) δ 198.6 (d, J=15.7 Hz), 149.5 (d, J=10.1 Hz), 141.6 (d, J=3.4 Hz), 141.5 (dd, J=69.2, 8.1 Hz), 129.5 (d, J=26.8 Hz), 122.6 (d, J=74.4 Hz), 117.7 (dd, J=164.5, 4.5 Hz), 110.7 (d, J=3.8 Hz), 108.0 (d, J=8.2 Hz), 43.5 (d, J=9.0 Hz), 42.8 (d, J=8.2 Hz), 41.8, 34.3 (d, J=111.6 Hz); $^{31}$P NMR (162 MHz, CDCl$_3$): δ 26.30 ppm; HRMS (ESI): m/z calcd. for C$_{21}$H$_{21}$N$_2$O$_3$P ([M+H]$^+$): 381.1363; Found: 381.1362.

j. Synthesis of 3-(2-oxido-1,3-diphenyl-1,3,2-diazaphospholidin-2-yl)hexanal (3k)

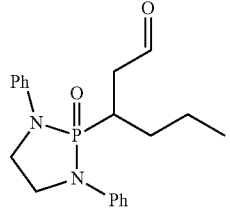

3k 25.9 mg, 73% yield; white solid; mp 105-106° C.; $R_f$=0.19 ($v_{Hexane}/v_{EtOAc}$=1:1), $v_{Hexane}/v_{EtOAc}/v_{DCM}$ (6/2/1) for column; IR v (KBr, cm$^{-1}$) 3060, 2930, 2874, 1718, 1599, 1508, 1500, 1491, 1481, 1273, 1220, 1128, 952; $^1$H NMR (400 MHz, CDCl$_3$) δ 9.55-9.51 (m, 1H), 7.38-7.31 (m, 8H), 7.09-7.04 (m, 2H), 3.93-3.71 (m, 4H), 3.07-2.95 (m, 1H), 2.84-2.72 (m, 1H), 2.40-2.28 (m, 1H), 1.77-1.68 (m, 2H), 1.25-1.11 (m, 2H), 0.76 (t, J=6.8 Hz, 3H); $^{13}$C NMR (100.5 MHz, CDCl$_3$) δ 200.3 (d, J=9.7 Hz), 141.8 (dd, J=7.5, 7.4 Hz), 129.5 (d, J=6.7 Hz), 122.7 (d, J=10.4 Hz), 118.0 (dd, J=10.5, 4.5 Hz), 44.4 (dd, J=11.9, 7.4 Hz), 43.8 (d, J=1.5 Hz), 34.0 (d, J=113.1 Hz), 31.5 (d, J=3.0 Hz), 21.1 (d, J=13.4 Hz), 13.7; $^{31}$P NMR (162 MHz, CDCl$_3$): δ 33.58 ppm; HRMS (ESI): m/z calcd. for C$_{20}$H$_{25}$N$_2$O$_2$P ([M+H]$^+$): 357.1726; Found: 357.1729.

k. Synthesis of (E)-3-(2-oxido-1,3-diphenyl-1,3,2-diazaphospholidin-2-yl)dec-4-enal (3l)

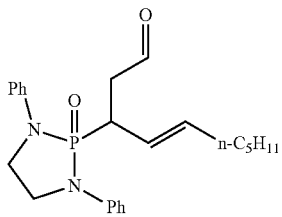

3l 11.2 mg, 27% yield; yellow oil; $R_f$=0.30 ($v_{Hexane}/v_{EtOAc}$=1:1), $v_{Hexane}/v_{EtOAc}/v_{DCM}$ (6/2/1) for column; IR v (KBr, cm$^{-1}$) 3061, 2955, 1926, 2856, 1724, 1599, 1498, 1269, 1228, 1124, 1035, 958; $^1$H NMR (400 MHz, CDCl$_3$) δ 9.54-9.52 (m, 1H), 7.41-7.28 (m, 8H), 7.11-7.03 (m, 2H), 5.33-5.23 (m, 1H), 5.08-5.00 (m, 1H), 3.84-3.61 (m, 5H), 3.07-2.98 (m, 1H), 2.53-2.42 (m, 1H), 1.93-1.84 (m, 2H), 1.31-1.14 (m, 6H), 0.87 (t, J=6.8 Hz, 3H); $^{13}$C NMR (100.5 MHz, CDCl$_3$) δ 199.7 (d, J=16.3 Hz), 141.7 (dd, J=46.9, 8.2 Hz), 129.5, 123.1 (d, J=8.2 Hz), 122.6 (d, J=61.1 Hz), 117.6 (dd, J=106.4, 4.5 Hz), 44.7 (d, J=7.5 Hz), 43.8 (d, J=7.5 Hz), 43.5, 38.4 (d, J=111.6 Hz), 32.5 (d, J=3.0 Hz), 31.3, 28.8 (d, J=3.8 Hz), 22.4, 14.0; $^{31}$P NMR (162 MHz, CDCl$_3$): δ 29.80 ppm; HRMS (ESI): m/z calcd. for C$_{24}$H$_{32}$N$_2$O$_2$P ([M+H]$^+$): 411.2196; Found: 411.2198.

1. Synthesis of 3-(2-oxido-1,3-diphenyl-1,3,2-diaza-phospholidin-2-yl)propanal (3m)

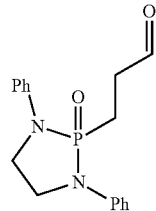

5.5 mg, 18% yield; white; $R_f$=0.38 ($v_{Hexane}/v_{EtOAc}/v_{DCM}$=1:2:4), $v_{Hexane}/v_{EtOAc}/v_{DCM}$ (1.5/1.5/4) for column; IR v (KBr, cm$^{-1}$) 3061, 2924, 2854, 1720, 1599, 1498, 1473, 1271, 1236, 1122, 1033, 997, 956; $^1$H NMR (400 MHz, CDCl$_3$) δ 9.48-9.46 (m, 1H), 7.38-7.28 (m, 8H), 7.09-7.04 (m, 2H), 3.83 (d, J=7.2 Hz, 4H), 2.57-2.41 (m, 4H); $^{13}$C NMR (100 MHz, CDCl$_3$) δ 199.4 (d, J=14.9 Hz), 141.3 (d, J=7.4 Hz), 129.6, 122.5, 116.9 (d, J=4.4 Hz), 43.7 (d, J=8.2 Hz), 37.5 (d, J=3.0 Hz), 20.5 (d, J=116.1 Hz); $^{31}$P NMR (162 MHz, CDCl$_3$): δ 30.67 ppm; HRMS (ESI): m/z calcd. for C$_{17}$H$_{20}$N$_2$O$_2$P ([M+H]$^+$): 315.1257; Found: 315.1248.

M. Synthesis of 3-methyl-3-(2-oxido-1,3-diphenyl-1,3,2-diazaphospholidin-2-yl)butanal (3p)

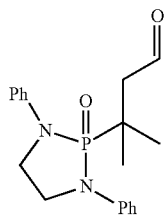

18.7 mg, 55% yield; white solid; mp 194-195° C.; $R_f$=0.37 ($v_{Hexane}/v_{EtOAc}$=1:1), $v_{Hexane}/v_{EtOAc}/v_{DCM}$ (6/2/1) for column; IR v (KBr, cm$^{-1}$) 2924, 2897, 2852, 1720, 1597, 1581, 1500, 1479, 1265, 1222, 1124, 1033, 950; $^1$H NMR (400 MHz, CDCl$_3$) δ 9.73-9.71 (m, 1H), 7.53-7.49 (m, 4H), 7.35-7.30 (m, 4H), 7.08 (tt, J=7.6, 1.2 Hz, 2H), 3.98-3.86 (m, 2H), 3.75-3.63 (m, 2H), 2.34 (dd, J=15.2, 2.8 Hz, 2H), 1.23 (d, J=17.2 Hz, 6H); $^{13}$C NMR (100.5 MHz, CDCl$_3$) δ 201.3 (d, J=8.9 Hz), 143.1 (d, J=6.7 Hz), 129.4, 123.4, 120.0 (d, J=4.1 Hz), 51.2, 45.7 (d, J=7.4 Hz), 41.5, 40.4, 24.2 (d, J=1.4 Hz); $^{31}$P NMR (162 MHz, CDCl$_3$): δ 35.02 ppm; HRMS (ESI): m/z calcd. for C$_{19}$H$_{23}$N$_2$O$_2$P ([M+H]$^+$): 343.1570; Found: 343.1577.

4. General Procedure for the Phosphite Addition to α,β-Unsaturated Ketones Employing NHP-Thioureas as Phosphonylation Reagent

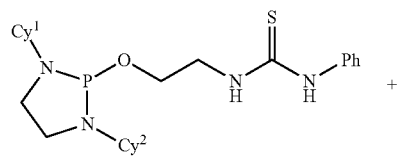 +

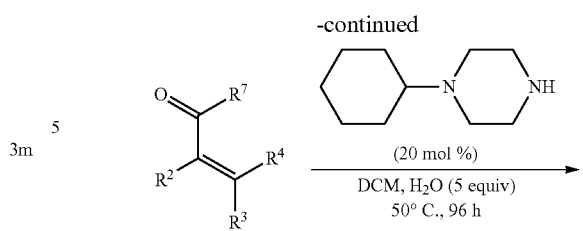

To a solution of NHP-thiourea (0.1 mmol), 1-cyclohexylpiperazine (0.02 mmol), H$_2$O (1.5 mmol) in DCM (0.5 mL) was added α,β-unsaturated ketone (0.3 mmol). The reaction mixture was heated in an oil bath at 50° C. for 96 h. After stirring for 96 h, the reaction mixture was cooled to room temperature and concentrated under reduced pressure. The residue was subjected to column chromatography on silica gel to give the corresponding product.

a. Synthesis of 4-(2-oxido-1,3-diphenyl-1,3,2-diazaphospholidin-2-yl)-4-phenylbutan-2-one (3q)

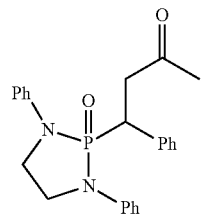

22.4 mg, 55% yield; white solid; mp 173-174° C.; $R_f$=0.29 ($v_{Hexane}/v_{EtOAc}$=1:1), $v_{Hexane}/v_{EtOAc}/v_{DCM}$ (6/2/1) for column; IR v (KBr, cm$^{-1}$) 3061, 3030, 2951, 2893, 1718, 1599, 1498, 1359, 1273, 1227, 1122, 956; $^1$H NMR (400 MHz, CDCl$_3$) δ 7.42-7.35 (m, 6H), 7.29-7.25 (m, 2H), 7.19-7.05 (m, 5H), 6.75-6.71 (m, 2H), 4.38-4.27 (m, 1H), 3.54-3.32 (m, 3H), 3.08-2.93 (m, 1H), 2.89-2.80 (m, 1H), 2.73-2.64 (m, 1H), 2.04 (s, 3H); $^{13}$C NMR (100.5 MHz, CDCl$_3$) δ 204.9 (d, J=14.9 Hz), 142.0 (dd, J=101.9, 8.1 Hz), 135.9 (d, J=6.7 Hz), 129.5 (d, J=22.3 Hz), 128.6 (d, J=6.0 Hz), 128.2 (d, J=3.7 Hz), 127.3 (d, J=3.7 Hz), 122.2 (d, J=45.4 Hz), 117.0 (dd, J=103.4, 4.5 Hz), 43.7 (d, J=7.5 Hz), 43.3, 41.9 (d, J=93.8 Hz), 30.1; $^{31}$P NMR (162 MHz, CDCl$_3$): δ 29.88 ppm; HRMS (ESI): m/z calcd. for C$_{24}$H$_{25}$N$_2$O$_2$P ([M+Na]$^+$): 427.1546; Found: 427.1543.

b. Synthesis of 4-(4-methoxyphenyl)-4-(2-oxido-1,3-diphenyl-1,3,2-diazaphospholidin-2-yl)butan-2-one (3r)

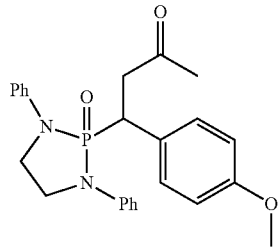

3r 8.5 mg, 20% yield; white solid; mp 157-158° C.; $R_f$=0.23 ($v_{Hexane}/v_{EtOAc}$=1:1), $v_{Hexane}/v_{EtOAc}/v_{DCM}$ (3/1/1) for column; IR v (KBr, cm$^{-1}$) 3059, 2953, 2895, 1716, 1599, 1514, 1498, 1271, 1224, 1178, 1035, 954; $^1$H NMR (400 MHz, CDCl$_3$) δ 7.42-7.36 (m, 6H), 7.29-7.25 (m, 2H), 7.13-7.05 (m, 2H), 6.72-6.63 (m, 4H), 4.30-4.20 (m, 1H), 3.76 (s, 3H), 3.51-3.36 (m, 3H), 3.03-2.92 (m, 1H), 2.92-2.85 (m, 1H), 2.83-2.75 (m, 1H), 2.03 (s, 3H); $^{13}$C NMR (100.5 MHz, CDCl$_3$) δ 205.0 (d, J=14.9 Hz), 158.7 (d, J=3.0 Hz), 142.1 (dd, J=101.2, 8.9 Hz), 129.629 (d, J=5.9 Hz), 129.621, 129.5, 129.4, 127.9 (d, J=6.7 Hz), 122.2 (d, J=42.4 Hz), 117.0 (dd, J=99.0, 4.5 Hz), 113.6 (d, J=3.0 Hz), 55.2, 43.7 (d, J=7.5 Hz), 43.5, 42.4 (d, J=7.4 Hz), 41.1 (d, J=108.7 Hz), 30.1; $^{31}$P NMR (162 MHz, CDCl$_3$): δ 30.54 ppm; HRMS (ESI): m/z calcd. for $C_{25}H_{27}N_2O_3P$ ([M+Na]$^+$): 457.1652; Found: 457.1663.

c. Synthesis of 4-(4-fluorophenyl)-4-(2-oxido-1,3-diphenyl-1,3,2-diazaphospholidin-2-yl)butan-2-one (3s)

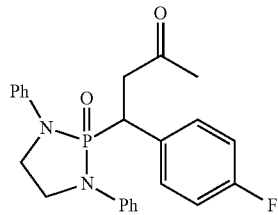

3s 21.0 mg, 50% yield; white solid; mp 183-184° C.; $R_f$=0.33 ($v_{Hexane}/v_{EtOAc}$=1:1), $v_{Hexane}/v_{EtOAc}/v_{DCM}$ (6/2/1) for column; IR v (KBr, cm$^{-1}$) 3059, 2943, 2889, 1718, 1599, 1508, 1500, 1491, 1271, 1226, 956; $^1$H NMR (400 MHz, CDCl$_3$) δ 7.43-7.36 (m, 6H), 7.27 (d, J=8.0 Hz, 2H), 7.14-7.06 (m, 2H), 6.86 (t, J=8.4 Hz, 2H), 6.73-6.67 (m, 2H), 4.34-4.24 (m, 1H), 3.55-3.39 (m, 3H), 3.03-2.89 (m, 2H), 2.86-2.77 (m, 1H), 2.04 (s, 3H); $^{13}$C NMR (100.5 MHz, CDCl$_3$) δ 204.7 (d, J=14.8 Hz), 161.8 (d, J=245.5), 141.9 (dd, J=99.7, 8.2 Hz), 131.8 (dd, J=6.7, 3.7 Hz), 130.1 (dd, J=8.2, 6.0 Hz), 129.6 (d, J=20.1 Hz), 122.4 (d, J=41.7 Hz), 117.0 (dd, J=96.7, 4.4 Hz), 115.1 (dd, J=20.8, 2.9 Hz), 43.9 (d, J=7.4 Hz), 43.5, 42.5 (d, J=8.2 Hz), 41.1 (d, J=108.6 Hz), 30.0; $^{31}$P NMR (162 MHz, CDCl$_3$): δ 29.61 ppm; HRMS (ESI): m/z calcd. for $C_{24}H_{24}FN_2O_2P$ ([M+Na]$^+$): 445.1452; Found: 445.1453.

d. Synthesis of 4-(4-chlorophenyl)-4-(2-oxido-1,3-diphenyl-1,3,2-diazaphospholidin-2-yl)butan-2-one (3t)

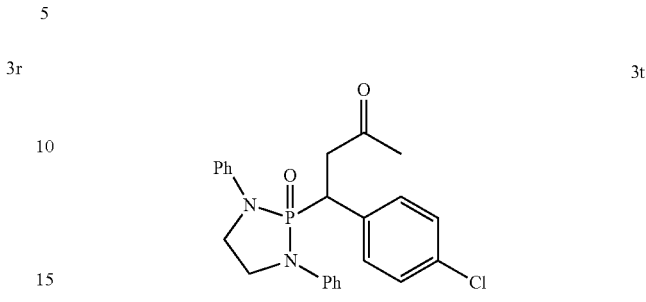

3t 21.2 mg, 48% yield; white solid; mp 186-187° C.; $R_f$=0.27 ($v_{Hexane}/v_{EtOAc}$=1:1), $v_{Hexane}/v_{EtOAc}/v_{DCM}$ (6/2/1) for column; IR v (KBr, cm$^{-1}$) 3061, 2953, 2895, 1722, 1599, 1496, 1477, 1359, 1271, 1222, 1124, 956; $^1$H NMR (400 MHz, CDCl$_3$) δ 7.43-7.35 (m, 6H), 7.27 (d, J=6.4 Hz, 2H), 7.16-7.07 (m, 4H), 6.66 (dd, J=8.8, 2.8 Hz, 2H), 4.34-4.23 (m, 1H), 3.54-3.39 (m, 3H), 3.03-2.90 (m, 2H), 2.86-2.77 (m, 1H), 2.03 (s, 3H); $^{13}$C NMR (100.5 MHz, CDCl$_3$) δ 204.6 (d, J=14.9 Hz), 141.9 (dd, J=101.2, 8.2 Hz), 134.7 (d, J=6.7 Hz), 133.1 (d, J=4.6 Hz), 129.9 (d, J=5.2 Hz), 129.6 (d, J=20.1 Hz), 128.4 (d, J=3.0 Hz), 122.5 (d, J=42.4 Hz), 117.1 (dd, J=97.5, 3.7 Hz), 44.0 (d, J=7.5 Hz), 43.4, 42.6 (d, J=7.4 Hz), 41.3 (d, J=107.9 Hz); $^{31}$P NMR (162 MHz, CDCl$_3$): δ 29.03 ppm; HRMS (ESI): m/z calcd. for $C_{24}H_{24}ClN_2O_2P$ ([M+Na]$^+$): 461.1156; Found: 461.1157.

e. Synthesis of 3-(2-oxido-1,3-diphenyl-1,3,2-diazaphospholidin-2-yl)cyclohexanone

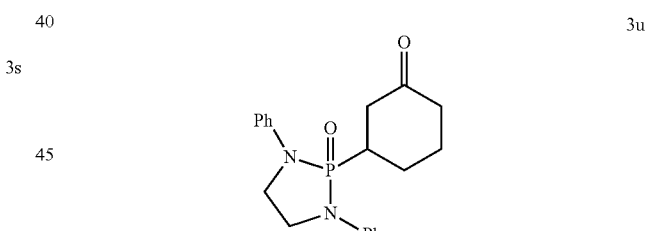

3u 21.0 mg, 59% yield; white solid; mp 226-227° C.; $R_f$=0.17 ($v_{Hexane}/v_{EtOAc}$=1:1), $v_{Hexane}/v_{EtOAc}/v_{DCM}$ (1/1/4) for column; IR v (KBr, cm$^{-1}$) 3059, 2935, 2893, 1712, 1599, 1500, 1479, 1271, 1220, 1126, 950; $^1$H NMR (400 MHz, CDCl$_3$) δ 7.42-7.30 (m, 8H), 7.10-7.03 (m, 2H), 3.92-3.75 (m, 4H), 2.73-2.60 (m, 1H), 2.52-2.44 (m, 1H), 2.31-2.15 (m, 3H), 2.11-1.95 (m, 2H), 1.63-1.45 (m, 2H); $^{13}$C NMR (100.5 MHz, CDCl$_3$) δ 208.6 (d, J=17.1 Hz), 141.9 (dd, J=39.4, 7.4 Hz), 129.6 (d, J=7.4 Hz), 122.7 (d, J=15.7 Hz), 117.9 (dd, J=58.8, 4.5 Hz), 44.7 (d, J=8.1 Hz), 44.1 (d, J=7.4 Hz), 41.5 (d, J=3.7 Hz), 40.5 (d, J=76.6 Hz), 38.9, 26.1 (d, J=19.4 Hz), 25.9 (d, J=4.5 Hz); $^{31}$P NMR (162 MHz, CDCl$_3$): δ 29.85 ppm; HRMS (ESI): m/z calcd. for $C_{20}H_{23}N_2O_2P$ ([M+Na]$^+$): 377.1389; Found: 377.1395.

f. Synthesis of 3-methyl-3-(2-oxido-1,3-diphenyl-1,3,2-diazaphospholidin-2-yl)cyclohexanone (3v)

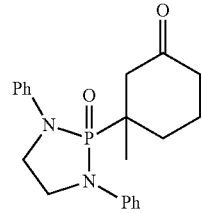

7.9 mg, 22% yield; white solid; mp 186-187° C.; $R_f$=0.20 ($v_{Hexane}/v_{EtOAc}$=1:1), $v_{Hexane}/v_{EtOAc}/v_{DCM}$ (4/1/1) for column; IR v (KBr, cm$^{-1}$) 3059, 2957, 2893, 1712, 1599, 1498, 1483, 1267, 1217, 1120, 954; $^1$H NMR (400 MHz, CDCl$_3$) δ 7.53-7.47 (m, 4H), 7.36-7.29 (m, 4H), 7.11-7.04 (m, 2H), 4.00-3.88 (m, 2H), 3.79-3.67 (m, 2H), 2.68 (dd, J=13.6, 10.8 Hz, 1H), 2.26-2.02 (m, 4H), 1.93-1.84 (m, 1H), 1.77-1.63 (m, 1H), 1.62-1.53 (m, 1H), 1.06 (d, J=18.4 Hz, 3H); $^{13}$C NMR (100.5 MHz, CDCl$_3$) δ 209.5 (d, J=15.6 Hz), 143.1 (dd, J=12.7, 6.7 Hz), 129.4 (d, J=4.5 Hz), 123.3 (d, J=4.5 Hz), 119.8 (dd, J=12.6, 3.7 Hz), 48.2 (d, J=2.2 Hz), 46.9, 45.69, 45.67 (d, J=8.2 Hz), 40.8, 31.0 (d, J=2.3 Hz), 21.7 (d, J=14.1 Hz), 19.2; $^{31}$P NMR (162 MHz, CDCl$_3$): δ 33.72 ppm; HRMS (ESI): m/z calcd. for C$_{21}$H$_{25}$N$_2$O$_2$P ([M+Na]$^+$): 391.1546; Found: 391.1545.

5. General Procedure for the Phosphite Addition to Nitroolefins Employing NHP-Thioureas as Phosphorous Reagents

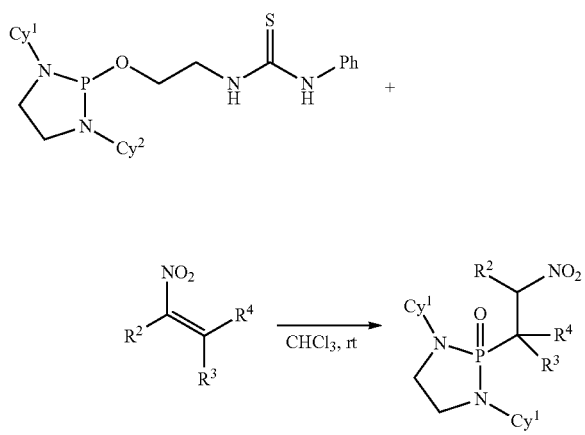

NHP-thioureas (0.1 mmol) and nitroalkenes (0.12 mmol) were dissolved in CHCl$_3$ (0.3 mL) in a 2 dram vial. The resulting reaction mixtures were stirred at room temperature for 4 h. After stirring for 4 h, the volatiles were removed under reduced pressure. The residue was subjected to column chromatography on silica gel to give the corresponding products.

a. Synthesis of 2-(2-nitro-1-phenylethyl)-1,3-diphenyl-1,3,2-diazaphospholidine 2-oxide (3$^{a1}$)

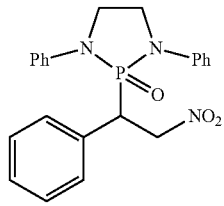 [SMILES: O=[N+]([O-])CC(c1ccccc1)P1(=O)N(c2ccccc2)CCN1c1ccccc1]

37.0 mg, 91% yield; white solid; mp 150° C. (decomp.); $R_f$ 0.20 ($v_{Hexane}/v_{EA}$=2:1), $v_{Hexane}/v_{EA}/v_{DCM}$ (8/2/1) for column; IR v (KBr, cm$^{-1}$) 3061, 2958, 2858, 1599, 1554, 1498, 1375, 1269, 1230, 1124, 958; $^1$H NMR (400 MHz, CDCl$_3$) δ 7.46-7.37 (m, 4H), 7.34-7.29 (m, 4H), 7.28-7.12 (m, 5H), 6.75-6.70 (m, 2H), 5.32-5.25 (m, 1H), 4.95-4.85 (m, 1H), 4.66-4.55 (m, 1H), 3.53-3.37 (m, 2H), 2.93-2.85 (m, 1H), 2.80-2.72 (m, 1H); $^{13}$C NMR (100 MHz, CDCl$_3$) δ 141.2 (dd, J=74.4, 8.2 Hz), 132.0 (d, J=7.4 Hz), 129.8 (d, J=5.2 Hz), 128.6 (d, J=3.7 Hz), 128.3 (d, J=3.7 Hz), 128.2 (d, J=5.2 Hz), 123.0 (d, J=44.6 Hz), 117.1 (dd, J=63.3, 4.5 Hz), 74.6 (d, J=5.9 Hz), 45.8 (d, J=102.7 Hz), 43.7 (d, J=8.2 Hz), 42.6 (d, J=8.1 Hz); $^{31}$P NMR (162 MHz, CDCl$_3$): δ 21.65 ppm; FIRMS (ESI$^+$): m/z calcd. for C$_{22}$H$_{22}$N$_3$O$_3$P [M+Na]$^+$: 430.1291; Found: 430.1293.

b. Synthesis of 2-(2-nitro-1-phenylethyl)-1,3-di-p-tolyl-1,3,2-diazaphospholidine 2-oxide (3b')

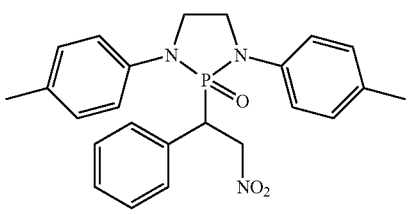

38.2 mg, 88% yield; white solid; mp 155° C. (decomp.); $R_f$ 0.20 ($v_{Hexane}/v_{EA}$=2:1), $v_{Hexane}/v_{EA}/v_{DCM}$ (8/2/1) for column; IR v (KBr, cm$^{-1}$) 3032, 2960, 2918, 2877, 1618, 1554, 1514, 1473, 1375, 1363, 1269, 1234, 964; $^1$H NMR (400 MHz, CDCl$_3$) δ 7.26-7.17 (m, 11H), 6.77-6.72 (m, 2H), 5.28-5.21 (m, 1H), 4.92-4.83 (m, 1H), 4.61-4.49 (m, 1H), 3.49-3.33 (m, 2H), 2.89-2.81 (m, 1H), 2.80-2.72 (m, 1H), 2.37 (s, 6H); $^{13}$C NMR (100 MHz, CDCl$_3$) δ 138.7 (dd, J=69.9, 8.1 Hz), 132.5 (d, J=48.3 Hz), 132.2 (d, J=6.7 Hz), 130.3 (d, J=3.0 Hz), 128.5 (d, J=3.0 Hz), 128.3 (d, J=5.2 Hz), 128.2 (d, J=3.7 Hz), 117.4 (dd, J=63.3, 3.8 Hz), 74.7 (d, J=5.9 Hz), 45.7 (d, J=102.7 Hz), 44.0 (d, J=8.2 Hz), 42.9 (d, J=9.0 Hz), 20.7 (d, J=2.2 Hz); $^{31}$P NMR (162 MHz, CDCl$_3$): δ 24.10 ppm; HRMS (ESI$^-$): m/z calcd. for C$_{24}$H$_{26}$N$_3$O$_3$P [M+Na]$^+$: 458.1604; Found: 458.1605.

c. Synthesis of 1,3-bis(4-methoxyphenyl)-2-(2-nitro-1-phenylethyl)-1,3,2-diazaphospholidine 2-oxide (3e)

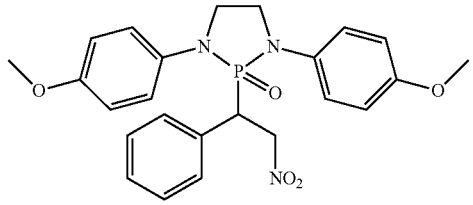

42.4 mg, 91% yield; white solid; mp 185° C. (decomp.); $R_f$ 0.16 ($v_{Hexane}/v_{EA}$=2:1), $v_{Hexane}/v_{EA}/v_{DCM}$ (1/1/4) for column; IR v (KBr, cm$^{-1}$) 3007, 2960, 2910, 2839, 1556, 1510, 1458, 1375, 1273, 1244, 1188, 1031, 962; $^1$H NMR (400 MHz, CDCl$_3$) δ 7.26-7.17 (m, 11H), 6.77-6.72 (m, 2H), 5.28-5.21 (m, 1H), 4.92-4.83 (m, 1H), 4.61-4.49 (m, 1H), 3.49-3.33 (m, 2H), 2.89-2.81 (m, 1H), 2.80-2.72 (m, 1H), 2.37 (s, 6H); $^{13}$C NMR (100 MHz, CDCl$_3$) δ 155.8 (d, J=21.6 Hz), 134.3 (dd, J=61.0, 8.2 Hz), 132.3 (d, J=6.7 Hz), 128.5 (d, J=3.0 Hz), 128.4 (d, J=5.2 Hz), 128.2 (d, J=3.7 Hz), 119.6 (dd, J=69.2, 3.8 Hz), 115.0 (d, J=8.2 Hz), 74.7 (d, J=5.3 Hz), 55.5 (d, J=3.7 Hz), 45.7 (d, J=103.4 Hz), 44.9 (d, J=8.2 Hz), 43.8 (d, J=8.2 Hz); $^{31}$P NMR (162 MHz, CDCl$_3$): δ 23.89 ppm; HRMS (ESI$^+$): m/z calcd. for C$_{24}$H$_{26}$N$_3$O$_5$P [M+Na]$^+$: 490.1502; Found: 490.1511.

d. Synthesis of 2-(2-nitro-1-(p-tolyl)ethyl)-1,3-diphenyl-1,3,2-diazaphospholidine 2-oxide (3e')

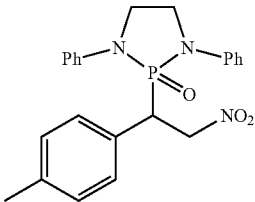 [SMILES: Cc1ccc(C(C[N+](=O)[O-])P2(=O)N(c3ccccc3)CCN2c2ccccc2)cc1]

379. mg, 90% yield; white solid; mp 168° C. (decomp.); $R_f$ 0.20 ($v_{Hexane}/v_{EA}$=2:1), $v_{Hexane}/v_{EA}/v_{DCM}$ (8/2/1) for column; IR v (KBr, cm$^{-1}$) 3061, 2916, 2893, 1599, 1554, 1498, 1371, 1269, 1236, 1120, 958; $^1$H NMR (400 MHz, CDCl$_3$) δ 7.46-7.37 (m, 4H), 7.34-7.29 (m, 4H), 7.15-7.11 (m, 2H), 7.00 (d, J=8.4 Hz, 2H), 6.60 (dd, J=8.0, 2.4 Hz, 2H), 5.29-5.21 (m, 1H), 4.91-4.82 (m, 1H), 4.61-4.50 (m, 1H), 3.53-3.37 (m, 2H), 2.95-2.87 (m, 1H), 2.84-2.78 (m, 1H), 2.29 (d, J=2.4 Hz, 3H); $^{13}$C NMR (100 MHz, CDCl$_3$) δ 141.3 (dd, J=75.9, 8.9 Hz), 138.2 (d, J=3.7 Hz), 129.8 (d, J=4.5 Hz), 129.3 (d, J=2.9 Hz), 128.8 (d, J=6.7 Hz), 128.1 (d, J=5.9 Hz), 122.9 (d, J=43.2 Hz), 117.1 (dd, J=61.0, 4.4 Hz), 74.8 (d, J=6.0 Hz), 44.4 (d, J=103.4 Hz), 43.7 (d, J=8.2 Hz), 42.6 (d, J=8.2 Hz), 21.1; $^{31}$P NMR (162 MHz, CDCl$_3$): δ 24.82 ppm; HRMS (ESI$^+$): m/z calcd. for C$_{23}$H$_{24}$N$_3$O$_3$P [M+Na]$^+$: 444.1447; Found: 444.1441.

e. Synthesis of 2-(1-(4-methoxyphenyl)-2-nitroethyl)-1,3-diphenyl-1,3,2-diazaphospholidine 2-oxide (3f')

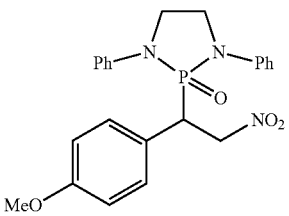 [SMILES: COc1ccc(C(C[N+](=O)[O-])P2(=O)N(c3ccccc3)CCN2c2ccccc2)cc1]

30.8 mg, 70% yield; white solid; mp 174° C. (decomp.); $R_f$ 0.20 ($v_{Hexane}/v_{EA}$=2:1), $v_{Hexane}/v_{EA}/v_{DCM}$ (8/2/1) for column; IR v (KBr, cm$^{-1}$) 3061, 2957, 2891, 1600, 1554, 1512, 1373, 1273, 1255, 1226, 1180, 1035, 958; $^1$H NMR (400 MHz, CDCl$_3$) δ 7.46-7.37 (m, 4H), 7.32 (t, J=8.4 Hz, 4H), 7.17-7.11 (m, 2H), 6.75-6.70 (m, 2H), 6.66-6.61 (m, 2H), 5.29-5.22 (m, 1H), 4.88-4.79 (m, 1H), 4.59-4.48 (m, 1H), 3.76 (s, 6H), 3.54-3.39 (m, 2H), 3.06-2.95 (m, 1H), 2.98-2.82 (m, 1H); $^{13}$C NMR (100 MHz, CDCl$_3$) δ 159.5 (d, J=2.9 Hz), 141.3 (dd, J=76.6, 8.9 Hz), 129.8 (d, J=3.0 Hz), 129.4 (d, J=5.2 Hz), 123.7 (d, J=6.7 Hz), 122.9 (d, J=42.4 Hz), 117.1 (dd, J=58.8, 4.5 Hz), 114.0 (d, J=3.0 Hz), 74.9 (d, J=7.4 Hz), 55.2, 45.0 (d, J=104.9 Hz), 43.7 (d, J=8.2 Hz), 42.6 (d, J=8.1 Hz); $^{31}$P NMR (162 MHz, CDCl$_3$): δ 25.10 ppm; HRMS (ESI$^+$): m/z calcd. for C$_{23}$H$_{24}$N$_3$O$_4$P [M+Na]$^+$: 460.1397; Found: 460.1389.

f. Synthesis of 2-(1-(4-(dimethylamino)phenyl)-2-nitroethyl)-1,3-diphenyl-1,3,2-diazaphospholidine 2-oxide (3g')

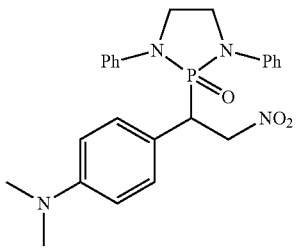 [SMILES: CN(C)c1ccc(C(C[N+](=O)[O-])P2(=O)N(c3ccccc3)CCN2c2ccccc2)cc1]

32.9 mg, 73% yield; white solid; mp 146° C. (decomp.); $R_f$ 0.14 ($v_{Hexane}/v_{EA}$=2:1), $v_{Hexane}/v_{EA}/v_{DCM}$ (3/1/1) for column; IR v (KBr, cm$^{-1}$) 3059, 2951, 2891, 1618, 1599, 1552, 1527, 1375, 1269, 1230, 1122, 956; $^1$H NMR (400 MHz, CDCl$_3$) δ 7.45-7.37 (m, 4H), 7.36-7.29 (m, 4H), 7.15-7.10 (m, 2H), 6.59-6.48 (m, 4H), 5.28-5.21 (m, 1H), 4.87-4.78 (m, 1H), 4.54-4.42 (m, 1H), 3.52-3.38 (m, 2H), 3.00-2.86 (m, 2H), 2.91 (s, 6H); $^{13}$C NMR (100 MHz, CDCl$_3$) δ 150.2 (d, J=2.2 Hz), 141.5 (dd, J=76.7, 8.9 Hz), 129.7 (d, J=2.2 Hz), 129.0 (d, J=5.2 Hz), 122.7 (d, J=41.0 Hz), 118.7 (d, J=7.5 Hz), 117.0 (dd, J=55.8, 4.8 Hz), 112.1 (d, J=2.2 Hz), 75.0 (d, J=7.4 Hz), 45.0 (d, J=104.2 Hz), 43.6 (d, J=7.5 Hz), 42.5 (d, J=8.2 Hz), 40.3; $^{31}$P NMR (162 MHz, CDCl$_3$): δ 26.06 ppm; HRMS (ESI$^+$): m/z calcd. for C$_{24}$H$_{27}$N$_4$O$_3$P [M+Na]$^+$: 473.1713; Found: 473.1710.

g. Synthesis of 2-(1-(4-fluorophenyl)-2-nitroethyl)-1,3-diphenyl-1,3,2-diazaphospholidine 2-oxide (3h')

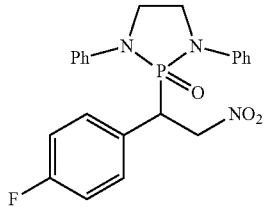 [SMILES: O=[N+]([O-])CC(c1ccc(F)cc1)P1(=O)N(c2ccccc2)CCN1c1ccccc1]

37.4 mg, 88% yield; white solid; mp 162° C. (decomp.); $R_f$ 0.20 ($v_{Hexane}/v_{EA}$=2:1), $v_{Hexane}/v_{EA}/v_{DCM}$ (8/2/1) for column; IR v (KBr, cm$^{-1}$) 3066, 2951, 2893, 1599, 1554, 1500, 1477, 1373, 1267, 1232, 1161, 1124, 1105, 956; $^1$H NMR (400 MHz, CDCl$_3$) δ 7.46-7.38 (m, 4H), 7.35-7.29 (m, 4H), 7.19-7.13 (m, 2H), 6.91 (t, J=8.4 Hz, 2H), 6.73-6.67 (m, 2H), 5.30-5.24 (m, 1H), 4.88-4.79 (m, 1H), 4.63-4.52 (m, 1H), 3.58-3.43 (m, 2H), 3.02-2.93 (m, 1H), 2.92-2.84 (m, 1H); $^{13}$C NMR (100 MHz, CDCl$_3$) δ 161.2 (d, J=3.7 Hz), 141.1 (dd, J=75.9, 8.9 Hz), 130.0, 129.9 (d, J=3.7 Hz), 127.9 (dd, J=4.6, 2.3 Hz), 123.2 (d, J=42.5 Hz), 117.2 (dd, J=59.5, 4.4 Hz), 115.2 (dd, J=21.6, 3.0 Hz), 74.8 (d, J=6.7 Hz), 45.0 (d, J=104.2 Hz), 43.9 (d, J=8.2 Hz), 42.8 (d, J=8.2 Hz); $^{31}$P NMR (162 MHz, CDCl$_3$): δ 23.33 ppm; HRMS (ESI$^+$): m/z calcd. for C$_{22}$H$_{21}$FN$_3$O$_3$P [M+Na]$^+$: 448.1197; Found: 448.1200.

h. Synthesis of 2-(1-(4-chlorophenyl)-2-nitroethyl)-1,3-diphenyl-1,3,2-diazaphospholidine 2-oxide (3i')

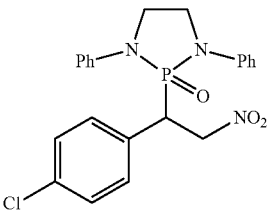 [SMILES: O=[N+]([O-])CC(c1ccc(Cl)cc1)P1(=O)N(c2ccccc2)CCN1c1ccccc1]

36.7 mg, 83% yield; white solid; mp 172° C. (decomp.); $R_f$ 0.22 ($v_{Hexane}/v_{EA}$=2:1), $v_{Hexane}/v_{EA}/v_{DCM}$ (8/2/1) for column; IR v (KBr, cm$^{-1}$) 3063, 2947, 2895, 1599, 1554, 1491, 1475, 1369, 1267, 1232, 1124, 956; $^1$H NMR (400 MHz, CDCl$_3$) δ 7.46-7.38 (m, 4H), 7.35-7.28 (m, 4H), 7.22-7.13 (m, 4H), 6.69-6.63 (m, 2H), 5.30-5.23 (m, 1H), 4.88-4.78 (m, 1H), 4.63-4.51 (m, 1H), 3.58-3.42 (m, 2H), 3.04-2.95 (m, 1H), 2.93-2.85 (m, 1H); $^{13}$C NMR (100 MHz, CDCl$_3$) δ 141.0 (dd, J=75.2, 8.2 Hz), 134.3 (d, J=4.4 Hz), 130.7 (d, J=6.7 Hz), 129.9 (d, J=3.8 Hz), 129.6 (d, J=5.2 Hz), 128.9 (d, J=2.9 Hz), 123.2 (d, J=43.2 Hz), 117.2 (dd, J=60.2, 4.4 Hz), 74.6 (d, J=6.0 Hz), 45.2 (d, J=103.4 Hz), 44.0 (d, J=8.2 Hz), 42.8 (d, J=8.2 Hz); $^{31}$P NMR (162 MHz, CDCl$_3$): δ 23.57 ppm; FIRMS (ESI$^+$): m/z calcd. for C$_{22}$H$_{21}$ClN$_3$O$_3$P [M+Na]$^+$: 464.0901; Found: 464.0911.

i. Synthesis of 2-(1-(4-bromophenyl)-2-nitroethyl)-1,3-diphenyl-1,3,2-diazaphospholidine 2-oxide (3j')

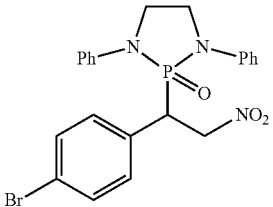

38.3 mg, 79% yield; white solid; mp 167° C. (decomp.); $R_f$ 0.22 ($v_{Hexane}/v_{EA}$=2:1), $v_{Hexane}/v_{EA}/v_{DCM}$ (8/2/1) for column; IR v (KBr, cm$^{-1}$) 3059, 2918, 2893, 159, 1554, 1500, 1477, 1371, 1265, 1228, 1120, 956; $^1$H NMR (400 MHz, CDCl$_3$) δ 7.46-7.38 (m, 4H), 7.36-7.28 (m, 6H), 7.18-7.13 (m, 2H), 6.62-6.57 (m, 2H), 5.30-5.23 (m, 1H), 4.88-4.78 (m, 1H), 4.61-4.49 (m, 1H), 3.58-3.42 (m, 2H), 3.04-2.95 (m, 1H), 2.93-2.85 (m, 1H); $^{13}$C NMR (100 MHz, CDCl$_3$) δ 141.0 (dd, J=75.2, 8.2 Hz), 131.8 (d, J=3.0 Hz), 131.2 (d, J=6.7 Hz), 129.9 (d, J=3.8 Hz), 129.8 (d, J=59 Hz), 123.2 (d, J=43.2 Hz), 122.4 (d, J=4.4 Hz), 117.2 (dd, J=59.6, 4.5 Hz), 74.5 (d, J=5.2 Hz), 45.3 (d, J=103.5 Hz), 44.0 (d, J=8.1 Hz), 42.8 (d, J=8.2 Hz); $^{31}$P NMR (162 MHz, CDCl$_3$): δ 23.34 ppm; HRMS (ESI$^+$): m/z calcd. for C$_{22}$H$_{21}$BrN$_3$O$_3$P [M+Na]$^+$: 508.0396; Found: 508.0418.

j. Synthesis of 2-(2-nitro-1-(4-(trifluoromethyl)phenyl)ethyl)-1,3-diphenyl-1,3,2-diazaphospholidine 2-oxide (3k')

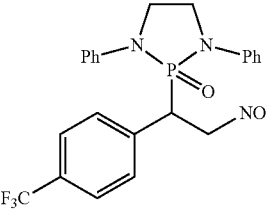

42.3 mg, 89% yield; white solid; mp 200° C. (decomp.); $R_f$ 0.26 ($v_{Hexane}/v_{EA}$=2:1), $v_{Hexane}/v_{EA}/v_{DCM}$ (8/2/1) for column; IR v (KBr, cm$^{-1}$) 3061, 2920, 2885, 1599, 1558, 1500, 1327, 1263, 1234, 1118, 1070, 960; $^1$H NMR (400 MHz, CDCl$_3$) δ 7.50-7.39 (m, 6H), 7.34-7.29 (m, 4H), 7.17 (t, J=7.2 Hz, 2H), 6.87 (dd, J=8.0, 2.0 Hz, 2H), 5.32-5.25 (m, 1H), 4.95-4.85 (m, 1H), 4.71-4.60 (m, 1H), 3.60-3.43 (m, 2H), 3.04-2.95 (m, 1H), 2.90-2.81 (m, 1H); $^{13}$C NMR (100 MHz, CDCl$_3$) δ 140.9 (dd, J=72.2, 8.2 Hz), 136.4 (d, J=6.0 Hz), 130.0 (d, J=5.3 Hz), 128.7 (d, J=5.2 Hz), 125.5 (d, J=3.8 Hz), 125.4 (d, J=3.7 Hz), 123.4 (d, J=41.7 Hz), 117.4 (dd, J=56.6, 3.7 Hz), 74.5 (d, J=5.2 Hz), 45.7 (d, J=102.8 Hz), 44.1 (d, J=8.2 Hz), 42.9 (d, J=8.9 Hz); $^{31}$P NMR (162 MHz, CDCl$_3$): δ 22.68 ppm; HRMS (ESI$^+$): m/z calcd. for C$_{23}$H$_{21}$F$_3$N$_3$O$_3$P [M+Na]$^+$: 498.1165; Found: 498.1167.

k. Synthesis of 2-(2-nitro-1-(o-tolyl)ethyl)-1,3-diphenyl-1,3,2-diazaphospholidine 2-oxide (3l')

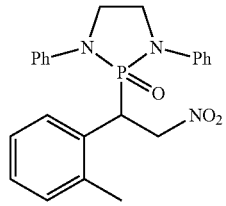 [SMILES: Cc1ccccc1C(C[N+](=O)[O-])P1(=O)N(c2ccccc2)CCN1c1ccccc1]

30.2 mg, 72% yield; white solid; mp 176-177° C.; $R_f$ 0.20 ($v_{Hexane}/v_{EA}$=2:1), $v_{Hexane}/v_{EA}/v_{DCM}$ (8/2/1) for column; IR v (KBr, cm$^{-1}$) 3092, 3018, 2951, 1599, 1550, 1500, 1371, 1269, 1232, 1116, 960; $^1$H NMR (400 MHz, CDCl$_3$) δ 7.44-7.35 (m, 6H), 7.28 (d, J=8.0 Hz, 2H), 7.17-7.01 (m, 5H), 6.82 (d, J=8.0 Hz, 1H), 5.35-5.29 (m, 1H), 4.95-4.81 (m, 2H), 3.53-3.43 (m, 2H), 3.06-2.95 (m, 1H), 2.91-2.82 (m, 1H), 1.73 (s, 3H); $^{13}$C NMR (100 MHz, CDCl$_3$) δ 141.5 (dd, J=61.1, 9.0 Hz), 138.3 (d, J=6.7 Hz), 131.1 (d, J=3.0 Hz), 130.5 (d, J=6.7 Hz), 129.8 (d, J=5.2 Hz), 128.0 (d, J=3.0 Hz), 127.1 (d, J=4.5 Hz), 125.9 (d, J=3.7 Hz), 122.8 (d, J=49.9 Hz), 116.8 (dd, J=63.3, 4.5 Hz), 76.2 (d, J=6.7 Hz), 43.6 (d, J=8.2 Hz), 42.2 (d, J=8.2 Hz), 41.7 (d, J=104.9 Hz); $^{31}$P NMR (162 MHz, CDCl$_3$): δ 25.38 ppm; HRMS (ESI$^+$): m/z calcd. for C$_{23}$H$_{24}$N$_3$O$_3$P [M+Na]$^+$: 444.1447; Found: 444.1455.

l. Synthesis of 2-(1-(2-fluorophenyl)-2-nitroethyl)-1,3-diphenyl-1,3,2-diazaphospholidine 2-oxide (3m')

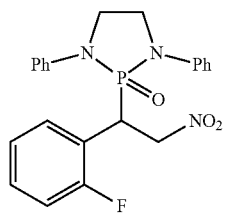 [SMILES: O=[N+]([O-])CC(c1ccccc1F)P1(=O)N(c2ccccc2)CCN1c1ccccc1]

30.2 mg, 71% yield; white solid; mp 158° C. (decomp.); $R_f$ 0.14 ($v_{Hexane}/v_{EA}$=3:1), $v_{Hexane}/v_{EA}/v_{DCM}$ (8/2/1) for column; IR v (KBr, cm$^{-1}$) 3076, 3043, 2960, 2879, 1599, 1554, 1492, 1473, 1267, 1234, 1128, 1107, 958; $^1$H NMR (400 MHz, CDCl$_3$) δ 7.43-7.28 (m, 8H), 7.24-7.17 (m, 1H), 7.15-7.09 (m, 2H), 6.98-6.89 (m, 2H), 6.76 (tt, J=7.6, 2.0 Hz, 1H), 5.28-5.21 (m, 1H), 5.00-4.84 (m, 2H), 3.61-3.46 (m, 2H), 3.17-3.09 (m, 1H), 3.05-2.97 (m, 1H); $^{13}$C NMR (100 MHz, CDCl$_3$) δ 160.8 (dd, J=248.6, 6.0 Hz), 141.2 (dd, J=78.2, 8.2 Hz), 130.0 (dd, J=8.2, 3.7 Hz), 129.7, 129.2, 124.2 (t, J=3.0 Hz), 123.0 (d, J=20.8 Hz), 119.5 (dd, J=14.2, 6.7 Hz), 117.3 (dd, J=24.5, 3.7 Hz), 115.9 (dd, J=22.3, 3.0 Hz), 74.3 (dd, J=5.9, 2.3 Hz), 43.8 (d, J=9.0 Hz), 42.8 (d, J=9.0 Hz), 39.4 (d, J=106.4 Hz); $^{31}$P NMR (162 MHz, CDCl$_3$): δ 23.10 (d, J=3.6 Hz) ppm; HRMS (ESI$^+$): m/z calcd. for C$_{22}$H$_{21}$FN$_3$O$_3$P [M+Na]$^+$: 448.1197; Found: 448.1188.

m. Synthesis of 2-(1-(2,4-dichlorophenyl)-2-nitroethyl)-1,3-diphenyl-1,3,2-diazaphospholidine 2-oxide (3n')

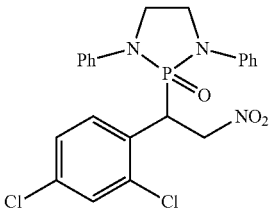 [SMILES: O=[N+]([O-])CC(c1ccc(Cl)cc1Cl)P1(=O)N(c2ccccc2)CCN1c1ccccc1]

38.5 mg, 81% yield; white solid; mp 188° C. (decomp.); $R_f$ 0.28 ($v_{Hexane}/v_{EA}$=2:1), $v_{Hexane}/v_{EA}/v_{DCM}$ (5/1/1) for column; IR v (KBr, cm$^{-1}$) 3028, 2939, 2856, 1599, 1560, 1552, 1500, 1477, 1373, 1269, 1116, 960; $^1$H NMR (400 MHz, CDCl$_3$) δ 7.42-7.27 (m, 6H), 7.23 (d, J=8.0 Hz, 2H), 7.19 (dd, J=2.4, 0.8 Hz, 1H), 7.14-7.01 (m, 3H), 6.87 (dd, J=8.8, 2.4 Hz, 1H), 5.17-5.01 (m, 2H), 4.93-4.83 (m, 1H), 3.69-3.52 (m, 2H), 3.48-3.39 (m, 1H), 3.25-3.17 (m, 1H); $^{13}$C NMR (100 MHz, CDCl$_3$) δ 141.2 (dd, J=31.3, 8.2 Hz), 135.9 (d, J=6.7 Hz), 134.5 (d, J=3.7 Hz), 129.8 (d, J=2.9 Hz), 129.6 (d, J=13.4 Hz), 129.5, 128.9 (d, J=6.7 Hz), 127.1 (d, J=3.8 Hz), 123.2 (d, J=8.9 Hz), 117.4 (d, J=5.2 Hz), 75.2 (d, J=6.0 Hz), 43.8 (d, J=9.7 Hz), 42.7 (d, J=9.7 Hz), 41.9 (d, J=104.2 Hz); $^{31}$P NMR (162 MHz, CDCl$_3$): δ 22.00 ppm; HRMS (ESI$^+$): m/z calcd. for C$_{22}$H$_{20}$Cl$_2$N$_3$O$_3$P [M+Na]$^+$: 498.0512; Found: 498.0518.

n. Synthesis of 2-(1-(2-bromo-4-chlorophenyl)-2-nitroethyl)-1,3-diphenyl-1,3,2-diazaphospholidine 2-oxide (3o')

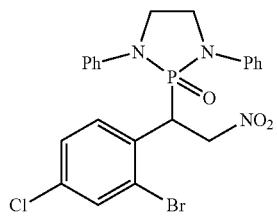 [SMILES: O=[N+]([O-])CC(c1ccc(Cl)cc1Br)P1(=O)N(c2ccccc2)CCN1c1ccccc1]

43.0 mg, 83% yield; white solid; mp 160° C. (decomp.); $R_f$ 0.30 ($v_{Hexane}/v_{EA}$=2:1), $v_{Hexane}/v_{EA}/v_{DCM}$ (8/2/1) for column; IR v (KBr, cm$^{-1}$) 3085, 2958, 2926, 1600, 1554, 1498, 1473, 1375, 1273, 1232, 1126, 958; $^1$H NMR (400 MHz, CDCl$_3$) δ 7.42-7.34 (m, 5H), 7.30-7.25 (m, 2H), 7.21 (d, J=8.0 Hz, 2H), 7.14-7.04 (m, 3H), 6.90 (dd, J=8.8, 2.84 Hz, 1H), 5.13-5.00 (m, 2H), 4.91-4.82 (m, 1H), 3.70-3.54 (m, 2H), 3.54-3.45 (m, 1H), 3.31-3.23 (m, 1H); $^{13}$C NMR (100 MHz, CDCl$_3$) δ 141.2 (dd, J=17.8, 7.4 Hz), 134.6 (d, J=3.7 Hz), 133.1 (d, J=2.2 Hz), 130.7 (d, J=6.7 Hz), 129.6 (d, J=23.1 Hz), 127.6 (d, J=3.0 Hz), 126.3, 123.2 (d, J=3.0 Hz), 117.5 (dd, J=5.9, 4.4 Hz), 75.5 (d, J=5.3 Hz), 44.7 (d, J=105.0 Hz), 43.8 (d, J=8.9 Hz), 42.6 (d, J=9.7 Hz); $^{31}$P NMR (162 MHz, CDCl$_3$): δ 21.86 ppm; HRMS (ESI$^+$): m/z calcd. for C$_{22}$H$_{20}$BrClN$_3$O$_3$P [M+Na]$^+$: 542.0006; Found: 542.0024.

o. Synthesis of 2-(1-(furan-2-yl)-2-nitroethyl)-1,3-diphenyl-1,3,2-diazaphospholidine 2-oxide (3p')

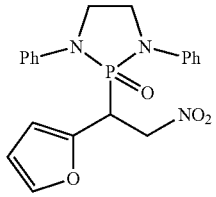 [SMILES: O=[N+]([O-])CC(c1ccco1)P1(=O)N(c2ccccc2)CCN1c1ccccc1]

22.2 mg, 56% yield; white solid; mp 120° C. (decomp.); $R_f$ 0.20 ($v_{Hexane}/v_{EA}$=2:1), $v_{Hexane}/v_{EA}/v_{DCM}$ (8/2/1) for column; IR v (KBr, cm$^{-1}$) 3007, 2957, 2852, 1600, 1554, 1498, 1473, 1307, 1267, 1236, 1155, 1126; $^1$H NMR (400 MHz, CDCl$_3$) δ 7.44-7.28 (m, 9H), 7.17-7.11 (m, 2H), 6.29 (dd, J=2.8, 2.0 Hz, 1H), 5.87 (t, J=3.6 Hz, 1H), 5.14-5.08 (m, 1H), 4.77-4.59 (m, 2H), 3.69-3.60 (m, 1H), 3.57-3.47 (m, 1H), 3.39-3.30 (m, 1H), 3.13-3.05 (m, 1H); $^{13}$C NMR (100 MHz, CDCl$_3$) δ 146.6 (d, J=10.4 Hz), 142.4 (d, J=3.8 Hz), 140.8 (dd, J=50.6, 8.2 Hz), 129.7 (d, J=20.8 Hz), 123.3 (d, J=64.0 Hz), 117.9 (dd, J=119.8, 3.7 Hz), 110.9 (d, J=3.7 Hz), 108.9 (d, J=8.2 Hz), 73.0 (d, J=5.9 Hz), 43.5 (d, J=8.9 Hz), 43.0 (d, J=8.2 Hz), 39.5 (d, J=105.7 Hz); $^{31}$P NMR (162 MHz, CDCl$_3$): δ 22.00 ppm; HRMS (ESI$^+$): m/z calcd. for C$_{20}$H$_{20}$N$_3$O$_4$P [M+Na]$^+$: 420.1084; Found: 420.1093.

p. Synthesis of 2-(2-nitro-1-(thiophen-2-yl)ethyl)-1,3-diphenyl-1,3,2-diazaphospholidine 2-oxide (3q')

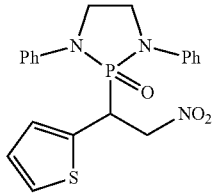 [SMILES: O=[N+]([O-])CC(c1cccs1)P1(=O)N(c2ccccc2)CCN1c1ccccc1]

23 mg, 57% yield; white solid; mp 122° C. (decomp.); $R_f$ 0.20 ($v_{Hexane}/v_{EA}$=2:1), $v_{Hexane}/v_{EA}/v_{DCM}$ (8/2/1) for column; IR v (KBr, cm$^{-1}$) 3014, 2957, 2881, 1599, 1558, 1498, 1471, 1267, 1228, 1126, 960; $^1$H NMR (400 MHz, CDCl$_3$) δ 7.45-7.30 (m, 8H), 7.19-7.12 (m, 3H), 6.89-6.85 (m, 1H), 6.44-6.41 (m, 1H), 5.30-5.23 (m, 1H), 4.91-4.80 (m, 1H), 4.76-4.67 (m, 1H), 3.61-3.47 (m, 2H), 3.19-3.06 (m, 2H); $^{13}$C NMR (100 MHz, CDCl$_3$) δ 140.9 (dd, J=67.7, 8.1 Hz), 134.4 (d, J=8.2 Hz), 129.8 (d, J=8.2 Hz), 127.0 (d, J=3.8 Hz), 126.7 (d, J=7.5 Hz), 125.5 (d, J=4.0 Hz), 123.2 (d, J=50.6 Hz), 117.6 (dd, J=91.6, 4.5 Hz), 75.9 (d, J=6.7 Hz), 44.2 (d, J=8.2 Hz), 43.1 (d, J=8.2 Hz), 41.1 (d, J=107.9 Hz); $^{31}$P NMR (162 MHz, CDCl$_3$): δ 23.08 ppm; HRMS (ESI$^+$): m/z calcd. for C$_{20}$H$_{20}$N$_3$O$_3$PS [M+Na]$^+$: 436.0855; Found: 436.0861.

q. Synthesis of 2-(1-cyclohexyl-2-nitroethyl)-1,3-diphenyl-1,3,2-diazaphospholidine 2-oxide (3r')

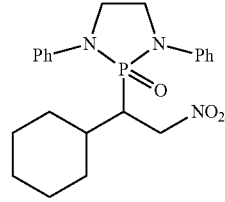 [SMILES: O=[N+]([O-])CC(C1CCCCC1)P1(=O)N(c2ccccc2)CCN1c1ccccc1]

19.9 mg, 48% yield; white solid; mp 168-169° C.; $R_f$ 0.17 ($v_{Hexane}/v_{EA}$=2:1), $v_{Hexane}/v_{EA}/v_{DCM}$ (8/2/1) for column; IR v (KBr, cm$^{-1}$) 2924, 2887, 2850, 1599, 1552, 1502, 1491, 1375, 1273, 1215, 1122, 962; $^1$H NMR (400 MHz, CDCl$_3$) δ 7.41-7.30 (m, 8H), 7.14-7.07 (m, 2H), 4.82-4.72 (m, 1H), 4.45-4.35 (m, 1H), 3.96-3.76 (m, 4H), 3.30-3.19 (m, 1H), 1.80-1.67 (m, 1H), 1.65-1.50 (m, 3H), 1.39 (d, J=13.2 Hz, 1H), 1.30 (d, J=13.2 Hz, 1H), 1.16-0.89 (m, 4H), 0.85-0.74 (m, 1H); $^{13}$C NMR (100 MHz, CDCl$_3$) δ 141.4 (dd, J=43.2, 8.2 Hz), 129.7 (d, J=2.3 Hz), 123.3 (d, J=46.2 Hz), 118.5 (dd, J=117.6, 4.5 Hz), 72.9 (d, J=3.0 Hz), 45.1 (d, J=8.1 Hz), 44.6 (d, J=3.7 Hz), 44.0 (d, J=96.0 Hz), 37.0, 33.0 (d, J=11.2 Hz), 28.7 (d, J=3.0 Hz), 26.8, 26.4, 25.6; $^{31}$P NMR (162 MHz, CDCl$_3$): δ 29.19 ppm; HRMS (ESI$^+$): m/z calcd. for C$_{22}$H$_{28}$N$_3$O$_3$P [M+Na]$^+$: 436.1760; Found: 436.1764.

r. Synthesis of 2-(1-nitropentan-2-yl)-1,3-diphenyl-1,3,2-diazaphospholidine 2-oxide (3s')

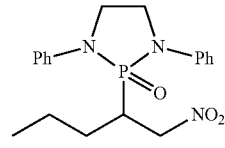 [SMILES: CCCC(C[N+](=O)[O-])P1(=O)N(c2ccccc2)CCN1c1ccccc1]

19.1 mg, 51% yield; white solid; mp 128-130° C.; $R_f$ 0.17 ($v_{Hexane}/v_{EA}$=2:1), $v_{Hexane}/v_{EA}/v_{DCM}$ (8/2/1) for column; IR v (KBr, cm$^{-1}$) 3061, 2964, 2931, 2895, 1600, 1560, 1500, 1481, 1267, 1220, 1126, 956; $^1$H NMR (400 MHz, CDCl$_3$) δ 7.41-7.31 (m, 8H), 7.14-7.08 (m, 2H), 4.87-4.78 (m, 1H), 4.25-4.16 (m, 1H), 3.97-3.76 (m, 4H), 3.38-3.26 (m, 1H), 1.74-1.61 (m, 1H), 1.31-1.14 (m, 3H), 0.74 (t, J=7.2 Hz, 3H); $^{13}$C NMR (100 MHz, CDCl$_3$) δ 141.2 (dd, J=11.9, 7.4 Hz), 129.7 (d, J=3.0 Hz), 123.3 (d, J=27.5 Hz), 118.1 (dd, J=22.3, 4.4 Hz), 75.8 (d, J=2.3 Hz), 44.9 (d, J=8.1 Hz), 44.4 (d, J=8.9 Hz), 38.2 (d, J=111.6 Hz), 30.1 (d, J=3.0 Hz), 20.5 (d, J=9.6 Hz), 13.7; $^{31}$P NMR (162 MHz, CDCl$_3$): δ 28.92 ppm; HRMS (ESI$^+$): m/z calcd. for C$_{19}$H$_{24}$N$_3$O$_3$P [M+Na]$^+$: 396.1447; Found: 396.1451.

s. Synthesis of 2-(1-nitro-3-phenylpropan-2-yl)-1,3-diphenyl-1,3,2-diazaphospholidine 2-oxide (3t')

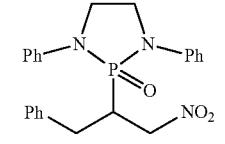 [SMILES: O=[N+]([O-])CC(Cc1ccccc1)P1(=O)N(c2ccccc2)CCN1c1ccccc1]

25.7 mg, 61% yield; white solid; mp 138-139° C.; $R_f$ 0.17 ($v_{Hexane}/v_{EA}$=2:1), $v_{Hexane}/v_{EA}/v_{DCM}$ (8/2/1) for column; IR v (KBr, cm$^{-1}$) 3056, 3022, 2957, 2924, 1599, 1558, 1492, 1377, 1271, 1220, 1118, 972; $^1$H NMR (400 MHz, CDCl$_3$) δ 7.44-7.33 (m, 6H), 7.25-7.09 (m, 7H), 6.92-6.87 (m, 2H), 4.95-4.86 (m, 1H), 4.34-4.24 (m, 1H), 3.80-3.64 (m, 3H), 3.62-3.54 (m, 1H), 3.30-3.20 (m, 1H), 3.04-2.95 (m, 1H), 2.64-2.52 (m, 1H); $^{13}$C NMR (100 MHz, CDCl$_3$) δ 141.1 (dd, J=41.7, 7.4 Hz), 136.9 (d, J=9.6 Hz), 129.8 (d, J=23.8 Hz), 128.7, 128.4, 127.1, 123.2 (d, J=30.6 Hz), 117.8 (dd, J=16.3, 5.2 Hz), 75.5 (d, J=3.0 Hz), 44.3 (d, J=8.9 Hz), 43.5 (d, J=9.0 Hz), 39.1 (d, J=111.7 Hz), 34.0 (d, J=2.3 Hz); $^{31}$P NMR (162 MHz, CDCl$_3$): δ 27.59 ppm; HRMS (ESI$^+$): m/z calcd. for C$_{23}$H$_{24}$N$_2$O$_2$P [M+Na]$^+$: 444.1447; Found: 444.1460.

t. Synthesis of (E)-2-(1-nitro-4-phenylbut-3-en-2-yl)-1,3-diphenyl-1,3,2-diazaphospholidine 2-oxide (3u')

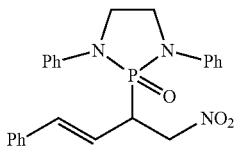 [SMILES: O=[N+]([O-])CC(/C=C/c1ccccc1)P1(=O)N(c2ccccc2)CCN1c1ccccc1]

12.1 mg, 28% yield; white solid; mp 142° C. (decomp.); $R_f$ 0.17 ($v_{Hexane}/v_{EA}$=2:1), $v_{Hexane}/v_{EA}/v_{DCM}$ (8/2/1) for column; IR v (KBr, cm$^{-1}$) 3024, 2914, 2881, 1599, 1554, 1500, 1491, 1265, 1226, 1122, 960; $^1$H NMR (400 MHz, CDCl$_3$) δ 7.45-7.37 (m, 6H), 7.36-7.26 (m, 5H), 7.19-7.15 (m, 4H), 6.17 (dd, J=16.0, 5.6 Hz, 1H), 5.76-5.67 (m, 1H), 5.08-5.02 (m, 1H), 4.47-4.39 (m, 1H), 4.19-4.06 (m, 1H), 3.82-3.69 (m, 4H); $^{13}$C NMR (100 MHz, CDCl$_3$) δ 140.9 (dd, J=47.6, 8.9 Hz), 136.2 (d, J=12.7 Hz), 135.4 (d, J=6.3 Hz), 129.9 (d, J=10.4 Hz), 128.8, 128.5 (d, J=1.5 Hz), 126.3 (d, J=1.5 Hz), 123.4 (d, J=71.4 Hz), 119.5 (d, J=10.4 Hz), 117.8 (dd, J=91.6, 4.5 Hz), 75.6 (d, J=4.5 Hz), 44.7 (d, J=12.7 Hz), 43.8 (d, J=7.4 Hz), 43.6; $^{31}$P NMR (162 MHz, CDCl$_3$): δ 24.56 ppm; HRMS (ESI$^+$): m/z calcd. for C$_{24}$H$_{24}$N$_3$O$_3$P [M+Na]$^+$: 456.1447; Found: 456.1448.

6. General Procedure for the Phosphite Addition to Maleimides Employing NHP-Thioureas as Phosphorous Reagents

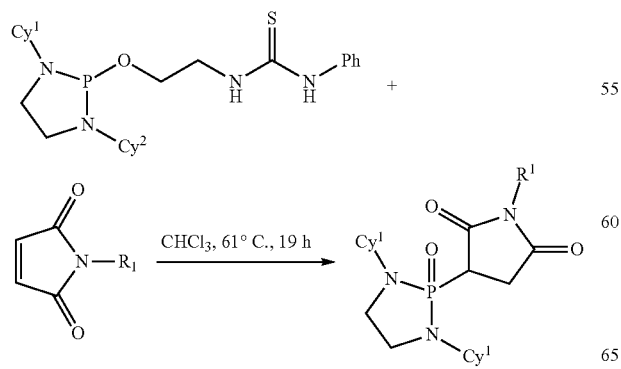

a. Synthesis of 3-(2-oxido-1,3-diphenyl-1,3,2-diazaphospholidin-2-yl)-1-phenylpyrrolidine-2,5-dione (3a")

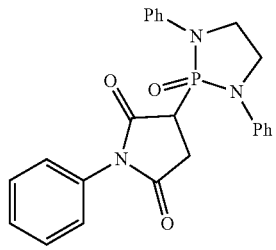 [SMILES: O=C1CC(P2(=O)N(c3ccccc3)CCN2c2ccccc2)C(=O)N1c1ccccc1]

1-Phenyl-1H-pyrrole-2,5-dione (8.65 mg, 0.05 mmol) and NHP-thiourea 1a" (32.7 mg, 0.075 mmol) were dissolved in CHCl3 (0.5 mL). Then the resulting reaction mixture was stirred at room temperature for 39 hours. After stirring for 39 hours, the reaction mixture was concentrated under reduced pressure. The residue was subjected to column chromatography on silica gel (gradient eluent of DCM:EtOAc 18/1 to 9/1) to give colorless semisolid 3a" (14.8 mg, 69% yield). Rf=0.22 (Hexanes:EtOAc=1:1).

b. Synthesis of 3-(2-oxido-1,3-di-p-tolyl-1,3,2-diazaphospholidin-2-yl)-1-phenylpyrrolidine-2,5-dione (3b")

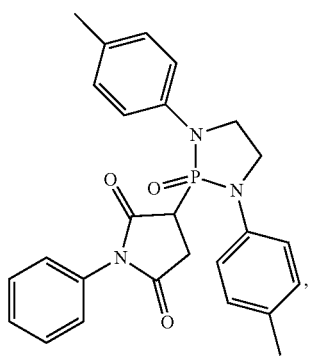

79% c. Synthesis of 3-(1,3-bis(4-methoxyphenyl)-2-oxido-1,3,2-diazaphospholidin-2-yl)-1-phenylpyrrolidine-2,5-dione (3c")

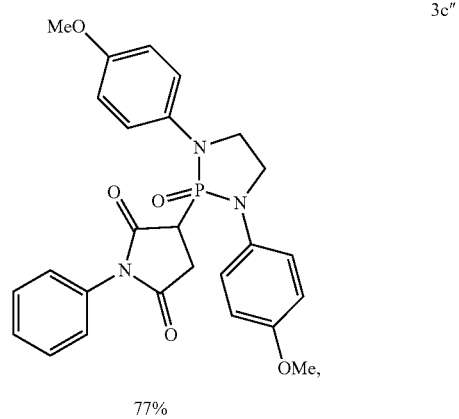 [SMILES: COc1ccc(N2CCN(c3ccc(OC)cc3)P2(=O)C2CC(=O)N(c3ccccc3)C2=O)cc1]

77%

103 d. Synthesis of 3-(2-oxido-1,3-diphenyl-1,3,2-diaza-phospholidin-2-yl)-1-(p-tolyl)pyrrolidine-2,5-dione (3e″)

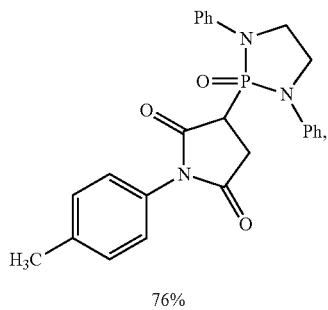

3e″

76% e. Synthesis of 1-(4-methoxyphenyl)-3-(2-oxido-1,3-diphenyl-1,3,2-diazaphospholidin-2-yl)pyrrolidine-2,5-dione (3f″)

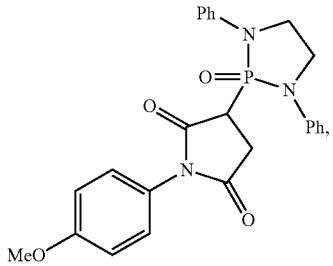

3f″

77% f. Synthesis of 1-(4-nitrophenyl)-3-(2-oxido-1,3-diphenyl-1,3,2-diazaphospholidin-2-yl)pyrrolidine-2,5-dione (3g″)

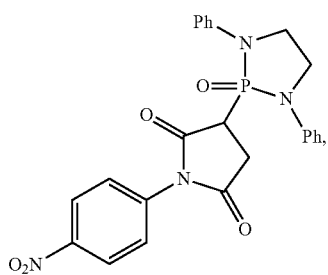

3g″

80%

104 g. Synthesis of 1-(4-bromophenyl)-3-(2-oxido-1,3-diphenyl-1,3,2-diazaphospholidin-2-yl)pyrrolidine-2,5-dione (3h″)

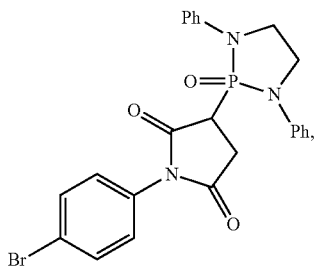

3h″

80% h. Synthesis of 1-(4-chlorophenyl)-3-(2-oxido-1,3-diphenyl-1,3,2-diazaphospholidin-2-yl)pyrrolidine-2,5-dione (3i″)

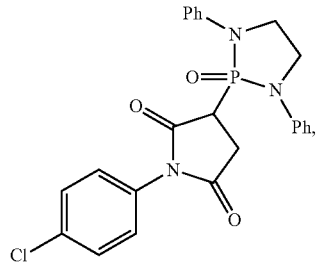

3i″

75% i. Synthesis of 1-(4-fluorophenyl)-3-(2-oxido-1,3-diphenyl-1,3,2-diazaphospholidin-2-yl)pyrrolidine-2,5-dione (3j″)

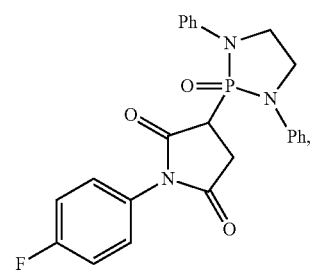

3j″

79% j. Synthesis of 1-(3-chlorophenyl)-3-(2-oxido-1,3-diphenyl-1,3,2-diazaphospholidin-2-yl)pyrrolidine-2,5-dione (3k″)

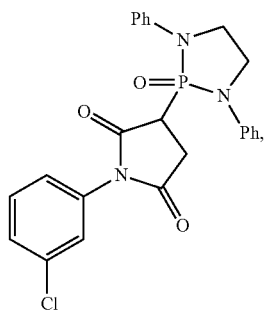

3k″

77% k. Synthesis of 1-(3,5-dichlorophenyl)-3-(2-oxido-1,3-diphenyl-1,3,2-diazaphospholidin-2-yl)pyrrolidine-2,5-dione (3l″)

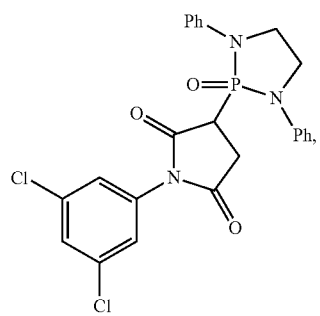

3l″

78% l. Synthesis of 1-(2,6-diisopropylphenyl)-3-(2-oxido-1,3-diphenyl-1,3,2-diazaphospholidin-2-yl)pyrrolidine-2,5-dione (3m″)

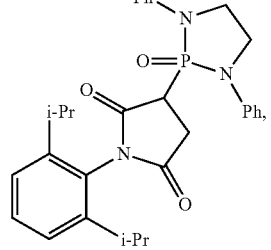

3m″

44% m. Synthesis of 3-(2-oxido-1,3-diphenyl-1,3,2-diazaphospholidin-2-yl)-1-(3,4,5-trimethoxyphenyl)pyrrolidine-2,5-dione (3n″)

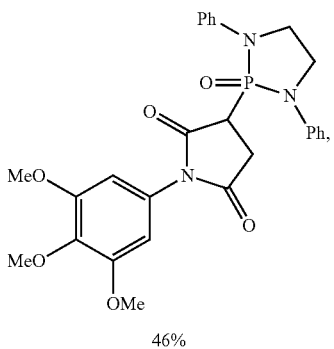

3n″

46% n. Synthesis of 3-(2-oxido-1,3-diphenyl-1,3,2-diazaphospholidin-2-yl)-1-(pyridin-3-yl)pyrrolidine-2,5-dione (3o″)

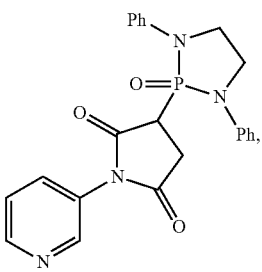

3o″

54% o. Synthesis of 1-(naphthalen-1-yl)-3-(2-oxido-1,3-diphenyl-1,3,2-diazaphospholidin-2-yl)pyrrolidine-2,5-dione (3p″)

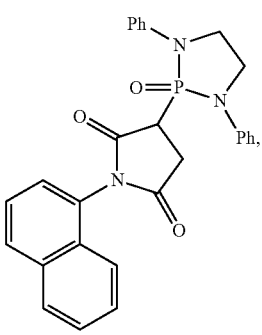

3p″

51%, dr: 36:47 p. Synthesis of 1-benzyl-3-(2-oxido-1,3-diphenyl-1,3,2-diazaphospholidin-2-yl)pyrrolidine-2,5-dione (3q")

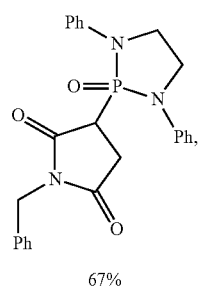

3q"

67% q. Synthesis of 1-cyclohexyl-3-(2-oxido-1,3-diphenyl-1,3,2-diazaphospholidin-2-yl)pyrrolidine-2,5-dione (3r")

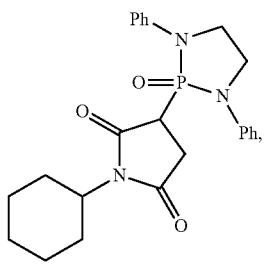

3r"

62%

7. General Procedure for the Large-Scale Reaction

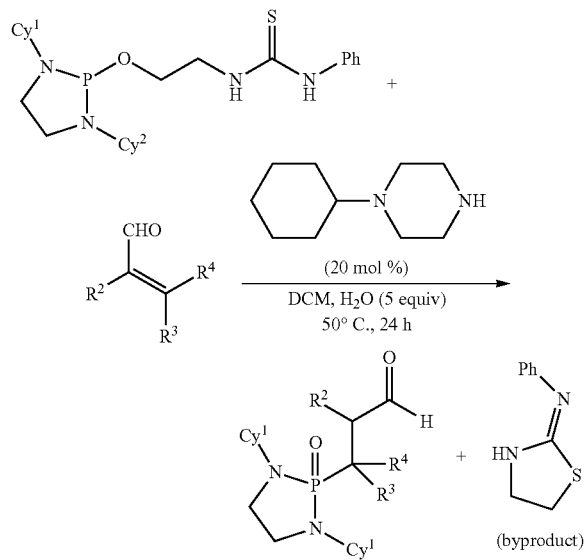

To a solution of NHP-thiourea (1.00 g, 2.3 mmol), 1-cyclohexylpiperazine (77.6 mg, 0.46 mmol), and H$_2$O (11.5 mmol) in DCM 11 mL) was added α,β-unsaturated aldehyde (0.87 mL, 6.9 mmol). The reaction mixture was heated in an oil bath at 50° C. for 24 h. After stirring for 24 h, the reaction mixture was cooled to room temperature and concentrated under reduced pressure. The residue was subjected to column chromatography on silica gel (Hexane/EA/DCM=6:2:1, Hexane/EA=1:2) to give the corresponding product (793 mg, 89%) and byproduct (Sommen et al. (2005) *Eur. J. Org. Chem.* 3128-3137) (334 mg, 82%), $^1$H NMR (400 MHz, CDCl$_3$) δ 7.28 (t, J=7.6 Hz, 2H), 7.13 (d, J=7.6 Hz, 2H), 7.04 (t, J=7.2 Hz, 1H), 3.82 (t, J=7.0 Hz, 2H), 3.30 (t, J=7.2 Hz, 2H).

8. Synthesis of 2-(3-hydroxy-1-phenylpropyl)-1,3-diphenyl-1,3,2-diazaphospholidine 2-oxide (4a)

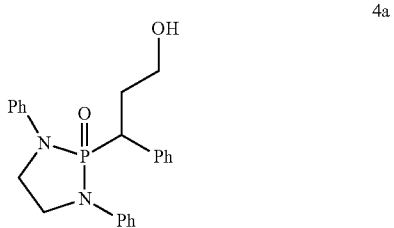 [SMILES: O=P1(C(CCO)c2ccccc2)N(c2ccccc2)CCN1c1ccccc1]

4a

To a solution of 3a (38.9 mg, 0.1 mmol) in MeOH (0.5 mL) was added NaBH$_4$ (7.9 mg, 0.2 mmol). After 2.5 h, the solution was quenched with distilled H$_2$O and the resulting mixture was extracted with EtOAc (3×5 mL). The organic phase was washed with brine, dried over Na$_2$SO$_4$, filtered, and evaporated under reduced pressure to afford the pure product 4a (39.6 mg, 99%). mp 158-160° C.; R$_f$=0.22 (ν$_{Hexane}$/ν$_{EtOAc}$=1:2); IR ν (KBr, cm$^{-1}$) 3335, 3057, 2935, 2885, 1599, 1500, 1471, 1273, 1215, 1159, 1132, 954; $^1$H NMR (400 MHz, CDCl$_3$) δ 7.44-7.33 (m, 6H), 7.25 (d, J=8.4 Hz, 2H), 7.22-7.15 (m, 3H), 7.11-7.04 (m, 2H), 6.76-6.71 (m, 2H), 3.91-3.81 (m, 1H), 3.73-3.66 (m, 1H), 3.53-3.45 (m, 1H), 3.44-3.35 (m, 2H), 2.90-2.58 (m, 4H), 2.15-2.02 (m, 1H); $^{13}$C NMR (100.5 MHz, CDCl$_3$) δ 142.1 (dd, J=81.1, 8.2 Hz), 136.4 (d, J=6.0 Hz), 129.5 (d, J=17.9 Hz), 128.9 (d, J=6.0 Hz), 128.2 (d, J=3.0 Hz), 127.3 (d, J=3.7 Hz), 122.2 (d, J=63.3 Hz), 117.1 (dd, J=141.4, 3.7 Hz), 61.3 (d, J=11.2 Hz), 44.7 (d, J=104.9 Hz), 44.0 (d, J=7.4 Hz), 42.4 (d, J=7.5 Hz), 33.1 (d, J=2.2 Hz); $^{31}$P NMR (162 MHz, CDCl$_3$): δ 31.33 ppm; HRMS (ESI): m/z calcd. for C$_{23}$H$_{25}$N$_2$O$_2$P ([M+Na]$^+$): 415.1551; Found: 415.1546.

9. Synthesis of (e)-ethyl 5-(2-oxido-1,3-diphenyl-1,3,2-diazaphospholidin-2-yl)-5-phenylpent-2-enoate (4b)

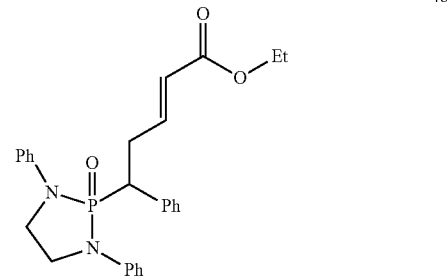

4b

To a solution of 3a (39.1 mg, 0.1 mmol) and 4 Å MS (51.9 mg) in 1,2-dichloroethane (0.5 mL) was added ethyl 2-(triphenylphosphoranylidene)acetate (42.3 mg, 0.12 mmol) at room temperature. After stirring for 2 h, volatiles were removed under reduced pressure. The residue was subjected to column chromatography (Hexanes/EtOAc/DCM=7/2/1) on silica gel to give white solid 4b (31.4 mg, 68%); white solid; mp 173-174° C.; $R_f$=0.54 ($v_{Hexane}/v_{EtOAc}$=1:1); IR v (KBr, cm$^{-1}$) 3028, 2928, 2891, 1718, 1655, 1600, 1500, 1475, 1307, 1273, 1220, 1151, 1118, 1035, 956; $^1$H NMR (400 MHz, CDCl$_3$) δ 7.41-7.33 (m, 6H), 7.28-7.23 (m, 2H), 7.22-7.15 (m, 3H), 7.11-7.05 (m, 2H), 6.72-6.68 (m, 2H), 6.62 (dt, J=15.6, 6.8 Hz, 1H), 5.66 (dt, J=15.6, 1.2 Hz, 1H), 4.04 (q, J=7.2 Hz, 2H), 3.80-3.69 (m, 1H), 3.46-3.28 (m, 3H), 2.85-2.69 (m, 3H), 1.17 (t, J=6.8 Hz, 3H); $^{13}$C NMR (100.5 MHz, CDCl$_3$) δ 166.0, 145.6 (d, J=17.1 Hz), 142.1 (dd, J=86.3, 8.2 Hz), 134.8 (d, J=6.7 Hz), 129.5 (d, J=20.0 Hz), 128.8 (d, J=5.9 Hz), 128.3 (d, J=3.0 Hz), 127.5 (d, J=3.7 Hz), 123.1, 122.2 (d, J=52.8 Hz), 117.0 (dd, J=113.9, 4.5 Hz), 60.1, 46.3 (d, J=104.2 Hz), 43.7 (d, J=7.5 Hz), 42.4 (d, J=7.5 Hz), 31.9, 14.1; $^{31}$P NMR (162 MHz, CDCl$_3$): δ 28.81 ppm; HRMS (ESI): m/z calcd. for C$_{27}$H$_{29}$N$_2$O$_3$P ([M+Na]$^+$): 483.1813; Found: 483.1808.

10. Synthesis of 3-(1,3-bis(4-bromophenyl)-2-oxido-1,3,2-diazaphospholidin-2-yl)-3-phenylpropanal (4c)

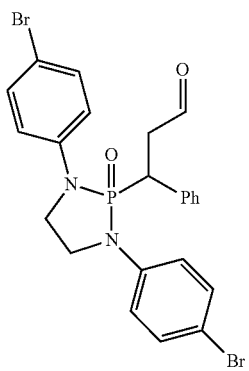

To a solution of 3a (39.1 mg, 0.1 mmol) in 1,2-dichloroethane (1.0 mL) were added benzoyl peroxide (4.2 mg, 0.012 mmol) and N-bromosuccinimide (45.2 mg, 0.25 mmol) at room temperature. After stirring for 3 h, volatiles were removed under reduced pressure. The residue was subjected to column chromatography (Hexanes/EtOAc/DCM=3/1/1) on silica gel to give off-white solid 4c (29.1 mg, 53%). mp 93-94° C.; $R_f$=0.48 ($v_{Hexane}/v_{EtOA}$=1:1); IR v (KBr, cm$^{-1}$) 3059, 2930, 2881, 1724, 1589, 1491, 1473, 1280, 1267, 1226, 1003, 960; $^1$H NMR (400 MHz, CDCl$_3$) δ 9.63-9.61 (m, 1H), 7.52-7.44 (m, 4H), 7.26-7.12 (m, 7H), 6.75-6.71 (m, 2H), 4.32-4.21 (m, 1H), 3.48-3.29 (m, 3H), 3.09-2.97 (m, 1H), 2.83-2.75 (m, 1H), 2.71-2.63 (m, 1H); $^{13}$C NMR (100.5 MHz, CDCl$_3$) δ 198.4 (d, J=15.6 Hz), 140.9 (dd, J=90.8, 8.2 Hz), 134.9 (d, J=6.7 Hz), 132.5 (d, J=14.1 Hz), 128.5 (d, J=3.8 Hz), 128.4 (d, J=6.0 Hz), 127.8 (d, J=3.7 Hz), 118.7 (dd, J=107.9, 4.5 Hz), 115.3 (d, J=52.9 Hz), 43.7 (d, J=7.4 Hz), 43.4, 42.4 (d, J=7.4 Hz), 40.6 (d, J=107.2 Hz); $^{31}$P NMR (162 MHz, CDCl$_3$): δ 29.26 ppm; HRMS (ESI): m/z calcd. for C$_{23}$H$_{22}$Br$_2$N$_2$O$_2$P ([M+H]$^+$): 546.9786; Found: 546.9780.

11. Synthesis of 3-(2-oxido-1,3-diphenyl-1,3,2-diazaphospholidin-2-yl)-3-phenylpropanoic Acid (4d)

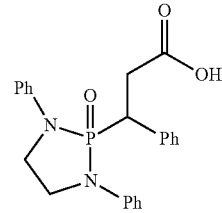

To a solution of 3a (39.0 mg, 0.1 mmol), NaClO$_2$ (13.4 mg, 0.14 mmol), and NaH$_2$PO$_4$ (13.1 mg, 0.1 mmol) in CH$_3$CN/H$_2$O (3/2, 0.5 mL) was added 30% H$_2$O$_2$ aq (13 µL). After stirring for 3 h, the solution was quenched with distilled H$_2$O and the resulting mixture was extracted with EtOAc (3×5 mL). The organic phase was washed with brine, dried over Na$_2$SO$_4$, filtered, and evaporated under reduced pressure to afford the crude product. The crude product was subjected to column chromatography (EtOAc/MeOH=95/5) on silica gel to give yellow oil 4d (16.2 mg, 40%).; $R_f$=0.19 ($v_{EtOAc}/v_{MeOH}$=95:5); IR v (KBr, cm$^{-1}$) 3433 (m), 3061, 2924, 2883, 1718 (m), 1599, 1491 (m), 1269, 1124, 1035, 960; $^1$H NMR (400 MHz, CD$_3$OD) δ 7.42-7.33 (m, 6H), 7.28 (d, J=8.0 Hz, 2H), 7.25-7.03 (m, 5H), 6.69 (dd, J=7.2, 2.0 Hz, 2H), 4.28-4.17 (m, 1H), 3.52-3.38 (m, 2H), 3.27-3.20 (m, 1H), 2.98-2.90 (m, 1H), 2.85-2.76 (m, 2H); $^{13}$C NMR (100.5 MHz, CD$_3$OD) δ 172.8 (d, J=18.6 Hz), 141.8 (dd, J=65.5, 8.2 Hz), 135.0 (d, J=6.7 Hz), 129.2 (d, J=10.4 Hz), 128.3 (d, J=5.9 Hz), 128.0 (d, J=3.7 Hz), 127.3 (d, J=3.7 Hz), 122.1 (d, J=64.0 Hz), 116.8 (dd, J=112.4, 4.4 Hz), 43.7 (d, J=8.2 Hz), 43.0 (d, J=102.7 Hz), 42.4 (d, J=2.2 Hz), 34.3; $^{31}$P NMR (162 MHz, CD$_3$OD): δ 27.28 ppm; HRMS (ESI): m/z calcd. for C$_{23}$H$_{24}$N$_2$O$_3$P ([M+Na]$^+$): 407.1525; Found: 407.1519.

12. Synthesis of 2-(2-(benzylamino)-1-phenylethyl)-1,3-diphenyl-1,3,2-diazaphospholidine 2-oxide (4e)

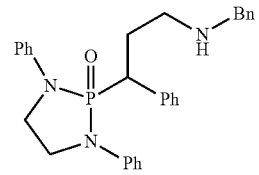

To a solution of 3a (39.3 mg, 0.1 mmol) and MgSO$_4$ (24.4 mg, 0.2 mmol) in toluene (0.5 mL) was added BnNH$_2$ (31.6 mg, 0.3 mmol). After stirring for 1 h, NaBH$_4$ (15.6 mg, 0.4 mmol) was added to the mixture and the resulting mixture was stirred for 14 h at room temperature. After stirring for 14 h, the reaction mixture was quenched with distilled H$_2$O and it was extracted with EtOAc (3×5 mL). The organic phase was washed with brine, dried over Na$_2$SO$_4$, filtered, and evaporated under reduced pressure to afford the crude product. The crude product was subjected to column chromatography (EtOAc/MeOH=98/2) on silica gel to give white solid 4e (24.6 mg, 52%). mp 156-157° C.; $R_f$=0.14 ($v_{EtOAc}/v_{MeOH}$=98:2); IR v (KBr, cm$^{-1}$) 3057, 3026, 2930, 2893, 1599, 1496, 1477, 1271, 1222, 1124, 954; $^1$H NMR (400 MHz, CDCl$_3$) δ 7.42-7.32 (m, 6H), 7.27-7.12 (m, 10H), 7.08-7.03 (m, 2H), 6.74-6.69 (m, 2H), 3.91-3.80 (m, 1H), 3.62 (dd, J=46.4, 13.2 Hz, 2H), 3.45-3.36 (m, 2H), 2.89-2.77 (m, 1H), 2.72-2.47 (m, 3H), 2.44-2.36 (m, 1H), 2.16-2.04 (m, 1H), 1.35 (br, 1H); $^{13}$C NMR (100.5 MHz, CDCl$_3$) δ

142.3 (dd, J=75.9, 8.2 Hz), 140.3, 136.0 (d, J=6.7 Hz), 129.4 (d, J=14.1 Hz), 129.0 (d, J=5.9 Hz), 128.3, 128.1 (d, J=3.0 Hz), 127.9, 127.1 (d, J=4.4 Hz), 126.8, 121.9 (d, J=49.8 Hz), 116.9 (dd, J=103.5, 4.5 Hz), 53.4, 47.5 (d, J=16.4 Hz), 45.0 (d, J=106.5 Hz), 43.7 (d, J=7.5 Hz), 42.4 (d, J=7.4 Hz), 29.6; $^{31}$P NMR (162 MHz, CDCl$_3$): δ 30.77 ppm; HRMS (ESI): m/z calcd. for C$_{30}$H$_{33}$N$_3$OP ([M+H]$^+$): 482.2361; Found: 482.2356.

1. Synthesis of 3-(2-oxido-1,3-diphenyl-1,3,2-diazaphospholidin-2-yl)-3-phenylpropanal oxime (4f)

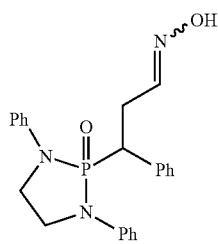

To a solution of 3a (29.6 mg, 0.076 mmol) and NH$_2$OH.HCl (5.6 mg, 0.076 mmol) in EtOH/H$_2$O (1:1, 0.5 mL) was added NaOH (9.0 mg, 0.152 mmol). After stirring for 2 h, the reaction mixture was quenched with distilled H$_2$O and the resulting mixture was extracted with DCM (3×5 mL). The organic phase was washed with brine, dried over Na$_2$SO$_4$, filtered, and evaporated under reduced pressure to afford the crude product 4f (26.6 mg, 86%, 55:45 mixture of E/Z isomers). R$_f$=0.19 (v$_{Hexane}$/v$_{EtOAc}$=1:1); IR v (KBr, cm$^{-1}$) 3255, 3059, 2941, 2887, 1599, 1496, 1269, 1124, 1035, 960; $^1$H NMR (400 MHz, DMSO-d$_6$) δ 10.76 (s, 1H, Z), 10.33 (s, 1H, E), 7.36-7.26 (m, 12H, Z+E), 7.22-7.10 (m, 10H, Z+E), 7.05-6.97 (m, 5H, Z+E), 6.67-6.59 (m, 4H, Z+E), 6.37 (t, J=4.8 Hz, 1H, Z), 3.99-3.84 (m, 2H, Z+E), 3.47-3.34 (m, 4H, Z+E), 3.05-3.91 (m, 3H, Z+E), 2.82-2.58 (m, 5H, Z+E); $^{13}$C NMR (100.5 MHz, DMSO-d$_6$) δ 148.4 (d, J=16.3 Hz), 147.9 (d, J=17.9 Hz), 143.0 (dd, J=8.1, 3.7 Hz), 142.3 (dd, J=8.2, 6.0 Hz), 135.7 (d, J=6.7 Hz), 135.3 (d, J=6.7 Hz), 129.8 (d, J=2.3 Hz), 129.7 (d, J=3.7 Hz), 129.0 (d, J=6.0 Hz), 128.8 (d, J=5.2 Hz), 128.54 (d, J=3.0 Hz), 128.51 (d, J=3.0 Hz), 127.68 (d, J=3.8 Hz), 127.61 (d, J=3.8 Hz), 122.2 (d, J=4.5 Hz), 121.7 (d, J=5.2 Hz), 117.2 (dd, J=6.7, 2.3 Hz), 116.4 (d, J=4.5 Hz), 45.1 (d, J=57.0 Hz), 44.0 (d, J=58.0 Hz), 43.5 (d, J=6.7 Hz), 42.4 (d, J=7.4 Hz), 29.8, 25.3; $^{31}$P NMR (162 MHz, DMSO-d$_6$): δ 24.53 (Z); 24.48 (F) ppm; HRMS (ESI): m/z calcd. for C$_{23}$H$_{24}$N$_3$O$_2$P ([M+H]$^+$): 406.1684; Found: 406.1679.

2. Synthesis of 1,3-bis(4-bromophenyl)-2-(2-nitro-1-phenylethyl)-1,3,2-diazaphospholidine 2-oxide (4a')

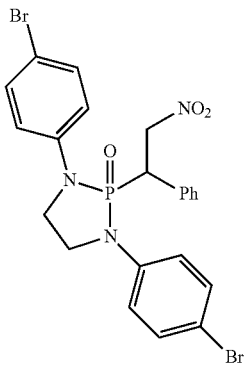 [SMILES: O=[N+]([O-])CC(c1ccccc1)P1(=O)N(c2ccc(Br)cc2)CCN1c1ccc(Br)cc1]

To a solution of 3a' (40.8 mg, 0.1 mmol) in 1,2-dichloroethane (1.0 mL) were added benzoyl peroxide (4.7 mg, 0.012 mmol) and N-bromosuccinimide (44.3 mg, 0.25 mmol) at room temperature. After stirring for 3 h, volatiles were removed under reduced pressure. The residue was subjected to column chromatography (Hexanes/DCM=1/1) on silica gel to give off-white solid 4a' (35.6 mg, 63%). mp 178° C. (decomp.); R$_f$ 0.31 (v$_{Hexane}$/v$_{DCM}$=1:1); IR v (KBr, cm$^{-1}$) 3028, 2957, 2875, 1591, 1556, 1491, 1473, 1363, 1309, 1267, 1234, 960; $^1$H NMR (400 MHz, CDCl$_3$) δ 7.56-7.48 (m, 4H), 7.30-7.15 (m, 7H), 6.75-6.70 (m, 2H), 5.26-5.19 (m, 1H), 4.91-4.81 (m, 1H), 4.59-4.48 (m, 1H), 3.49-3.32 (m, 2H), 2.87-2.79 (m, 1H), 2.75-2.66 (m, 1H); $^{13}$C NMR (100 MHz, CDCl$_3$) δ 140.2 (dd, J=78.1, 8.9 Hz), 132.8 (d, J=3.0 Hz), 131.6 (d, J=6.7 Hz), 128.9 (d, J=3.0 Hz), 128.6 (d, J=3.7 Hz), 128.1 (d, J=5.2 Hz), 118.7 (dd, J=63.3, 4.5 Hz), 116.0 (d, J=42.5 Hz), 74.3 (d, J=5.2 Hz), 45.7 (d, J=104.2 Hz), 43.7 (d, J=7.4 Hz), 42.6 (d, J=8.2 Hz); $^{31}$P NMR (162 MHz, CDCl$_3$): δ 24.58 ppm; HRMS (ESI$^+$): m/z calcd. for C$_{22}$H$_{20}$Br$_2$N$_3$O$_3$P [M+Na]$^+$: 585.9501; Found: 585.9494.

3. Synthesis of tert-butyl (2-(2-oxido-1,3-diphenyl-1,3,2-diazaphospholidin-2-yl)-2-phenylethyl)carbamate (4b')

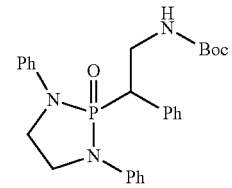

To a solution of 3a' (40.6 mg, 0.1 mmol) in MeOH/THF (3:1, 2.0 mL) were added NiCl$_2$H$_2$O (59.6 mg, 0.25 mmol) and NaBH$_4$ (38.1 mg, 1 mmol) at -10° C. After stirring for 2 h at -10° C., the reaction mixture was warmed up to room temperature, then di-tert-butyl dicarbonate (68.3 mg, 0.3 mmol) was added to the mixture and kept stiring for anther 2.5 h. The reaction was quenched with 1N NaHCO$_3$ aq., and the organic solvents were evaporated. The aqueous phase was extracted with DCM, and dried over anhydrous Na$_2$SO$_4$. After removal of solvent, the residue was purified by flash column chromatography to afford 4b' (41.6 mg, 88%); white solid; mp 180-181° C.; R$_f$ 0.41 (v$_{Hexane}$/v$_{EA}$=1:1), v$_{Hexane}$/v$_{EA}$/v$_{DCM}$ (8/2/1) for column; IR v (KBr, cm$^{-1}$) 3448, 3057, 2976, 2889, 1710, 1599, 1500, 1365, 1271, 1170, 1126, 954; $^1$H NMR (400 MHz, CDCl$_3$) δ 7.41-7.32 (m, 6H), 7.27 (dd, J=8.0, 0.8 Hz, 2H), 7.24-7.13 (m, 3H), 7.10-7.05 (m, 2H), 6.67 (dd, J=7.2, 1.6 Hz, 2H), 5.67 (b, 1H), 3.90-3.70 (m, 3H), 3.50-3.41 (m, 1H), 3.41-3.33 (m, 1H), 2.86 (b, 1H), 2.70 (b, 1H), 1.41 (s, 9H); $^{13}$C NMR (100 MHz, CDCl$_3$) δ 155.7, 141.9 (dd, J=90.8, 8.2 Hz), 134.9, 129.6 (d, J=13.4 Hz), 128.7 (d, J=5.2 Hz), 128.3 (d, J=3.0 Hz), 127.6, 122.3 (d, J=59.5 Hz), 116.9 (dd, J=98.2, 4.4 Hz), 79.3, 47.5 (d, J=102.7 Hz), 43.8 (d, J=7.4 Hz), 42.4 (d, J=7.5

Hz), 40.7; $^{31}$P NMR (162 MHz, CDCl$_3$): δ 29.07 ppm; HRMS (ESI$^+$): m/z calcd. for C$_{27}$H$_{32}$N$_3$O$_3$P [M+Na]$^+$: 500.2073; Found: 500.2076.

4. Synthesis of diethyl (2,5-dioxo-1-phenylpyrrolidin-3-yl)phosphonate

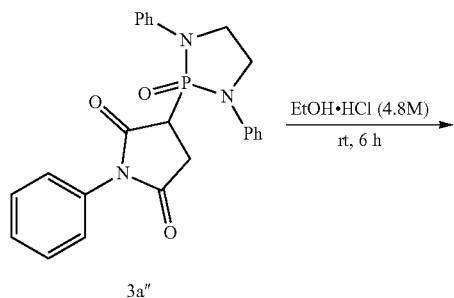

5. Multiplex Roles Of NHP-Thioureas in the Phospha-Michael Addition

Following ongoing efforts in the construction of C—P bonds using the bifunctional N-heterocyclic phosphine (NHP)-thioureas (Scheme 6, a), it was hypothesized that the roles of NHP-thioureas in the phospha-Michael addition would contain: (1) a Brønsted acid motif as an internal nucleophile that could promote the transformation of P(III) to P(V) without additives (Scheme 6, b) (Mulla et al. (2016) *J. Org. Chem.* 81: 77-88; Mulla and Kang (2016) *J. Org. Chem.*); (2) the hydrogen bonding of the aldehyde group with a Brønsted acid and the optimum length of the tether may efficiently inhibit the undesired 1,2-addition (Scheme 6, c); 3) due to the hydrogen bonding with the Brønsted acid, α,β-unsaturated ketones could effectively form the iminium intermediate with amines to ultimately undergo phospha-Michael addition reaction (Scheme 6, d).

SCHEME 6.

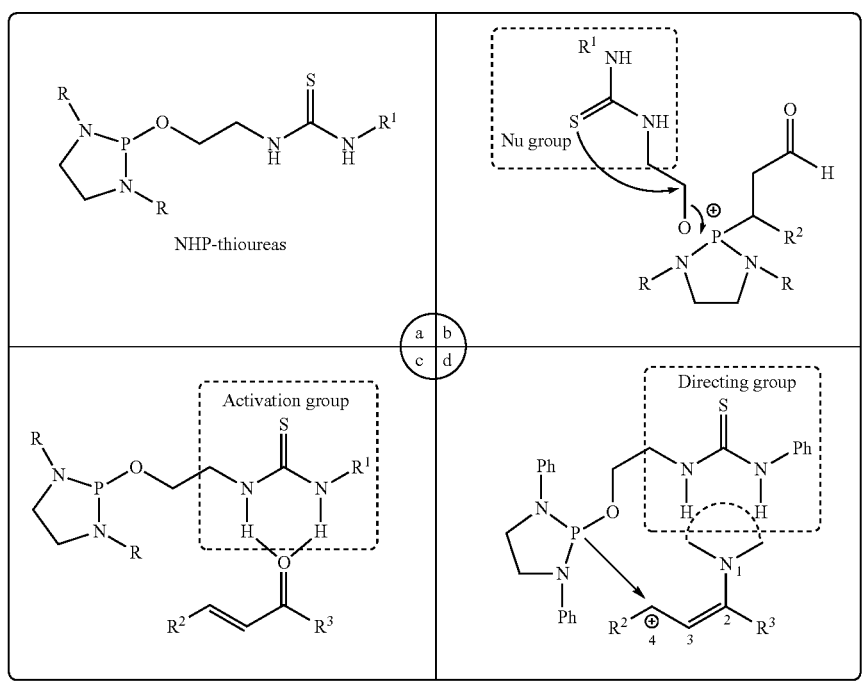

-continued

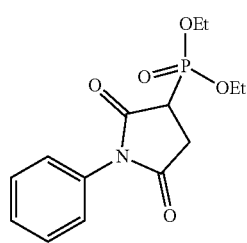

6. Optimization of Phospha-Michael Addition Reaction

To test the amine-catalyzed phospha-Michael addition reaction without nucleophile additives, NHP-thiourea 1a, transcinnamaldehyde 2a, and amines (1-10) in CH$_2$Cl$_2$ were used to screen for the optimal reaction conditions described in Table 1. First, the catalytic activity of the amines was evaluated. Morpholine 1 with 20 mol % loading demonstrated the catalytic turnover of the reaction, providing the phospha-Michael adduct 3a with 28% yield under additive-free reaction conditions. Next, various heterocyclic amines (entries, 2-4) including pyrrolidine (entry 5) were tested; among the evaluated amines, thiomorpholine provided the highest product yield (entry 2, 65%). Without wishing to be bound by theory, this may be due to the strong nucleophilicity. However, the acyclic amine was inferior to the cyclic amine (entry 6 vs 2). With the advantage of strong nucleophilic amines for iminium intermediate formation, N-alkyl or aryl substituted piperidines were explored for optimization of the catalysis system (entries 7-14). Gratifyingly, optimized reaction conditions of this phospha-Michael addition reaction were obtained using 1-cyclohexylpiperazine 8 with addition of 5.0 equivalents of $H_2O$ (entry 14, 95%); the addition of large excess of $H_2O$ was found to cause significant decomposition of N-heterocyclic phosphine (1,3,2-diazaphospholidine) to ethylenedianiline, resulting in a reduced product yield (entry 13, 76%).

TABLE 1

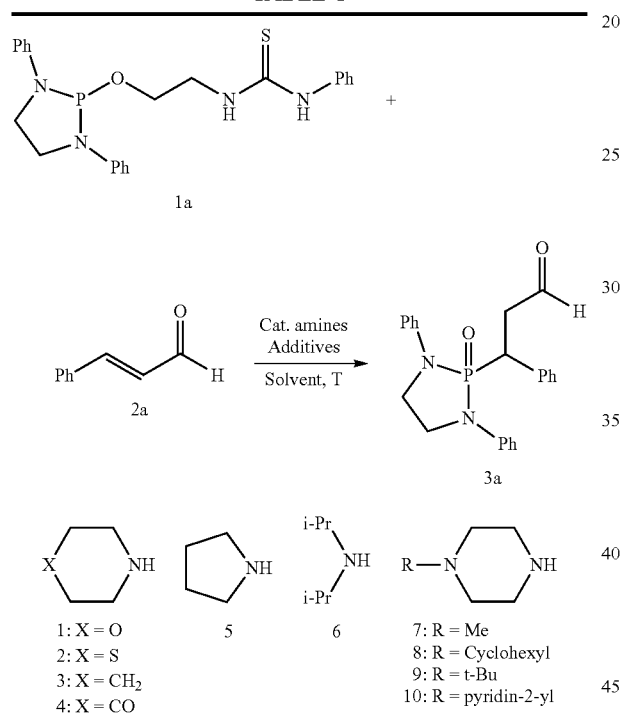

| entry | amines (mol %) | solvent | t (° C.) | additive (equiv) | 3a yield (%) |
|---|---|---|---|---|---|
| 1 | 1 (20) | DCM | 50 | — | 28 |
| 2 | 2 (20) | DCM | 50 | — | 65 |
| 3 | 3 (20) | DCM | 50 | — | 58 |
| 4 | 4 (20) | DCM | 50 | — | 28 |
| 5 | 5 (20) | DCM | 50 | — | 47 |
| 6 | 6 (20) | DCM | 50 | — | 52 |
| 7 | 7 (20) | DCM | 50 | — | 67 |
| 8 | 8 (20) | DCM | 50 | — | 71 |
| 9 | 9 (20) | DCM | 50 | — | 69 |
| 10 | 10 (20) | DCM | 50 | — | 40 |
| 11 | 8 (20) | DCM(dry) | 50 | — | 59 |
| 12 | 8 (20) | DCM(dry) | 50 | 4 Å MS | 23 |
| 13 | 8 (20) | DCM(dry) | 50 | $H_2O$ (1.0) | 75 |
| 14 | 8 (20) | DCM(dry) | 50 | $H_2O$ (5.0) | 80 |
| 15 | 8 (20) | DCM(dry) | 50 | $H_2O$ (8.0) | 76 |
| 16 | 8 (20) | DCM(dry) | 50 | $H_2O$ (10.0) | 72 |
| 17 | 8 (20) | DCM(dry) | 50 | $H_2O$ (15.0) | 72 |
| 18 | 8 (20) | DCE(dry) | 50 | $H_2O$ (5.0) | 71 |
| 10 | 8 (20) | $CHCl_3$(dry) | 50 | $H_2O$ (5.0) | 67 |
| 20 | 8 (20) | THF(dry) | 50 | $H_2O$ (5.0) | 70 |
| 21 | 8 (20) | $CH_3CN$(dry) | 50 | $H_2O$ (5.0) | 58 |

TABLE 1-continued

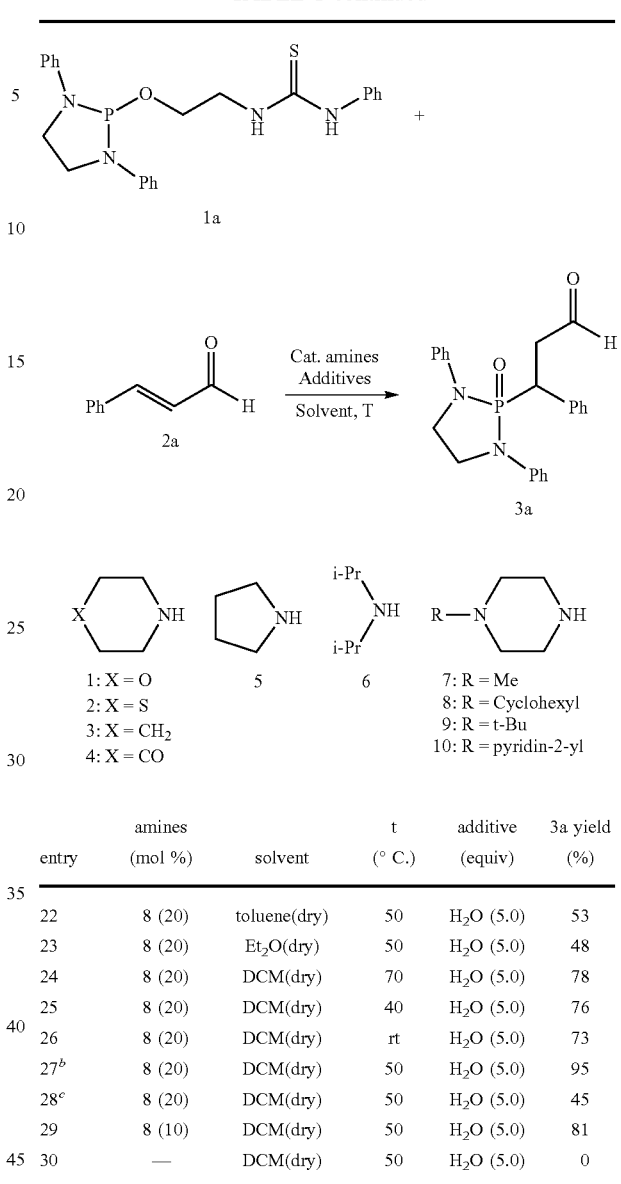

| entry | amines (mol %) | solvent | t (° C.) | additive (equiv) | 3a yield (%) |
|---|---|---|---|---|---|
| 22 | 8 (20) | toluene(dry) | 50 | $H_2O$ (5.0) | 53 |
| 23 | 8 (20) | $Et_2O$(dry) | 50 | $H_2O$ (5.0) | 48 |
| 24 | 8 (20) | DCM(dry) | 70 | $H_2O$ (5.0) | 78 |
| 25 | 8 (20) | DCM(dry) | 40 | $H_2O$ (5.0) | 76 |
| 26 | 8 (20) | DCM(dry) | rt | $H_2O$ (5.0) | 73 |
| 27[b] | 8 (20) | DCM(dry) | 50 | $H_2O$ (5.0) | 95 |
| 28[c] | 8 (20) | DCM(dry) | 50 | $H_2O$ (5.0) | 45 |
| 29 | 8 (10) | DCM(dry) | 50 | $H_2O$ (5.0) | 81 |
| 30 | — | DCM(dry) | 50 | $H_2O$ (5.0) | 0 |

[a]Reaction

[a] Reaction conditions: 1a (0.1 mmol), 2a (0.2 mmol) and catalysts (20 mol %) in solvent (2.0 mL) for 6 h.
[b] 0.3 mmol of 2a was added.
[c] 0.12 mmol of 1a was added.

7. Scope of NHP-Thioureas

Next, a systematic study of the effect of Brønsted acid motif on the intramolecular nucleophilic substitution reaction process was conducted (Table 2). The phenyl-substituted parent thiourea 1a generated the phospha-Michael adduct 3a in excellent yield (95%) with exclusivity 1,4 addition product (entry 1). Following optimization studies of the bifunctional NHPs revealed that the length of the tether between the NHP motif and a Brønsted acid played a pivotal role in effective hydrogen-bonding activation of the aldehyde. For example, NHPs with a longer tether provided lower product yields (entry 1 vs entries 2-3).

TABLE 2
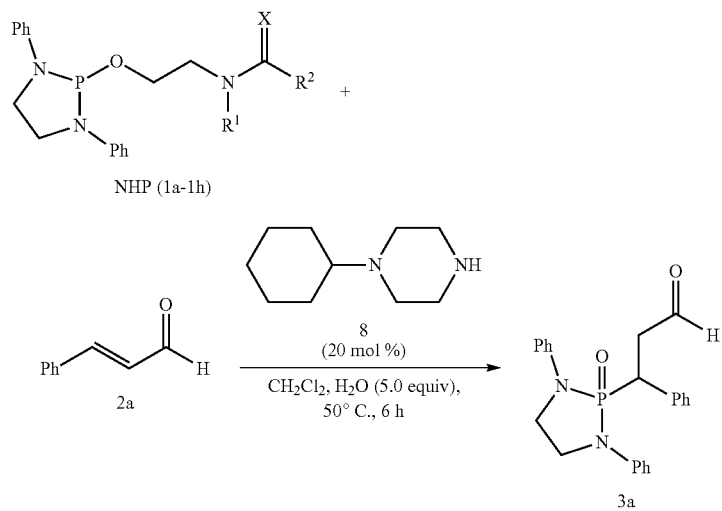
| entry | NHP | yield[b] |
|---|---|---|
| 1 | | 1a, n = 1; 95% |
| 2 | | 1b, n = 2; 87% |
| 3 | | 1c, n = 3; 80% |
| 4 | 1d | 67% |
| 5 | 1e | 56% |
| 6 | 1f | 66% |
| 7 | 1g | 33% |

TABLE 2-continued

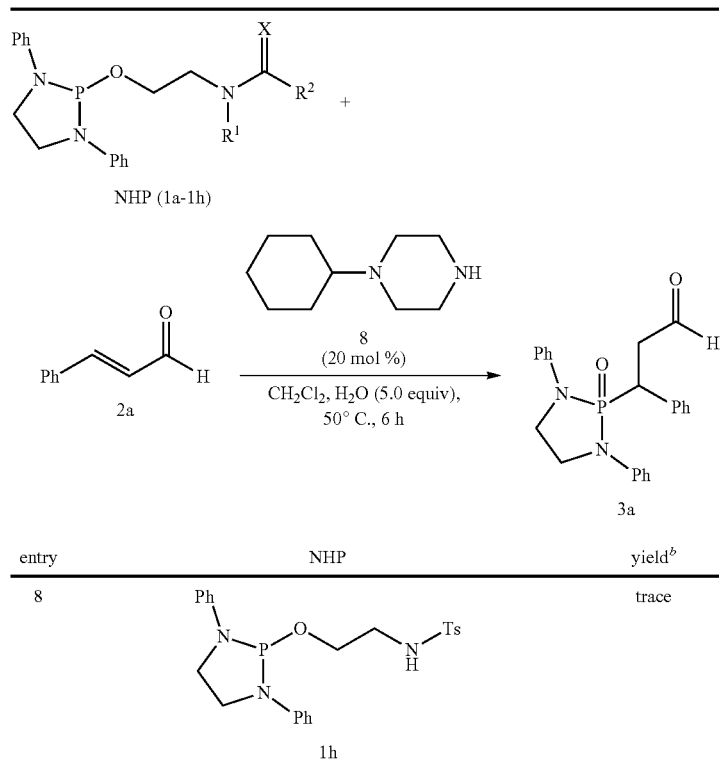

| entry | NHP | yield[b] |
|---|---|---|
| 8 | 1h | trace |

In order to investigate the electronic effects of the thiourea motif on this substitution reaction, 4-MeO- and 3,5-(CF$_3$)-phenyl thiourea-NHPs (1d-e) were subjected to the standard reaction conditions using 8 as catalyst, and the results showed that none of them were superior to the parent thiourea (entries 4-5 vs 1). Having a methyl substituent on the nitrogen atom at the Brønsted acid motif, the reaction also provided a lower yield (entry 6-7), presumably due to impeding of intramolecular nucleophilic substitution reaction sequence. The replacement of thiourea group with sulfonamide significantly reduced the reaction efficiency (entry 8). Lastly, the use of triethyl or diethylphosphite, previously known phosphonylation reagents (Maerten et al. (2007) *J. Org. Chem.* 72: 8893-8903; Moonen et al. (2005) *Angew. Chem. Int. Ed.* 44: 7407-7411; Zhao et al. (2009) *Chem. Eur. J.* 15: 2738-2741; Simoni et al. (1998) *Tetrahedron Lett.* 39: 7615-7618; Li et al. (2014) *Tetrahedron: Asymmetry* 25: 989-996; Strappaveccia et al. (2016) *Org. Biomol. Chem.* 14: 3521-3525; Wen et al. (2010) *Chem. Comm.* 46: 4806-4808), did not proceed to the phospha-Michael adducts under this standard reaction conditions in the absence of nucleophile additives.

8. Scope of a, b-Unsaturated Aldehydes for Phospha-Michael Addition

With the optimized reaction conditions established, the scope of this reaction was explored by treating NHP-thioureas and aldehydes (Scheme 7). The electronic effects of the NHP motifs (1i-1j) on this reaction had a negligible influence (3b-3c) whereas the steric effects induced by the ortho-substituents on the NHP motif (1k) completely suppressed the reactivity of this phospha-Michael reaction (3d). Aldehydes with para-substituted phenyl rings containing electron-donating groups (Me, 2e and OMe, 2f) or withdrawing groups (F, 2g and Br, 2h) were well tolerated and provided the corresponding products in high to excellent yields (3e-3h). In addition, a Michael acceptor with ortho-substituted phenyl ring (2i) proceeded smoothly to furnish the phospha-Michael adduct in excellent yield (3i, 90%). Heteroaromatic α,β-unsaturated aldehyde (2j) was also succeeded in producing the desired adduct in a moderate yield (3j, 64%). Furthermore, aliphatic α,β-unsaturated aldehyde, (E)-hex-2-enal (2k), was also suitable for this reaction to produce the corresponding product (3k) in 73% yield. Moreover, (2E,4E)-deca-2,4-dienal (2l) with the NHP-thiourea (1a) delivered an allylphosphonate in an acceptable yield (3l, 27%). Finally, the reactivity of acrolein was studied, but a poor product yield was obtained due to the instability of the product (3m).

SCHEME 7.

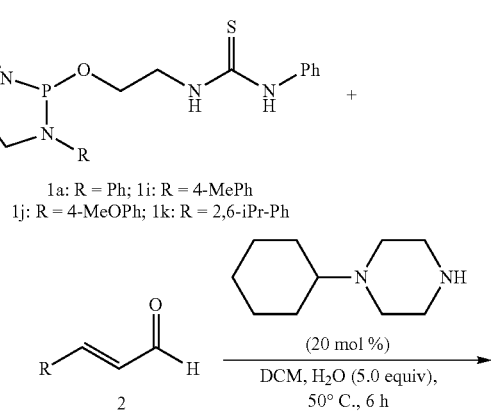

1a: R = Ph; 1i: R = 4-MePh
1j: R = 4-MeOPh; 1k: R = 2,6-iPr-Ph

-continued

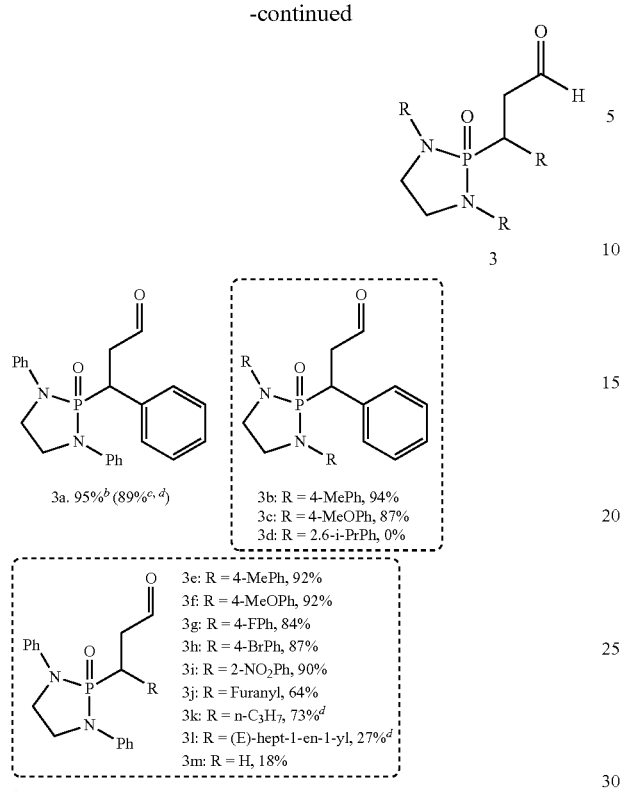

*Reaction conditions: 1 (0.1 mmol), 2 (0.3 mmol), H₂O (0.5 mmol), and 8 (20 mol %) in CH₂Cl₂ (0.5 mL) at 50° C. for 6 h. [b]Isolated yield. [c]Scale-up experiment with 2.3 mmol 1a loading. [d]Reaction run for 24 h.

9. Phospha-Michael Addition Reaction with Variously Substituted a, b-Unsaturated Aldehydes To further explore the influence of steric hindrance on the Michael acceptor, several α,β-unsaturated aldehydes containing various substituents were examined under the standard reaction conditions (Scheme 8). The results showed that α,β-unsaturated aldehydes with α-substituents (2n, 2o) inhibited the phospha-Michael process, probably due to the challenge of forming the iminium intermediates. On the other hand, 3-methylbut-2-enal (2p) was smoothly converted to the corresponding tetra-substituted phosphonate in 55% yield.

SCHEME 8.

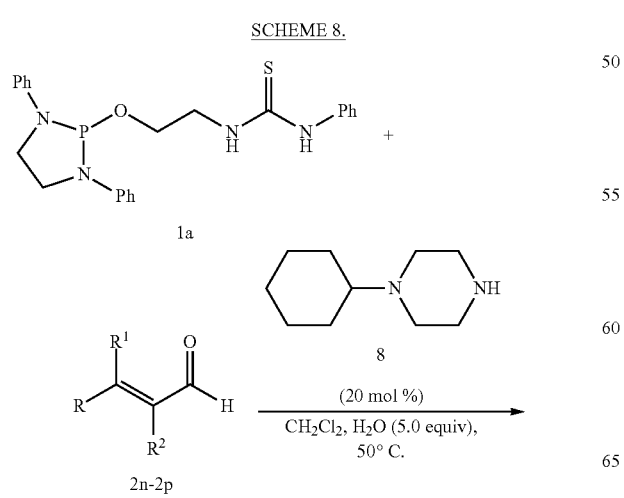

-continued

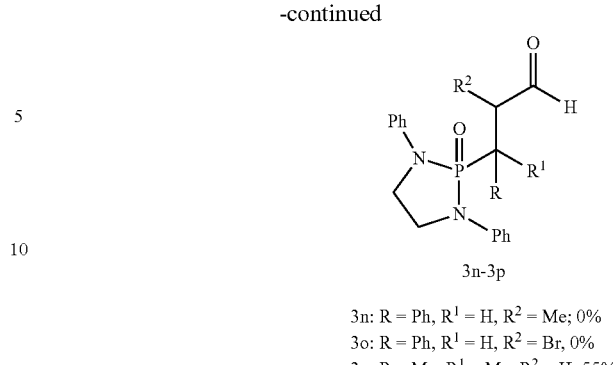

10. Scope of α, β-Unsaturated Ketones for Phospha-Michael Addition Reaction

With the potential of strong hydrogen bonding activation of the ketone group with thiourea Brønsted acid for the iminium formation, the possibility of phospha-Michael addition of enones utilizing the multi-functional NHP-thioureas was evaluated. A moderate yield of the product was obtained when (E)-4-phenylbut-3-en-2-one (2q) was employed as a Michael acceptor in our catalysis system (Scheme 9, 3q). The reaction is compatible with both electron-donating (OMe) and electron-withdrawing (F, Cl) groups on the enones (2r-2t). The reactivity of cyclohex-2-enone (2u) and 3-methylcyclohexenone (2v) were also investigated under the optimized reaction conditions, and the corresponding products (3u, 3v) were obtained in moderate yields, affording a tetra-substituted phosphonate (3v).

Scheme 9.

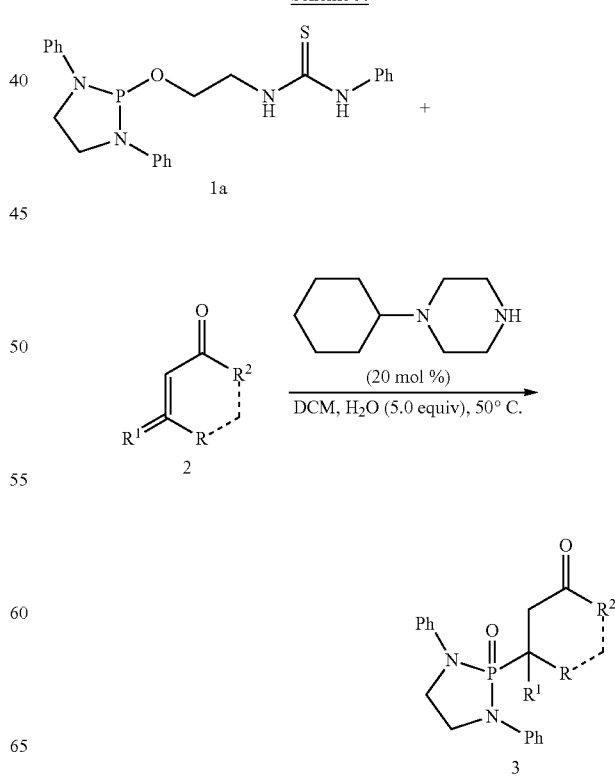

-continued

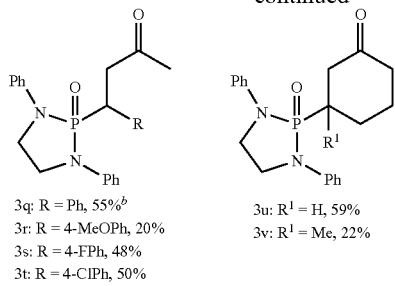

3q: R = Ph, 55%[b]
3r: R = 4-MeOPh, 20%
3s: R = 4-FPh, 48%
3t: R = 4-ClPh, 50%

3u: R¹ = H, 59%
3v: R¹ = Me, 22%

[a]Reaction conditions: 1a (0.1 mmol), 2 (0.3 mmol), H$_2$O (1.5 mmol), and 8 (20 mol %) in CH$_2$Cl$_2$ (0.5 mL) at 50° C., for 96 h. [b]Isolated yield.

11. Proposed Mechanism of Phospha-Michael Addition

On the basis of the observed experimental results and related previous works (Mulla et al. (2016) *J. Org. Chem.* 81: 77-88; Mulla and Kang (2016) *J. Org. Chem*), a plausible mechanism is depicted in Scheme 10. With a hydrogen-bond activation of the α,β-unsaturated ketone 2 by NHP-thiourea 1, amine 8 can effectively form an iminium intermediate A. A would be in equilibrium with a transient benzylic carbocation-stabilized enamine intermediate A1 also characterized as stable allylic carbocation to increase their chemoselectivity through hydrogen bond between the enamine intermediate and thiourea group. A1 subsequently undergoes a nucleophilic addition with the NHP 1 to form a C—P bond and enamine intermediate B. A sequential deprotonation/intramolecular nucleophilic substitution reaction provided a phosphonate intermediate C and thiazolidine byproduct D (Mulla et al. (2016) *J. Org. Chem.* 81: 77-88; Mulla and Kang (2016) *J. Org. Chem*). After hydrolysis of C, the corresponding product 3 is generated.

Scheme 10.

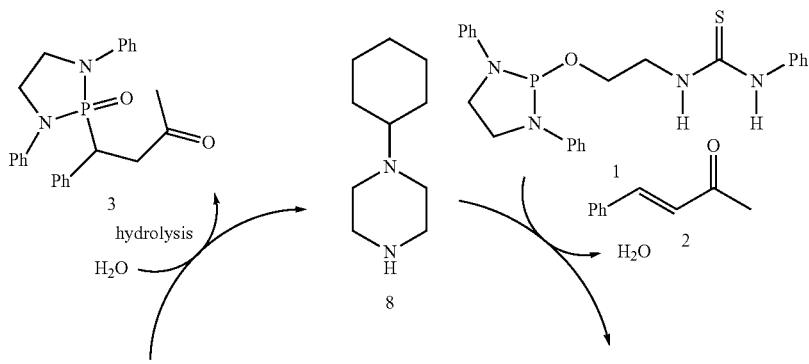

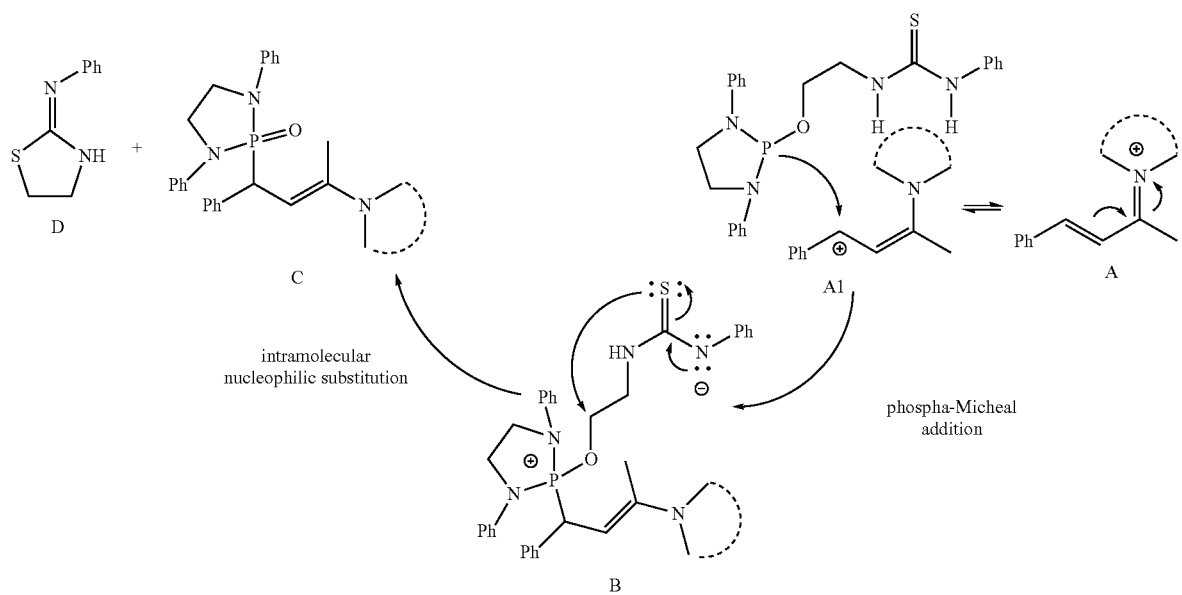

12. Synthetic Manipulation of Phospha-Michael Adduct 3a

To explore the synthetic utility of the Michael-adduct 3a, synthetic manipulations were carried out (Scheme 11). Firstly, a reduction of aldehyde 3a to an alcohol 4a was achieved with NaHB$_4$ in 99% yield. Wittig reaction of 3a afforded γ-vinyl diazaphosphonate 4b in 68% yield. Bromination of 3a using NBS and benzoyl peroxide produced only N-aryl-brominated product 4c. Additionally, oxidation of the aldehyde 3a to the corresponding carboxylic acid 4d was achieved with NaClO$_2$/H$_2$O$_2$ conditions (Dalcanale et al. (1986) *J. Org. Chem.* 51: 567-569). Moreover, considering a significant application of the P—N ligands to the bidentate ligands (Braunstein and Naud (2001) *Angew. Chem. Int. Ed.* 40: 680-699), reductive amination of 3a with BnNH$_2$/NaBH$_4$ was carried out to afford the corresponding product 4e in 52% overall yield. Finally, treatment of 3a with NH$_2$OH.HCl provided β-oximephosphonate 4f in high yield (86%).

13. Optimization of Phospha-Michael Addition Using Nitroolefins

NHP-thiourea 1a' and (E)-(2-nitrovinyl)benzene 2a' were used as model substrates to screen for optimal reaction conditions (Table 3). The initial solvent studies revealed that the halogenated solvent (CHCl$_3$) proved to be superior to the non-halogenated solvents and polar solvents (entry 2 vs entries 6-7), providing 64% yield of the desired products without additives or catalysts. A slight increment of the ratio of Michael acceptor 2a' helped to improve the product yield (entry 8, 75%). A significant improvement in reactivity for this phospha-Michael reaction was observed in higher solvent concentration conditions, which also reduced the reaction time drastically (entry 9, 91%, 4 h).

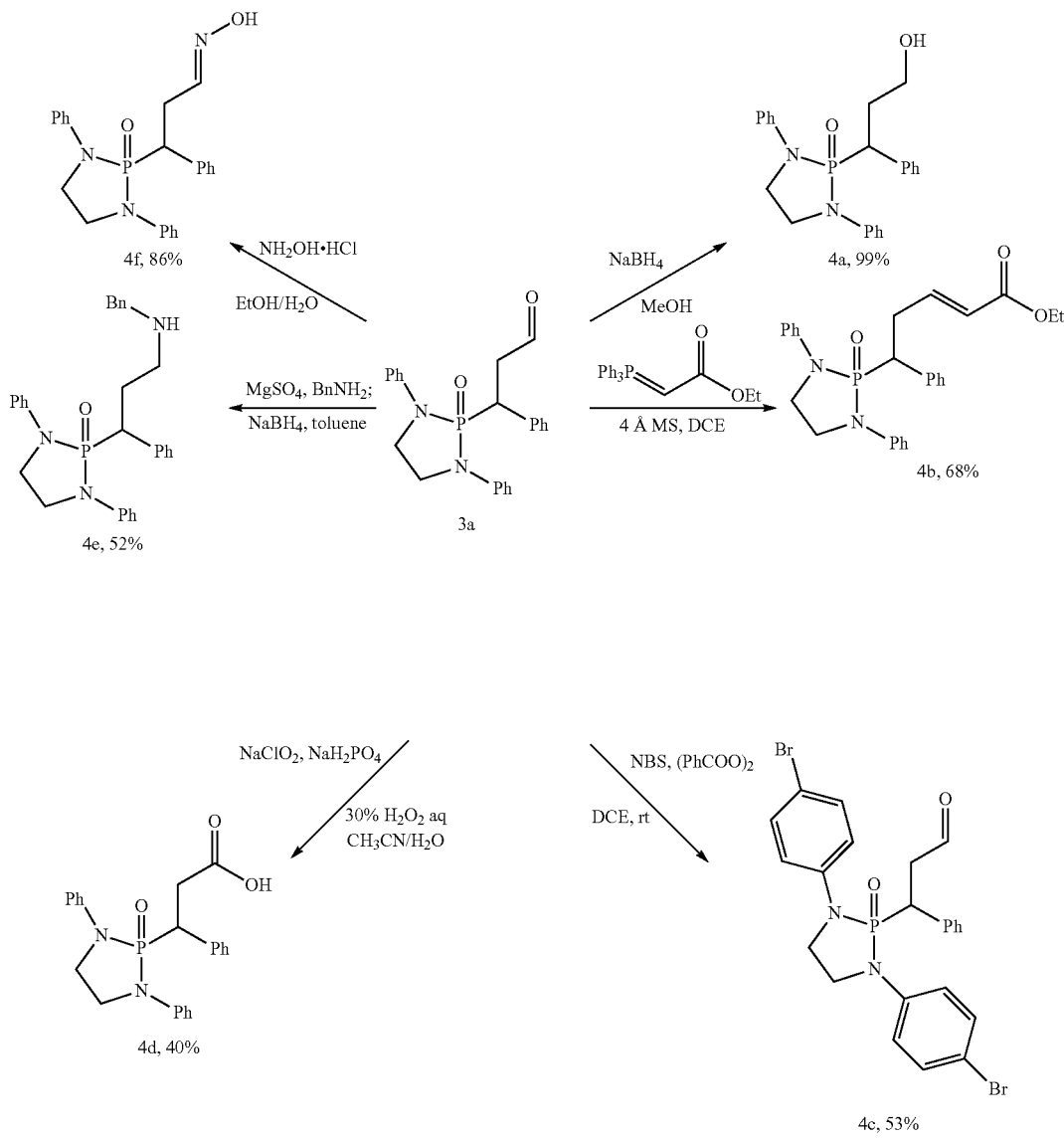

Scheme 11.

TABLE 3

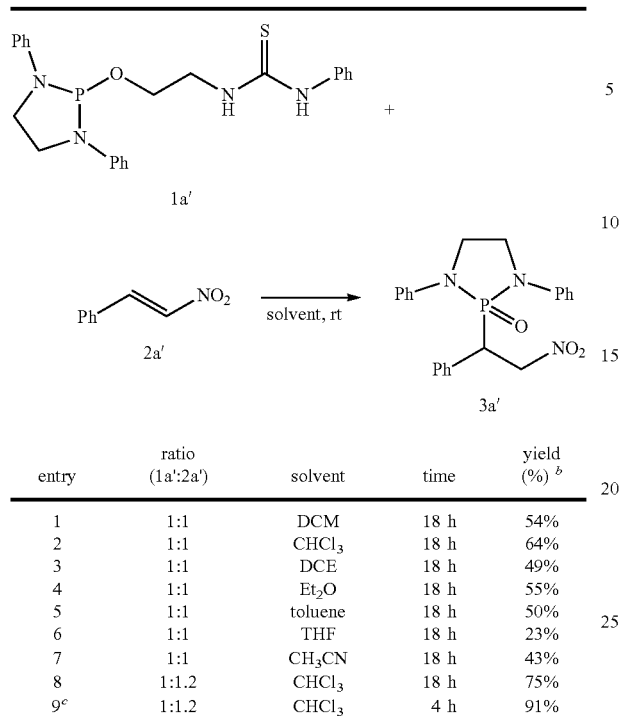

| entry | ratio (1a':2a') | solvent | time | yield (%) [b] |
|---|---|---|---|---|
| 1 | 1:1 | DCM | 18 h | 54% |
| 2 | 1:1 | CHCl$_3$ | 18 h | 64% |
| 3 | 1:1 | DCE | 18 h | 49% |
| 4 | 1:1 | Et$_2$O | 18 h | 55% |
| 5 | 1:1 | toluene | 18 h | 50% |
| 6 | 1:1 | THF | 18 h | 23% |
| 7 | 1:1 | CH$_3$CN | 18 h | 43% |
| 8 | 1:1.2 | CHCl$_3$ | 18 h | 75% |
| 9[c] | 1:1.2 | CHCl$_3$ | 4 h | 91% |

[a] Reaction conditions: 1a' (0.1 mmol), 2a' (0.1-0.12 mmol), and solvent (0.5 mL) for 4-18 h.
[b] Isolated yield (%).
[c] 0.3 mL solvent was used.

14. Scope of NHP-Thioureas Using Nitroolefins

Next, the effect of Brønsted acid motif on the intramolecular nucleophilic substitution reaction process of this phospha-Michael reaction was investigated (Table 4). The parent NHP-thiourea 1a' generated the phospha-Michael adduct 3a' in 91% yield (Table 4, entry 1). Further optimization studies of the bifunctional NHPs disclosed that the tether length between the NHP motif and a Brønsted acid may have a direct influence on the effective hydrogen-bond activation of the nitro group. NHPs with a lengthy tether reduced the efficiency of this transformation and resulted in lower product yields (entry 1 versus entries 2-3). For instance, a drastic decrement of the product yield was observed with the NHP-thiourea having a four-carbon length tether (entry 3). In addition, the electronic effects of the thiourea motif on this substitution reaction were also investigated. NHPs with a strongly electron-donating group (4-methoxyphenyl thiourea, 1d') and an electron-withdrawing group (3,5-bis(trifluoromethyl)phenyl, 1e') on the thiourea moiety were subjected to the standard reaction conditions yet both of them showed inferior results than the parent NHP-thiourea 1a' (entry 1 vs entries 4-5). Without wishing to be bound by theory, these outcomes may indicate a relationship between suitable hydrogen bond-activation of the nitroalkenes by a Brønsted acid and the nucleophilicity of an in-situ-generated anionic thiourea intermediate for the intramolecular nucleophilic substitution reaction. Having a methyl substituent on the nitrogen atom of the Brønsted acid motif such as N-methyl thiourea 1f' and N-methyl amide 1g', the reaction efficiency was significantly reduced (entries 6-7). Finally, replacement of a thiourea group with a sulfonic acid amide-reduced the reaction efficiency (entry 8).

TABLE 4

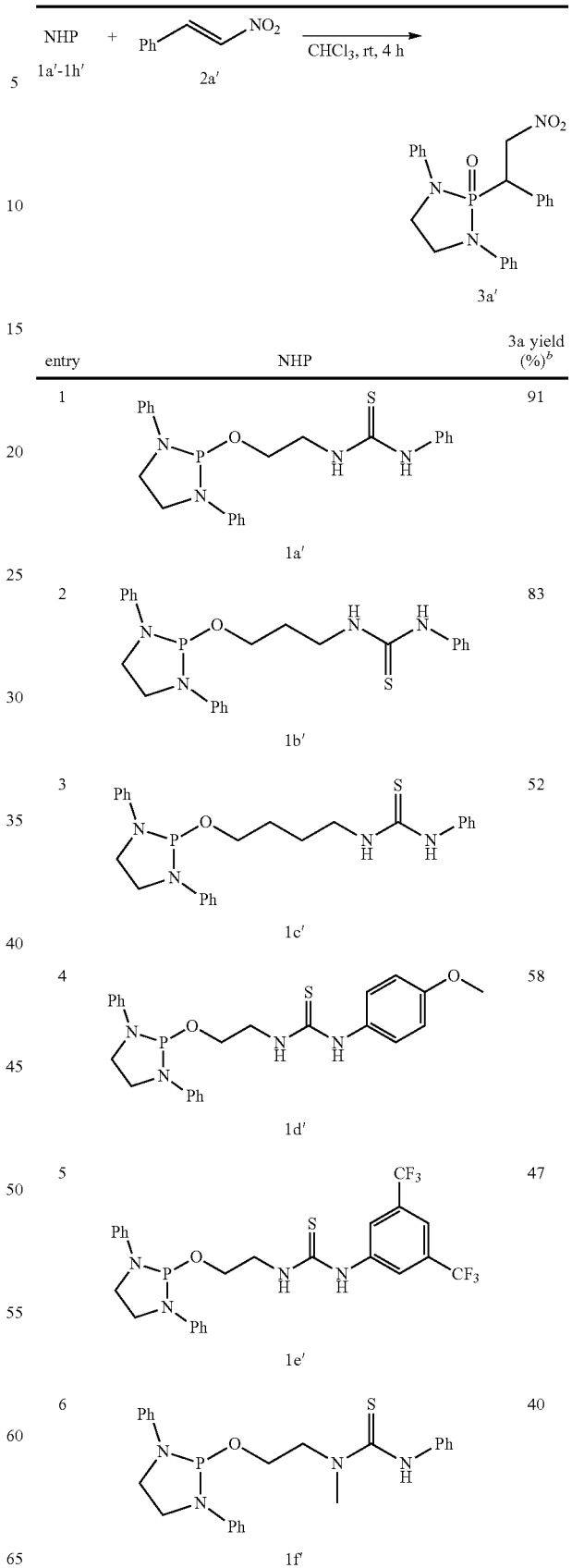

TABLE 4-continued

NHP + Ph—CH=CH—NO$_2$ →(CHCl$_3$, rt, 4 h) [product 3a']

1a'-1h'    2a'

[Structure of 3a': phospholidine ring with N-Ph, N-Ph, P=O, O-CH$_2$CH$_2$-CH(Ph)-CH$_2$NO$_2$]

3a'

| entry | NHP | 3a yield (%)[b] |
|---|---|---|
| 7 | 1g' (structure with N-methyl benzamide) | 0 |
| 8 | 1h' (structure with NHTs) | trace |

[a] Reaction conditions: 1a'-1h' (0.1 mmol), 2a' (0.12 mmol), and CHCl$_3$ (0.3 mL) at rt for 4 h.
[b] Isolated yield.

15. Scope of Nitroalkenes and NHP-Thioureas for Phospha-Michael Reaction

Having the optimized reaction conditions, the scope of this reaction was studied by treating NHP-thioureas with nitroalkenes (Table 5). The study of electronic and steric effects of the NHP motif on this transformation was performed under the standard reaction conditions. While the electronics have a negligible influence (3b'-3c'), the steric effects of the ortho-substituents on the NHP motif 1k' suppressed the reaction completely (3d'). Gratifyingly, this phospha-Michael addition reaction tolerated a wide range of functional groups on the nitroalkenes including electron-donating groups (3e'-3g') and electron-withdrawing groups (3h'-3k'), and provided good to high yields. Nitroalkenes with di-substituted phenyl groups were also viable substrates for this phospha-Michael reaction and afforded the corresponding β-nitrodiazaphosphonates in high yields (3n', 3o'). Heteroaromatic nitroalkenes were also succeeded in producing the desired adduct in 56-57% yields (3p', 3q'). Aliphatic nitroalkenes such as (E)-(2-nitrovinyl)cyclohexane 2r', (E)-1-nitropent-1-ene 2s', and (E)-(3-nitroallyl)benzene 2t' also proved to be useful substrates under the standard reaction conditions (3r'-3t'). Finally, highly conjugated nitroalkenes, ((1E,3E)-4-nitrobuta-1,3-dien-1-yl)benzene 2u', furnished an allylphosphonate compound 3u' in an acceptable yield (28%).

TABLE 5

[Structure: NHP-thiourea with phospholidine N-Ph, N-Ph, P-O-CH$_2$CH$_2$-NH-C(=S)-NH-Ph]

1a': R = Ph
1i': R = 4-MePh
1j': R = 4-MeOPh
1k': R = 2,6-iPrPh

2a'-2u' →(CHCl$_3$, rt, 4-6 h) 3a'-3u'

| Product No. | Yield (%) |
|---|---|
| 3a' | 91 |
| 3b' | 88 |
| 3c' | 91 |
| 3d' (R = 2,6-iPr) | 0 |
| 3e' | 90 |
| 3f' | 70 |
| 3g' | 73 |
| 3h' | 88 |
| 3i' | 86 |
| 3j' | 79 |
| 3k' | 89 |
| 3l' | 72 |
| 3m' | 71 |
| 3n' | 81 |
| 3o' | 83 |
| 3p' | 56 |
| 3q' | 57 |
| 3r' | 48 |
| 3s' | 51 |
| 3t' | 61 |
| 3u' | 28 |

[a] Reaction conditions: 1 (0.1 mmol), 2 (0.12 mmol), and CHCl$_3$ (0.3 mL) at rt for 4 h.
[b] Isolated yield.
[c] Reaction run for 6 h.

16. Synthetic Utility of Phospha-Michael Adduct 3a

Next, the synthetic utilities of the phospha-Michael adducts was explored (Scheme 12). The regioselective bromination of electron-rich aromatic ring 3a' was performed using NBS and benzoyl peroxide in which only N-aryl-brominated product 4a' was obtained in 63% yield. The reduction of a nitro group to an amine was achieved under the modified nickel boride conditions, and it provided N-Boc-protected β-aminodiazaphosphonate 4b' in 88% yield (Alcaine et al. (2011) Org. Biomol. Chem. 9: 2777-2783).

SCHEME 12.

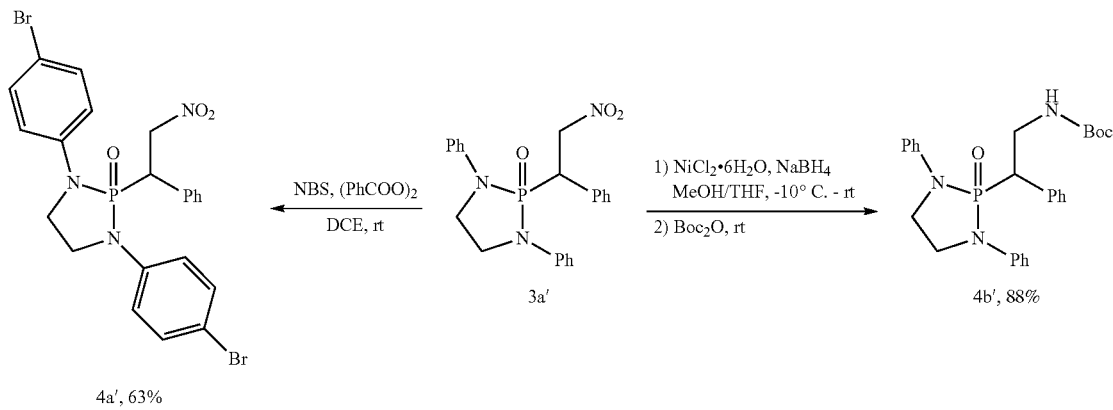

4a', 63%    3a'    4b', 88%

17. Proposed Mechanism of Phospha-Michael Addition to Nitroolefins

On the basis of experimental observations and previous works (Mulla et al. (2016) *J. Org. CHem.* 81: 77-88; Mulla and Kang (2016) *J. Org. Chem.* 81: 4550-4558), a rational mechanism for the formation of 3a' was theorized (Scheme 13). The Michael addition of NHP-thiourea 1a' to nitroalkene 2' activated through a hydrogen bonding with a thiourea motif may generate diazaphosphonium intermediate A. The sequential proton transfer/tautomerization process furnishes an anionic thiourea intermediate B. The anionic thiourea-initiated intramolecular nucleophilic substitution reaction responses to the formation of β-nitrodiazaphosphonate 3a' and thiazolidine byproduct C.

E. References

Trost, B. M., *Science* 1991, 254, 1471-1477.
Trost, B. M., *Angew. Chem. Int. Ed.* 1995, 34, 259-281.
Rulev, A. Y., *RSC Adv.* 2014, 4, 26002-26012.
Enders, D.; Saint-Dizier, A.; Lannou, M.-I.; Lenzen, A., *Eur. J. Org. Chem.* 2006, 2006, 29-49.
Maerten, E.; Cabrera, S.; Jorgensen, K. A., *J. Org. Chem.* 2007, 72, 8893-8903.
Moonen, K.; Van Meenen, E.; Verwée, A.; Stevens, C. V., *Angew. Chem. Int. Ed.* 2005, 44, 7407-7411.
Laghzizil, A.; Elhrech, N.; Britel, O.; Bouhaouss, A.; Ferhat, M., *J. Fluorine Chem.* 2000, 101, 69-73.
Moiseev, D. V.; Patrick, B. O.; James, B. R., *Inorg. Chem.* 2007, 46, 11467-11474.

SCHEME 14.

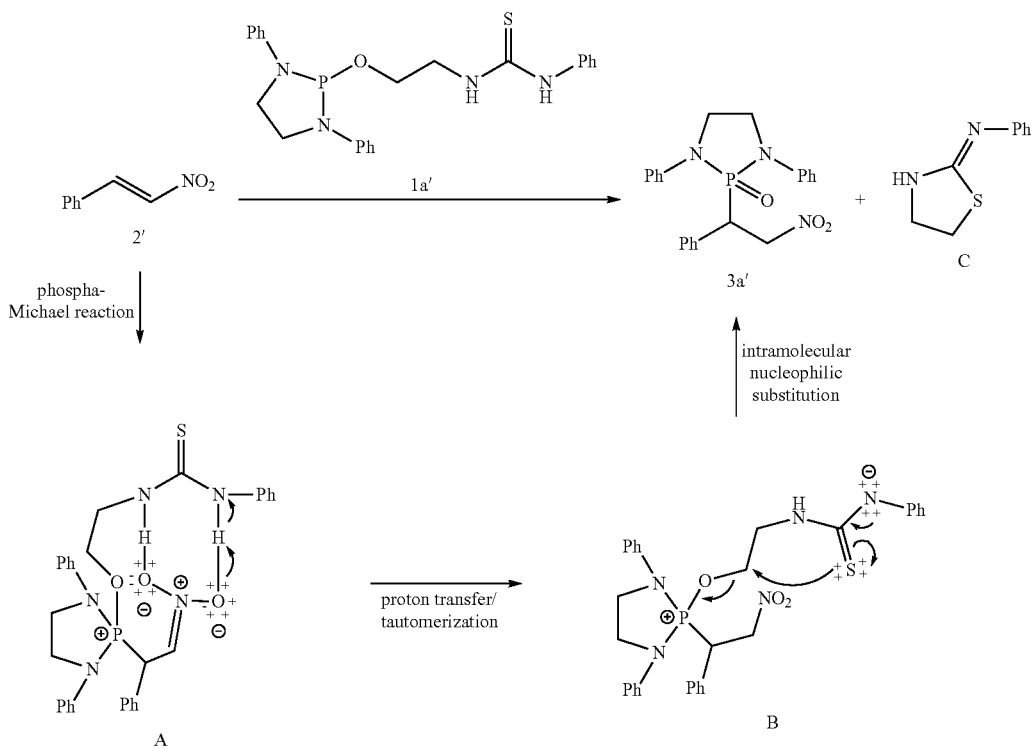

Luo, X.; Zhou, Z.; Li, X.; Liang, X.; Ye, J., *RSC Adv.* 2011, 1, 698-705.

Zhao, D.; Yuan, Y.; Chan, A. S. C.; Wang, R., *Chem. Eur. 1* 2009, 15, 2738-2741.

Simoni, D.; Invidiata, F. P.; Manferdini, M.; Lampronti, I.; Rondanin, R.; Roberti, M.; Pollini, G. P., *Tetrahedron Lett.* 1998, 39, 7615-7618.

Li, G.; Wang, L.; Yao, Z.; Xu, F., *Tetrahedron: Asymmetry* 2014, 25, 989-996.

Strappaveccia, G.; Bianchi, L.; Ziarelli, S.; Santoro, S.; Lanari, D.; Pizzo, F.; Vaccaro, L., *Org. Biomol. Chem.* 2016, 14, 3521-3525.

Wen, S.; Li, P.; Wu, H.; Yu, F.; Liang, X.; Ye, J., *Chem. Comm.* 2010, 46, 4806-4808.

Russo, A.; Lattanzi, A., *Eur. J. Org. Chem.* 2010, 2010, 6736-6739.

Rai, V.; Namboothiri, I. N. N., *Tetrahedron: Asymmetry* 2008, 19, 2335-2338.

Zhu, Y.; Malerich, J. P.; Rawal, V. H., *Angew. Chem. Int. Ed.* 2010, 49, 153-156.

Fu, X.; Jiang, Z.; Tan, C.-H., *Chem. Commun.* 2007, 5058-5060.

Wang, J.; Heikkinen, L. D.; Li, H.; Zu, L.; Jiang, W.; Xie, H.; Wang, W., *Adv. Synth. Catal.* 2007, 349, 1052-1056.

Lenker, H. K.; Richard, M. E.; Reese, K. P.; Carter, A. F.; Zawisky, J. D.; Winter, E. F.; Bergeron, T. W.; Guydon, K. S.; Stockland, R. A., *J. Org. Chem.* 2012, 77, 1378-1385.

Li, Z.; Ni, Y.; Qiu, F.; Ying, A.; Xu, S.; Wang, Y., *Catal. Lett.* 2014, 144, 1810-1818.

Sobhani, S.; Bazrafshan, M.; Delluei, A. A.; Parizi, Z. P., *Appl. Catal., A* 2013, 454, 145-151.

Sobhani, S.; Parizi, Z. P.; Rezazadeh, S., *J. Organomet. Chem.* 2011, 696, 813-817.

Hosseini-Sarvari, M.; Etemad, S., *Tetrahedron* 2008, 64, 5519-5523.

Kluender, H.; Benz, G.; Brittelli, D.; Bullock, W.; Combs, K.; Dixon, B.; Schneider, S.; Wood, J.; Vanzandt, M.; Wolanin, D. In US Pat. Appl. US 95-539409 951106, Chem. Abstr 1998; p 161412.

Schwender, C. F.; Beers, S. A.; Malloy, E.; Demarest, K.; Minor, L.; Lau, K. H. W., *Bioorg. Med. Chem. Lett.* 1995, 5, 1801-1806.

Jomaa, H.; Wiesner, J.; Sanderbrand, S.; Altincicek, B.; Weidemeyer, C.; Hintz, M.; Türbachova, I.; Eberl, M.; Zeidler, J.; Lichtenthaler, H. K.; Soldati, D.; Beck, E., *Science* 1999, 285, 1573-1576.

Andaloussi, M.; Henriksson, L. M.; Więckowska, A.; Lindh, M.; Björkelid, C.; Larsson, A. M.; Suresh, S.; Iyer, H.; Srinivasa, B. R.; Bergfors, T.; Unge, T.; Mowbray, S. L.; Larhed, M.; Jones, T. A.; Karlén, A., *J. Med. Chem.* 2011, 54, 4964-4976.

Ikemura, K.; R. Tay, F.; Nishiyama, N.; H. Pashley, D.; Endo, T., *Dent. Mater. J.* 2006, 25, 566-575.

Mulla, K.; Aleshire, K. L.; Forster, P. M.; Kang, J. Y., *J. Org. Chem.* 2016, 81, 77-88.

Mulla, K.; Kang, J. Y., *J. Org. Chem.* 2016.

Wang, F.; Wang, S.; Zhu, X.; Zhou, S.; Miao, H.; Gu, X.; Wei, Y.; Yuan, Q., *Organometallics* 2013, 32, 3920-3931.

Zhang, A.; Cai, L.; Yao, Z.; Xu, F.; Shen, Q., *Heteroat. Chem.* 2013, 24, 345-354.

Dalcanale, E.; Montanari, F., *J. Org. Chem.* 1986, 51, 567-569.

Braunstein, P.; Naud, F., *Angew. Chem. Int. Ed.* 2001, 40, 680-699.

Palacios, F.; Alonso, C.; de los Santos, J. M., *Chem. Rev.* 2005, 105, 899-932.

Juaristi, E.; Soloshonok, V. A., *Enantioselective synthesis of beta-amino acids*. John Wiley & Sons, 2005.

Yokomatsu, T.; Sato, M.; Shibuya, S., *Tetrahedron: Asymmetry* 1996, 7, 2743-2754.

Bigge, C. F.; Johnson, G.; Ortwine, D. F.; Drummond, J. T.; Retz, D. M.; Brahce, L. J.; Coughenour, L. L.; Marcoux, F. W.; Probert, A. W., *J. Med. Chem.* 1992, 35, 1371-1384.

Kinney, W. A.; Abou-Gharbia, M.; Garrison, D. T.; Schmid, J.; Kowal, D. M.; Bramlett, D. R.; Miller, T. L.; Tasse, R. P.; Zaleska, M. M.; Moyer, J. A., *J. Med. Chem.* 1998, 41, 236-246.

Kinney, W. A.; Lee, N. E.; Garrison, D. T.; Podlesny, E. J.; Simmonds, J. T.; Bramlett, D.; Notvest, R. R.; Kowal, D. M.; Tasse, R. P., *J. Med. Chem.* 1992, 35, 4720-4726.

Schweitzer, B. A.; Loida, P. J.; Thompson-Mize, R. L.; CaJacob, C. A.; Hegde, S. G., *Bioorg. Med. Chem. Lett.* 1999, 9, 2053-2058.

Wester, R. T.; Chambers, R. J.; Green, M. D.; Murphy, W. R., *Bioorg. Med. Chem. Lett.* 1994, 4, 2005-2010.

Yang, Q.; Li, C.; Cheng, M.-X.; Yang, S.-D., *ACS Catal.* 2016, 6, 4715-4719.

Cai, Y.; Li, Y.; Zhang, M.; Fu, J.; Miao, Z., *RSC Adv.* 2016, 6, 69352-69356.

Turcheniuk, K. V.; Poliashko, K. O.; Kukhar, V. P.; Rozhenko, A. B.; Soloshonok, V. A.; Sorochinsky, A. E., *Chem. Commun.* 2012, 48, 11519-11521.

Radwan-Olszewska, K.; Palacios, F.; Kafarski, P., *J. Org. Chem.* 2011, 76, 1170-1173.

Pudovik, A. N.; Konovalova, I. V., *Synthesis* 1979, 81-96.

Dingwalla, J. G.; Ehrenfreund, J.; Hall, R. G., *Tetrahedron* 1989, 45, 3787-3808.

Wang, J.; Heikkinen, L. D.; Li, H.; Zu, L.; Jiang, W.; Xie, H.; Wang, W., *Adv. Synth. Catal.* 2007, 349, 1052-1056.

Terada, M.; Ikehara, T.; Ube, H., *J. Am. Chem. Soc.* 2007, 129, 14112-14113.

Abbaraju, S.; Bhanushali, M.; Zhao, C.-G., *Tetrahedron* 2011, 67, 7479-7484.

Alcaine, A.; Marques-Lopez, E.; Merino, P.; Tejero, T.; Herrera, R. P., *Org. Biomol. Chem.* 2011, 9, 2777-2783.

Sohtome, Y.; Horitsugi, N.; Takagi, R.; Nagasawa, K., *Adv. Synth. Catal.* 2011, 353, 2631-2636.

Jiang, Z.; Zhang, Y.; Ye, W.; Tan, C.-H., *Tetrahedron Lett.* 2007, 48, 51-54.

Li, Y.-G.; Liu, Y.-S.; Miao, F.-M.; Liu, X.-L.; Cao, J.-H.; Zhou, W.; Wen, M.-X., *Phosphorus, Sulfur, Silicon, Relat. Elem.* 1990, 47, 229-242.

Yamamoto, H.; Hanaya, T.; Kawamoto, H.; Inokawa, S.; Yamashita, M.; Armour, M. A.; Nakashima, T. T., *J. Org. Chem.* 1985, 50, 3516-3521.

Yamashita, M.; Sugiura, M.; Tamada, Y.; Oshikawa, T.; Clardy, J., *Chem. Lett.* 1987, 16, 1407-1408.

Enders, D.; Tedeschi, L.; Bats, J. W., *Angew. Chem. Int. Ed.* 2000, 39, 4605-4607.

Tronchet, J. M. J.; Pallie, K. D.; Barbalat-Rey, F., *J. Carbohydr. Chem.* 1985, 4, 29-52.

Yamashita, M.; Sugiura, M.; Oshikawa, T.; Inokawa, S., *Synthesis* 1987, 62-64.

Hanaya, T.; Yamamoto, H.; Yamamoto, H., *Bull. Chem. Soc. Jpn.* 1992, 65, 1154-1156.

Robbie, A. J.; Cowley, A. R.; Jones, M. W.; Dilworth, J. R., *Polyhedron* 2011, 30, 1849-1856.

Bernacki, A. L.; Zhu, L.; Hennings, D. D., *Org. Lett.* 2010, 12, 5526-5529.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for preparing a product compound having a structure represented by a formula:

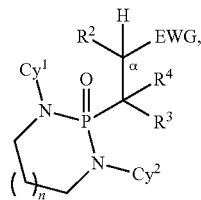

wherein n is 0 or 1;
wherein each of $Cy^1$ and $Cy^2$ is independently selected from:
  aryl substituted with 0, 1, 2, or 3 groups independently selected from halogen, hydroxyl, amine, alkylamino, dialkylamino, C1-C4 alkyl, and C1-C4 alkoxy;
  a 5- or 6-membered heteroaryl having 1, 2, or 3 ring-members selected from O, S, and $NR^1$ and substituted with 0, 1, 2, or 3 groups independently selected from halogen, hydroxyl, amine, alkylamino, dialkylamino, C1-C4 alkyl, and C1-C4 alkoxy;
  a 5- or 6-membered cycloalkyl substituted with 0, 1, 2, or 3 groups independently selected from halogen, hydroxyl, amine, alkylamino, dialkylamino, C1-C4 alkyl, and C1-C4 alkoxy; and
  a 5- or 6-membered heterocycloalkyl having 1, 2, or 3 ring-members selected from O, S, and $NR^1$ and substituted with 0, 1, 2, or 3 groups independently selected from halogen, hydroxyl, amine, alkylamino, dialkylamino, C1-C4 alkyl, and C1-C4 alkoxy;
wherein each $R^1$ is independently selected from hydrogen, C1-C4 alkyl, aryl, 5- or 6-membered heteroaryl, 5- or 6-membered cycloalkyl, and —(C1-C4 alkyl)aryl, and substituted with 0, 1, 2, or 3 groups independently selected from halogen, hydroxyl, amine, alkylamino, dialkylamino, C1-C4 alkyl, and C1-C4 alkoxy;
wherein $R^2$ is selected from hydrogen, halogen, hydroxyl, amine, alkylamino, dialkylamino, C1-C4 alkyl, C1-C4 alkoxy, and an electron-withdrawing group; and
wherein $R^3$ is selected from hydrogen, hydroxyl, amine, alkyl amine, dialkylamine, C1-C4 alkyl, C1-C8 alkenyl, C1-C4 alkoxy, —C(O)OH, —C(O)$OR^5$, —C(O)$R^5$, —C(O)$NHR^6$, aryl, a 5- or 6-membered heteroaryl having 1, 2, or 3 ring-members selected from O, S, and $NR^1$, a 5- or 6-membered cycloalkyl, (C1-C4 alkyl)aryl, and (C1-C4 alkenyl)aryl, and substituted with 0, 1, 2, or 3 groups independently selected from halogen, hydroxyl, amine, alkylamino, dialkylamino, C1-C4 alkyl, and C1-C4 alkoxy; or
wherein $R^2$ and $R^3$, together with the intervening atoms, comprise a 5- or 6-membered cycloalkyl or a 5- or 6-membered heterocycloalkyl having 1, 2, or 3 ring-members selected from O, S, and $NR^1$, substituted with 0, 1, 2, or 3 groups independently selected from oxo, hydroxyl, halogen, C1-C4 alkyl, C1-C4 alkoxy, —C(O)OH, —C(O)$OR^5$, —C(O)$R^5$, and —C(O)$NHR^6$;
wherein EWG is an electron-withdrawing group; and
wherein $R^4$ is selected from hydrogen, hydroxyl, amine, alkyl amine, dialkylamine, C1-C4 alkyl, C1-C8 alkenyl, C1-C4 alkoxy, —C(O)OH, —C(O)$OR^5$, —C(O)$R^5$, —C(O)$NHR^6$, aryl, a 5- or 6-membered heteroaryl having 1, 2, or 3 ring-members selected from O, S, and $NR^1$, a 5- or 6-membered cycloalkyl, (C1-C4 alkyl)aryl, and (C1-C4 alkenyl)aryl, and substituted with 0, 1, 2, or 3 groups independently selected from halogen, hydroxyl, amine, alkylamino, dialkylamino, C1-C4 alkyl, and C1-C4 alkoxy; or
wherein EWG and $R^4$, together with the intervening atoms, comprise a 5- or 6-membered cycloalkyl or a 5- or 6-membered heterocycloalkyl having 1 or 2 ring-members selected from O, S, and $NR^1$, substituted with 0, 1, 2, or 3 groups independently selected from hydroxyl, halogen, oxo, C1-C4 alkyl, C1-C4 alkoxy, —C(O)OH, —C(O)$R^5$, —C(O)$OR^5$, and —C(O)$NHR^6$; provided that the first atom of EWG adjacent to the position denoted α is substituted with oxo;
wherein each $R^5$ is independently selected from hydrogen and C1-C4 alkyl; and
wherein each $R^6$ is independently selected from hydrogen, C1-C4 alkyl, and aryl substituted with 0, 1, 2, or 3 groups independently selected from halogen, hydroxyl, amine, alkylamino, dialkylamino, C1-C4 alkyl, and C1-C4 alkoxy;
the method comprising the step of reacting a first compound having a structure represented by a formula:

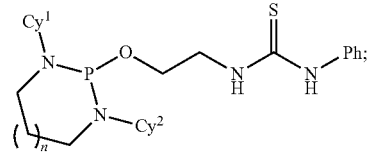

with a second compound having a structure represented by a formula:

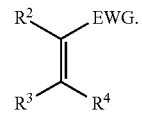

2. The method of claim 1, wherein the electron-withdrawing group is selected from nitro, cyano, —C(O)OH, —C(O)$R^5$, —C(O)$OR^5$, and —C(O)$NHR^6$.

3. The method of claim 1, wherein each of $Cy^1$ and $Cy^2$ is phenyl.

4. The method of claim 1, wherein n is 0.

5. A method for preparing a product compound having a structure represented by a formula:

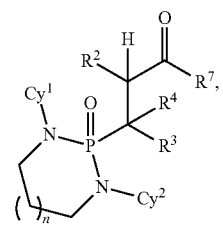

wherein n is 0 or 1;
wherein each of Cy¹ and Cy² is independently selected from:
  aryl substituted with 0, 1, 2, or 3 groups independently selected from halogen, hydroxyl, amine, alkylamino, dialkylamino, C1-C4 alkyl, and C1-C4 alkoxy;
  a 5- or 6-membered heteroaryl having 1, 2, or 3 ring-members selected from O, S, and NR¹ and substituted with 0, 1, 2, or 3 groups independently selected from halogen, hydroxyl, amine, alkylamino, dialkylamino, C1-C4 alkyl, and C1-C4 alkoxy;
  a 5- or 6-membered cycloalkyl substituted with 0, 1, 2, or 3 groups independently selected from halogen, hydroxyl, amine, alkylamino, dialkylamino, C1-C4 alkyl, and C1-C4 alkoxy; and
  a 5- or 6-membered heterocycloalkyl having 1, 2, or 3 ring-members selected from O, S, and NR¹ and substituted with 0, 1, 2, or 3 groups independently selected from halogen, hydroxyl, amine, alkylamino, dialkylamino, C1-C4 alkyl, and C1-C4 alkoxy;
wherein each R¹ is independently selected from hydrogen, C1-C4 alkyl, aryl, 5- or 6-membered heteroaryl, 5- or 6-membered cycloalkyl, and —(C1-C4 alkyl)aryl, and substituted with 0, 1, 2, or 3 groups independently selected from halogen, hydroxyl, amine, alkylamino, dialkylamino, C1-C4 alkyl, and C1-C4 alkoxy;
wherein R² is selected from hydrogen, halogen, hydroxyl, amine, alkylamino, dialkylamino, C1-C4 alkyl, C1-C4 alkoxy, and an electron-withdrawing group; and
wherein R³ is selected from hydrogen, hydroxyl, amine, alkyl amine, dialkylamine, C1-C4 alkyl, C1-C8 alkenyl, C1-C4 alkoxy, —C(O)OH, —C(O)OR⁵, —C(O)R⁵, —C(O)NHR⁶, aryl, a 5- or 6-membered heteroaryl having 1, 2, or 3 ring-members selected from O, S, and NR¹, a 5- or 6-membered cycloalkyl, (C1-C4 alkyl)aryl, and (C1-C4 alkenyl)aryl, and substituted with 0, 1, 2, or 3 groups independently selected from halogen, hydroxyl, amine, alkylamino, dialkylamino, C1-C4 alkyl, and C1-C4 alkoxy; or
wherein R² and R³, together with the intervening atoms, comprise a 5- or 6-membered cycloalkyl or a 5- or 6-membered heterocycloalkyl having 1, 2, or 3 ring-members selected from O, S, and NR¹, substituted with 0, 1, 2, or 3 groups independently selected from oxo, hydroxyl, halogen, C1-C4 alkyl, C1-C4 alkoxy, —C(O)OH, —C(O)OR⁵, —C(O)R⁵, and —C(O)NHR⁶;
wherein R⁷ is selected from hydrogen, hydroxyl, amine, alkyl amine, dialkylamine, C1-C4 alkyl, and C1-C4 alkoxy; and
wherein R⁴ is selected from hydrogen, hydroxyl, amine, alkyl amine, dialkylamine, C1-C4 alkyl, C1-C8 alkenyl, C1-C4 alkoxy, —C(O)OH, —C(O)OR⁵, —C(O)R⁵, —C(O)NHR⁶, aryl, a 5- or 6-membered heteroaryl having 1, 2, or 3 ring-members selected from O, S, and NR¹, a 5- or 6-membered cycloalkyl, (C1-C4 alkyl)aryl, and (C1-C4 alkenyl)aryl, and substituted with 0, 1, 2, or 3 groups independently selected from halogen, hydroxyl, amine, alkylamino, dialkylamino, C1-C4 alkyl, and C1-C4 alkoxy; or
wherein R⁷ and R⁴, together with the intervening atoms, comprise a 5- or 6-membered cycloalkyl or a 5- or 6-membered heterocycloalkyl having 1 or 2 ring-members selected from O, S, and NR¹, substituted with 0, 1, 2, or 3 groups independently selected from hydroxyl, halogen, oxo, C1-C4 alkyl, C1-C4 alkoxy, —C(O)OH, —C(O)R⁵, —C(O)OR⁵, and —C(O)NHR⁶;

wherein each R⁵ is independently selected from hydrogen and C1-C4 alkyl; and
wherein each R⁶ is independently selected from hydrogen, C1-C4 alkyl, and aryl substituted with 0, 1, 2, or 3 groups independently selected from halogen, hydroxyl, amine, alkylamino, dialkylamino, C1-C4 alkyl, and C1-C4 alkoxy;
the method comprising the step of reacting a first compound having a structure represented by a formula:

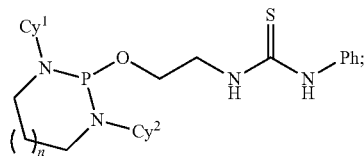

with a second compound having a structure represented by a formula:

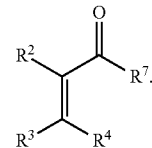

6. The method of claim 5, wherein each of Cy¹ and Cy² is phenyl.

7. The method of claim 5, wherein n is O.

8. The method of claim 5, wherein reacting is in the presence of a catalyst.

9. The method of claim 5, wherein the second compound has a structure represented by a formula:

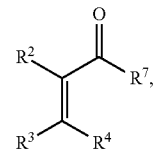

wherein R⁷ is selected from hydrogen, hydroxyl, amine, alkyl amine, dialkylamine, C1-C4 alkyl, and C1-C4 alkoxy.

10. The method of claim 5, wherein R⁷ and R⁴, together with the intervening atoms, comprise a 5- or 6-membered cycloalkyl or a 5- or 6-membered heterocycloalkyl having 1 or 2 ring-members selected from O, S, and NR¹, substituted with 0, 1, 2, or 3 groups independently selected from hydroxyl, halogen, oxo, C1-C4 alkyl, C1-C4 alkoxy, —C(O)OH, —C(O)R⁵, —C(O)OR⁵, and —C(O)NHR⁶.

11. The method of claim 10, wherein the second compound has a structure selected from:

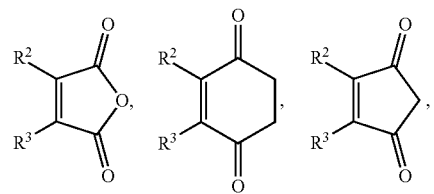

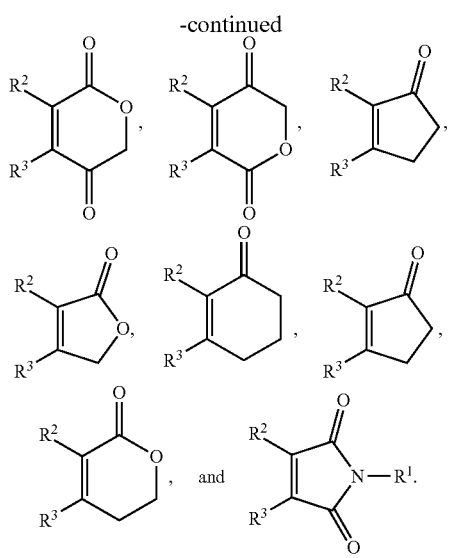
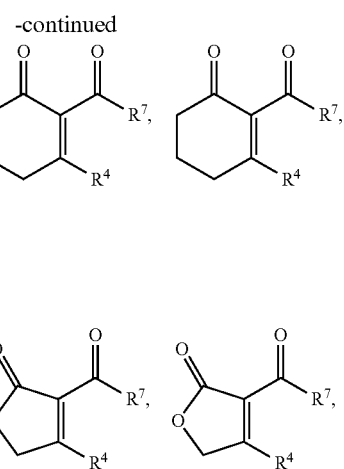
12. The method of claim 5, wherein the second compound has a structure selected from:
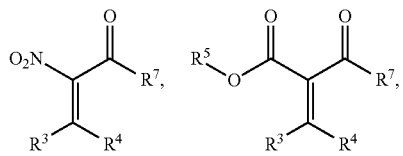
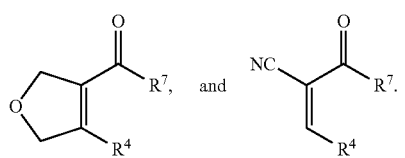
* * * * *